(12) United States Patent
Harp

(10) Patent No.: US 7,666,186 B2
(45) Date of Patent: Feb. 23, 2010

(54) SURGICAL SYSTEM WITH A BLADE

(75) Inventor: Richard J. Harp, Carlsbad, CA (US)

(73) Assignee: SurgiTech, LLC, Charlotte, NC (US)

(*) Notice: Subject to any disclaimer, the term of this patent is extended or adjusted under 35 U.S.C. 154(b) by 233 days.

(21) Appl. No.: 11/258,841

(22) Filed: Oct. 25, 2005

(65) Prior Publication Data

US 2006/0206117 A1 Sep. 14, 2006

Related U.S. Application Data

(63) Continuation-in-part of application No. 10/675,068, filed on Sep. 29, 2003, now Pat. No. 7,390,330.

(60) Provisional application No. 60/414,690, filed on Sep. 27, 2002, provisional application No. 60/621,843, filed on Oct. 25, 2004, provisional application No. 60/621,853, filed on Oct. 25, 2004, provisional application No. 60/701,727, filed on Jul. 22, 2005.

(51) Int. Cl.
*A61B 17/00* (2006.01)
(52) U.S. Cl. ....................................... 606/85
(58) Field of Classification Search .................. 606/85, 606/170, 171, 177
See application file for complete search history.

(56) References Cited

U.S. PATENT DOCUMENTS

| | | | |
|---|---|---|---|
| 3,642,002 A | 2/1972 | Otterstrom | |
| 3,978,862 A | 9/1976 | Morrison | |
| 4,867,155 A | 9/1989 | Isaacson | |
| 5,092,873 A | 3/1992 | Simpson et al. | |
| 5,195,519 A | 3/1993 | Angelsen | |
| 5,222,966 A | 6/1993 | Perkins et al. | |
| 5,411,513 A | 5/1995 | Ireland et al. | |
| 5,540,693 A | 7/1996 | Fisher | |
| 5,562,695 A | 10/1996 | Obenchain | |
| 5,643,304 A | 7/1997 | Schechter et al. | |
| 5,651,781 A | 7/1997 | Grace | |

(Continued)

FOREIGN PATENT DOCUMENTS

EP 0 716 831 B1 3/1999

(Continued)

OTHER PUBLICATIONS

International Preliminary Examination Report in corresponding International application No. PCT/US03/30906, dated Apr. 26, 2005, 4 pp.

(Continued)

*Primary Examiner*—Michael J Milano
*Assistant Examiner*—Victor X Nguyen
(74) *Attorney, Agent, or Firm*—Knobbe, Martens, Olson & Bear LLP

(57) ABSTRACT

A reciprocating surgical file system for precisely removing bone and/or other tissue is described. The system allows a user to maneuver the system and navigate into hard-to-access sites under a direct vision mechanism. A transmission mechanism converts rotary motion from a motor into reciprocating motion and provides it to the surgical file for precision removal of bone or other tissue. A pulsatile pump mechanism is operatively coupled with the transmission mechanism and provides irrigating fluid to the surgical site.

24 Claims, 86 Drawing Sheets

U.S. PATENT DOCUMENTS

| | | | |
|---|---|---|---|
| 5,669,923 A | 9/1997 | Gordon | |
| 5,846,244 A | 12/1998 | Cripe | |
| 5,983,136 A * | 11/1999 | Kamen | 604/21 |
| 6,001,115 A | 12/1999 | Ahola et al. | |
| 6,048,345 A | 4/2000 | Berke et al. | |
| 6,063,050 A | 5/2000 | Manna et al. | |
| 6,309,106 B1 | 10/2001 | Hooley | |
| 6,485,517 B1 * | 11/2002 | Michelson | 623/17.11 |
| 7,077,803 B2 | 7/2006 | Kasahara et al. | |
| 7,189,240 B1 | 3/2007 | Dekel | |
| 7,316,683 B2 | 1/2008 | Kasahara et al. | |
| 7,390,330 B2 | 6/2008 | Harp | |
| 2004/0122459 A1 | 6/2004 | Harp | |
| 2006/0058732 A1 | 3/2006 | Harp | |
| 2006/0079919 A1 | 4/2006 | Harp | |
| 2006/0161189 A1 | 7/2006 | Harp | |
| 2006/0200153 A1 | 9/2006 | Harp | |
| 2006/0200154 A1 | 9/2006 | Harp | |
| 2006/0200155 A1 | 9/2006 | Harp | |
| 2008/0058820 A1 | 3/2008 | Harp | |

FOREIGN PATENT DOCUMENTS

| | | |
|---|---|---|
| JP | 2002177317 | 6/2002 |
| WO | WO 89/09028 A1 | 10/1989 |
| WO | WO 99/39724 A1 | 8/1999 |
| WO | WO 01/08571 A1 | 2/2001 |
| WO | WO 01/13802 A1 | 3/2001 |
| WO | WO 01/66021 A1 | 9/2001 |
| WO | WO 02/36023 A1 | 5/2002 |
| WO | WO 2004/002331 A1 | 1/2004 |
| WO | WO 2004/080316 A1 | 9/2004 |

OTHER PUBLICATIONS

International Search Report in corresponding International application No. PCT/US03/30906, mailed May 24, 2004, 7 pp.

K. Tomita, MD, Ph.D. and N. Kawahara, MD, Ph.D.; The Threadwire Saw: a New Device for Cutting Bone; *The Journal of Bone and Joint Surgery*; Dec. 1996; vol. 78-A (12); pp. 1915-1917.

Jeong Tae Kim, M.D., Ph.D. and Seok Kwun Kim, M.D., Ph.D.; Endoscopically Assisted, Intraorally Approached Corrective Rhinoplasty; *Department of Plastic and Reconstructive Surgery at the Dong-A-University College of Medicine and Institute of Medical Science*; Jul. 2001; vol. 108, No. 1; pp. 199-205.

* cited by examiner

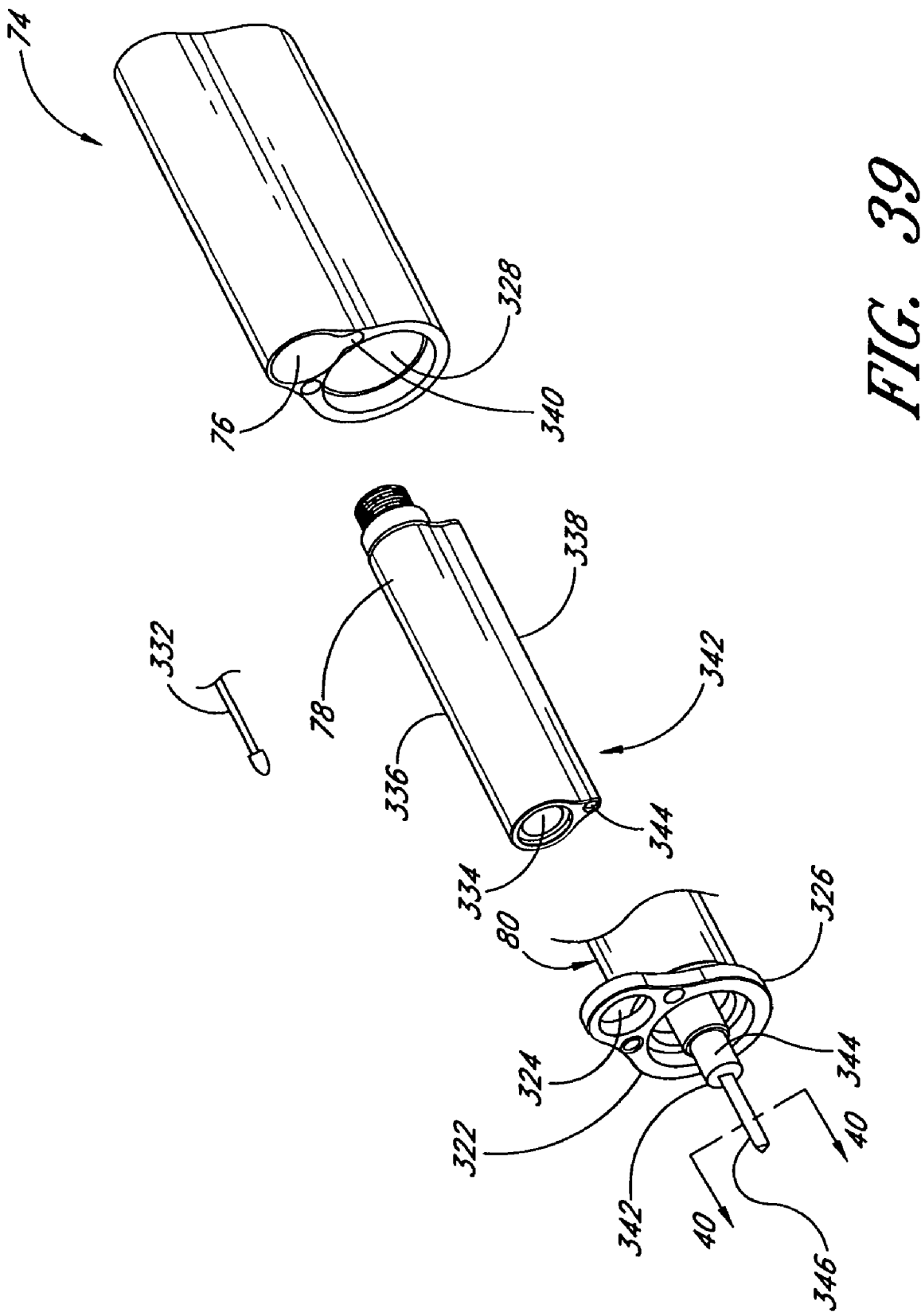

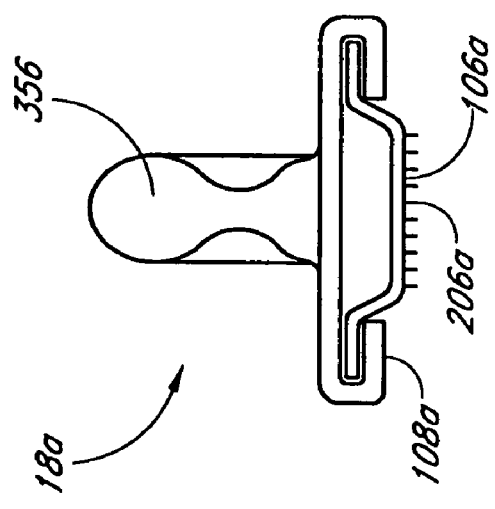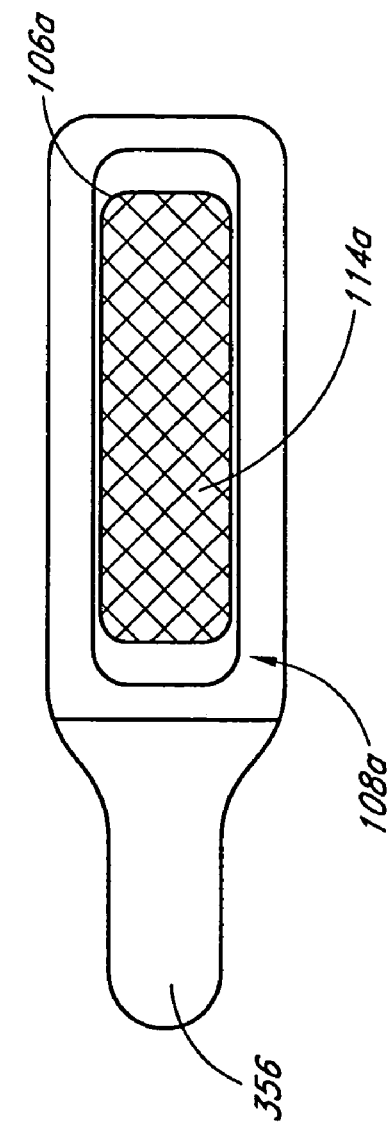

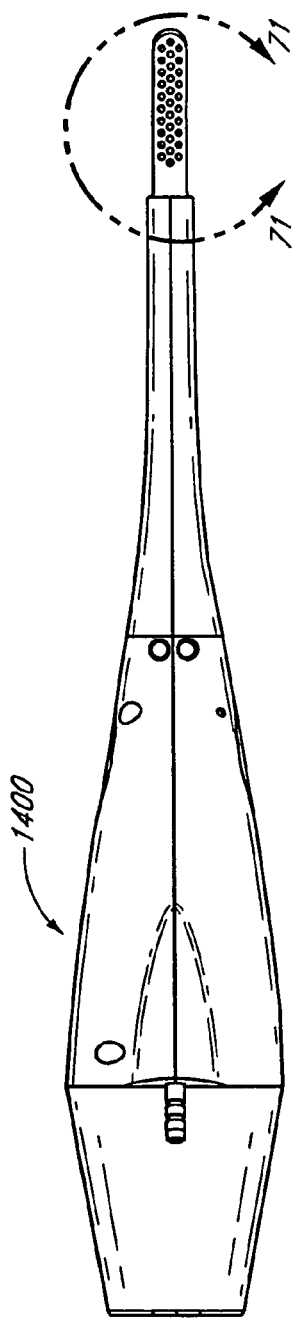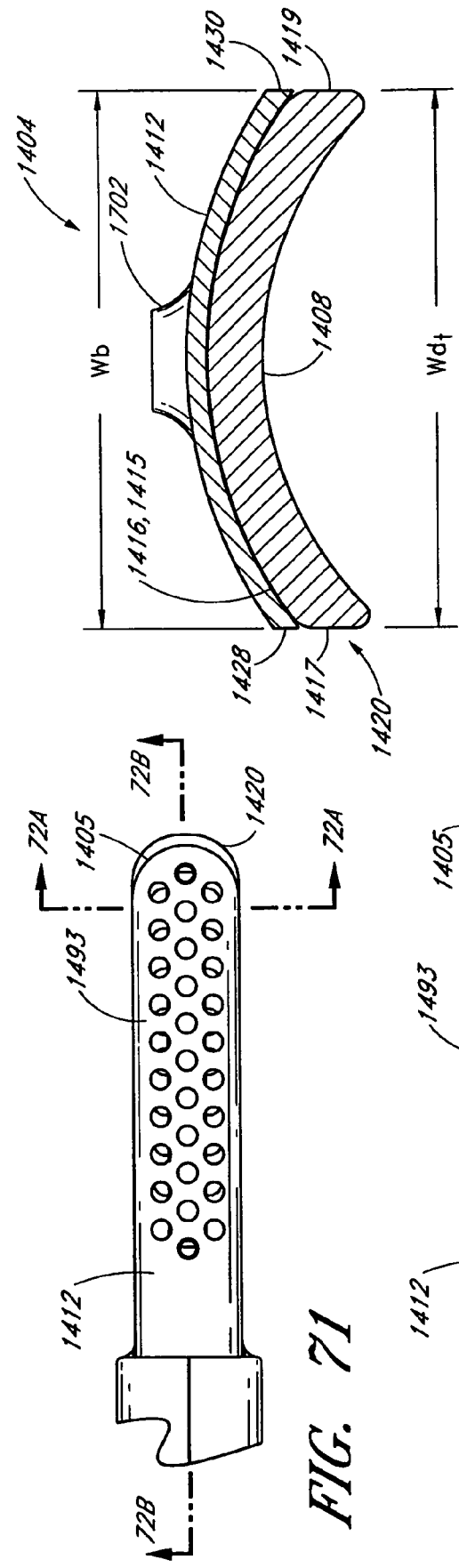
FIG. 70
FIG. 71
FIG. 72A
FIG. 72B

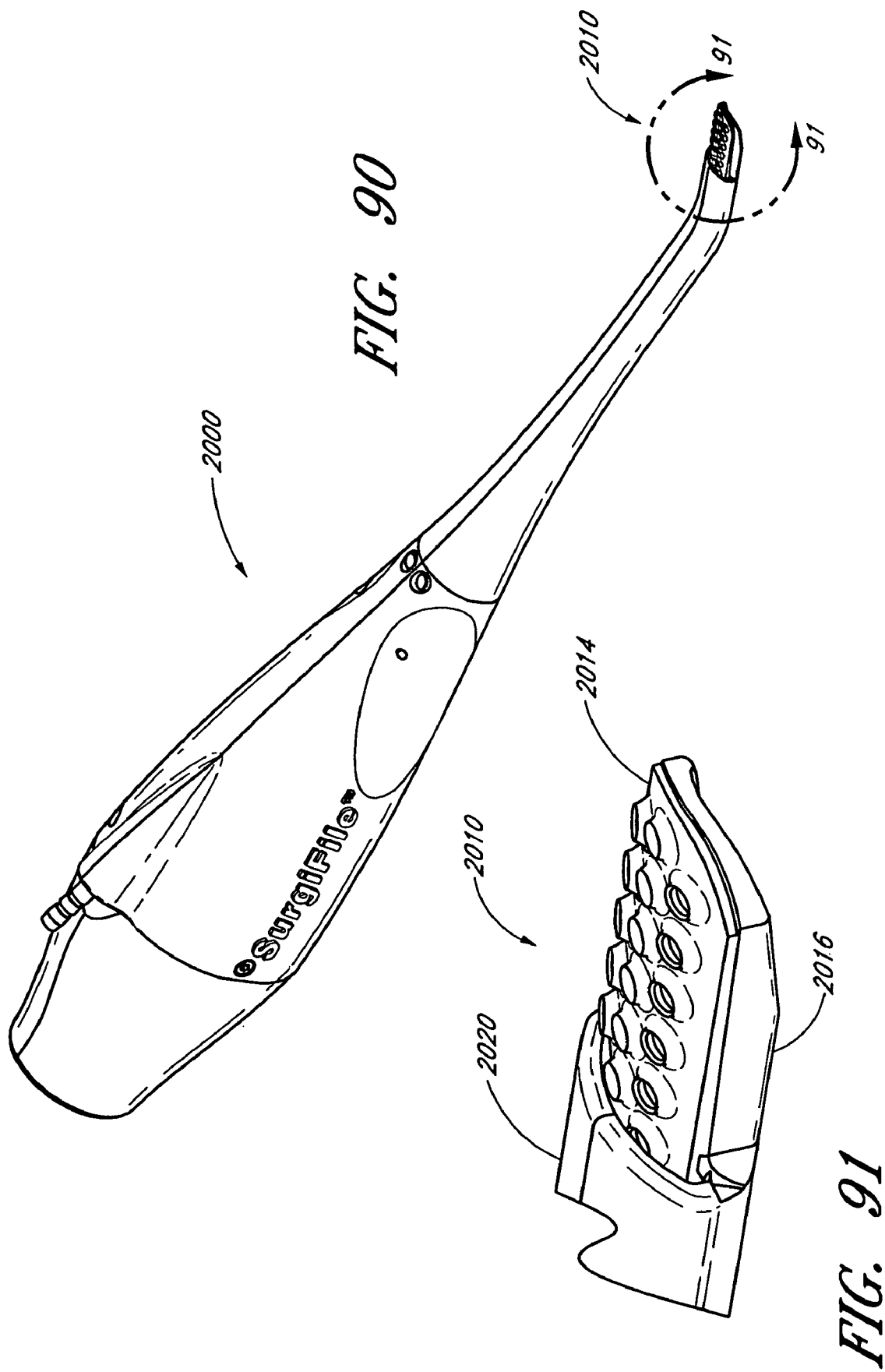

SURGICAL SYSTEM WITH A BLADE

RELATED APPLICATIONS

This application is a continuation-in-part of U.S. patent application Ser. No. 10/675,068, entitled RECIPROCATING SURGICAL FILE, filed Sep. 29, 2003, now U.S. Pat. No. 7,390,330, which claims the benefit of U.S. Provisional Application No. 60/414,690, filed Sep. 27, 2002, and this application also claims the priority benefit under 35 U.S.C. § 119(e) of U.S. Provisional Application No. 60/621,843, filed Oct. 25, 2004, U.S. Provisional Application No. 60/621,853, filed Oct. 25, 2004, and U.S. Provisional Application No. 60/701,727, filed Jul. 22, 2005, all of which are hereby incorporated by reference in their entireties.

BACKGROUND OF THE INVENTION

1. Field of the Invention

The invention relates generally to systems and methods for tissue cutting and removal. More particularly, the invention relates to a reciprocating surgical file system for cutting, removing, grinding, shaping and sculpturing bone and/or tissue material under direct vision.

2. Description of the Related Art

Adjacent spinal vertebrae are spaced by intervertebral discs that are tough and semi-elastic. The discs act as a flexible spacer between the vertebrae that makeup the backbone. Vertebrae are shaped to provide a bony tubular shaped tunnel between upper and lower pairs of vertebrae and this tunnel is made-up in part by the spacing disc. These tubular shaped tunnels are called neuroforamen and serve as a passageway foSSr nerve roots. The size of the neuroforamen tubular shaped tunnels is a close fit for the nerve roots that pass through these tunnels on their way from the spinal cord to the arms, legs and other muscles.

Each year millions of people encounter neck and back injuries. Many million suffer from truly problematic back pain that either keeps them out of work or debilitates them in some way. Many vertebral and disc injuries result in pain from nerve irritation and compression.

When an intervertebral disc is damaged, often it is because of a physical overrotation between two vertebrae and normal wear and tear. When a vertebra is overrotated, small facet joints called the zygopophyseal capsules that are located to the left and right sides of the disc are damaged. When the body incurs damage to these small joints, unwanted osteophytes and bony overgrowths frequently occur at the edges of these tiny joints. The unwanted bony overgrowth restricts the neuroforamen and pinches the delicate and sensitive nerve roots.

Also, with age, for many people, the sensation of thirst is somewhat reduced. As a result, sometimes less water is consumed than needed by the body. The intervertebral discs depend on water as well as other materials to maintain a healthy function. When a disc loses a part of its fluid mass it tends to desiccate. When a disc is desiccated it reduces in height and reduces the space between the two vertebras it is connected to, that is, the neuroforamen becomes constricted and pinches nerve roots.

Pinched nerves that are constrained in between vertebras can cause neck and back pain. The bony overgrowth and a reduction in the space between vertebras pinch the nerves causing irritation, pain and numbness. The pinching can potentially result in a loss of use of the limbs controlled by the affected nerve.

Thus, when intervertebral discs are damaged from accident, age and/or general wear and tear the intervertebral nerve roots in the neuroforamen are irritated and pinched and can cause unwanted involuntary muscular contractions. The muscle contractions can come in the form of a continuous low-grade ache or become more severe as a spasm. The muscle contractions can act to further compress the space between the vertebras, which further pinches the nerve. This becomes a severely painful, self-destructive and self-feeding problem.

One current technology to treat a patient with nerve compression that causes pain and numbness involves the removal of the disc and fusion of the vertebra below with the vertebra above it. Vertebral fusion removes a disc that was flexible and fuses one vertebra together with the adjacent vertebra resulting in a rigid joint between two vertebrae. This causes added strain on the disc above and below the now rigid bone fusion. Sometimes the attempted fusion of one vertebra onto another vertebra is unsuccessful and does not provide the intended fusion.

Disadvantageously, the intervertebral fusion is an invasive and relatively complicated procedure. In addition, and undesirably, the fusion process can result in a long hospital stay for the patient, a long recuperation and rehabilitation period and high costs for both the patient and care providers.

SUMMARY OF THE INVENTION

Embodiments of the invention overcome some or all of the above disadvantages by providing systems and methods for tissue cutting and removal including a reciprocating surgical file and a direct vision apparatus. Some embodiments provide surgical instrumentation that allows a surgeon to navigate into small neuroforamina next to delicate nerves under direct or indirect vision, and locate and remove obstructions of tissue that can cause nerve compression and irritation. Advantageously, this offers many patients a minimally invasive surgical option that can result in shorter hospital stays and lower cost.

In some embodiments, a surgical instrument comprises a handle assembly and a distal assembly connected to the handle assembly. The distal assembly comprises: a blade having a first width, a lower blade structure having an upper face which has a second width extending between a first lateral side and a second lateral side, the blade being movably mounted to the lower blade structure and slidably coupling with the lower blade structure, wherein the first width is equal to or less than the second width. In some embodiments, the first width is at least about 95% of the second width. In some embodiments, the first width is at least about 80% of the second width. In some embodiments, the blade comprises an exposed cutting surface, the cutting surface configured to perform at least one of grinding, filing, and cutting of tissue. In some embodiments, the blade is axially movable along the lower blade structure. In some embodiments, at least a portion of the lower blade structure is tapered in the distal direction. In some embodiments, the distal assembly forms an minimally traumatic tip that is dimensioned so as to fit into a neuroforamen without appreciable trauma to a nerve extending through the neuroforamen. In some embodiments, the lower blade structure defines a shield on one side of the distal assembly, and the blade is disposed on another side of the distal assembly. In some embodiments, the blade and the upper face are curved about a long axis of the lower blade structure. In some embodiments, the lower blade structure defines a fluid delivery channel, and the blade is axially moveable between a proximal position and a distal position. A window for expelling fluid is at a distal end of the fluid delivery channel which is defined between the blade and the lower blade structure when the occupies a proximal position.

In some embodiments, the blade has a cutting zone comprising a cutting surface. The cutting surface can be convex. In some embodiments, the cutting zone comprises cutting elements configured to remove tissue. In some variations, the cutting elements are self-sharpening. The cutting elements can be spaced evenly or unevenly along the cutting zone.

In some embodiments, a surgical instrument has a distal assembly comprising a blade and a lower blade structure. The blade can have a first blade edge and a second blade edge. The lower blade structure comprises an upper face between a first structure edge and a second structure edge. The blade is positioned upon the upper face and is movable relative to a lower blade structure. The first blade edge is proximate to the first structure edge and the second blade edge is proximate to the second structure edge. In some embodiments, the first blade edge and the second blade edge are opposing, longitudinally extending lateral edges of the blade. The first and second blade edges define a blade width. The first structure edge and the second structure edge are opposing, longitudinally extending lateral edges of the lower blade structure. The first and second structure edges define a lower blade structure width. The blade width is equal to or greater than the lower blade width. A blade width is defined between the first blade edge and the second blade edge, a lower blade structure width is defined between the first structure edge and the second structure edge. The blade width is substantially similar to the lower blade structure width. The periphery of at least a portion of the blade has a similar shape to a periphery of at least a portion of the lower blade structure. In some embodiments, at least a portion of a surface of the blade conforms to a periphery of at least a portion of the lower blade structure. In some embodiments, the lower blade structure has a shield surface opposing the upper face, and the shield surface forms a tip that curves towards the blade. The lower blade structure has a shield surface opposing the upper face, and at least a portion of the shield surface is convex towards the blade. In some embodiments, the lower blade structure has a shield surface opposing the upper face, and at least a portion of the shield surface is concave towards a nerve extending through a neuroforamen, when the lower blade structure is positioned at least partially in the neuroforamen. In some embodiments, the lower blade structure has a shield surface opposing the upper face, and at least a portion of the shield surface is concave about a longitudinal axis of the lower blade structure. In some embodiments, the lower blade structure has a longitudinally extending fluid delivery channel disposed along the lower blade structure and a plurality of channels in communication with the delivery channel. In some embodiments, the blade further comprises a plurality of throughholes, the blade is movable between a proximal position and a distal position, at least one throughhole is positioned near the first structure edge and at least one throughhole is positioned near the second structure edge. In some embodiments, the lower blade structure further comprises an elongate delivery channel and a plurality of channels. The elongate delivery channel extends along the lower blade structure. The plurality of channels are in communication with the delivery channel. At least one of the delivery channels is aligned with at least one of the throughhole blade. In some embodiments, the distal assembly forms a tip that is dimensioned so as to fit into a neuroforamen without producing appreciable trauma to a nerve extending through the neuroforamen.

In some embodiments, an instrument comprises a blade and a lower blade structure. The blade has an upper filing surface. The blade is slidably coupled with the lower blade structure. The blade and the lower blade structure are each convex away from the upper filing surface. In some embodiments, the distal assembly further comprises a tip. The tip is dimensioned so as to fit into a neuroforamen without producing appreciable trauma to a nerve extending through the neuroforamen. In some embodiments, the blade has a first transverse width and the lower blade structure has a second transverse width. The first transverse width is about the same as the second transverse width. In some embodiments, the blade has a first transverse width and the lower blade structure has a second transverse width. The first transverse width is less than the second transverse width. In some embodiments, the blade has a first transverse width and the lower blade structure has a second transverse width. The first transverse width is greater than the second transverse width. In some embodiments, the blade has a first transverse width and the lower blade structure has a second transverse width. The first transverse width is less than about 95% of the second transverse width.

In some embodiments, the blade has a cutting zone having a transverse width that is generally similar to a transverse width of the blade. In some embodiments, the cutting zone has a transverse width that is generally similar to a transverse width of a lower blade structure. In some embodiments, the cutting zone comprises one or more of the following: cutting teeth, filing elements, sharpened edges, and the like. In some embodiments, the cutting zone has a generally rectangular shape. In some embodiments, the cutting zone is an array of cutting elements positioned evenly or unevenly through the cutting zone. In some embodiments, the cutting zone is an array of cutting elements forming throughholes. The cutting elements can be positioned evenly or unevenly through the cutting zone.

In some embodiments, an instrument has a distal assembly for removing tissue. The distal assembly forms an atraumatic tip that is dimensioned so as to fit into a neuroforamen without appreciable trauma to the nerve extending through the neuroforamen. In some variations, the distal assembly has a movable blade configured to remove tissue.

In some embodiments, a surgical instrument comprises a filing surface configured to cut, grind, and/or file tissue. A shield surface is coupled to the filing surface. The instrument is configured to be positioned at least partially in a neuroforamen having a nerve extending therethrough. At least a portion of the shield surface is concave towards the nerve when the instrument is positioned at least partially in the neuroforamen. In some variations, the neuroforamen is a vertebral foramen.

In some embodiments, a surgical instrument comprises a filing surface configured to cut, grind, and/or file tissue. A shield surface is coupled to the filing surface. At least a portion of the shield surface is convex towards the filing surface. In some variations, the instrument is configured to be positioned at least partially in a mammalian neuroforamen having a nerve extending therethrough.

In some embodiments, a surgical instrument comprises means for grinding a first tissue, means for shielding a second tissue from the means for grinding when the second tissue is in proximity to the first tissue, and at least part of the means for shielding is convex towards the means for grinding.

In some embodiments, an instrument has a distal assembly that forms an atraumatic tip. The atraumatic tip is dimensioned so as to fit into a vertebral foramen, having nerve extending through the vertebral foremen, without appreciable trauma to the nerve. The distal tip can have an actuatable member for cutting, filing, and/or grinding tissue. The tissue can be bone tissue.

In some embodiments, a method of treating a patient is provided. The method comprises placing a distal assembly of an instrument at least partially in a neuroforamen having a nerve extending therethrough. At least a portion of the distal assembly is concave towards the nerve. Tissue is removed from the patient by operating the distal assembly. In some variations, the removing of tissue comprises at least one of cutting, filing, and grinding. In some embodiments, the removing of tissue comprises at least one of cutting, filing, and grinding. In some embodiments, the method further comprises oscillating a blade of the distal assembly to remove the tissue. In some embodiments, the method further comprises coupling a powered handpiece to the distal assembly of the instrument, and the powered handpiece has a drive system for driving a movable blade of the distal assembly. In some embodiments, the powered handpiece is a rotary handpiece and the instrument further comprises a mechanical transmission that converts rotary motion of the powered handpiece to reciprocating, linear motion. In some embodiments, the method further comprises positioning an access device in a patient's body, and advancing the distal assembly through the access device until the distal assembly reaches a target location for tissue removal. In some embodiments, the tissue is removed by reciprocating a blade while at least a portion of the distal assembly remains in the neuroforamen.

In some embodiments, method of treating a patient comprises: placing a distal assembly of an instrument at least partially into a neuroforamen between target tissue and a nerve; removing the target tissue from surrounding tissue with the distal assembly; after removing the target tissue, drawing the target tissue into the distal assembly; and moving the target tissue through the distal assembly. In some embodiments, the drawing the target tissue into the distal assembly comprises drawing the target tissue through an inlet port of the distal assembly and through a lumen extending from the inlet port through the distal assembly. In some embodiments, the method further comprises: delivering irrigation fluid out of the distal assembly as the distal assembly removes the target tissue such that the irrigation fluid is mixed with the target tissue; and drawing the mixture of target tissue and irrigation fluid into and through the distal assembly. In some embodiments, the distal assembly is substantially L-shaped and has a cutting blade for removing tissue.

In some embodiments, a surgical instrument comprises a housing that contains a drive system. A distal assembly has a distal tip configured to perform at least one of grinding tissue, filing tissue, and cutting tissue. The distal assembly extends from the housing and engages the drive system of the housing. A lumen extends through the housing and the distal assembly. The lumen is configured to receive at least a portion of an endoscope such that an optical element of the endoscope is positioned to provide endoscopic viewing of the distal tip. In some embodiments, the instrument is further configured to permit releasable engagement of the endoscope to the housing. In some embodiments, the distal tip is curved and comprises a blade and a lower blade structure. The blade is slidably disposed on the lower blade structure. In some embodiments, the distal assembly has a longitudinal axis, wherein the endoscope provides viewing of the distal tip when the distal tip is offset from the longitudinal axis.

In some embodiments, a surgical instrument comprises a body assembly that has a distal tip configured to remove bone from a mammal. The body assembly is configured to hold releasably an endoscope such that the endoscope is positioned to provide viewing of the distal tip when the distal tip removes bone. In some embodiments, the surgical instrument further comprises a passageway extending through the body assembly, wherein the passageway is sized to receive the endoscope. In some embodiments, the distal assembly has a curved distal tip that comprises a movable blade coupled to a lower blade structure. In some embodiments, the body assembly has a longitudinal axis, wherein the endoscope provides viewing of the distal tip when the distal tip is offset from the longitudinal axis. In some embodiments, the surgical instrument further comprises the endoscope.

In some embodiments, a method of assembling an instrument is provided. The method comprises placing a distal end of a visualization instrument into a body assembly. The body assembly has an outwardly extending distal assembly which is configured to remove bone from a mammal. The distal end of the visualization instrument is advanced through a lumen extending through the distal assembly. The distal end of the visualization instrument is positioned so that the visualization instrument is capable of providing viewing of at least a portion of the distal assembly. In some embodiments, the method further comprises locking the visualization instrument to the body assembly. In some embodiments, the body assembly has a longitudinal axis. The visualization instrument is configured to provide viewing of a distal tip of the distal assembly when the distal tip is offset from the longitudinal axis. In some embodiments, the distal assembly is configured to perform at least one of grinding tissue, filing tissue, cutting tissue, when driven by a drive system of the housing. In some embodiments, the method further comprising removing the visualization instrument out of the lumen after performing a surgical procedure. In some embodiments, the visualization instrument is an endoscope.

In some embodiments, a surgical distal module comprises a distal body configured to attach to a handle assembly. The surgical distal module further comprises a blade coupled to the distal body. The blade is configured to be slidably moved in a reciprocating linear way by rotary motion emanating from the handle assembly. The module is further configured to remove bone from a mammal. In some variations, the module further comprises a protrusion extending from the distal body. The protrusion is configured to be gripped by a clinician while the blade removes the bone. The protrusion can be dimensioned so as to be gripped between a thumb and a finger of a user. In some embodiments, the module further comprising a protrusion extending from the distal body, wherein the protrusion is configured to be gripped by a clinician while the blade removes the bone. In some embodiments, the protrusion is dimensioned so as to be gripped between a thumb and a finger of a user. In some embodiments, further comprising a transmission that converts the rotary motion to linear reciprocating motion. The transmission can be a toroidal drive system. In some embodiments, the blade and the protrusion are on substantially opposite sides of the distal tip body. In some embodiments, the module comprises a coupling assembly at a proximal end of the distal body. The coupling assembly is configured to releasably couple to the handle assembly. In some embodiments, the blade has a convex surface. In some embodiments, the convex surface is configured to perform at least one of grinding, cutting, or filing the bone. In some embodiments, the blade has a concave surface configured to perform at least one of grinding, filing, and cutting the bone.

In some embodiments, a blade for removing tissue comprises an elongated blade body having an upper surface and an opposing lower surface. A plurality of raised cutting elements extends from the upper surface, each of the cutting elements defining a cutting edge for removing tissue. The cutting edge is substantially parallel to at least one of the upper surface and lower surface. In some embodiments, the cutting elements are adapted to remove bone by at least one of grinding, cutting, and filing. In some embodiments, the raised cutting elements each have a throughhole extending through the elongated blade body. In some embodiments, the elongated blade body has an arcuate transverse axis. In some embodiments, the cutting edge is substantially flat. In some embodiments, the cutting edge is substantially parallel to the transverse axis. In some embodiments, the cutting edge is arcuate. In some embodiments, the raised cutting elements each have a substantially frusto-conical shape. In some embodiments, the raised cutting elements are substantially self-sharpening. In some embodiments, the blade is movably coupled to a lower blade structure of a surgical instrument. In some embodiments, the blade is dimensioned so as to fit at least partially within a neuroforamen.

In some embodiments, a blade for removing tissue comprises a blade body having an upper face and a lower face. The upper face and the lower face extend between a first edge and a second edge. A plurality of raised elements for removing tissue is provided. The raised elements extend from the upper face. Each of the raised elements has a cutting edge that is substantially concentric to an arcuate transverse axis of the blade body. In some embodiments, the blade body is dimensioned so as to fit at least partially within a neuroforamen. In some embodiments, the raised elements form an array of cutting elements that effectively remove tissue when the blade is actuated. In some embodiments, the raised elements each have a throughhole extending through the blade body. In some embodiments, the cutting edge is substantially flat. In some embodiments, the raised elements are substantially frusto-conical in shape. In some embodiments, the cutting edge is defined at a junction of an outer surface and an inner surface of the cutting element. In some embodiments, the raised elements are substantially self-sharpening.

In some embodiments, a blade for removing tissue comprises a blade body that has an upper face and a lower face. The upper face and the lower face extend between a first edge and a second edge. A plurality of cutting elements for removing tissue extend from the upper face. Each of the raised elements has a cutting edge that is substantially concentric to an curved transverse axis of the blade body.

In some embodiments, a surgical instrument comprises a blade for removing tissue. The blade has a plurality of throughholes. A lower blade structure couples to the blade. The lower blade structure comprises a fluid delivery channel that extends substantially along a long axis of the lower blade structure. At least a portion of the fluid delivery channel is aligned with at least one of the throughholes in the blade so as to permit flow through the at least one of the throughholes. The blade is configured to move along the long axis with respect to the lower blade structure. In some embodiments, the instrument is configured to produce pulsatile flow of fluid when the blade is moved reciprocally along the long axis. In some embodiments, the instrument is configured to produce a substantially pulsatile flow of fluid when the blade is moved reciprocally along the long axis, and while the fluid is supplied to the fluid delivery channel at a substantially constant pressure. In some embodiments, at least one of the throughholes is adjacent to the fluid delivery channel such that fluid can flow substantially continuously through the at least one of the throughholes. In some embodiments, at least one of the throughholes is aligned with the fluid delivery channel to permit fluid through the at least one of the throughholes when the blade is in a first position with respect to the lower blade structure, and wherein the at least one of the throughholes is not aligned with the fluid delivery channel when the blade is in a second position with respect to the lower blade structure. In some embodiments, the fluid delivery channel comprises a elongate portion extending along the long axis and a plurality of side channels extending from the elongate portion. In some embodiments, the instrument is configured to permit fluid flow from at least one side channel through at least one of the throughholes when the at least one throughhole is aligned with the at least one side channel. In some embodiments, the instrument is configured to substantially obstruct fluid flow from the at least one side channel through the at least one of the throughholes when the at least of the one throughholes is not aligned with the at least one side channel. In some embodiments, the blade is configured to move reciprocally such that the at least one of the throughholes and at least one of the side channels are alternatingly aligned and not aligned.

In some embodiments, a surgical instrument comprises means for removing tissue from a mammal and means for delivering fluid through the means of removing tissue. Movement of the means for removing tissue produces substantially pulsatile flow.

In some embodiments, a surgical instrument comprises a blade configured to remove tissue from a patient. A lower blade structure couples with the blade. Reciprocating motion of the blade with respect to the lower blade structure generates substantially pulsatile flow of fluid through the blade when the fluid is supplied to the lower blade structure at a substantially constant pressure.

In some embodiments, the tissue is bone. In some embodiments, the lower blade structure comprises a fluid delivery channel configured to permit fluid flow therethrough. In some embodiments, the blade comprises at least one throughhole that is adjacent to the fluid delivery channel such that fluid can flow substantially continuously through the at least one throughhole. In some embodiments, the blade comprises at least one throughhole that is aligned with the fluid delivery channel to permit fluid through the at least one throughhole when the blade is in a first position with respect to the lower blade structure, and wherein the at least one throughhole is not aligned with the fluid delivery channel when the blade is in a second position with respect to the lower blade structure. In some embodiments, the fluid delivery channel comprises an elongate portion extending along a long axis of the lower blade structure and a plurality of side channels extending from the elongate portion. In some embodiments, the blade comprises at least one throughhole, wherein the instrument is configured to obstruct substantially fluid flow from the at least one of the plurality of side channels through the at least one throughhole when the at least one throughhole is not aligned with the at least one of the plurality of side channels. In some embodiments, the blade is configured to move reciprocally such that the at least one throughhole and at least one of the plurality of side channels are alternatingly aligned and not aligned.

Kits can be provided that include at least one of the components, devices, or assemblies disclosed herein. The kits can include instructions for using the components, devices, or assemblies in a procedure. The instructions can be recorded on a suitable recording medium. For example, the instructions may be printed on a substrate, such as paper, plastic, packaging, etc. As such, the instructions may be present in the kits as a package insert, in the labeling of the container of the kit or components thereof (e.g., packaging, sub-packaging, etc.). In other embodiments, the instructions are present as an electronic storage data file present on a suitable computer readable storage medium. The instructions may take any form, including complete instructions for how to use, assemble, or perform other methods described herein.

Embodiments of the invention can desirably be adapted and tailored to serve at least three surgical fields. These include, but are not limited to, neurosurgery, orthopaedic surgery and plastic surgery. The neurosurgical embodiments enable surgeons to safely enlarge the constricted neuroforamen and provide more space for the nerve roots to pass through the rigid bony vertebral structure, thereby relieving the nerve pinching and compression.

The orthopaedic embodiments provide improved bone and/or tissue removal instrumentation and methodology, for example, for orthopaedic surgical procedures such as knee surgery. The plastic surgery embodiments provide improved bone and/or tissue sculpturing instrumentation and methodology, for example, for cosmetic surgical procedures such as nose reshaping or rhinoplasty.

Some embodiments include a surgical instrument comprising a blade; a housing in which the blade moves, the housing having a long axis; a transmission that converts rotary motion to reciprocating, linear motion, wherein the transmission is coupled to the blade such that the blade moves reciprocally in the housing; a first opening in the housing through which a portion of the blade is exposed; and a cutting surface on the exposed portion of the blade, the surface configured to perform at least one of grinding, filing, and cutting of tissue.

In some embodiments the housing is concave about at least a portion of its long axis, such as at least a distal portion of its long axis. In some embodiments, the housing is convex about at least a portion of its long axis, such as at least a distal portion of its long axis. In some embodiments, the first opening is in an opening surface on the housing. In some embodiments, the housing is curved along its long axis, to assist in placing the surgical instrument in the body of a patient. In some embodiments the blade is substantially flat.

In some embodiments, the housing is curved along its long axis in a direction toward the opening surface. Some embodiments further comprise at least one bearing retainer for reducing friction. In some embodiments the at least one bearing retainer has at least one slot configured to transmit fluid toward a distal end of the instrument. Some embodiments further comprise at least one fiberoptic in or on the housing, for transmission of at least one of a video signal and illumination light. In some embodiments the housing has at least a second opening at a distal end of the housing.

Some embodiments further comprise at least two lenses coupled to the at least one fiberoptic. In some embodiments, at least one of the at least two lenses is disposed at a distal end of the housing, and another of the at least two lenses is disposed in proximity to the first opening in the housing. Some embodiments further comprise a pump for pumping fluid through the surgical instrument. In some embodiments the pump is mechanically coupled to the transmission. In some embodiments, the transmission comprises: two surfaces that are a substantially fixed distance apart; a cam that rotates about a central axis, the central axis being at an angle to a plane extending between the two surfaces; and the cam having a curvilinear body, the body having a nonuniform thickness, wherein the body continuously contacts the two surfaces as the cam rotates about the central axis, such that the two surfaces remain at the substantially fixed distance apart as they move linearly in response to the cam's rotation about the central axis.

In some embodiments, the cam's central axis is substantially parallel to a direction of the linear motion of the two surfaces. In some embodiments, the central axis is substantially perpendicular to the plane extending between the two surfaces. In some embodiments the two surfaces move linearly back and forth in reciprocating motion in response to the cam's rotation about the central axis. In some embodiments the curvilinear body has a shape comprising at least two toruses, the at least two toruses being partially superimposed, and each of the at least two toruses has a central axis, wherein the central axes of the at least two toruses are at an angle to each other. In some embodiments at least one bearing comprises the two surfaces. In some embodiments two bearings respectively comprise the two surfaces.

In some embodiments the curvilinear body is disposed at an angle to the central axis of the cam. Some embodiments include an apparatus for translating a rotary motion to a linear motion, the apparatus comprising: two surfaces that are a substantially fixed distance apart; and a cam that rotates about a central axis, the central axis being at an angle to a plane extending between the two surfaces; the cam having a curvilinear body, the body having a nonuniform thickness, wherein the body continuously contacts the two surfaces as the cam rotates about the central axis, such that the two surfaces remain at the substantially fixed distance apart as they move linearly in response to the cam's rotation about the central axis.

In some embodiments, the cam's central axis is substantially parallel to a direction of the linear motion of the two surfaces. In some embodiments the central axis is substantially perpendicular to the plane extending between the two surfaces. In some embodiments the two surfaces move linearly back and forth in reciprocating motion in response to the cam's rotation about the central axis. In some embodiments the curvilinear body has a shape comprising at least two toruses, the at least two toruses being partially superimposed, and each of the at least two toruses has a central axis, wherein the central axes of the at least two toruses are at an angle to each other.

In some embodiments at least one bearing comprises the two surfaces. In some embodiments two bearings respectively comprise the two surfaces. In some embodiments the curvilinear body is disposed at an angle to the central axis of the cam. In some embodiments a pump comprises: a fluid path; two plungers configured to at least partially occlude the fluid path; a cam configured to cause the two plungers to at least partially occlude the fluid path alternatingly; and at least one check valve along the fluid path for reducing backflow of fluid within the fluid path.

In some embodiments the cam translates in a direction that is substantially perpendicular to a long axis of at least one of the two plungers. In some embodiments the cam translates in a direction that is substantially perpendicular to a long axis of each of the two plungers. In some embodiments, the pump comprises: a fluid path; two plungers configured to at least partially occlude the fluid path; a cam configured to cause the two plungers to at least partially occlude the fluid path alternatingly; and at least one check valve along the fluid path for reducing backflow of fluid within the fluid path.

In some embodiments the cam translates in a direction that is substantially perpendicular to a long axis of at least one of the two plungers. In some embodiments the cam translates in a direction that is substantially perpendicular to a long axis of each of the two plungers. Some embodiments of the instrument further comprise at least one opening in the exposed portion of the blade, for transmitting fluid. In some embodiments the cutting surface comprises an abrasive material. In some embodiments the cutting surfaces comprises diamond. In some embodiments the blade comprises stainless steel.

In some embodiments, a blade may have one or more throughholes. As used herein, the term "throughholes" has a broad meaning that includes, but is not limited to, any channel or passageway that permits fluid flow from one side of structure to another.

Some embodiments further comprise a handpiece coupled to the housing. Some embodiments further comprise a video camera. In some embodiments the camera is configured to couple with a fiberoptic that extends to a distal end of the housing. In some embodiments a video camera is located in the handpiece. Some embodiments further comprise a watertight seal in the handpiece. In some embodiments the handpiece is configured to contain the video camera in a chamber such that the watertight seal reduces or prevents ingress of at least one of water and bacteria from outside the handpiece into the chamber containing the video camera in the handpiece.

Some embodiments further comprise a motor in the handpiece, the motor configured to power the rotary motion. In some embodiments the motor comprises a gas turbine. Some embodiments further comprise a cord configured to couple to a proximal end of the surgical instrument, the cord comprising at least one of a fiberoptic, an electrical line, an irrigation channel, a suction line, and a gas tube for powering a gas turbine motor in the surgical instrument.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 39 is an exploded perspective view of a surgical file powered handpiece illustrating features and advantages in accordance with another embodiment of the invention.

FIG. 44 is a simplified front view of a distal cutting assembly of the surgical file instrument of FIG. 43.

FIG. 45 is a simplified bottom view of the distal cutting assembly of FIG. 44.

FIG. 70 is an elevation view of the surgical instrument of FIG. 69.

FIG. 71 is an enlarged top view of the surgical instrument of FIG. 70 taken along 71-71.

FIG. 72A is a cross-sectional view of the surgical instrument of FIG. 71 taken along the line 72A-72A.

FIG. 72B is a cross-sectional view of the surgical instrument of FIG. 71 taken along the line 72B-72B.

FIG. 90 is a perspective view of another embodiment of a surgical instrument.

FIG. 91 is a perspective view of a distal tip of the surgical instrument of FIG. 90.

DETAILED DESCRIPTION OF THE PREFERRED EMBODIMENTS

The preferred embodiments of the invention described herein relate generally to systems and methods for tissue cutting and removal and, in particular, to a reciprocating surgical file system for cutting, removing, shaping and sculpturing bone and/or tissue material under direct vision.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
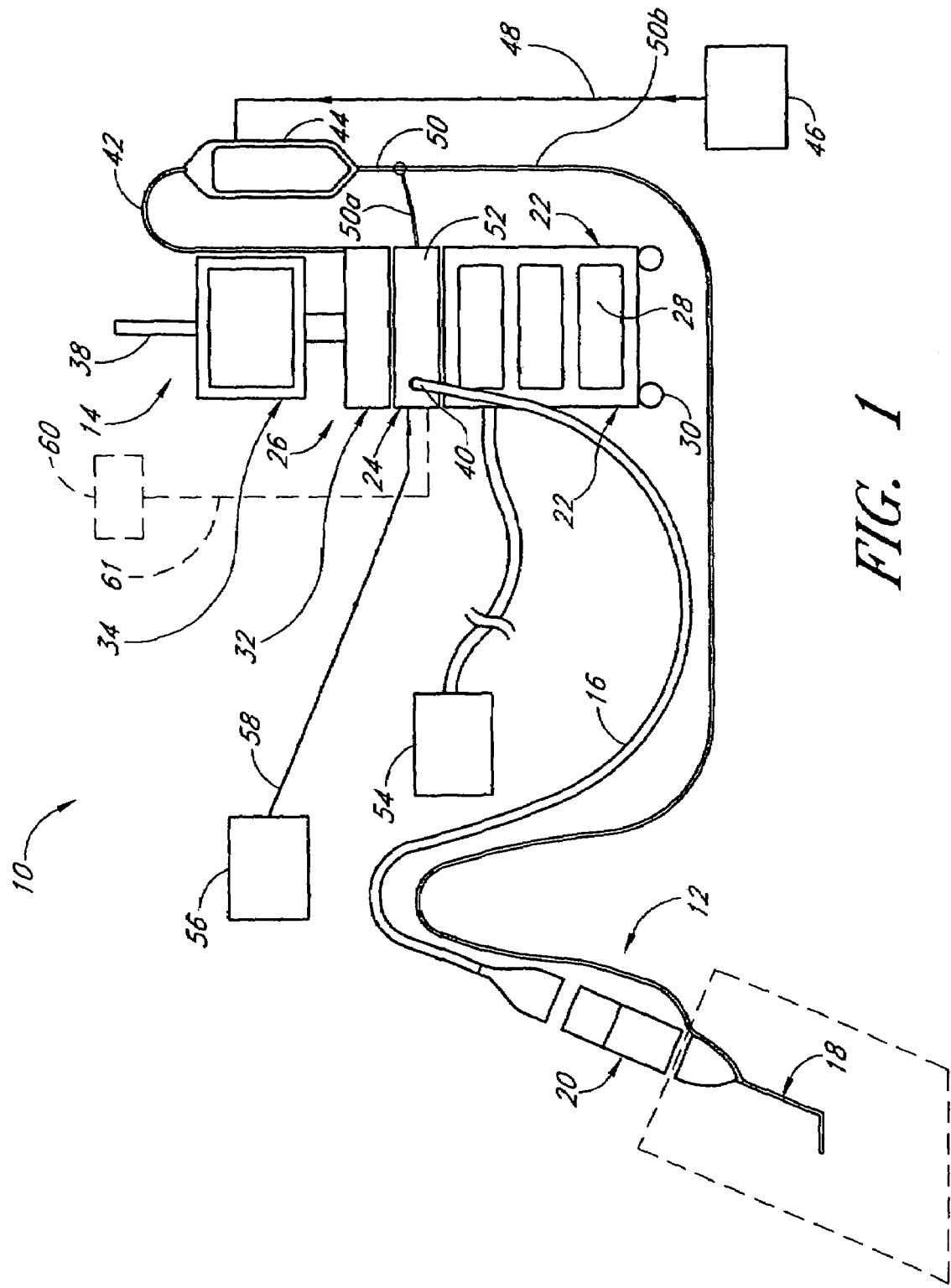
FIG. 1 is a schematic view of a surgical file system illustrating features and advantages in accordance with an embodiment of the invention.
Figure 2:
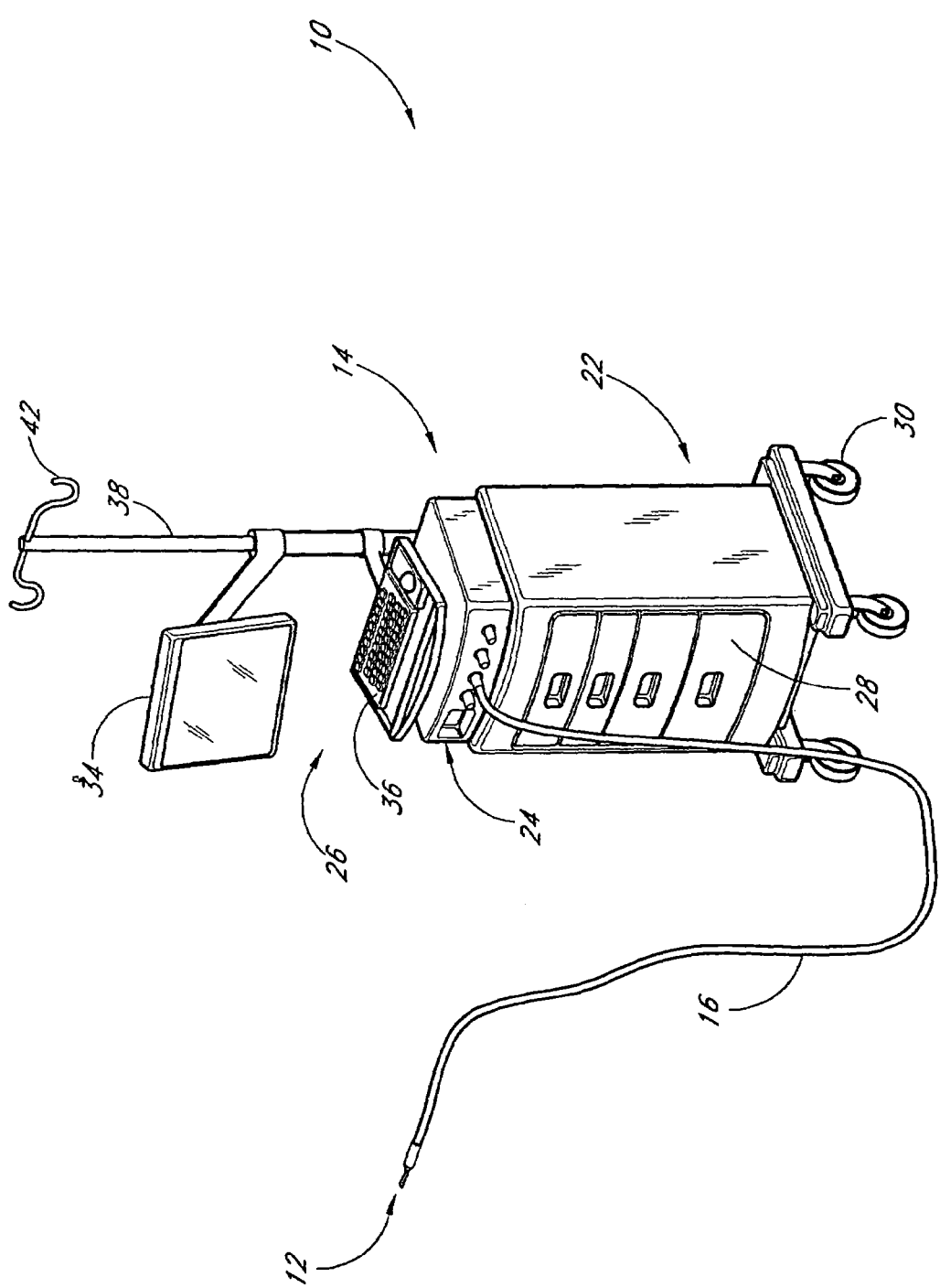
FIG. 2 is a perspective view of the surgical file system of FIG. 1.

FIGS. 1 and 2 show a surgical file system 10 generally comprising a motorized reciprocating surgical file instrument, apparatus, assembly or device 12 and a mobile portable control system 14 connected via a flexible umbilical cable 16. The surgical file device 12 generally comprises a distal tip assembly 18 and a powered handpiece 20. Reciprocating as used herein generally includes back and forth motion and to and from motion.

The system 14 generally comprises a mobile portable stand, cabinet or trolley 22 that supports a controller or control unit or box 24 and a computer system 26. In on embodiment, the system 14 has a footprint of about 0.2 m² (2 square feet (ft²)) and a height of about 1.8 m (6 feet (ft)). In modified embodiments, other suitable dimensions may be efficaciously used, as needed or desired. The system 14 may also utilize wireless communication.

The cabinet 22 has a plurality of drawers or compartments 28 to store system parts, including spare parts, such as cables, connection lines, powered hand piece 20 and an array of various disposable distal cutting tip assemblies, for example, for neurosurgery, orthopaedic surgery and plastic surgery. The storage drawers 28 also serve to store instructions.

The cabinet 22 has a plurality of wheels 30 such as caster wheels to enable movement of the system 14. In the illustrated embodiment, the cabinet 22 has four wheels 30. The caster wheels 30 have wheel locks or other suitable fastening mechanisms to enable stationarily locking the unit at the desired position in the operating room or other area.

The computer system 26 comprises a central processing unit (CPU) 32, a monitor 34, a keyboard 36 including a mouse and a color printer to produce color pictures. The CPU 32 may be supported on (see, for example, FIG. 1) or within (see, for example, FIG. 2) the movable cabinet 22. The CPU 32 includes a video processing system, such as but not limited to a data acquisition board and the like, to process video signals from the surgical file device 12 and supply the signals to the monitor or video display 34. The CPU 32 has a printer port to interface it with the color printer.

The display monitor 34 can comprise any one of a number of suitable commercially available monitors. In one embodiment, the display 34 is a 17-inch (43 cm) liquid crystal display (LCD) monitor.

The storage cabinet 22 includes a substantially vertical pole or rod 38 to support the monitor 34. The height and tilt angle of the display 34 is adjustable to allow suitable viewing for the operating surgeons. In one embodiment, the monitor 34 is positioned at a height of about 1.5 meters (5 feet). As discussed further below, the monitor 34 can display a magnified visual picture of the view from the distal end of the cutting tip assembly 18.

The cabinet 22 includes one or more hooks or supports 42 for mounting of an irrigation fluid bag, container or pouch 44. The hooks 42 can be positioned at a suitable position, for example, on the pole 38. The irrigation bag 44 is provided sterile irrigation water from a source 46 through a feedline 48. The sterile water is transported to the distal cutting tip assembly 18 during device operation through feed line 50.

In one embodiment, sterile water is provided to the distal cutting tip assembly 18 through the control unit 24 via feedline 50a. In a modified embodiment, the sterile water is provided directly to the distal cutting tip assembly 18 via feedline 50b.

The control unit 24 is supported at a suitable working height by the cabinet structure 22. The control unit 24 is operatively interfaced or connected the cable 16 at its proximal end 40. In the illustrated embodiment, the cable 16 connects to a front face 52 of the control box 24. The control box 24 and the CPU 32 can be housed in a single unit.

The control unit 24 and the computer system 26 are powered by a conventional 115-Volt AC electrical power supply 54, for example, by connecting a male plug to a wall receptacle. In modified embodiments, the system may be powered by a portable power supply such as a generator and the like.

In one embodiment, the control unit 24 connects to a pressurized gas or air source supply 56 via feedline 58. As discussed further below, the pressurized gas is used to power an air turbine motor of the powered handpiece 20. The pressurized gas is supplied by the hospital or house supply. In modified embodiments, a portable pressurized gas source such a cylinder may be efficaciously used, as needed or desired.

In one embodiment, the pressurized gas and the irrigation water are supplied from the control unit 24 and through the umbilical cable 16 to the surgical file device 12. In addition, the cable 16 provides video signals from the surgical file device 12 to the control unit 24 and computer system 26. The umbilical cable 16 provides a mechanical and waterproof connection for electrical, video, pressurized gas and irrigation water supply. In modified embodiments, one or more of the electrical and video signals, gas and water may be transmitted through separate cables with efficacy, as needed or desired.

The cable 16 can be any suitable length, for example, about 16 feet long. The cable 16 is sterilizable. The cable 16 may also be used to provide a suction line, as needed or desired.

The control box 24 houses switches and valves to control the flow of the pressurized gas and irrigation water. The control unit 24 has electrical controls for the handpiece 20 and video signals for the computer system 26. The control unit 24 may also include sensors such as pressure sensors, flow rate sensors and the like to monitor the flow of the pressurized gas and irrigation water.

Software is provided that interfaces with the control unit 24 to monitor and control system operation and perform various other related functions. For example, the software allows the operating room personnel to enter the patient identification and date and other pertinent data into the computer for record reference.

The software also allows operating room personnel to change video picture zoom ratios and to control and modify details of the picture for clarity. The computer-based system enables the operating personnel to save pictures of the patient's anatomy, including before and after pictures, to a computer file and to print out color pictures in seconds.

The software is used to control the pressurized gas and irrigation liquid flow to the surgical file device 12. The software can also be used to turn the device 12 on and off and control the frequency of cutting blade reciprocation during filing procedures.

The control unit 24 accommodates connection to existing cauterizing equipment. As discussed further below, and as shown in phantom in FIG. 1, the control unit 24 can be connected to a cauterizing system 60 through connection line 61 to stop or prevent undesirable bleeding during surgery.

In brief, to enable the surgeon to stop the bleeding of freshly cut bone tissue, the cutting blade surface can feature an electrically conductive surface that is operatively connected to an electric circuit, for example, 60. This allows a controlled pulse of electricity to generate a small amount of heat applied directly onto the bone surface to coagulate the blood and stop the bleeding at the freshly cut bone surface only, while insulating delicate nerve roots from unwanted heat damage. The irrigation water also works in conjunction to assist in keeping heat precisely localized and preventing heat injury to the nearby delicate nerve roots and spinal cord.

Figure 3:
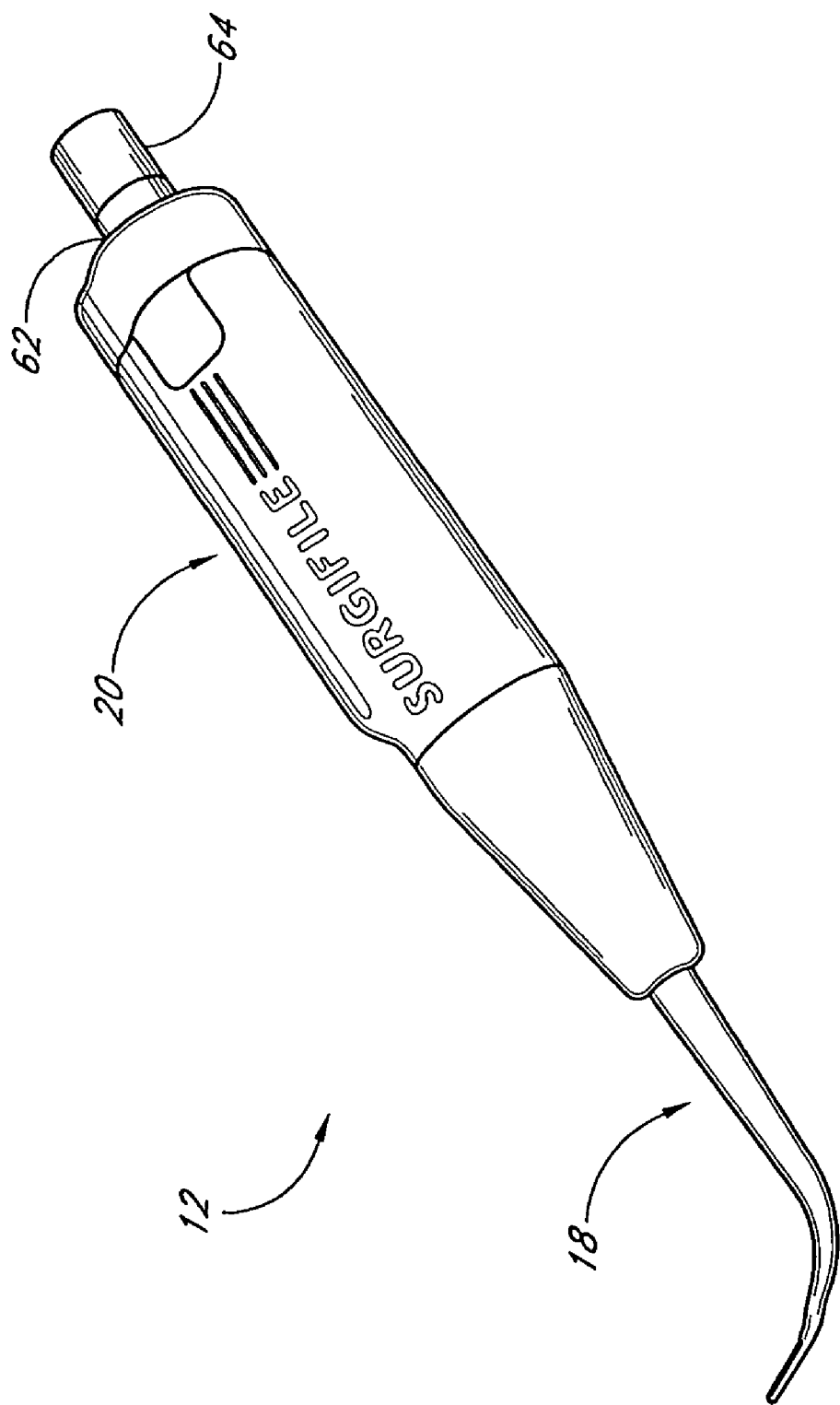
FIG. 3 is a perspective view of a surgical file device with a curved distal tip configuration illustrating features and advantages in accordance with an embodiment of the invention.
Figure 4:
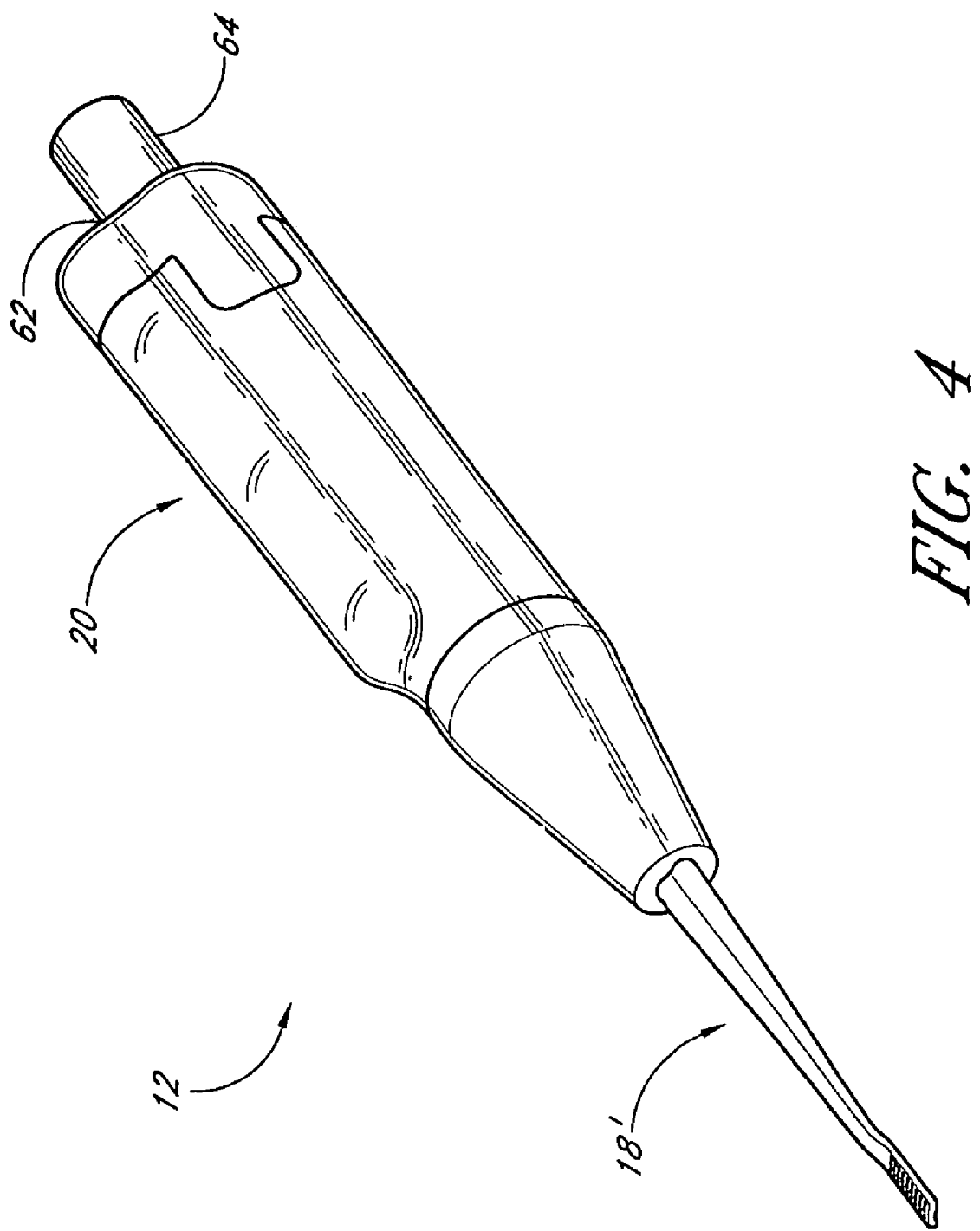
FIG. 4 is a perspective view of a surgical file device with a straight distal tip configuration illustrating features and advantages in accordance with another embodiment of the invention.

FIG. 3 shows the surgical file device 12 with a distal tip assembly 18 having a generally curved and/or angled configuration. FIG. 4 shows the surgical file device 12 with a distal tip assembly 18' having a generally straight configuration. The powered handpiece 20 has at its proximal end 62 a quick connect docking feature 64 to enable connection to the umbilical cable 16 that provides a mechanical and waterproof connection for electrical, pressurized gas and irrigation water supply.

Figure 5:
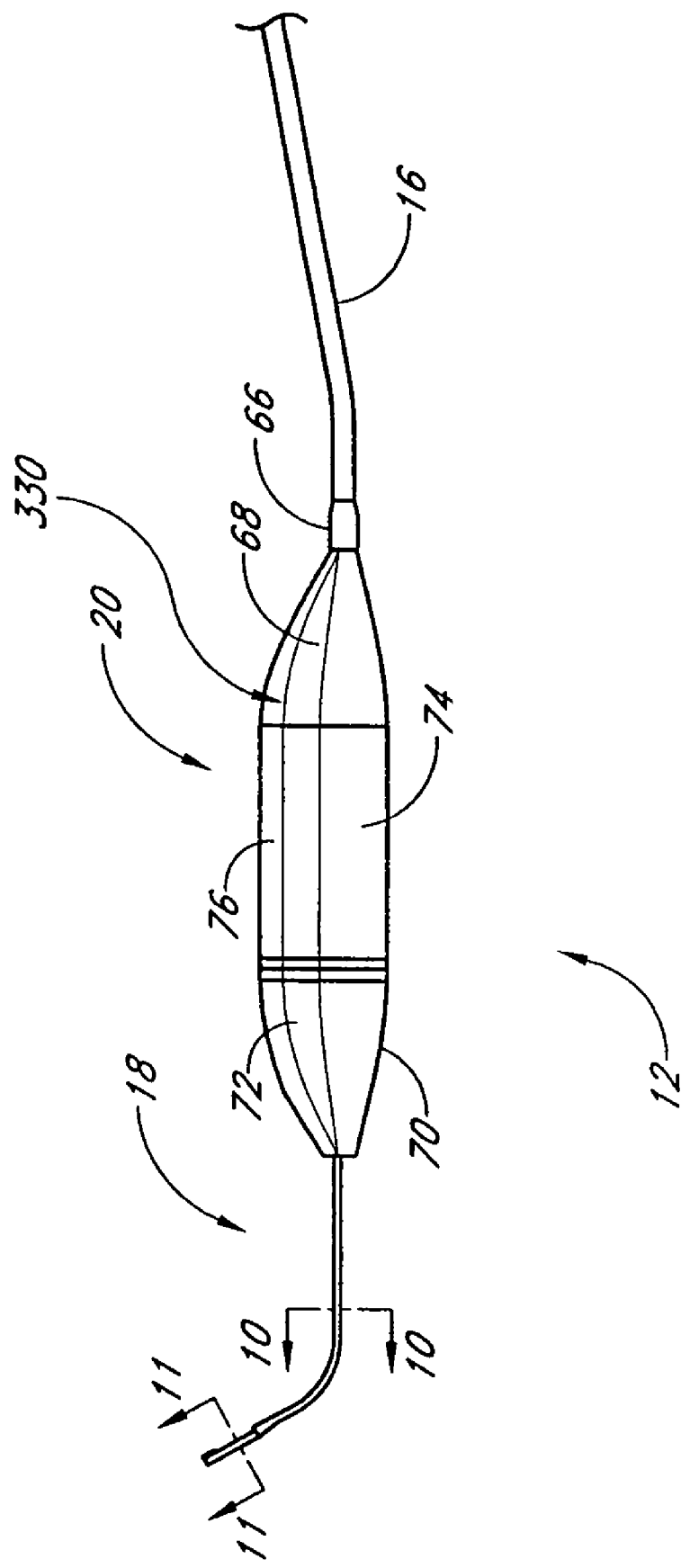
FIG. 5 is a side view of a surgical file device illustrating features and advantages in accordance with an embodiment of the invention.

FIG. 5 shows the surgical file device 12 connected to the umbilical cable 16 at its distal end 66. The interface or connection between a proximal end 330 of the powered handpiece 18 and the cable 16 includes a cover or housing 68. In the illustrated embodiment, the cover 68 is generally frusto-conical in shape, though in modified embodiments other suitable shapes such as cylindrical and the like may be efficaciously utilized, as needed or desired.

The distal tip assembly 18 at its proximal portion or end 70 includes a cover or housing 72. In the illustrated embodiment, the cover 72 is generally frusto-conical in shape, though in modified embodiments other suitable shapes such as cylindrical and the like may be efficaciously utilized, as needed or desired.

The powered handpiece 20 includes a cover 74 intermediate the front and back covers 68 and 72. In the illustrated embodiment, the cover 74 is generally cylindrical in shape and can include a longitudinally extending bulging portion 76 for housing a video camera. In other embodiments, the cover 74 may be efficaciously contoured in suitable ergonomic shapes that facilitate operation by a surgeon or other operator.

The covers 68, 72, 74 can be formed from a number of suitably durable materials. In one embodiment, the covers 68, 72, 74 are formed from a suitable plastic such as a thermoplastic. In another embodiment, the covers 68, 72, 74 are formed from a suitable metal such as stainless steel. In modified embodiments, other suitable plastics, metals, alloys, ceramics, combinations thereof, among others, may be efficaciously utilized, as needed or desired. Suitable surface coatings or finishes may be applied, as required or desired.

The covers 68, 72, 74 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Figure 6:
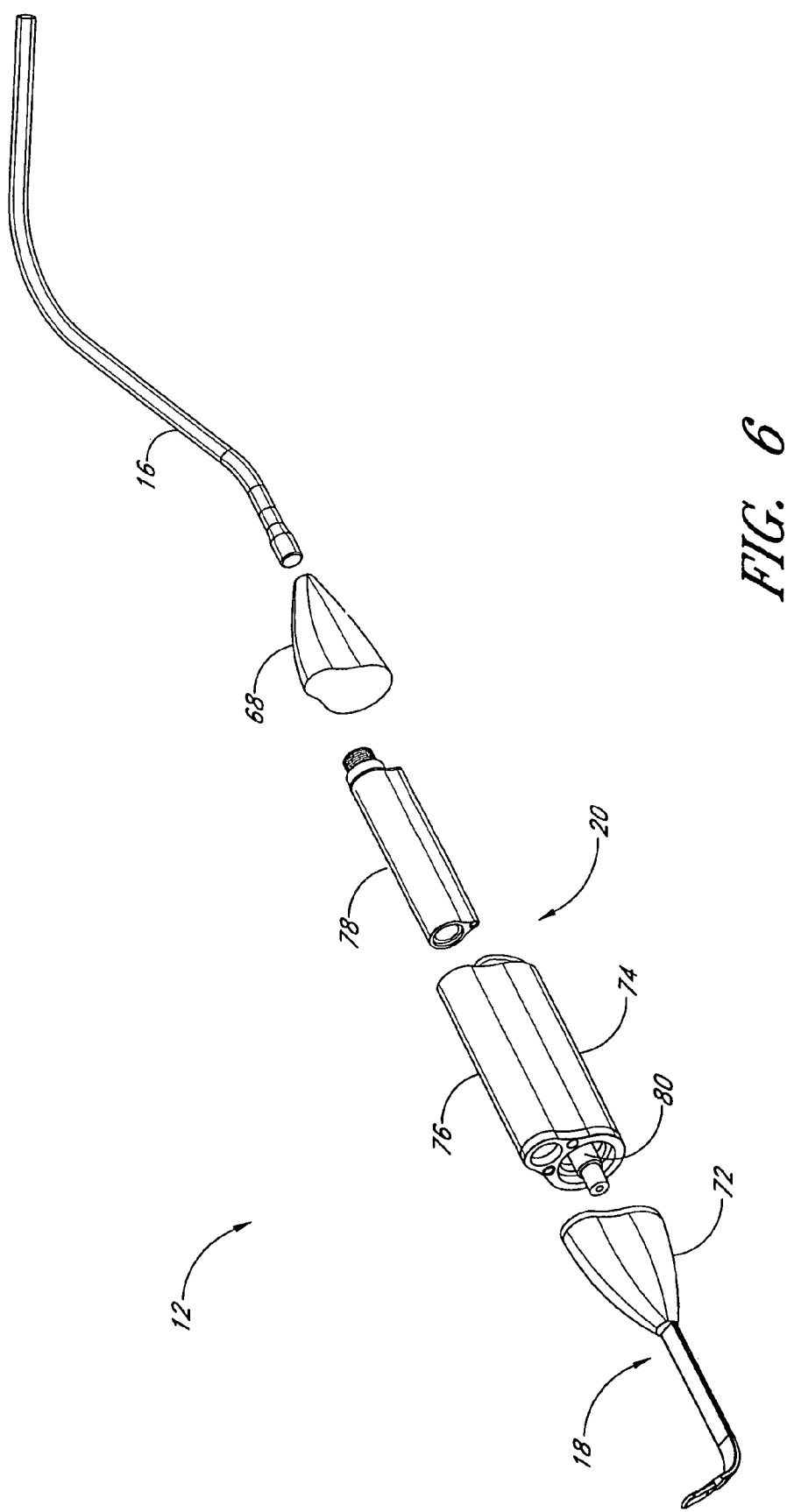
FIG. 6 is a partially exploded view of the surgical file device of FIG. 5.
Figure 7:
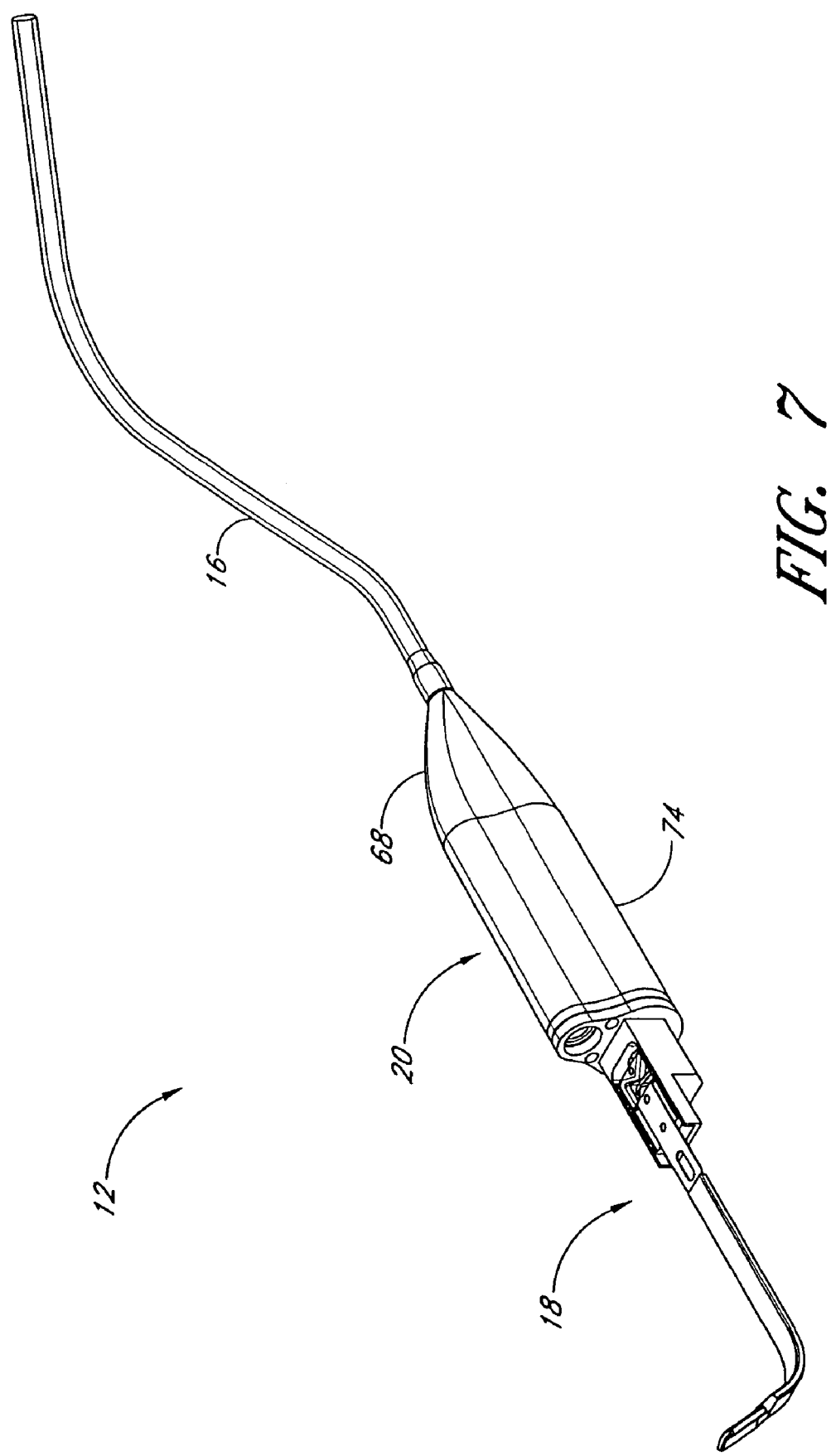
FIG. 7 is a perspective view of the surgical file device of FIG. 5 with the distal cover removed illustrating features and advantages in accordance with an embodiment of the invention.

FIG. 6 shows a partially exploded view of the surgical file device 12. As discussed further below, the powered handpiece 20 includes a video camera 78 and a micro-motor 80 that provides rotary motion which is converted to linear reciprocating motion within the distal tip assembly 18. FIG. 7 shows another perspective view of the surgical file device 12 with the distal cover 72 removed illustrating some of the features of the distal tip assembly.

Distal Tip Assembly

Figure 8:
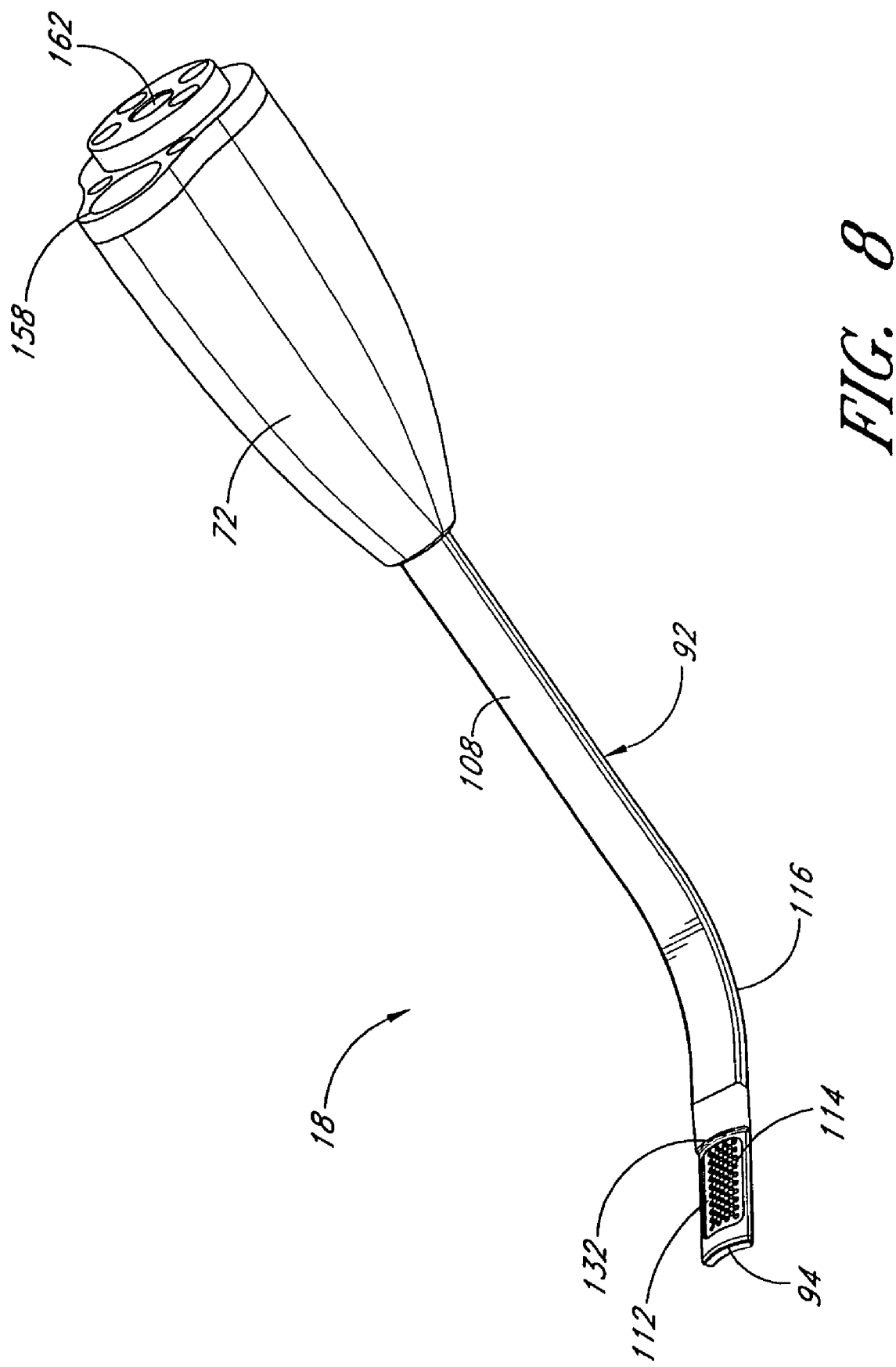
FIG. 8 is a perspective view of a distal tip assembly of the surgical file device of FIG. 5.
Figure 9:
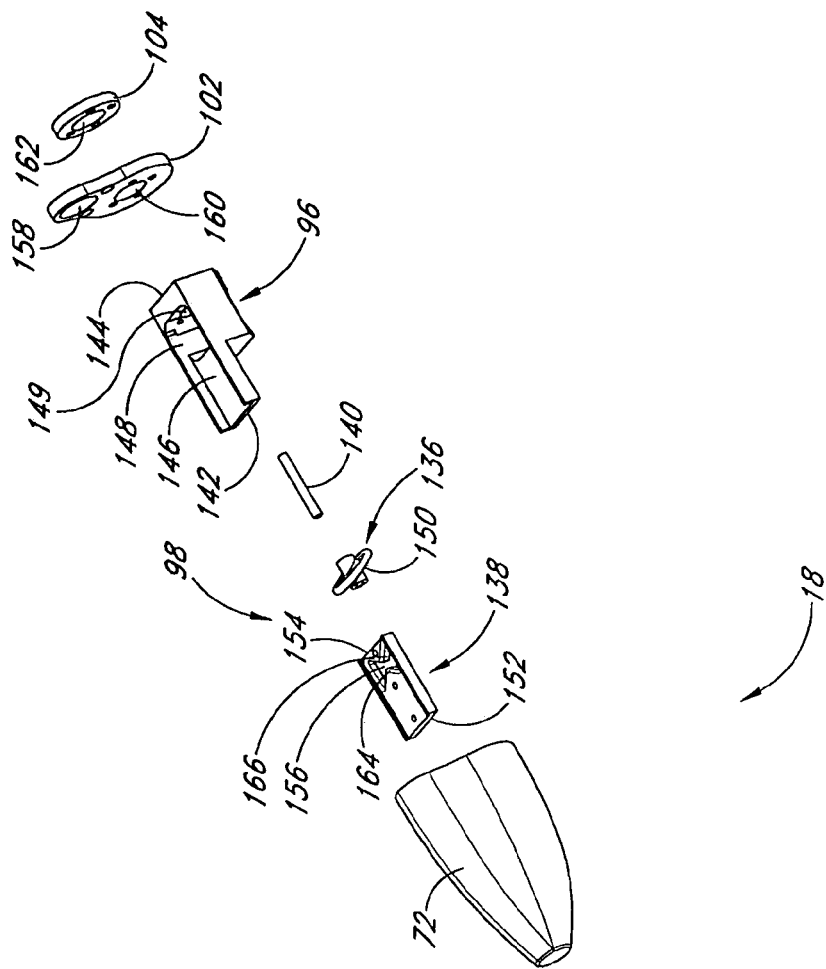
FIG. 9 is a simplified exploded perspective view of the distal tip assembly of FIG. 8 illustrating features and advantages in accordance with an embodiment of the invention.

FIGS. 8 and 9 show the distal tip assembly 18 in greater detail. In one embodiment, the composite tip 18 has a length of about 10 cm (4 inches) to about 15 cm (6 inches), including all values and sub-ranges therebetween. In one embodiment, the composite tip 18 has a length of about 5 cm (2 inches) to about 30 cm (12 inches), including all values and sub-ranges therebetween. In modified embodiments, other suitable lengths may be efficaciously utilized, as needed or desired.

The distal tip assembly 18 is sterile to maintain appropriate surgical standards and is provided in a sterile packaging. In one embodiment, the distal tip assembly 18 is for one time use and is disposable thereafter. As described further below, embodiments of the distal tip assembly 18 include a cartilage or other tissue and bone removal file with vision, illumination, irrigation and cauterization features.

The distal tip assembly 18 generally comprises a distal tip portion 92 that has a distal-most end 94 and a proximal portion extending into the cover 72 that encloses a housing 96 that receives a toroidal power converter system 98 and a water pump system. The distal tip assembly 18 further includes an interface member 102 and a coupling 104 that facilitate connection between the distal tip assembly 18 and the powered handpiece 20.

In some embodiments, the distal tip portion 92 generally comprises a reciprocating cutting or filing blade 106 that is enclosed in a protective case or shield 108. The shield 108 has an aperture, window, opening 112 to expose a cutting surface 114 of the filing blade 106 proximate the distal end 94. Desirably, the shielded blade 106 permits surgical bone and/or tissue removal substantially without risk of damage to nearby delicate tissues such as nerve tissue.

The distal tip portion 92 can be configured to be small and thin so it is minimally intrusive and can go around corners and into any small inaccessible blind channels where nerves are located. The distal tip portion 92 can be configured to fit any desired cavity or contoured shape. The tip portion 92 can be supplied in a variety of sizes and shapes to suit a particular application such as, but not limited to, neurosurgery, orthopaedic surgery and plastic surgery.

The blade cutting surface 114 can be located on the end of an extension with a bend 116 of any desired angle. In the illustrated embodiment of FIGS. 8 and 9, the tip portion 92 has a curved, angled or bent configuration with the bend 116. In another embodiment, the distal tip portion 92 has a substantially straight and/or planar (flat) configuration.

The tip portion 92 further includes a linear bearing retainer 118 within the shield 108. The reciprocating blade 106 is precision fitted within the bearing retainer 118 that allows free linear motion of the reciprocation blade stroke. Advantageously, the bearing retainer 118 provides low friction bearing surfaces for the reciprocating motion of the blade 106.

The bearing retainer 118 comprises a plurality of stationary linear bearings 120 which are positioned on the top, bottom and both sides of the reciprocation blade. The top linear bearing 120 has an aperture, opening or window 122 that is substantially aligned with the shield aperture 112 to expose the blade-cutting surface 114. In one embodiment, the tip portion 92 (and hence the lengths of the blade cutting surface 114 and the apertures 112, 122) are configured so that substantially the entire blade cutting surface 114 is exposed during the full blade reciprocation cycle.

The bearing retainer 118 can be formed from a number of suitably durable materials. In one embodiment, the bearing retainer 118 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The bearing retainer 118 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

As described in more detail below, the distal tip portion 92 further includes a pair of fiber optic probes 124, 126 that are part of an on-board optical illumination and vision system. The fiber optic probes 124, 126 optically connect or interface at their proximal ends to the video camera 78.

The bottom or lower fiber optic probe 124 is below the lower bearing 120. The fiber optic probe 124 may be housed within the shield 108 or it may have its independent protective jacket below the shield 108. The fiber optic probe 124 has a distal end 128 at about the distal-most end 94 of the tip portion 92.

The top or lower fiber optic probe 126 is above the upper bearing 120. The fiber optic probe 126 may be housed within the shield 108 or it may have its independent protective jacket above the shield 108. The fiber optic probe 126 has a distal end 130 proximal to a proximal end 132 of the aperture 112 and/or the cutting surface 114.

The shield 108 can include the aperture 112 on any one of its sides depending on the positioning of the cutting surface 114. This includes the top (as shown in, for example, FIGS. 8 and 9), the bottom and the sides of the shield 108 and even its distal end 134. The shield 108 has a longitudinally extending cavity that houses the blade 106, the bearing retainer 118 and in some embodiments the fiber optic probes 124, 126. In the illustrated embodiment, the distal end 134 closes the longitudinal shield cavity.

In one embodiment, the shield 108 is capable of deflecting and bends at predetermined and/or low loads (for example about 2 lbs.) in order to prevent injury or damage to tissue, such as nerve tissue, engaged by the shield 108. The shield 108 has a predetermined stress-strain curve and spring constant to provide the desired deflection and can comprise, for example, a suitable polymer and the like. The shield 108 may bend at the bend location 116 or at a location proximate to the contact with the tissue. One or more of the associated tip portion 92 components such as the blade 106, bearings 120 and the fiber optic probes 124, 126 can also bend with the shield 108, as needed or desired.

The shield 108 can be formed from a number of suitably durable materials. In one embodiment, the shield 108 is formed from a suitable plastic such as a thermoplastic. In another embodiment, the shield 108 is formed from a polymer that is flexible or can bend under a predetermined load. In modified embodiments, other suitable plastics, metals, alloys, ceramics, combinations thereof, among others, may be efficaciously utilized, as needed or desired. Suitable surface coatings or finishes may be applied, as required or desired.

The shield 108 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The shield 108, the bearing retainer 118 and the fiber optic probes 124, 126 generally conform in shape to the longitudinal profile of the blade 106. In the illustrated embodiment of FIGS. 8 and 9, this is a curved, angled or bent profile with a bend at around 116.

Figure 10:
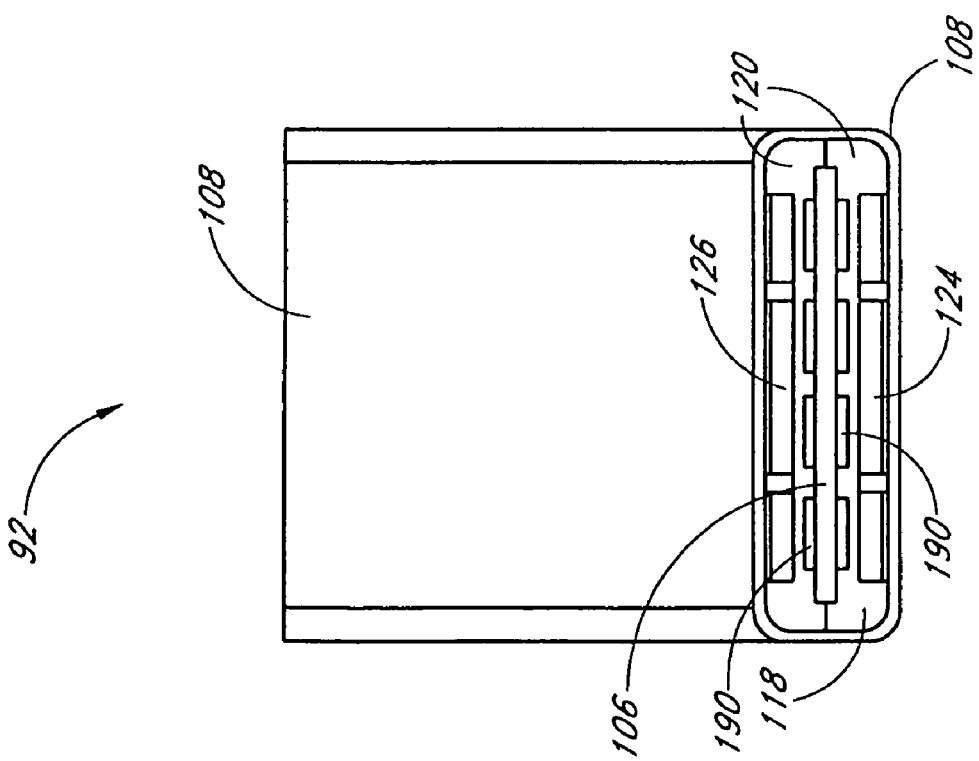
FIG. 10 is a sectional view along line 10-10 of FIG. 5 illustrating features and advantages in accordance with an embodiment of the invention.

FIG. 10 shows a cross-sectional view of the distal tip portion 92 at a location proximal to the aperture 112 and the bend 116. The blade 106 is substantially centrally located within the shield or outer jacket 108. The blade 106 is precision fitted within the bearing retainer 118 including the linear bearings 120. The respective lower and upper fiber optic probes 124, 126 are buffered from the blade 106 by the stationary bearings 120.

The cutting blade linear bearing 120 has a series of shallow slots 190 running substantially longitudinally in line with the proximal to distal axis. The slots 190 serve as water passageways to enable irrigation water to be transported from a proximal to a distal location. The irrigation water serves several functions and provides several advantages.

The water is a lubricant for the interface between the moving blade 106 and the stationary linear bearings 120, which in one embodiment are positioned on the top and bottom and both sides of the reciprocation blade 106. The water cools the blade and bearing material, and in the embodiment the bearing material is plastic, prevents the plastic bearing material from getting hot and softening. The water also serves to wet the cutting blade surface. The water is also used to clean tissue and transport the cut tissue away from the cutting blade 106. Additionally, water transported across the linear blade 106 intimately irrigates the volume of water in the distal blade area to clear the optical vision field for clear viewing.

Figure 11:
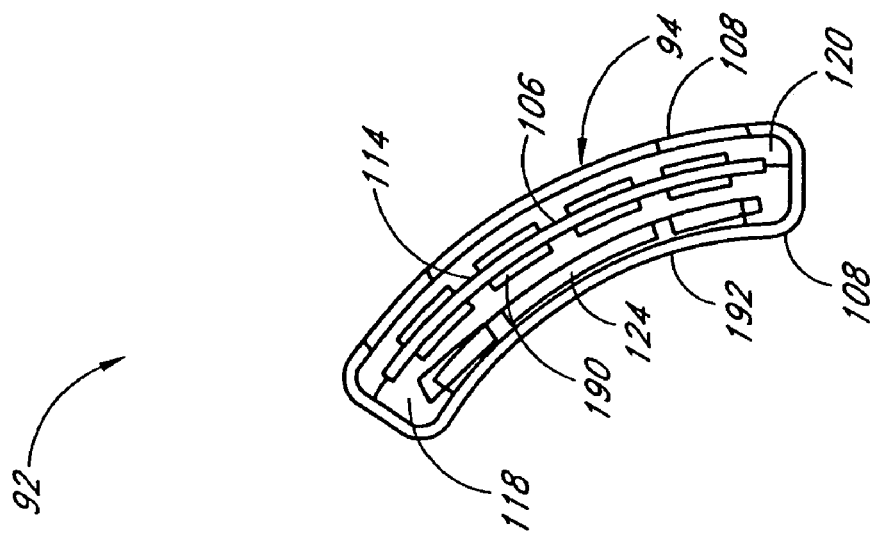
FIG. 11 is a sectional view along line 11-11 of FIG. 5 illustrating features and advantages in accordance with an embodiment of the invention.

FIG. 11 shows a cross-sectional view of the distal tip portion 92 at the shield aperture 112. The cutting surface 114 of the blade 106 is exposed and is above the lower bearing 120, the lower fiber optic probe 124 and a lower portion 192 of the shield 108. The drawing also shows portions of the shield 108 and the upper bearing 120 at the tip distal end 94. In this embodiment, the cross-sectional profile of the cutting surface 114 is convex and the associated portions of the shield 108, bearings 120 and lower fiber optic probe 124 generally conform to this shape.

In one embodiment, and as described further below, the toroidal drive system 98 is substantially mounted within the housing 96 and generally comprises a rotatable toroid drive 136 and a drive slide 138. A drive shaft 140 is connected to the handpiece motor 80 and transfers rotary motion to the toroid drive 136 which engages the linear slider 138 to convert rotary motion into reciprocating motion that is provided to the blade 106 for performing bone and/or tissue removal operations. In modified embodiments, other suitable rotary to reciprocating motion mechanisms or devices may be used, as needed or desired, to reciprocatingly drive the blade 106.

As discussed further below, the drive shaft 140 is connected to the toroid drive 136 and has a specially designed female receptor hole. The receptor hole allows the drive shaft 140 to substantially irrotationally mate with a power drive shaft of the motor 80.

The housing 96 has a distal end 142 and a proximal end 144 and a generally flat recessed surface 146 extending from the distal end 142 towards the proximal end 144. The linear slide 138 is reciprocatingly seated on or within the recessed surface 146. The housing 96 includes a cavity 148 intermediate the recessed surface 146 and the housing proximal end 144 that receives the rotatable toroid drive 136. The housing proximal end 144 has an opening 149 that receives a power shaft of the handpiece motor 80 that connects to the drive shaft 140.

The housing 96 can be formed from a number of suitably durable materials. In one embodiment, the housing 96 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The housing 96 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired. The housing 96 and bearing retainer 118 may comprise an integral unit, for example, they may be formed by molding and the like.

The toroid drive 136 is connected with the drive shaft 140. The toroid drive 136 has an outer rim 150 that is engaged with the slider 138 and transmits rotary motion that is converted into reciprocating motion by the slider 138.

The slide plate 138 has a distal end 152, a proximal end 154 and a specially contoured slot 156 proximate to the proximal end 152 with a pair of generally opposed bearing surfaces 164, 166. As described in greater detail below, the slot 156 receives the rotating outer rim 150 of the toroid drive 136.

The blade 106 is connected to the slide 138. As described in greater detail below, this connection utilizes shear pins to provide a safety mechanism against blade buckling.

The slide 138 can be formed from a number of suitably durable materials. In one embodiment, the slide 138 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The slide 138 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The interface member 102 has an opening 158 which allows passage of the fiber optic probes 124, 126 for connection to the camera 78. The interface member 102 has an opening 160 that receives that receives a power shaft of the handpiece motor 80 that connects to the drive shaft 140.

The coupling 104 has an opening 162 that receives that receives a power shaft of the handpiece motor 80 that connects to the drive shaft 140. The openings 149, 160 and 162 are substantially aligned with one another.

The interface member 102 and coupling 104 can be formed from a number of suitably durable materials. In one embodiment, the interface member 102 and coupling 104 are formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The interface member 102 and coupling 104 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Blade Embodiments

Embodiments of the invention provide reciprocating cutting blade for precision bone and/or tissue removal. In one embodiment, the reciprocating cutting blade is shielded or covered or guarded on five sides to provide a shielded surgical file. As used herein, the term "blade" is a broad term and includes, without limitation, any of various grinders, filers, cutters, surfaces that are configured to grind, file, and/or cut tissue.

The shielded file can be flat, planar, convex or concave in its cross-section. The shielded file can extend generally straight or be curved, angled or bent along its longitudinal axis. Advantageously, the angled configuration allows the cutting surface to travel around a corner to reach into usually inaccessible body cavities. Desirably, this provides the ability to remove unwanted tissue in a blind tunnel or body cavity while enabling direct vision through the illumination and vision probes.

The shielded file can be dimensioned in a number of manners. The shielded file can be any length or width suitable for the human or mammalian anatomy proportions. For other non-medical applications, the shielded file can be of any length or width to suit the material removal application.

The thickness of the shielded file can be varied to be very thin. In one embodiment, the thickness can be of the order of $1/10^{th}$ of an inch. Advantageously, this enables the shielded file to fit into small spaces such as between a nerve and the foramen opening that it is passing through. In other embodiments, the thickness of the shielded file can be greater, as needed or desired.

The cutting blade can be shaped and contoured in several configurations. In one embodiment, the reciprocating cutting blade is straight and planer (in one flat plane). In another embodiment the reciprocating cutting blade that is curved convex or concave in its cross sectional shape. In yet another embodiment, the reciprocating cutting blade that is substantially straight in its longitudinal axis. In still another embodiment, the reciprocating cutting blade is curved in its longitudinal axis.

The thickness of the cutting blade drive 106 can be varied. In one embodiment, the cutting blade thickness is in the range from about 100 microns or μm (0.004 inches) to about 300 μm (0.012 inches). In another embodiment, the cutting blade thickness is in the range from about 50 μm (0.002 inches) to about 600 μm (0.024 inches). In yet another embodiment, the cutting blade thickness is in the range from about 25 μm (0.001 inches) to about 2.5 mm (0.1 inches). In modified embodiments, other suitable dimensions may be efficaciously utilized, as needed or desired.

The cutting blade 106 can be formed from a number of suitably durable materials. In one embodiment, the cutting blade 106 is formed from steel. In another embodiment, the cutting blade 106 comprises spring stainless steel. In modified embodiments, other suitable metals, alloys, plastics, ceramics, hard carbon (e.g., graphite, diamond, etc.), composites, laminates, combinations thereof, among others, may be efficaciously utilized, as needed or desired. Suitable surface coatings or finishes may be applied, as required or desired.

The cutting blade 106 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

In one embodiment, the cutting blade 106 is flexible. Advantageously, this allows the cutting blade to be easily bent, angled or curved along its length as it is enclosed in a bent, angled or curved outer shield 108. In another embodiment, the cutting blade is substantially rigid. This can be suitable for blade configurations that are generally straight. The rigid blade may also be bent by suitable techniques, as needed or desired. In modified embodiments, the cutting blade 106 may efficaciously comprise one or more flexible portions and one or more rigid portions, as needed or desired.

Figure 12:
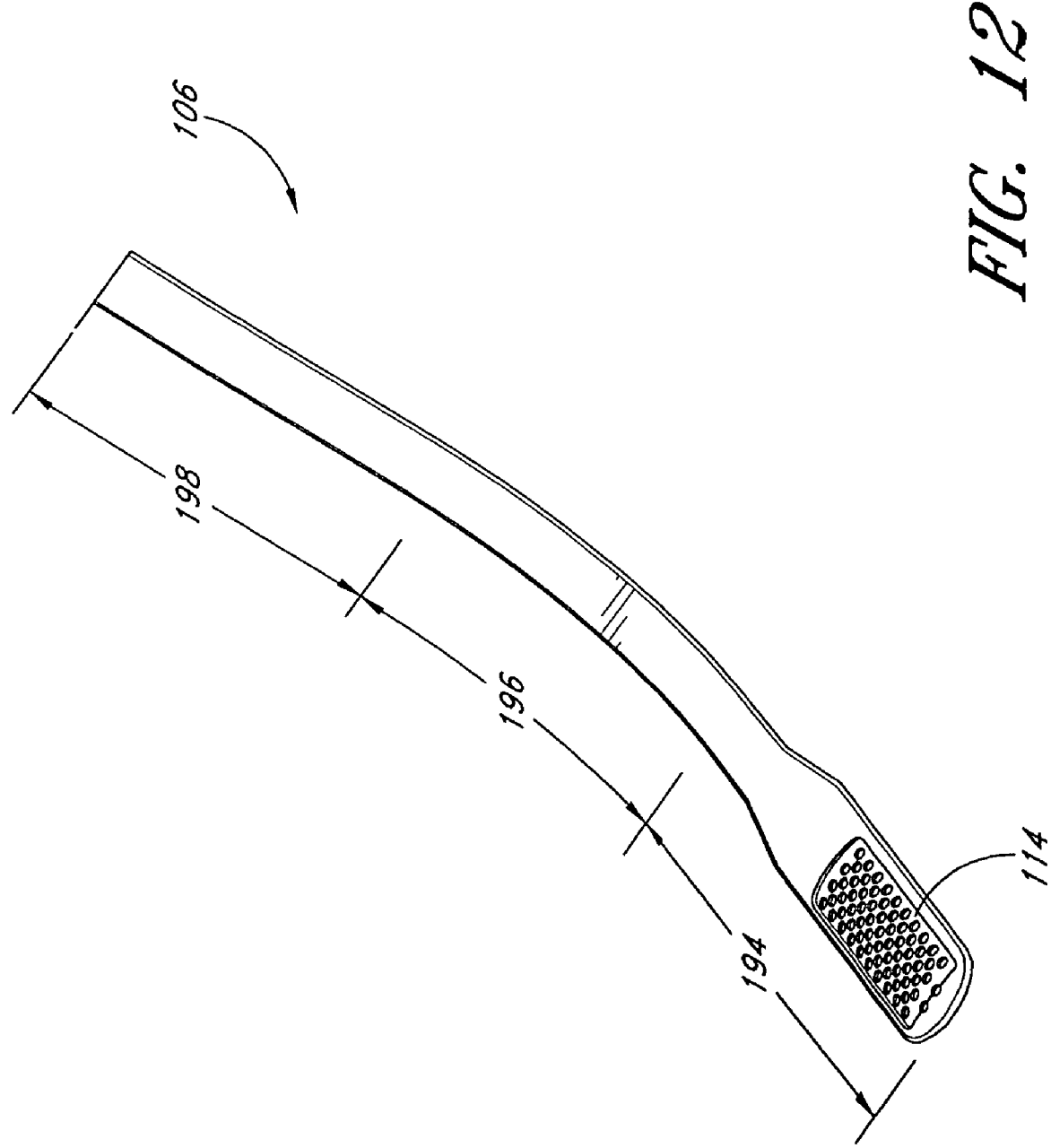
FIG. 12 is a simplified perspective view of a surgical cutting blade illustrating features and advantages in accordance with an embodiment of the invention.

FIG. 12 shows an embodiment of the cutting blade 106. The blade 106 comprises a thin flexible material that is capable of bending along its length. The blade 106 includes a distal section or portion 194 with the cutting surface 114, a medial section or portion 196 and a proximal section or portion 198. When enclosed within the curved, angled or bent shield 108 the blade 106 flexes like a thin spring to conform to the shape of the shield or guide cover 108. Thus, the medial section 196 is curved, angled or bent while the respective distal and proximal sections 194, 198 extend generally straight.

Figure 13:
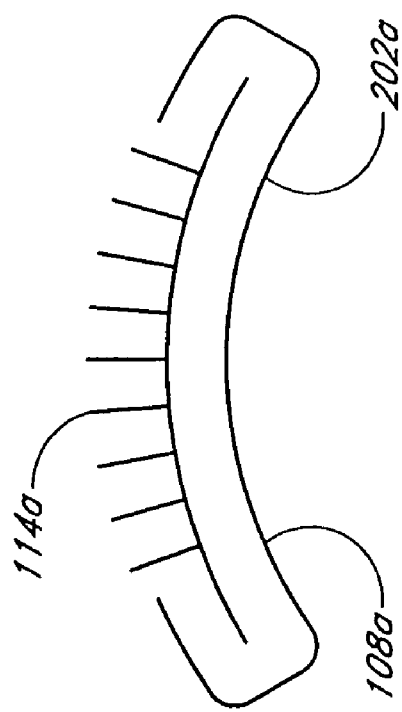
FIG. 13 is a simplified schematic cross-section view of a convex surgical file cutting surface illustrating features and advantages in accordance with an embodiment of the invention.

FIG. 13 shows a cross-section of a cutting surface 114a and an associated portion 202a of the shield 108a having a generally convex configuration suited for some particular bone and/or tissue removal applications. The convex curvature of the cutting surface 114a can also be advantageous in providing enhanced rigidity to the thin cutting surface 114a and/or the associated blade 106.

Figure 14:
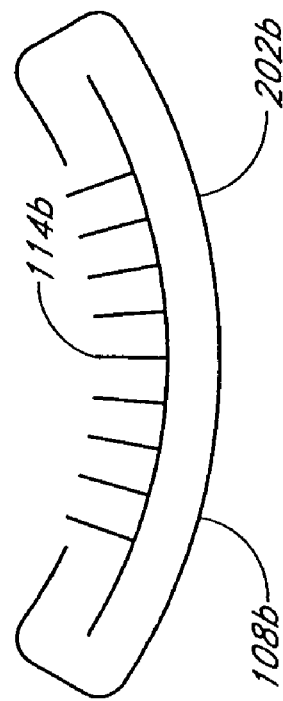
FIG. 14 is a schematic cross-section view of a concave surgical file cutting surface illustrating features and advantages in accordance with another embodiment of the invention.

FIG. 14 shows a cross-section of a cutting surface 114b and an associated portion 202b of the shield 108b having a generally concave configuration suited for particular bone and/or tissue removal applications. The concave curvature of the cutting surface 114b can also be advantageous in providing enhanced rigidity to the thin cutting surface 114b and/or the associated blade 106.

Figure 15:
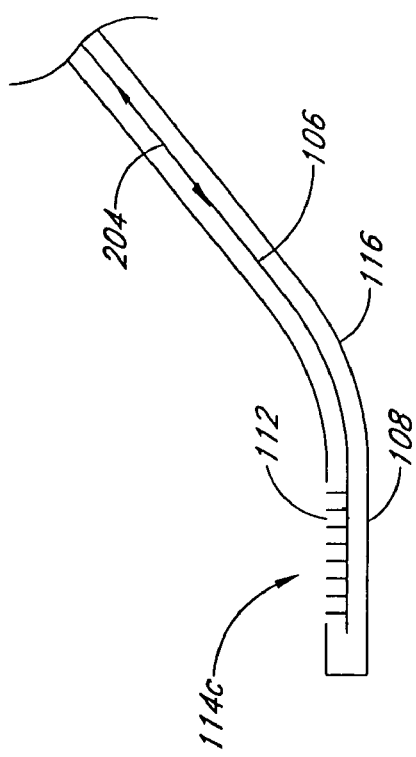
FIG. 15 is a schematic side view sectional view of surgical file distal tip with a top cutting surface illustrating features and advantages in accordance with an embodiment of the invention.

FIG. 15 shows a lengthwise-section of the distal tip portion 92 having a cutting surface 114c on the top or upper side of the reciprocating blade 106 within the non-moving shield 108. This configuration is suited for some particular bone and/or tissue removal applications. The bend 116 allows the cutting surface 114c to pass into a cavity that involves traveling around a corner. The direction of blade travel is generally denoted by arrows 204.

Figure 16:
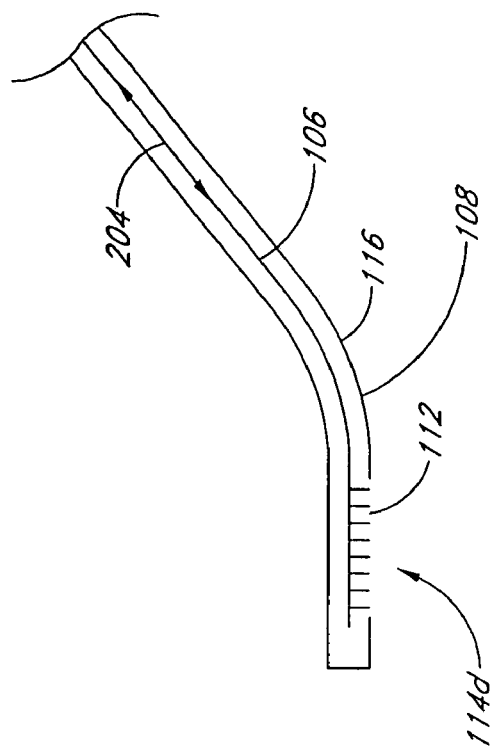
FIG. 16 is a schematic side sectional view of a surgical file distal tip with a top cutting surface illustrating features and advantages in accordance with another embodiment of the invention.

FIG. 16 shows a lengthwise-section of the distal tip portion 92 having a cutting surface 114d on the bottom or lower side of the reciprocating blade 106 within the non-moving shield 108. This configuration is suited for some particular bone and/or tissue removal applications. The bend 116 allows the cutting surface 114d to pass into a cavity that involves traveling around a corner. The direction of blade travel is generally denoted by arrows 204.

Figure 17:
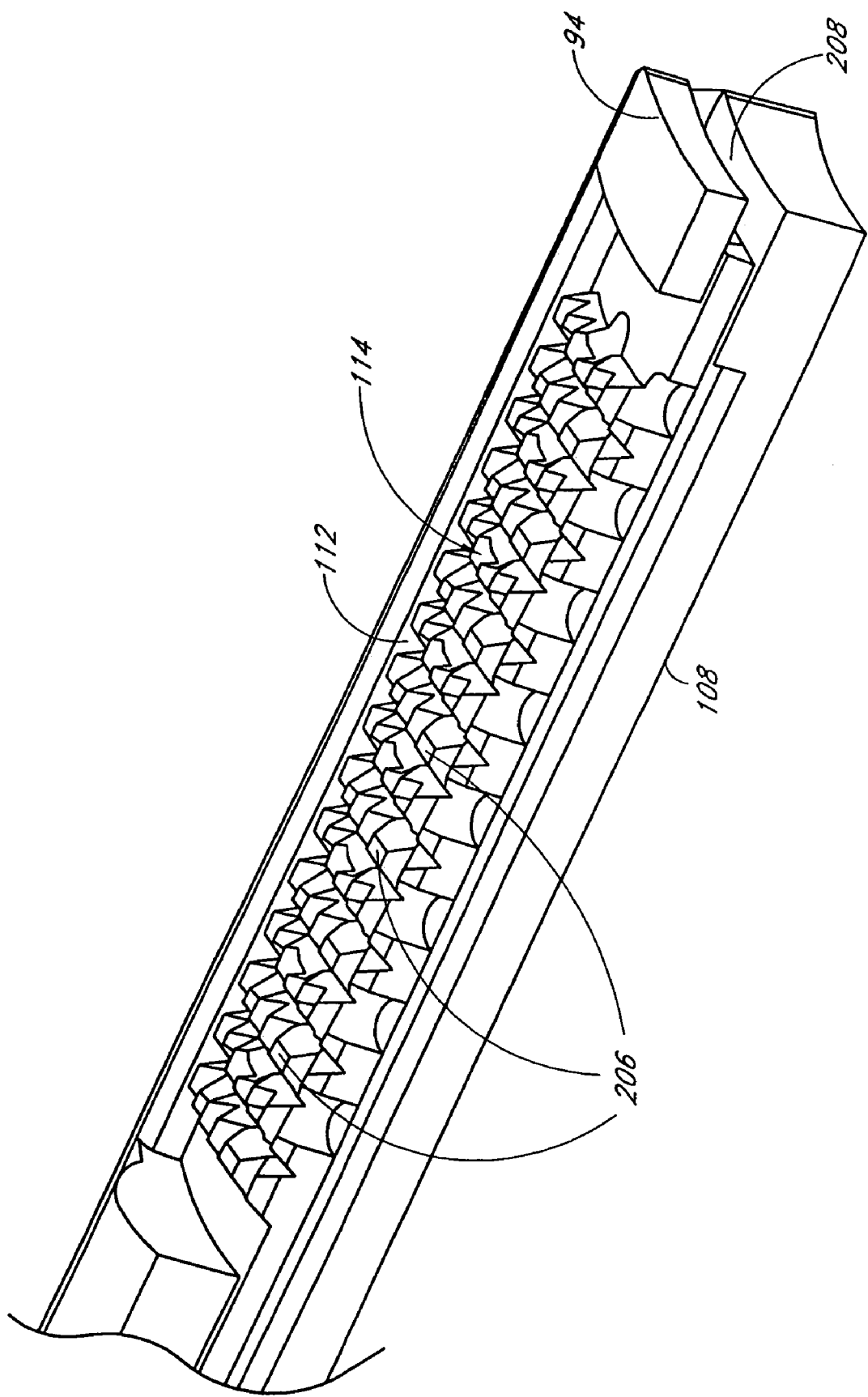
FIG. 17 is a perspective view of a surgical file cutting surface with abrasives illustrating features and advantages in accordance with an embodiment of the invention.

FIG. 17 shows the cutting surface 114 including an abrasive material or abrasives 206 for cutting, removing, filing or grinding bone and/or tissue materials. For clarity, one side of the shield 108 has been removed in the drawing. Any one of a number of suitable abrasives may be used that are safe to use within a patient's body or are biocompatible and hard. In one embodiment, the abrasives 206 comprise embedded diamonds or diamond particles.

Also shown in FIG. 17 is a lateral slot or opening at the tip portion distal end 94. Advantageously, the distal opening 208 allows the removal of any bone and/or tissue debris that may collect within the distal and provides for flushing out of the debris as the blade cutting surface 114 reciprocates and the irrigation fluid flows out of the instrument.

Figure 18:
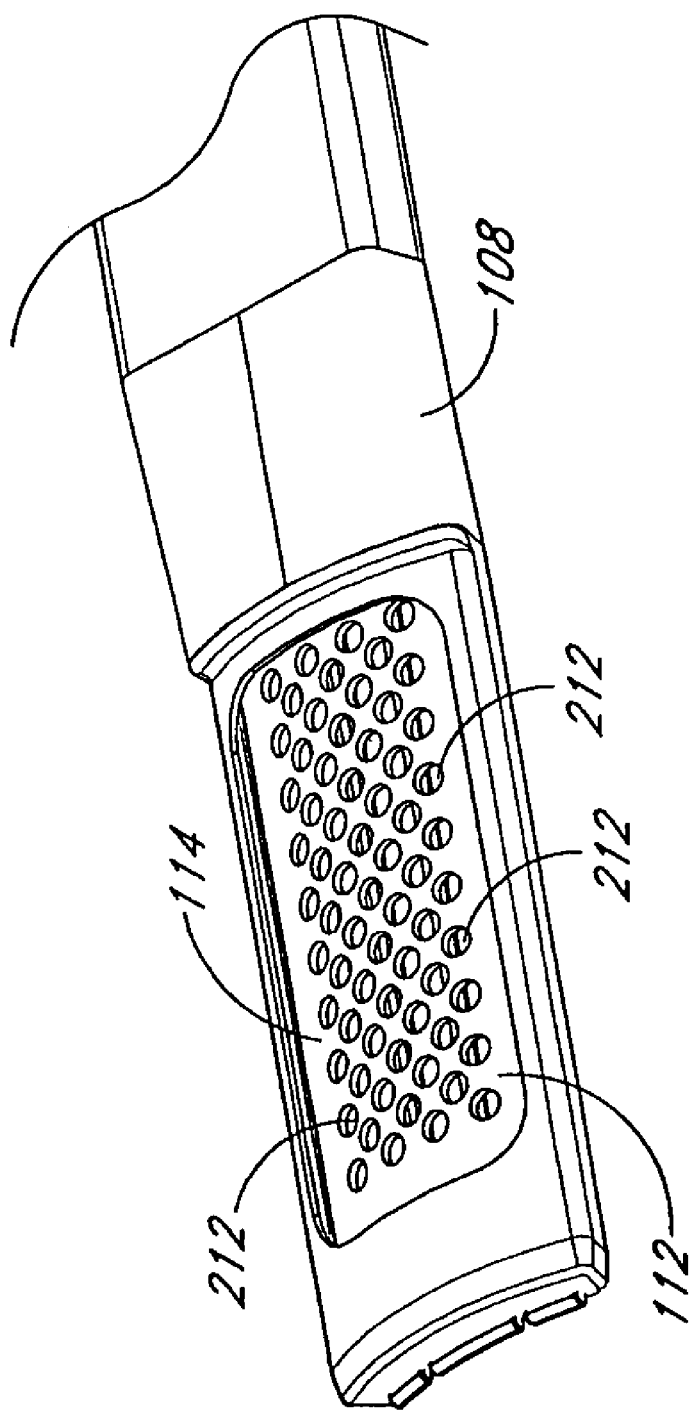
FIG. 18 is a perspective view of a surgical file cutting surface with irrigation fluid openings illustrating features and advantages in accordance with an embodiment of the invention.

FIG. 18 shows the blade cutting surface 114 including a plurality of micro holes or openings 212 for the flow of irrigation fluid therethrough. For clarity the abrasives are not shown in the drawing. The holes 212 are in fluid, liquid or hydraulic communication with the longitudinal slots 190 of the lower linear bearing 120. The slots 190 of the upper linear bearing 120 also provide irrigation water to the cutting area.

Figure 19:
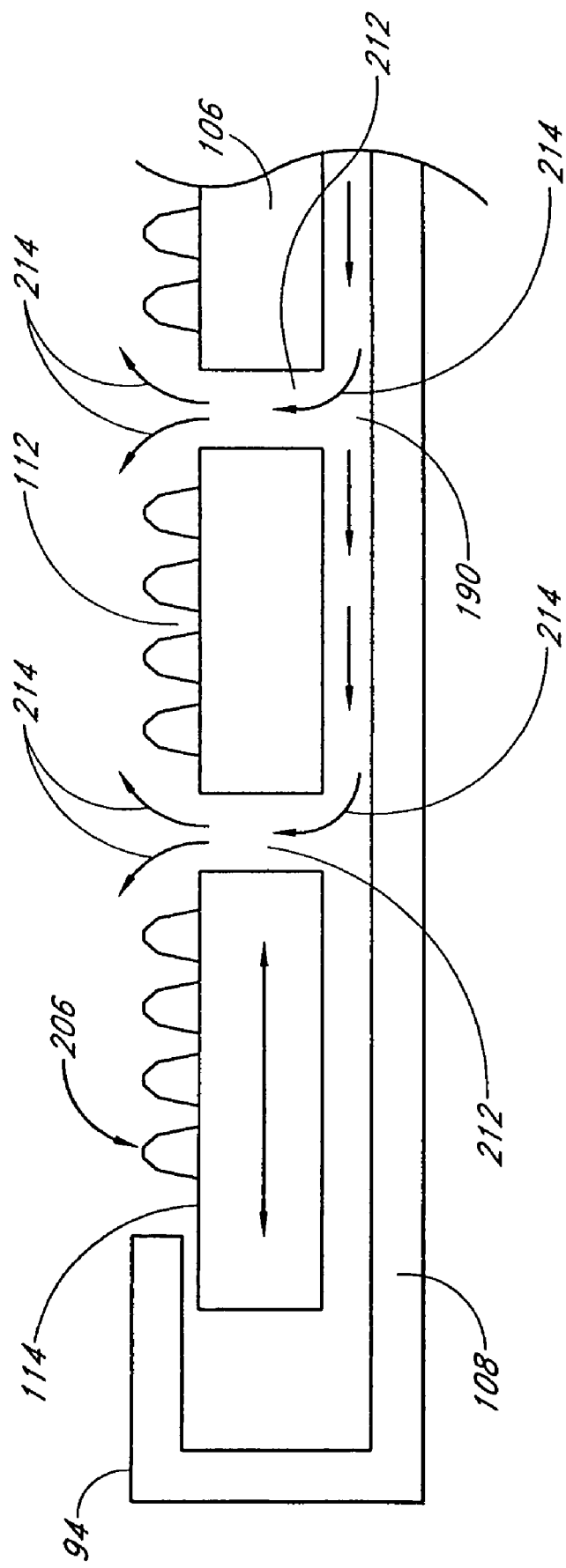
FIG. 19 is a schematic view of a surgical file cutting blade with irrigation fluid flow therethrough illustrating features and advantages in accordance with an embodiment of the invention.

FIG. 19 schematically depicts the fluid, liquid or hydraulic communication between the bearing slot(s) 190 and the cutting surface holes 212. The flow of water from the bearing slots(s) 190 and the micro hole openings 212 is generally indicated by arrows 214. The water is forced to flow up, down or out through the openings 212 in the cutting blade surface 114 and away from the blade cutting surface 114. The water washes away cut material and keeps debris from clogging the cutting surface 114 to maintain optimum cutting and material removal performance, and to keep the cutting area cool to prevent tissue necrosis damage.

The water also flows over the moving (reciprocating) cutting blade 106 and drive mechanism or bearings 120 to provide cooling and lubrication. The water can be forced into the cutting cavity 112 to flush away micro cutting debris and maintain a clear field of view for video navigation and visualization. The water can be forced into the cutting area cavity 112 to clean and remove freshly cut bone cells and bone fragments to prevent repopulation and unwanted bone growth in the area.

Figure 20:
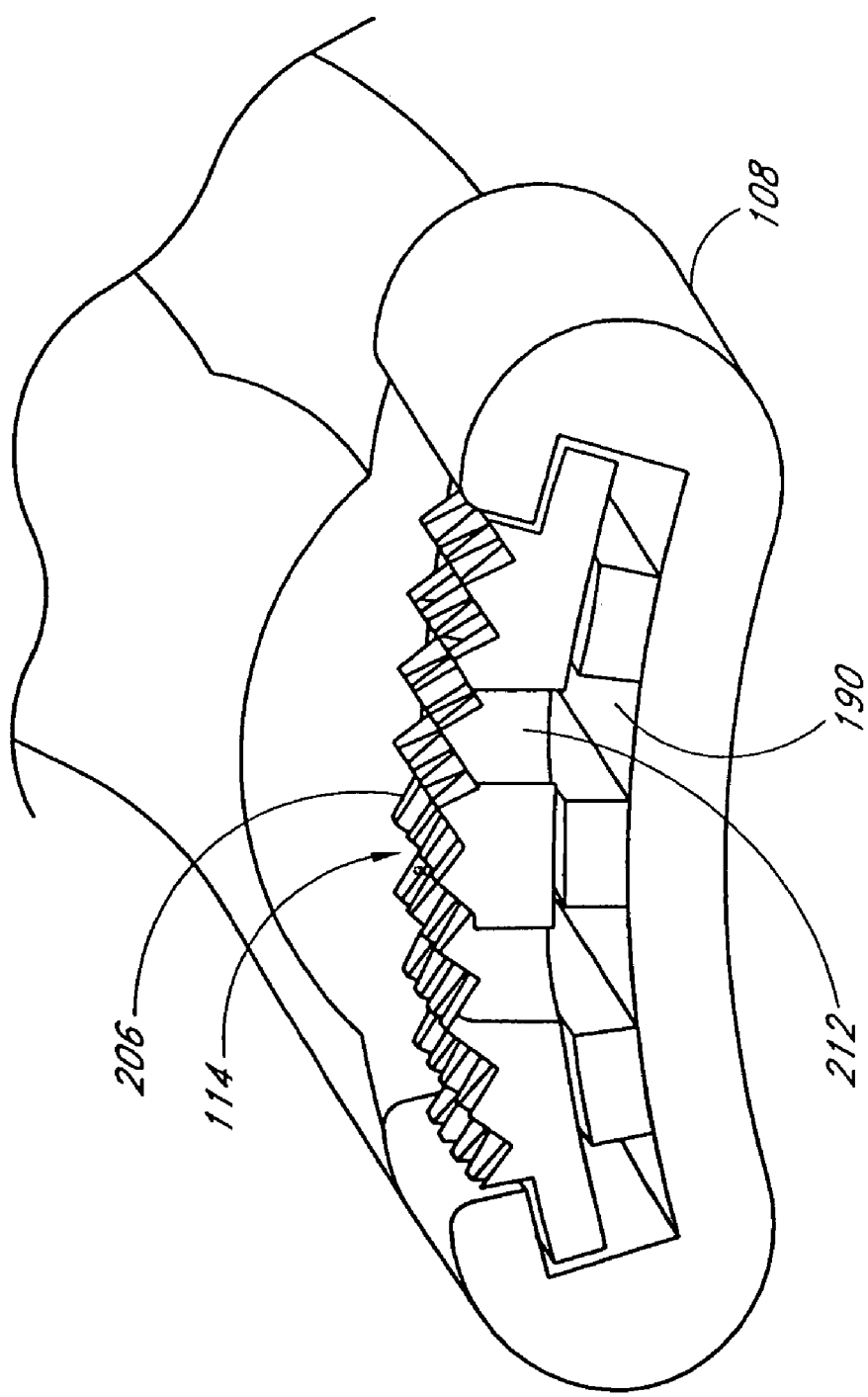
FIG. 20 is a cross-section view of a surgical file distal cutting tip with irrigation fluid passageways illustrating features and advantages in accordance with an embodiment of the invention.

FIG. 20 is another schematic depiction showing the fluid, liquid or hydraulic communication between the irrigation fluid holes 212 and the bearing irrigation passageways 190. The drawing also shows the abrasive material or abrasives 206 of the blade cutting surface 114.

Figure 21:
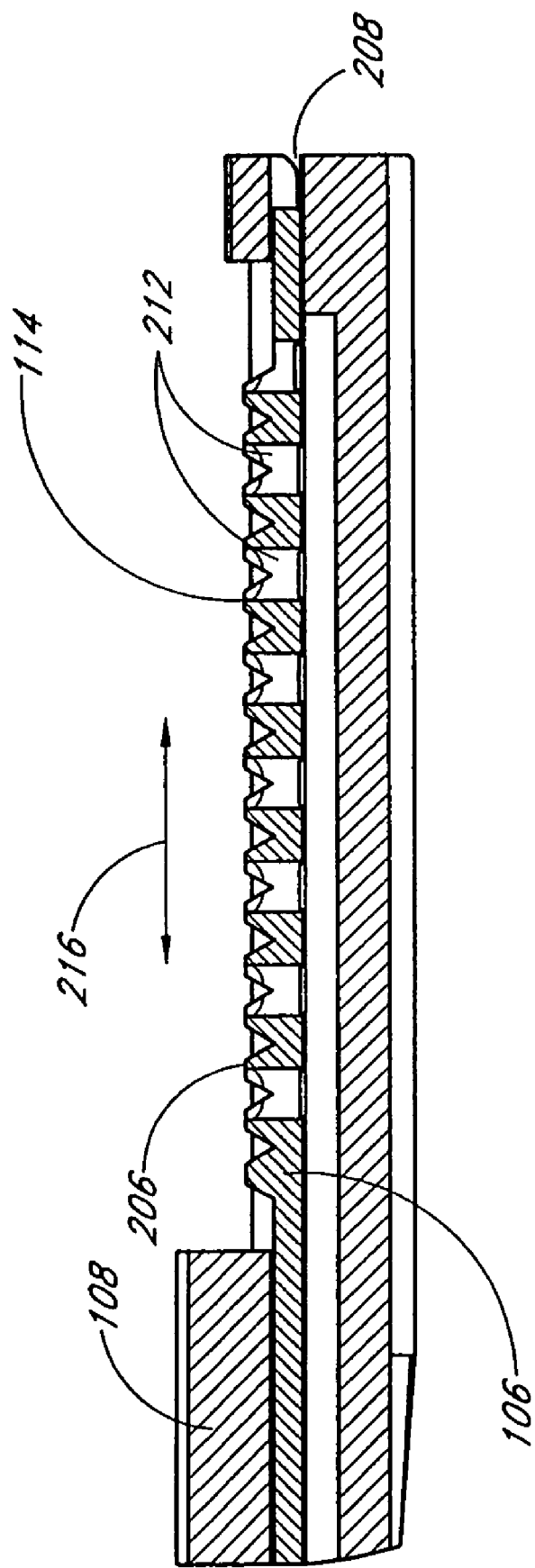
FIG. 21 is a side sectional view of a surgical file distal cutting tip with a linear reciprocation stroke illustrating features and advantages in accordance with an embodiment of the invention.

FIG. 21 shows the reciprocation blade stroke direction as generally indicated by arrows 216. The free linear motion of the reciprocation blade stroke is a linear stroke. In one embodiment, for applications within the human body, the linear stroke is in the range from about 2.5 mm (0.1 inches) to about 7.6 mm (0.3 inches), including all values and sub-ranges therebetween. In another embodiment, the linear stroke is in the range from about 1.3 mm (0.05 inches) to about 12.7 mm (0.5 inches), including all values and sub-ranges therebetween. In yet another embodiment, the linear stroke is in the range from about 0.25 mm (0.01 inches) to about 25.4 mm (1 inch), including all values and sub-ranges therebetween. In modified embodiments, the linear stroke may efficaciously be lower or higher depending on the particular application, as needed or desired.

Cauterization

In accordance with one embodiment, the surgical file instrument 12 can stop the small amount of bleeding of freshly cut or sculpture shaped bone or other tissue by accommodating connection to existing cauterizing equipment 60. In this embodiment, the special feature the system has is a non-electrically conductive shield 108, which is covering an electrically conductive metal file blade 106.

When bleeding of the freshly cut bone is detected, the file cutting blade 106 can be brought back into contact with the freshly shaped bone that may be bleeding slightly. A pulse of electricity can be momentarily applied that will flow from the metal blade file surface into the bleeding bone or other tissue surfaces. This will heat the bleeding bone or other tissue surfaces, coagulate the blood flow and advantageously stop the bleeding of the bone and/or tissue surface. Desirably, the irrigation flow facilitates localizing the heat and cooling while the shield 108 protects the adjacent nerves and spine from heat.

Illumination and Vision Probes

Figure 22:
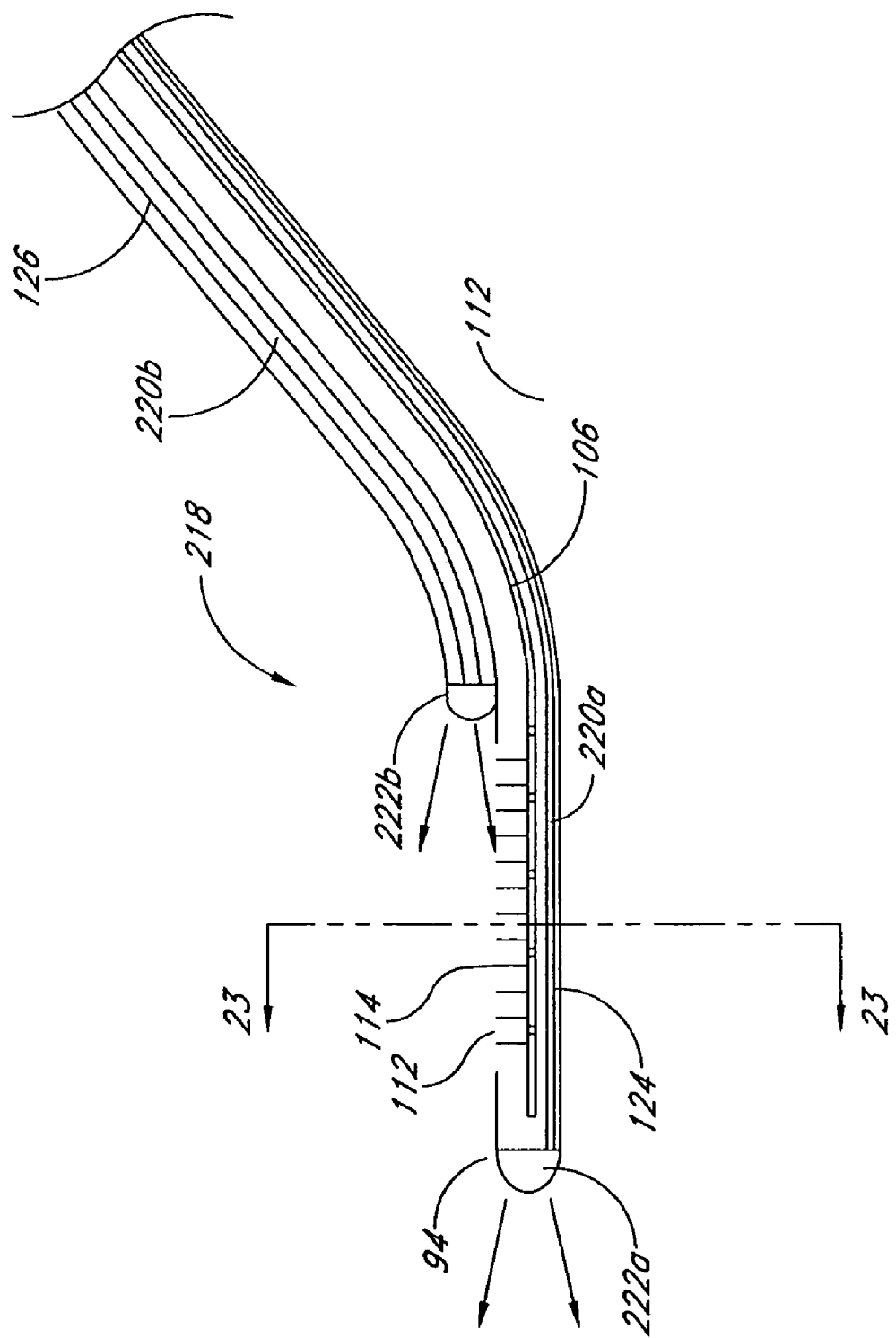
FIG. 22 is a side sectional view of a surgical file distal cutting tip with fiber optic probes illustrating features and advantages in accordance with an embodiment of the invention.

FIG. 22 shows a fiber optic vision system 218 including the fiber optic probes 124 and 126. The fiber optic vision system 218, in some surgical embodiments, enables surgeons to visually see and verify the presence of unwanted bone and cartilage buildup that is causing nerve root compression and damage to normal body functions. This information on the unwanted material can be documented and recorded by saving visual pictures into a computer database and printing color pictures immediately for reference and record.

The lower fiber optic probe 124 includes a plurality of optical fibers 220a that optically terminates at a distal lens array or arrangement 222a. The lens array 222a is positioned at substantially the tip distal end 94. The fiber optic probe 124 may be placed within the shield 108 or it may have a separate housing. The lower fiber optic probe 124 generally follows the longitudinal profile of the distal tip portion 92, the blade 106 and/or the shield 108.

The upper fiber optic probe 126 includes a plurality of optical fibers 220b that optically terminates at a distal lens array or arrangement 222b. The lens array 222b is positioned proximal to the blade cutting surface 114. The fiber optic probe 126 may be placed within the shield 108 or it may have a separate housing. The upper fiber optic probe 126 generally follows the longitudinal profile of the distal tip portion 92, the blade 106 and/or the shield 108.

Advantageously, the fiber optic vision system 218 enables visual viewing of the patient's body cavities all during insertion and placement of the cutting blade. This is intended to enable the surgeon to safely navigate the tiny body cavities such as neuroforamina and other tubular canals, and avoid damage to fragile nerve roots.

Figure 23:
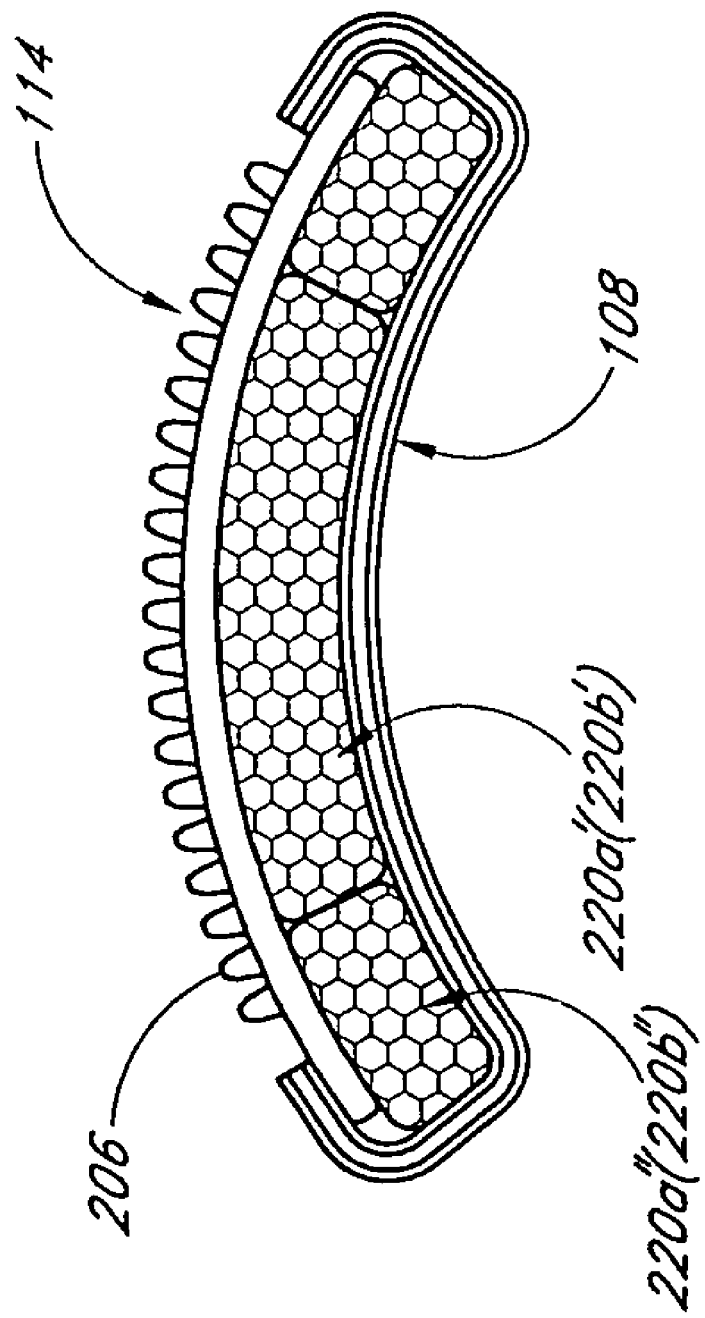
FIG. 23 is a sectional view along line 23-23 of FIG. 22 illustrating features and advantages in accordance with an embodiment of the invention.

FIG. 23 shows the optical fibers 220a in more detail. The upper optical fibers 220b (220b', 220b'') have a similar configuration and functioning though they may have a different curvature or be flat and planar. The optical fibers 220a comprise a central plurality of optical vision fibers 220a' flanked by light or illumination fibers 220a''. The optical vision fibers 220a' are connected at their proximal end to the video camera 78.

The fiber optical illumination fibers 220a'' illuminate the body cavity and enable video visualization. An LED located at the proximal end of the fiber optics illumination fibers 220a'' is used transmit light to the distal end of the illumination fibers 220a'' to provide illuminating light. Advantageously, the direct vision optical system 218 enables surgeons to safely navigate into blind cavities of the human body and to illuminate and see specific body anatomy such as nerves and bony buildups that could be irritating and pressing against nerves causing nerve compression.

In the illustrated embodiment, the direct vision optical system 218 desirably provides an integrated illumination and optical vision system. The optics for vision and illumination are included within the distal tip assembly 18 which in some embodiments is a docking sterile one time use assembly.

Figure 24:
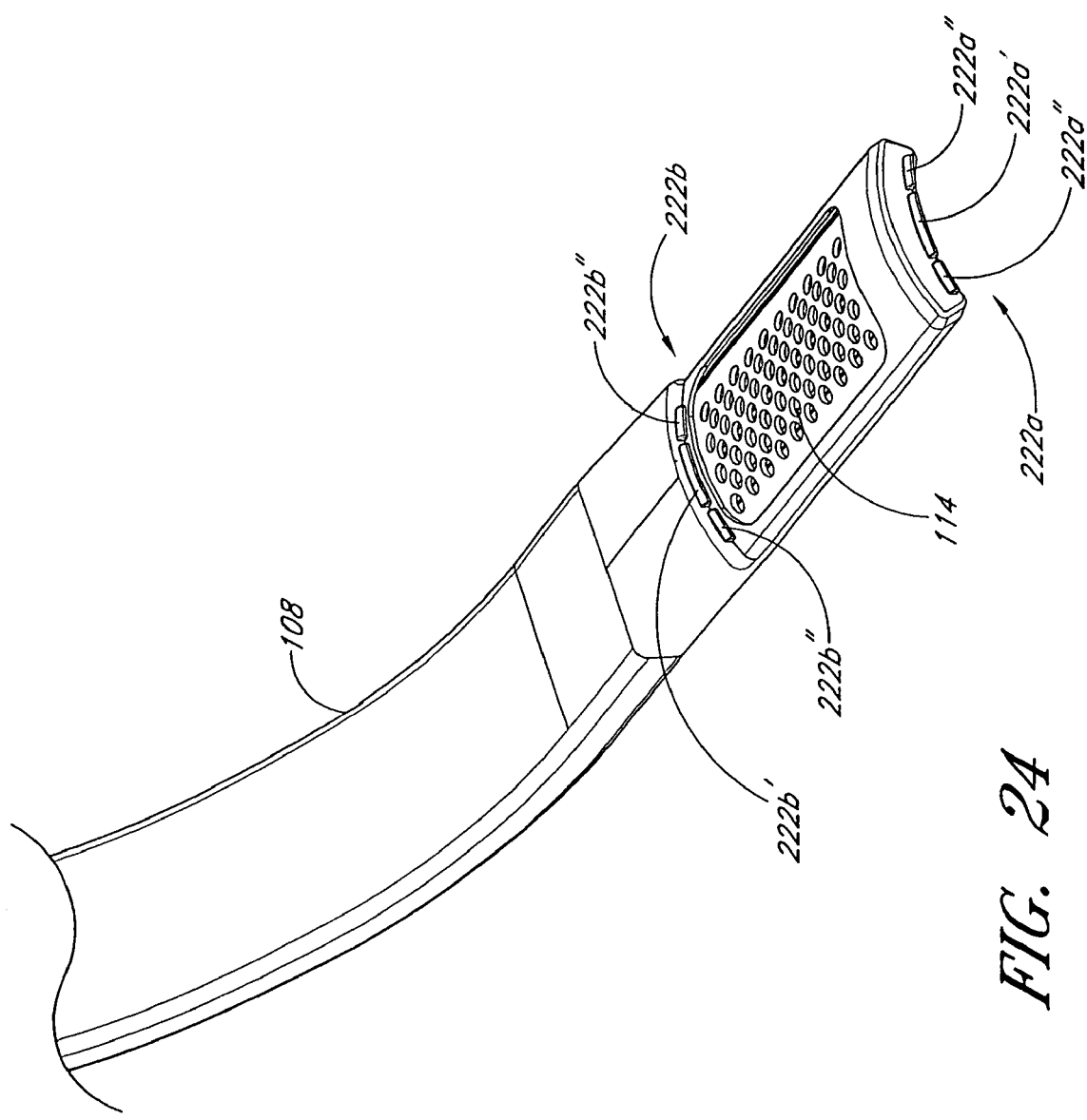
FIG. 24 is a simplified side sectional view of a surgical file distal cutting tip with an illumination and vision system illustrating features and advantages in accordance with an embodiment of the invention.

Referring in particular to FIG. 24, the distal optical system lenses arrangements 222a and 222b are each arrayed in three segments. The lower optical segments 222a are arranged with a video imaging lens 222a' centered medially and with illuminating lenses 222a'' positioned on the right and left lateral sides. The upper optical segments 222b are arranged with a video imaging lens 222b' centered medially and with illuminating lenses 222b'' positioned on the right and left lateral sides.

Figure 25:
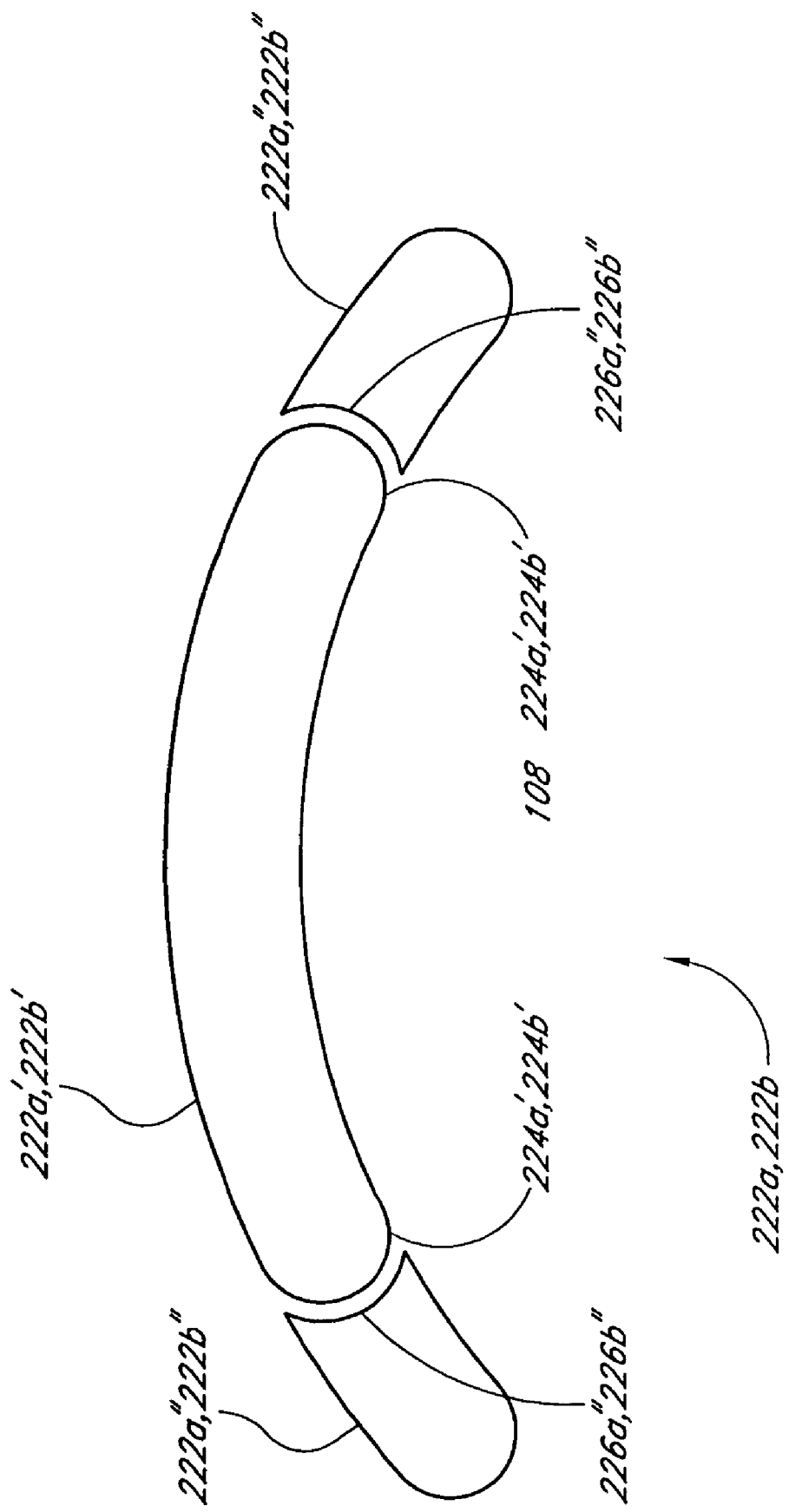
FIG. 25 is a schematic view of an arrangement of lenses of a surgical file illumination and vision system illustrating features and advantages in accordance with an embodiment of the invention.

FIG. 25 shows the lens arrays 222a, 222b in more detail. The lateral sides of the central lenses 222a', 222b' have a respective semi-arc male shape 224a', 224b' to each of their left and right sides. The illuminating lenses 222a'', 222b'' are shaped to have mating female semi-arc medial sides 226a'', 226b'' on there medial sides which mate into the male mating features 224a', 224b' of the central lens sides.

Advantageously, such mating lens arrays 222a, 222b can accommodate a wide range of instrument sizes while using substantially the same basic lens assembly design. Different lenses may be used in the design and the curvature of the lens array adjusted and changed to provide the desired illumination and/or field of view. For example, for a particular medial video imaging lens 222a', 222b' the curvature of the side illuminating lenses 222a'', 222b'' can be adjusted or changed to illuminate the desired field of view. This desirably saves on cost since micro lenses are very expensive to tool up and make. The distal tip assembly 18 can have numerous sizes with varying cross sections of the distal tip portion 92 depending on the particular application and advantageously substantially the same basic lens assembly design 222a, 222b can be utilized with the different sizes.

Additionally the mating lenses 222a', 222b' and 222a", 222b" allow the black out of the respective mating surfaces 224a', 224b' and 226a" and 226b" to substantially prevent illumination light from passing laterally into the imaging lens 222a', 222b' and degrading the optical quality of the resulting picture. A lens set comprising the central imaging lens 222a', 222b' and one each right and left illuminating lenses 222a", 222b" can be assembled onto a wide range of instrument disposable cutting tips 18 in an assembly that has an optical distal lens system which is very thin in cross section and that the lenses follow the instrument cross sectional curve. Advantageously, for embodiments of the invention and in particular the neurosurgery embodiments, having a very thin cross section enables the instruments distal tip to fit into the tiny space between a nerve root and its neuroforamen opening.

Figure 26:
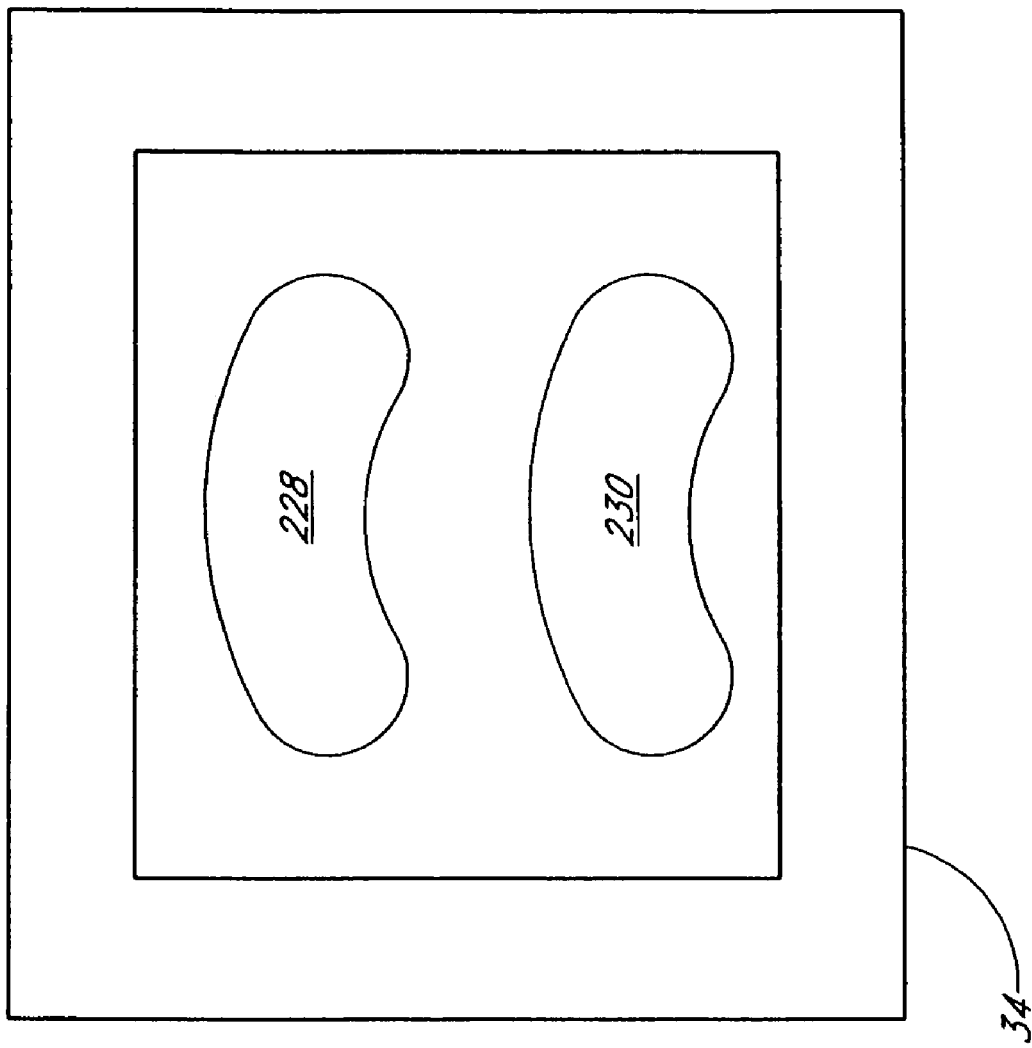
FIG. 26 is a schematic view of display images provided by a surgical file illumination and vision system illustrating features and advantages in accordance with an embodiment of the invention.

As shown in FIG. 26 the images from the direct vision optical system 218 can be viewed on the LCD monitor 34. The drawing shows an example of the display with a view 228 from the upper fiberoptic 126 looking onto the blade 106 and a view 230 from the lower fiberoptic 124 looking out from the instrument distal end 92.

Toroidal Transmission System

The toroidal transmission or power conversion system 98 is a mechanical conversion device that converts rotary to reciprocating motion or action. The powered handpiece 20 houses a rotating motor 80 to power the cutting action of the tissue removal instrument or blade 106. The rotating mechanical action of the motor 80 is converted into reciprocating mechanical motion of a suitable reciprocal stroke length. It is desirable that the mechanical motion conversion device be simple and have few parts.

Having a video camera system mounted directly into a reciprocating motion mechanical device can create a stability problem with respect to inherent vibration that is usually inherent in all reciprocating motion mechanical devices. Advantageously, the toroidal drive system 98 of embodiments of the invention provides a desirable solution for the vibration problem since it has low or minimum levels of associated vibration. This advantageously provides a stable platform for the capture of high quality pictures by the video system including the camera 78 housed in the handpiece 20.

The toroidal drive system 98 inherently has few parts and can be built to be very low vibration due to low mass of the reciprocating components. Thus, the toroidal drive system 98 can provide the powered handpiece 20 with a stable platform and a smooth running mechanical action. The transmission system of embodiments of the invention has utility in a number of fields and applications where conversion of rotary motion to reciprocating motion is desired.

Figure 27:
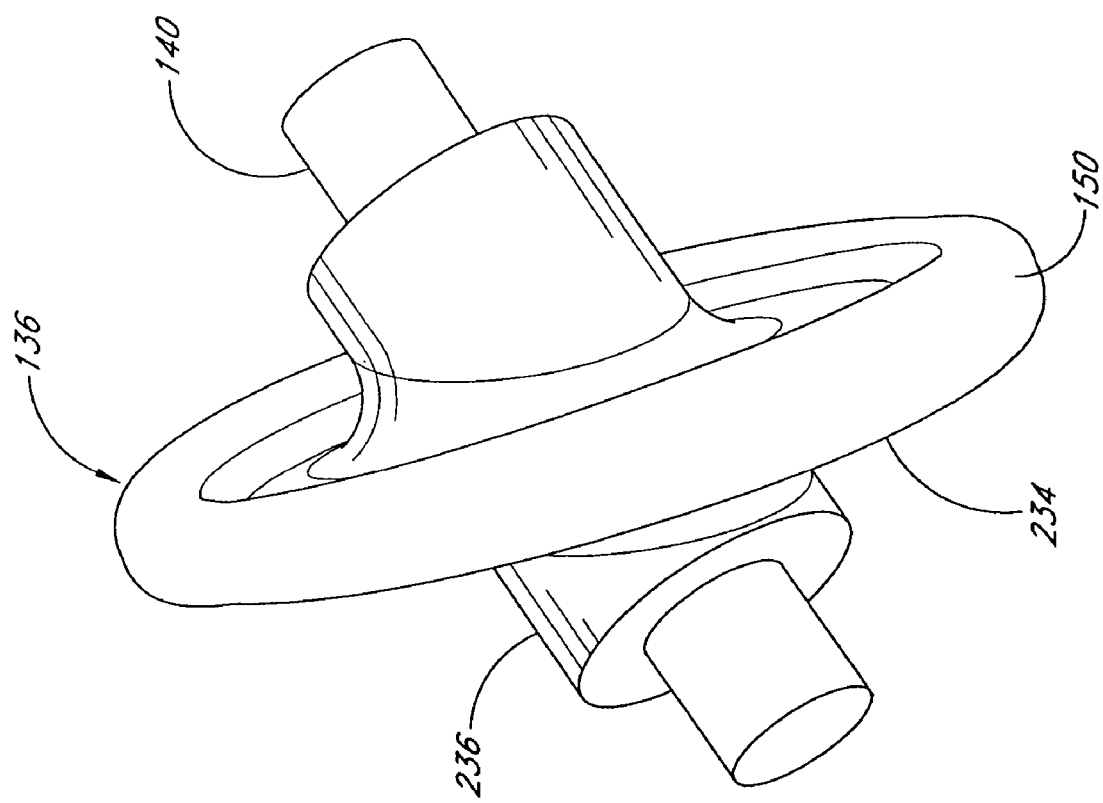
FIG. 27 is a simplified perspective view of a dual torus and drive shaft illustrating features and advantages in accordance with an embodiment of the invention.
Figure 28:
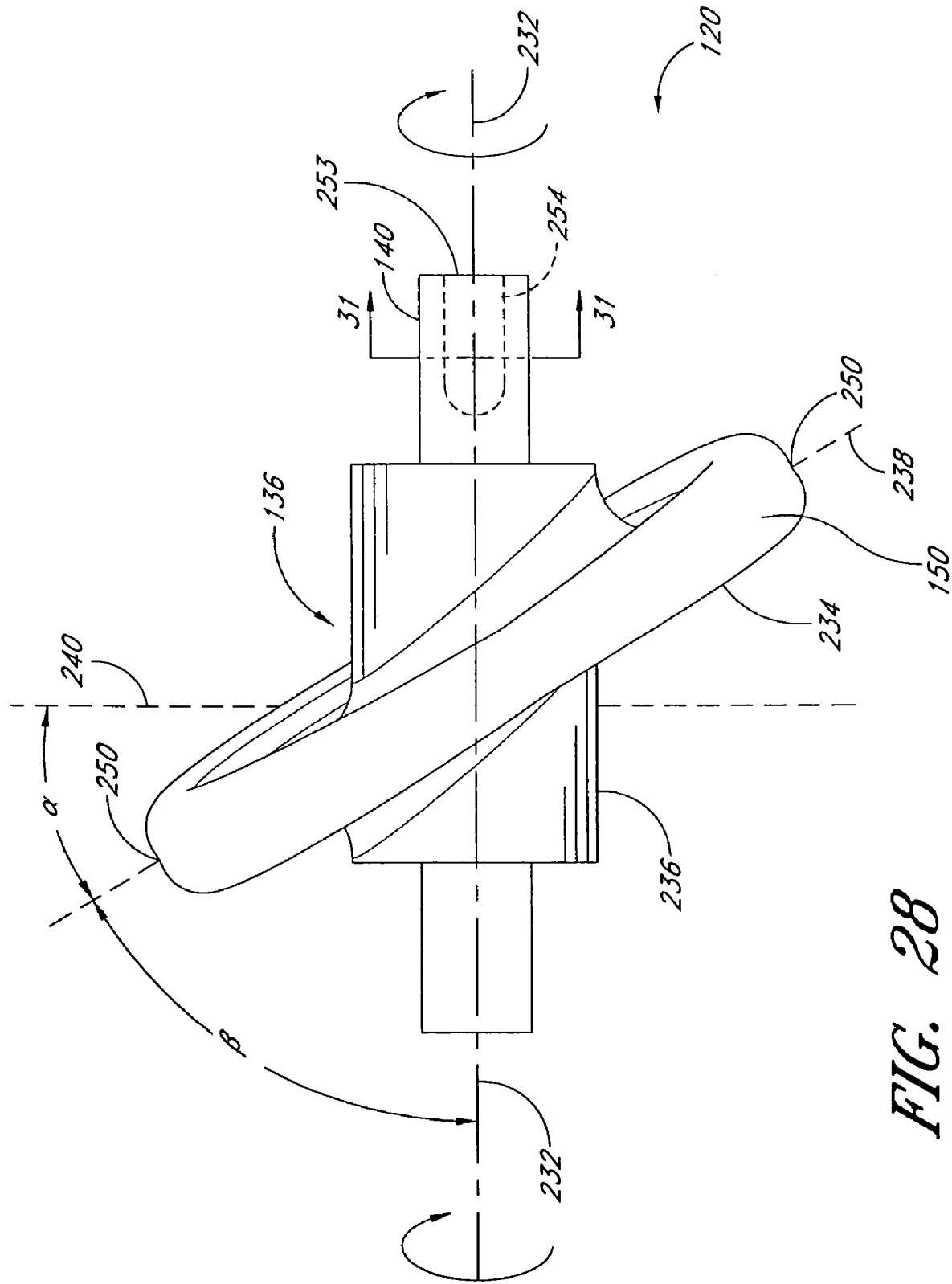
FIG. 28 is a simplified side view of the dual torus and drive shaft of FIG. 27.

FIGS. 27 and 28 show the toroid drive 136 and the female receptor drive shaft 140. In one embodiment, the toroid drive 136 and the drive shaft 140 comprise an integral unit and are formed as a single piece. In another embodiment, the toroid drive 136 and the drive shaft 140 can be rigidly connected to one another.

The toroid drive 136 and the drive shaft 140 can be formed from a number of suitably durable materials. In one embodiment, the toroid drive 136 and the drive shaft 140 are formed from a suitable plastic by molding. The plastic material may comprise a suitable thermoplastic. In modified embodiments, other suitable plastics, metals, alloys, ceramics, combinations thereof, among others, may be efficaciously utilized, as needed or desired. Suitable surface coatings or finishes may be applied, as required or desired.

The toroid drive 136 and the drive shaft 140 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The toroid drive 136 and the drive shaft 140 are rotatable about a substantially central rotation axis 232. The toroid drive 136 has a generally circular or curvilinear cam portion 234 and a generally central shank portion 236. As discussed further below, the cam 234 has a specially designed generally circular or curvilinear outer rim 150 with a varying or non-uniform thickness.

The cam 234 and/or the outer rim 150 have a substantially central side view plane 238. The cam 234 and/or the outer rim 150 are tilted relative to a vertical plane or axis 240 by a predetermined angle $\alpha$ and hence to the rotation axis by an angle $\beta$ where $\beta=90°-\alpha$. Thus, typically $\beta$ and $\alpha$ are less than 90°.

In one embodiment, $\alpha$ is about 20° and $\beta$ is about 70°. In another embodiment, $\alpha$ is in the range from about 10° to about 40° and $\beta$ is in the range from about 50° to about 80°, including all values and sub-ranges therebetween. In yet another embodiment, $\alpha$ is in the range from about 5° to about 80° and $\beta$ is in the range from about 10° to about 85°, including all values and sub-ranges therebetween. In modified embodiments, $\alpha$ and $\beta$ may be lower or higher, as needed or desired.

Figure 29:
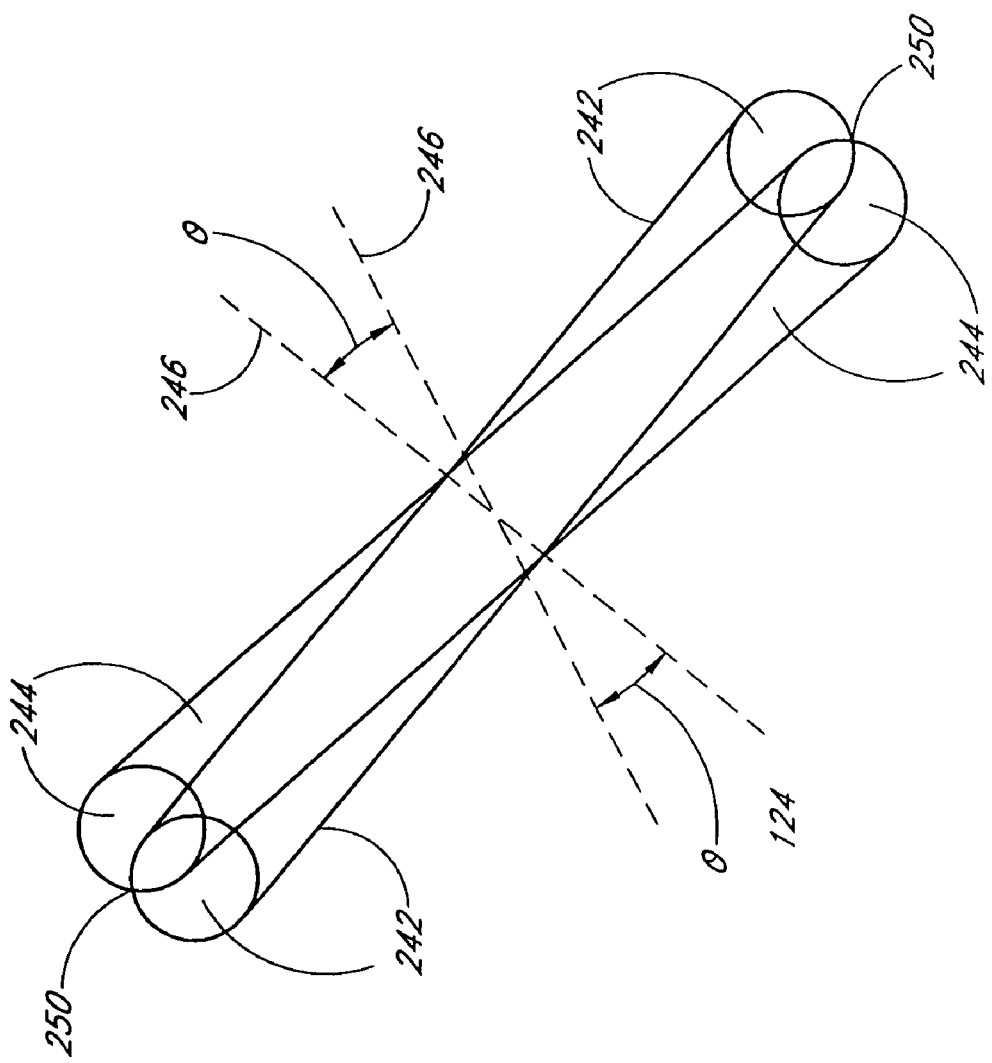
FIG. 29 is a simplified schematic view of a dual torus partial superposition illustrating features and advantages in accordance with an embodiment of the invention.

As schematically illustrated in FIG. 29, in one embodiment, the cam 234 and/or the outer rim 150 are designed to provide a variable thickness for the outer rim 150 by the partial superimposition of two toruses or toroids 242, 244 of substantially uniform rim thickness with respective central axes 246, 248. By controlling the degree of superposition, the rim 150 of variable and controlled thickness is created. Thus, the transmission or power conversion system 98 is also referred to as a "hybrid dual or twin toroid" system.

Advantageously, the outer rim 150 thickness is varied such that the rim 150 substantially continuously contacts the bearing surfaces 164 and 166 as the cam 234 rotates about the central axis 232. Thus, desirably the two surfaces 164 and 166 can remain at a substantially fixed distance apart as they move linearly back and forth in reciprocating motion in response to the cam's rotation about the central axis 232.

In the illustrated embodiment, the torus central axes 246, 248 are at an offset angle $\theta$ to produce the desired variable thickness rim 150. The slightly dimpled or grooved surface 250 is indicative of the partial superposition of the two toruses or toroids 242, 244. In modified embodiments, more than two toruses and/or toruses with variable rim thickness may be utilized to create the desired outer rim profile.

Advantageously, the dual torus or toroid (one toroid partially inside another) configuration provides an elegant solution of for maintaining a uniform distance between the bearing surfaces 164, 166 or driven rollers. The rotation of the toroid or torus cam 234 moves the outer rim 150 in a reciprocating motion with the motion being generally parallel to the rotary axis 232. The reciprocating motion of the slide plate 138 is also generally parallel to the rotary axis 232 which is then transmitted to the blade 106.

Figure 30:
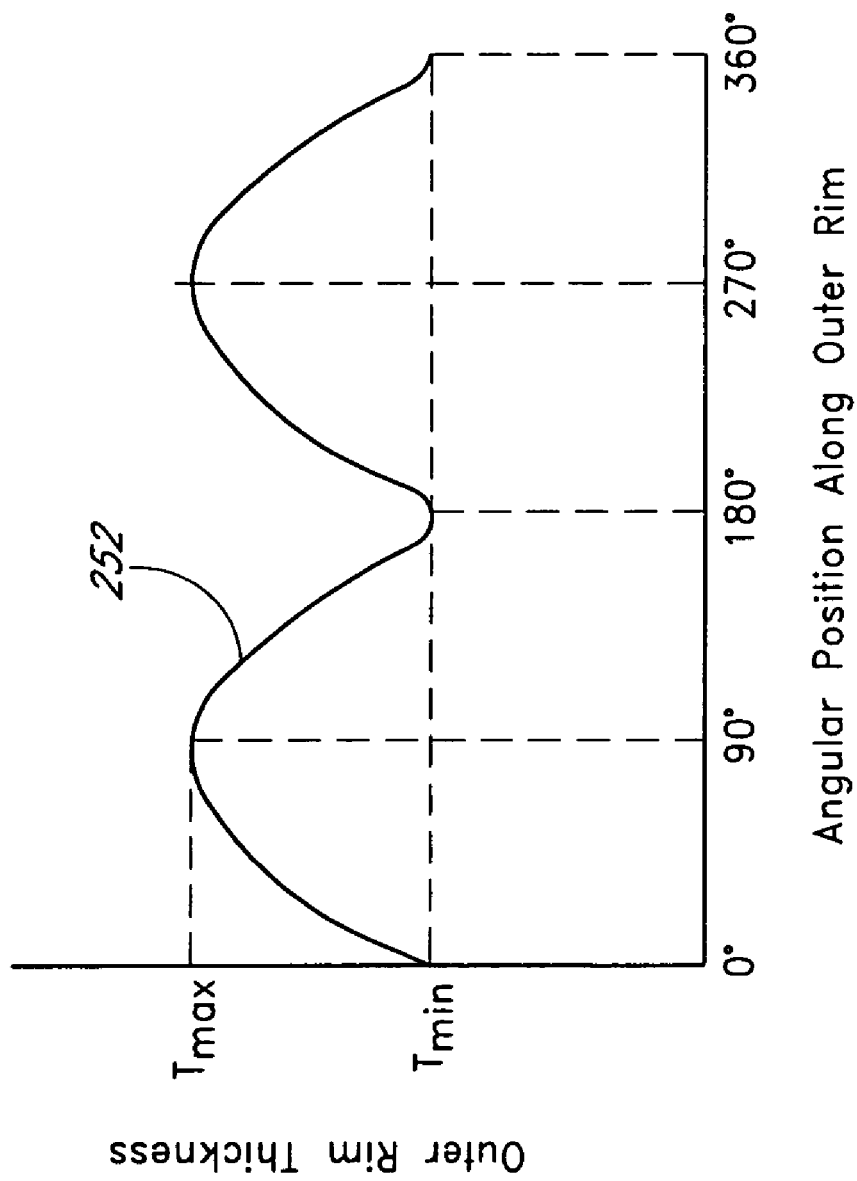
FIG. 30 is a schematic graphical representation of variation in outer rim thickness of a dual torus or toroid illustrating features and advantages in accordance with an embodiment of the invention.

FIG. 30 shows the thickness profile of the outer rim 150 in accordance with one embodiment. The thickness varies across the rim 150 in a generally offset sinusoidal profile with a minimum thickness $T_{min}$ and a maximum thickness $T_{max}$. In modified embodiments, other suitable rim thickness profiles may be efficaciously utilized, as needed or desired.

The disposable cutting blade assembly 18 includes the integrated transmission system 98 within the distal cover 72. The transmission system 98 converts the rotary motion of the drive motor 80 into the reciprocating motion of the tissue-cutting blade 106. The transmission system 98 is a sterile assembly of the disposable cutting blade assembly 18 that is sterile packaged.

The transmission system 98 is an internal mechanism and is generally housed within the housing 96. This is important in that the "one time use disposable" tip assembly 18 embodiments because easy separation from the re-sterilizable motor drive portion of the powered handpiece 20. In theses embodiments, the powered handpiece 20 with its rotary motor 80 comprises an independent assembly from the disposable distal cutting tip assembly 18. Numerous sizes and shapes of distal cutting tip portion 92 are available to be connected onto the motor drive powered handpiece 20.

Since the disposable distal cutting tip assembly 18 has an internal mechanism to convert rotary motion into reciprocating motion, it advantageously enables a simple and cost effective means of disconnecting the two assemblies 18 and 20. The drive shaft 140 at its proximal end 253 includes a female receptor hole 254 that is configured to substantially irrotationally mate with a matching male distal shaft drive protruding out of the motor drive 80.

Figure 31A:
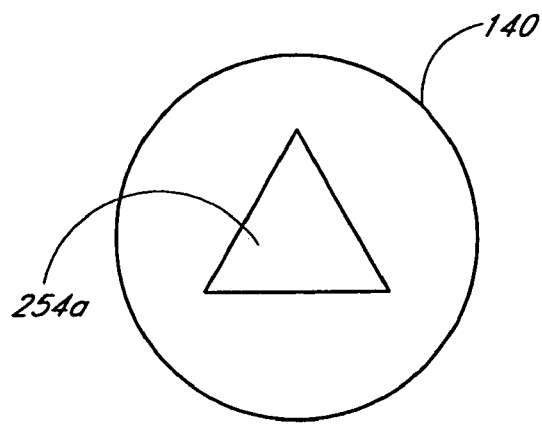
FIG. 31A is a sectional view along line 31-31 of FIG. 28 illustrating features and advantages in accordance with an embodiment of the invention.

FIG. 31A shows a simple female triangular hole 254a in the drive shaft 140 that can engage a triangular shaped distal shaft drive protruding out of the motor drive assembly. When the distal tip assembly 18 and the powered handpiece 20 are connected both the female triangular receptor hole 254a and the motor's male triangular drive shaft can rotate in tandem. The male and female features are free to mesh and align during the axial motion of connecting the disposable cutting tip assembly 18 onto the reusable sterilizable motor handpiece 20.

A triangular shaped male mating drive is desirable because it facilitates sterilization of the male triangular shaft. The surfaces that are steam sterilized and reused are desirably simple surfaces that are easy to wash and clean. The surfaces should also enable reliable cleaning prior to sterilization. A triangular male shaft has three flat surfaces that are both easy to see and clean.

Figure 31B:
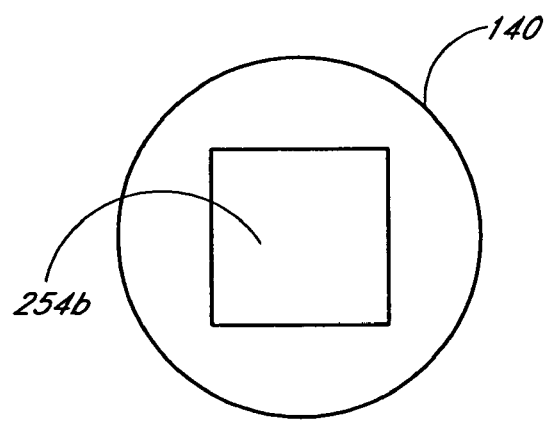
FIG. 31B is a sectional view along line 31-31 of FIG. 28 illustrating features and advantages in accordance with another embodiment of the invention.
Figure 31C:
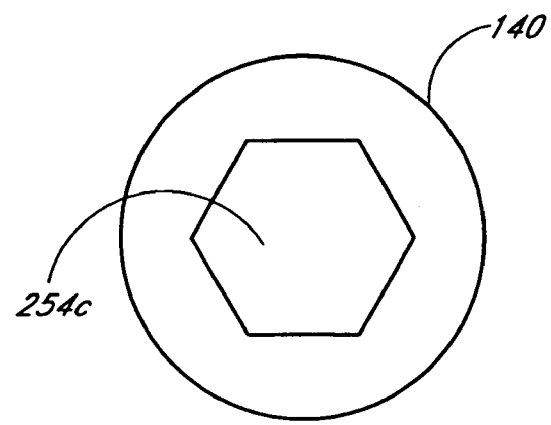
FIG. 31C is a sectional view along line 31-31 of FIG. 28 illustrating features and advantages in accordance with yet another embodiment of the invention.

In modified embodiments, other suitable male-female mating drive polygonal or non-polygonal interlocking configurations may be utilized with efficacy, as needed or desired. For example, FIG. 31B shows a generally square or rectangular female receptor hole 254b and FIG. 31C shows a generally hexagonal female receptor hole 254c.

Figure 32:
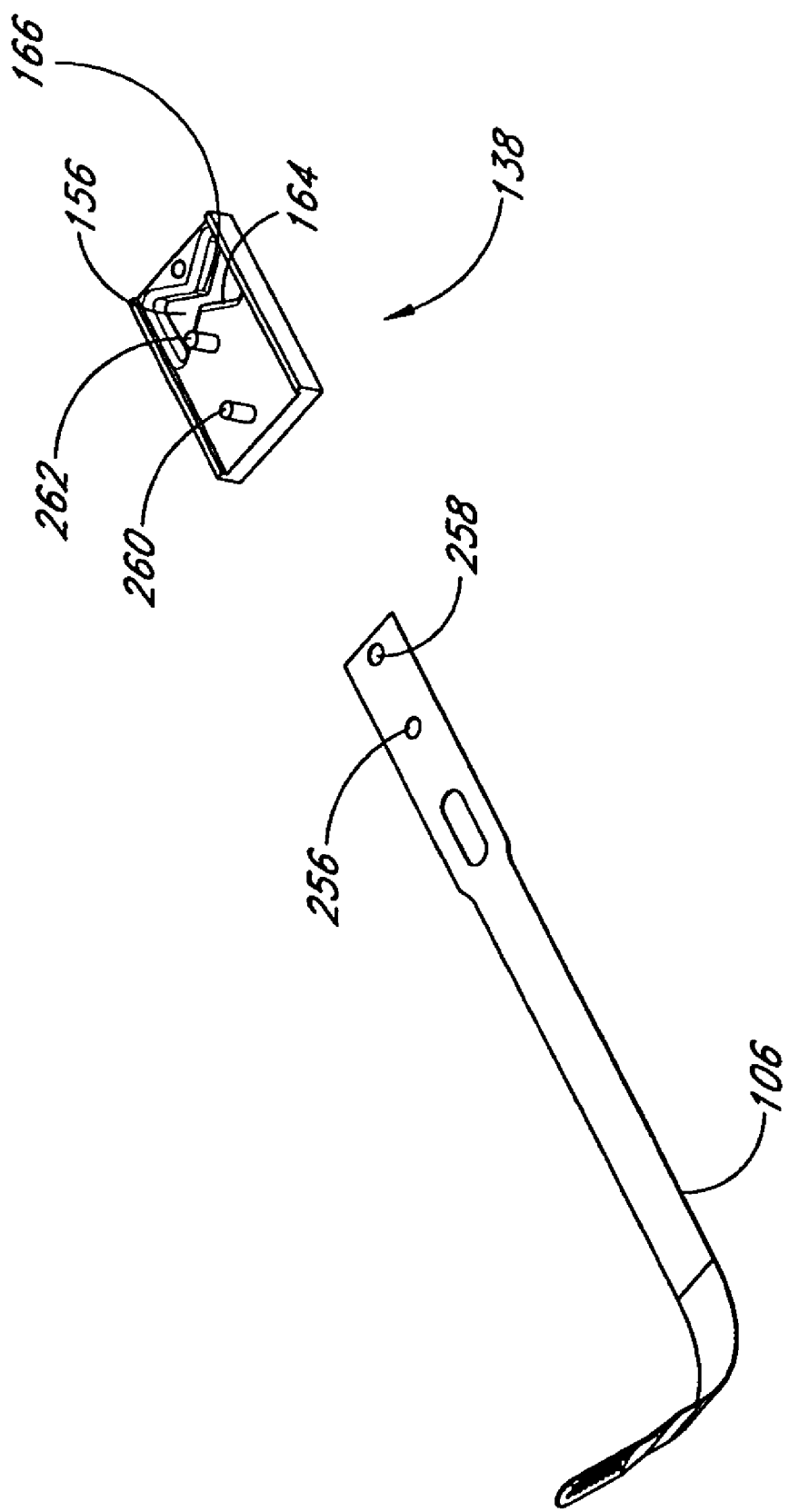
FIG. 32 is a perspective view of a distal cutting blade and a reciprocating slide plate that connects to the blade illustrating features and advantages in accordance with an embodiment of the invention.
Figure 33:
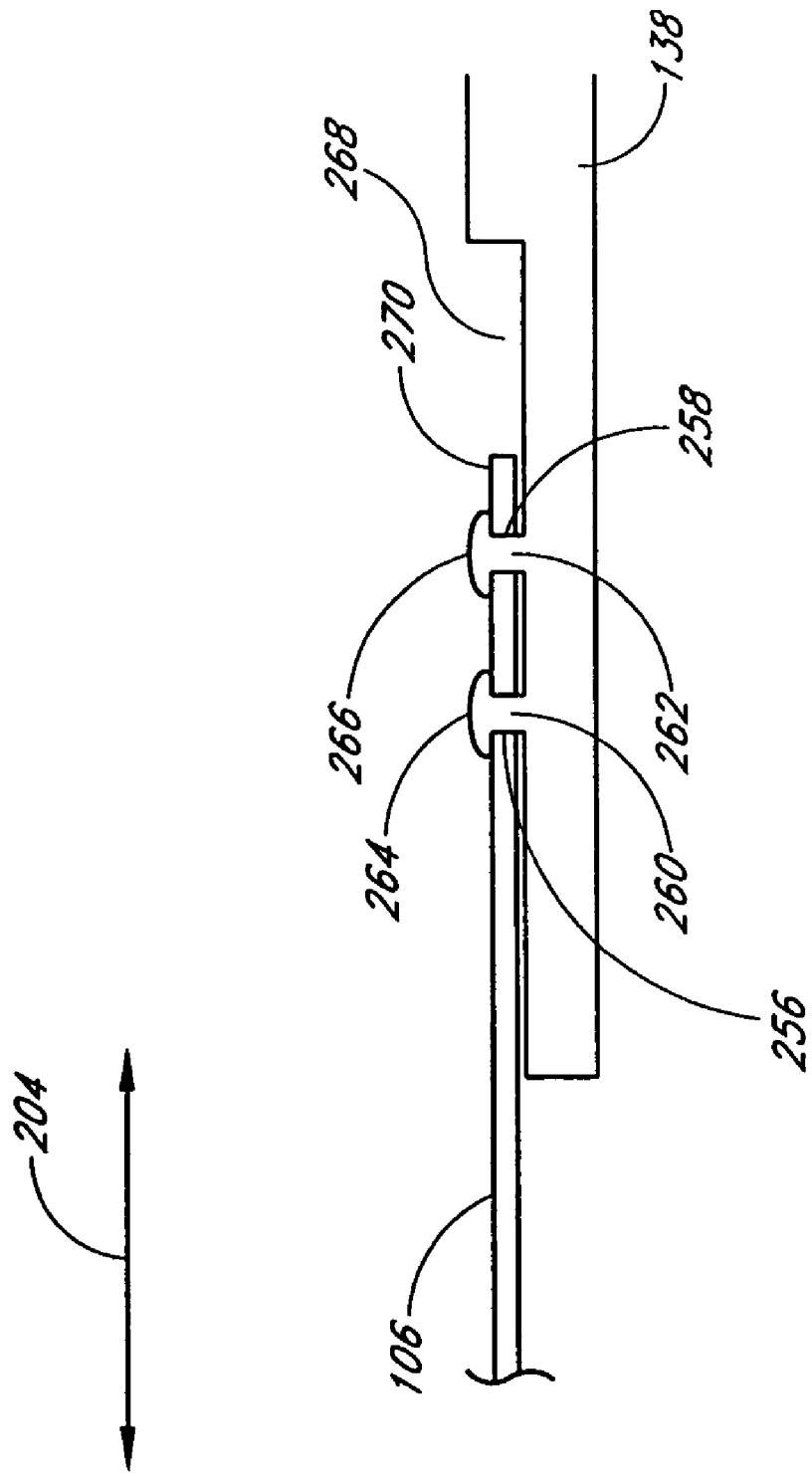
FIG. 33 is a schematic side view of a distal cutting blade connected to a slide blade illustrating features and advantages in accordance with an embodiment of the invention.

FIGS. 32 and 33 show the cutting blade 106 and the drive slide 138. The outer rim 150 of the toroid drive 136 engages the slide slot 156 and abuts against the bearing surfaces 164, 166 as it rotates to reciprocatingly displace the slide 138 connected to the blade 106. The slide 138 can be generally above the toroid drive 136 or it can be generally below the toroid drive 136. In modified embodiments, the slide 138 can be to the sides of the toroid drive 136 as long as the outer rim 150 rotates within the slide slot 156 and causes the slide to move in a reciprocating motion.

It is important that the distal filing blade 106 maintain its structural rigidity and not to fail in a buckling mode that would cause the file blade 106 to become bent or distorted into a shape that may result in an undesirable thicker profile. To safeguard against this, in one embodiment, a safety shear system is provided.

The slide 138 includes a pair of posts or pins 260, 262 that engage respective blade holes 256, 258. In one embodiment, the posts 260, 262 are formed from a molding process in which the slide 138 including the posts 260, 262 comprises a plastic. The posts 260, 262 in one embodiment are heat staked and the like to mushroom and form respective heads 264, 266 to affix the blade 106 and the slide 138. The mushroomed pins 260, 262 prevent undesirable blade buckling by being configured to shear at a force much lower than the force that could potentially buckle the file blade 106.

Thus, advantageously, the file blade 106 is driven by a structure that has an intentional weak point that will shear away the driving reciprocating action of the blade drive 106 to prevent a potential distal blade 106 buckling. The configuration of the shear pins 260, 262 is tailored to the specific file blade configuration (which varies in width and length and cross sectional curve). Thus, the shear pin connection including the diameter and/or cross-section of the mushroomed heads 264, 266 and/or the shank portions of the pins 260, 262 is configured such that the mushroomed pins 260, 262 shear at a force lower than a force that would buckle the specific distal cutting blade 106 and allow safe disengagement and disconnection of the blade 106 from the slide 138.

Advantageously, the diameter(s) of the pins 260, 262 provides a desirable shear pin safety mechanism. The pins 260, 262 allow the connection between the drive slide 138 and the blade 106 to shear at a predetermined force. This force can be determined for a particular cutting blade configuration by a number of methods including modeling, numerical analysis, computer simulation, experimental and empirical testing and the like, among others. Accordingly, each differing cutting blade 106 is provided with a shear connection feature to shear and stop the blade driving action before the blade could conceivably buckle. A clearance space 268 in the slide 138 is provided in the proximal direction behind a blade proximal end 270 to allow the blade 106 to move proximally in the slide part 138 when shear disconnection occurs so that the blade 106 is substantially decoupled from the reciprocating motion.

The safety shear force $F_{shear}$ can be calculated as a function of the blade buckling force $F_{buckle}$ in a number of ways to provide suitable protection. In one embodiment, the shear force $F_{shear}$ is about $\frac{1}{3}^{rd}$ of the blade buckle force $F_{buckle}$. In another embodiment, the shear force $F_{shear}$ is in the range from about $0.25F_{buckle}$ to about $0.75F_{buckle}$, including all values and sub-ranges therebetween. In yet another embodiment, the shear force $F_{shear}$ is in the range from about $0.1F_{buckle}$ to about $0.9F_{buckle}$, including all values and sub-ranges therebetween. In modified embodiments, the shear force $F_{shear}$ may be lower or higher, as needed or desired.

FIGS. 32 and 33 illustrate a connection between the blade 106 and the slide plate 138 in accordance with an embodiment that provides a safety shear decoupling between the 106 and the slide plate 138. In modified embodiments, as the skilled artisan will appreciate, the blade 106 and the slide 138 may be connected utilizing other suitable techniques, as needed or desired.

Figure 34:
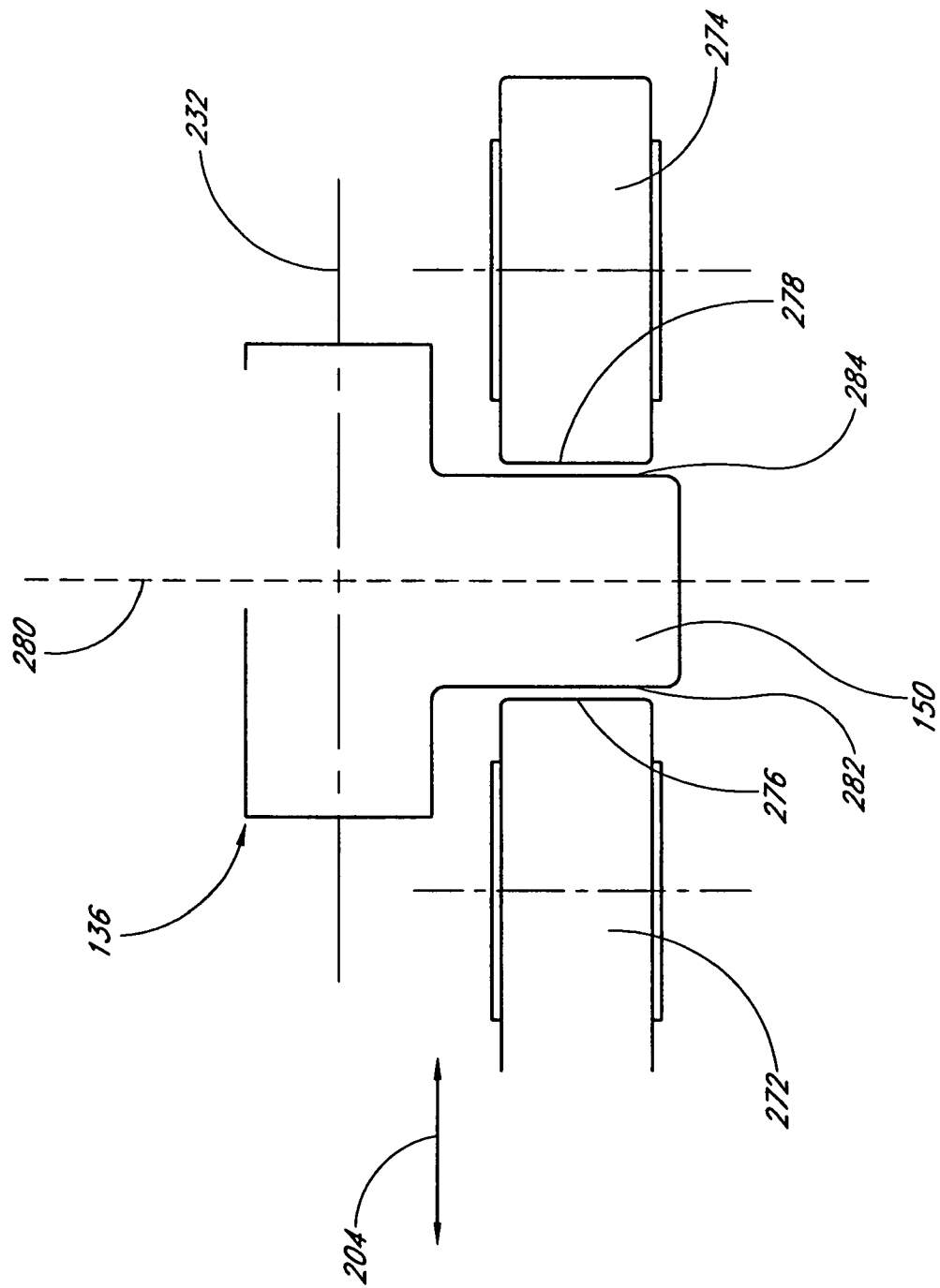
FIG. 34 is a schematic view of toroid drive and associated bearings illustrating features and advantages in accordance with an embodiment of the invention.

FIG. 34 shows the hybrid dual toroid drive 136 with a pair of associated bearings 272, 274 operatively mounted on the slide plate 138. The bearings 272, 274 and their toroid abutting surfaces 276, 278 are spaced by a predetermined distance that allows the variable thickness cam outer rim 150 to be in substantially continuous contact while rotating. In this embodiment, the rotation axis 232 is substantially perpendicular to a plane 280 between the bearing surfaces 276, 278.

The specially configured bearing abutting surfaces 282, 284 of the outer rim 150 advantageously provide an increased surface contact area with respective bearing surfaces 276, 278. This desirably decreases the pressure load between driving toroidal surfaces 282, 284 and the driven linear slide follower bearings 272, 274 and their respective surfaces 276, 278. The bearings 272, 274 also provide for a low friction contact with the driving toroidal surfaces 282, 284 and advantageously improve wear-resistant properties.

Figure 35:
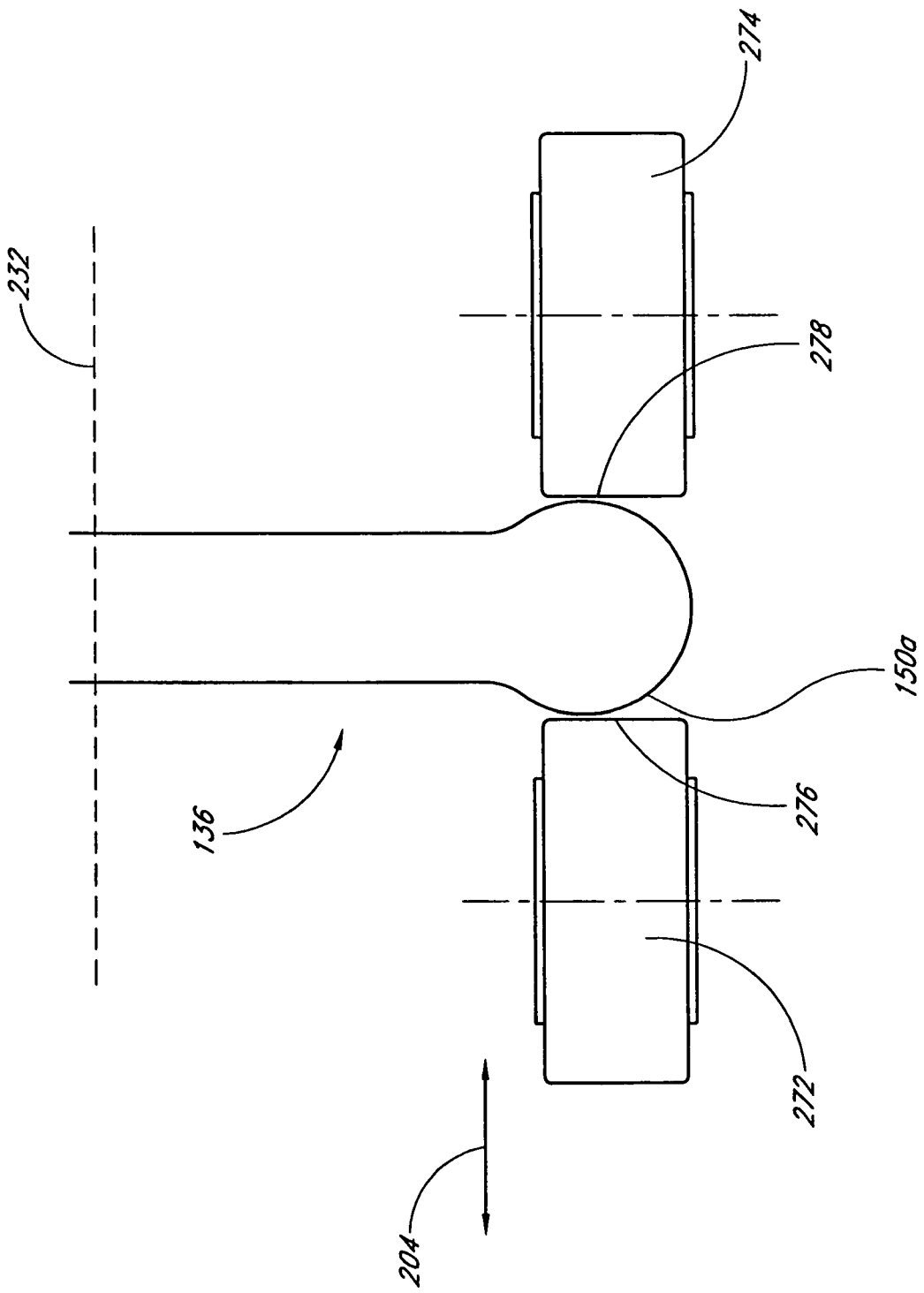
FIG. 35 is a schematic view of toroid drive and associated bearings illustrating features and advantages in accordance with another embodiment of the invention.

FIG. 35 shows a modified embodiment wherein the toroid drive 136 has an outer rim 150a that substantially contacts the bearing surfaces 276, 278 mounted on the slide 138 in a low surface area or point contact arrangement. In further embodiments, the cam outer rim 150 can directly contact the slide bearing surfaces 164 and 166, as needed or desired.

Figure 36:
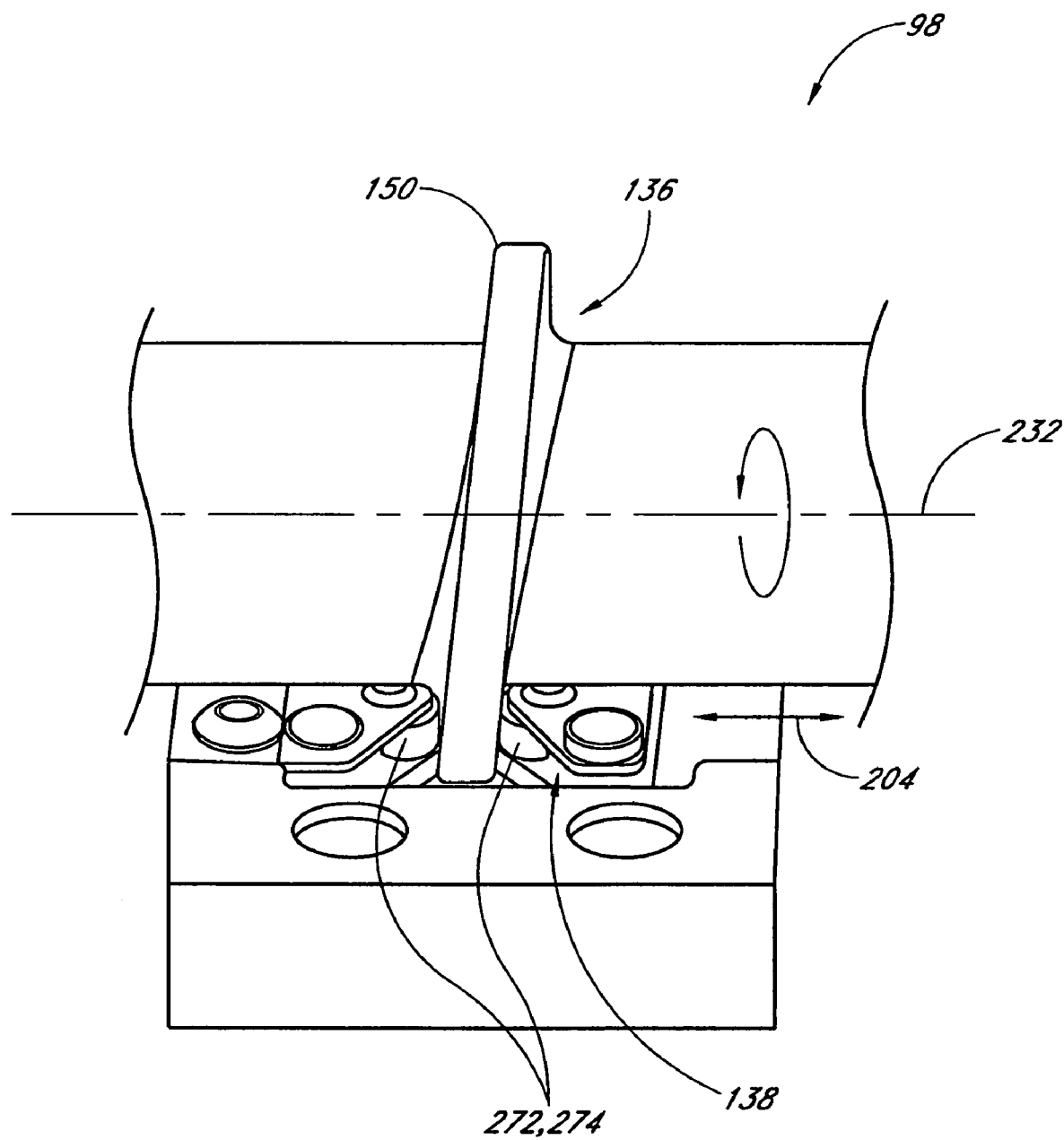
FIG. 36 is a perspective view of a surgical file transmission system in a test set-up illustrating features and advantages in accordance with an embodiment of the invention.

FIG. 36 shows the operation of the toroidal transmission and power converter system 98 in a laboratory system set-up. Rotation of the toroid drive 136 is about the central rotary axis 232 is converted into linear reciprocating motion of the slide 138 as generally indicated by arrows 204. The slide is connected to the cutting blade 106. Also shown are the slide bearings 272 and 274.

Irrigation Pump System

A pulsatile water pump system 290 is incorporated into the disposable cutting blade assembly 18 and is housed within the distal cover 72. The pulsating water pump 290 supplies sterile water into a patient and in one embodiment is disposed after one use to insure no "patient to patient" bio-contamination. The pulsatile pump system of embodiments of the invention has utility in a number of fields and applications where fluid transport is desired. In one embodiment, a pulse of water is provided after each linear motion stroke.

The integrated cutting blade water pump system 290 is advantageously driven by blade motion and insures that the blade 106 will automatically be cooled and lubricated whenever the cutting blade 106 is in reciprocating motion. In modified embodiments, an external pump system may be utilized, as needed or desired.

The water pump system 290 lubricates the reciprocating blade moving parts. The water pump system 290 cools the reciprocating blade moving parts. The water pump system 290 provides clear water for optical vision capability.

The pulsating water pump system 290 more effectively clears debris from the cutting blade surface for better cutting performance by providing pulsed jets of irrigation fluid. The pulsatile water pump system 290 is driven by reciprocating cutting blade motion pumps water whenever reciprocating blade 106 is driven. In modified embodiments, the system may have a manual override feature for pump operation.

Figure 37:
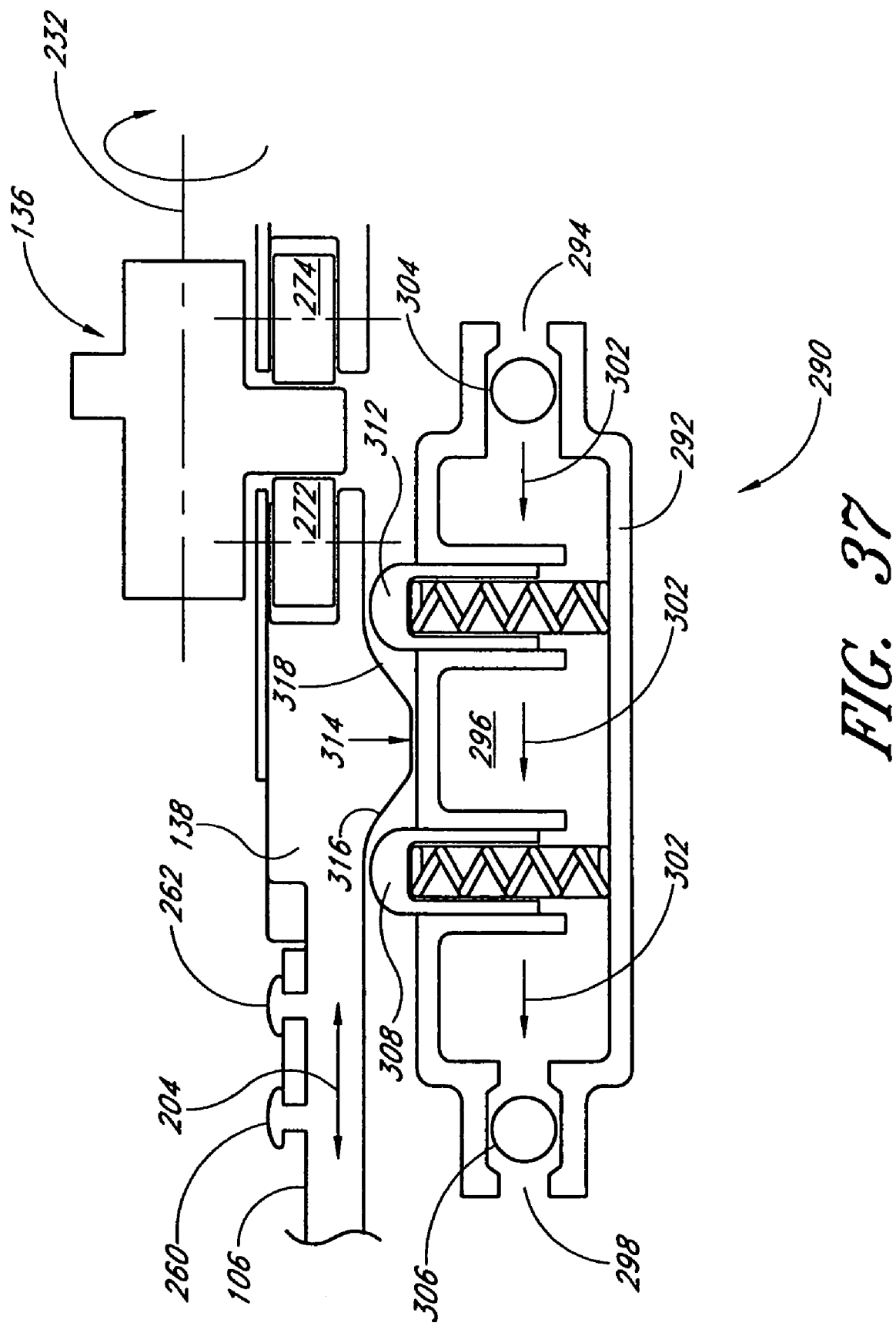
FIG. 37 is a side cross-sectional view of a surgical file pulsatile pump system illustrating features and advantages in accordance with an embodiment of the invention.

FIG. 37 shows the pulsatile dual direction water pump system 290 in accordance with an embodiment. The pump system 290 has a stationary pump body 292 that includes an inlet 294, a flow chamber 296 and an outlet 298. The inlet 294 is fed water from the umbilical cord 16 or through another feedline. The outlet 298 provides water to the bearing retainer 118 within the blade shield 108. The general direction of flow or the fluid path through the pump 290 is generally indicated by arrows 302.

The inlet 294 has a one-way or check valve 304 and the outlet 298 has a one-way or check valve 306 to prevent undesired back-flow. Any one of a number of suitable valves may be used such as, but not limited to, pressure relief valves, ball-spring devices and the like.

The pump system 290 includes a pair of spaced spring-biased or -loaded plungers 308, 312. In modified embodiments, other suitable resilient biasing or loading mechanisms may be efficaciously utilized, as needed or desired. The plungers 308, 312 can move back and forth into the pump chamber 296 to selectively occlude the pump chamber 296 and/or fluid path 302 to displace fluid and pulsatingly pump it to the desired site. Water is drawn in from the inlet 294 through the valve 304 as the plungers 308, 312 move back towards their undepressed position.

The slide 138 has a lower surface 314 with a pair of specially contoured and spaced cam surfaces 316, 318 that operatively couple the slide 138 with the pump plungers 308, 312. During a forward linear stroke motion the distal cam surface 316 contacts or abuts the distal plunger 308 and depresses it to pump water out of the outlet 298. During a backward linear stroke motion the proximal cam surface 318 contacts or abuts the proximal plunger 312 and depresses it to pump water out of the outlet 298.

Thus, the reciprocating linear stroke blade drive motion moves cam surfaces 316, 318 to alternatingly depress pump plungers and thereby pump water in a pulsing modality whenever the driven cutting blade 106 is moved through a linear stroke by the transmission system 98. Desirably, the transmission system 98 provides the motion, force or energy to substantially simultaneously and synchronously drive the reciprocating blade 106 and the pulsatile pump system 290.

In embodiments of the invention, the water pump 290 is integrated into the reciprocating blade mechanism. The pulsatile (pulsating with each linear stroke) water pump feature pulses a jet of water out through the cutting blade irrigation holes 212 to keep the cutting surface 114 clean for optimum cutting action. The pulse powered pump 290 is powered by the reciprocating action of the cutting blade 106. Advantageously, this direct drive eliminates a separate pump drive source. This desirably saves parts and cost by eliminating a separate water pump.

The disposable cutting tip assembly 18 is sterile. It incorporates the water pump 290 which is also sterile. The pump 290 is very close or proximate to the site where the pressurized water is provided. Advantageously, this reduces pressure losses that would be incurred if the pump is at a distance from the point of use. It desirably also solves the problem of sterilizing a far away water pump.

When the reciprocating blade device 106 is cutting it should be provided lubrication and cooling and the cutting surface 114 should desirably also remain clean and clear of tissue debris. The water pump 290 pumps water when the cutting surface 114 is activated as the same drive mechanism drives both. Thus, an operator need not remember to activate the pump 290 since its operation is automatically actuated with cutting blade 106. Desirably, this provides a safety feature to prevent damage, galling, a freeze up and also prevents cutting debris buildup and thermal glazing.

The pump system 290 can be formed from a number of suitably durable materials. In one embodiment, the pump system 290 is formed from a suitable plastic. The plastic material may comprise a suitable thermoplastic. In modified embodiments, other suitable plastics, metals, alloys, ceramics, combinations thereof, among others, may be efficaciously utilized, as needed or desired. Suitable surface coatings or finishes may be applied, as required or desired.

The pump system 290 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Figure 38:
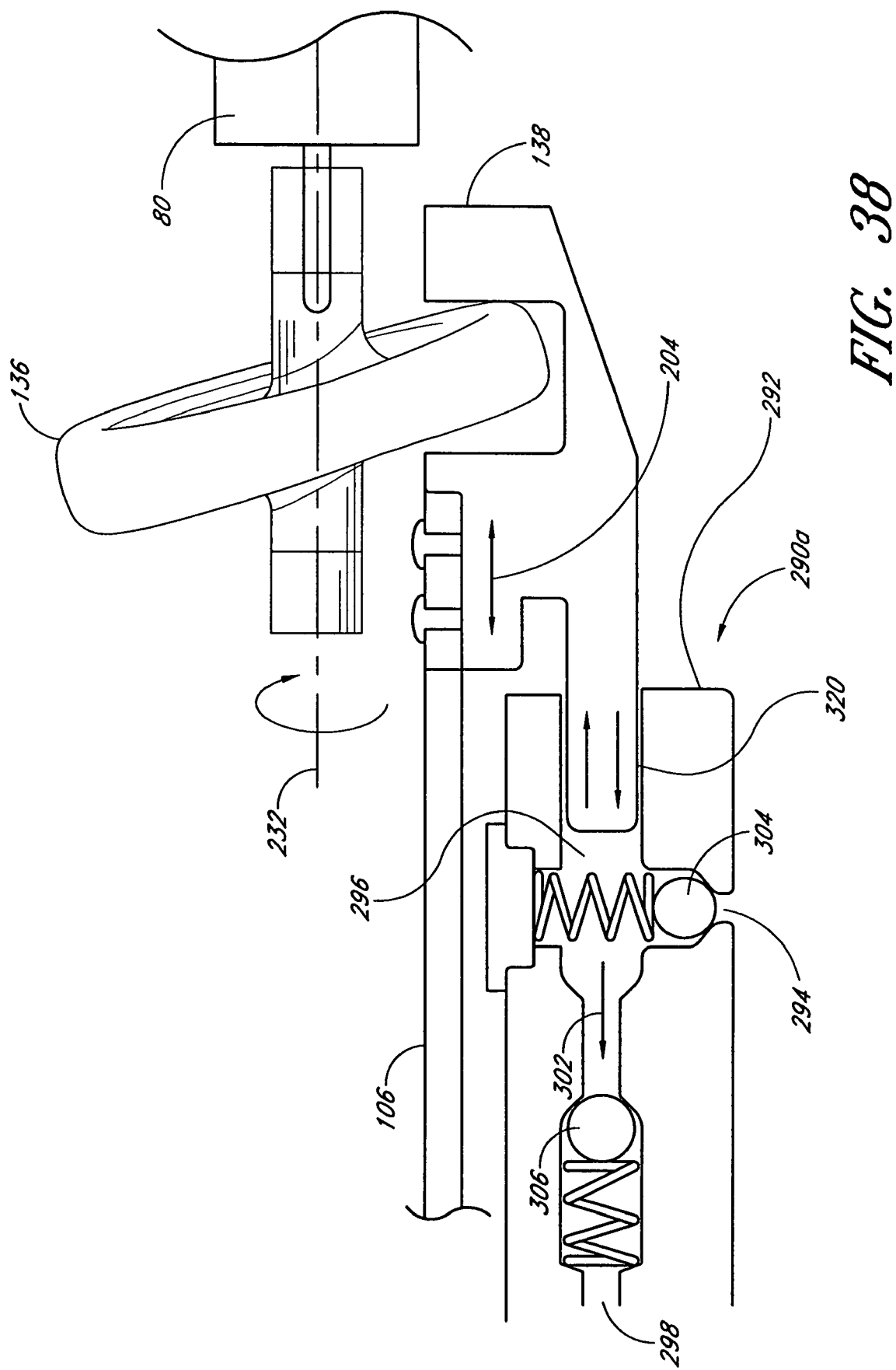
FIG. 38 is a side cross-sectional view of a surgical file pulsatile pump system illustrating features and advantages in accordance with another embodiment of the invention.

FIG. 38 shows a pulsatile single direction eater pump system 290a in accordance with another embodiment. The pump system 290a includes a plunger 320 connected to the slide 138. During forward linear stroke motion the plunger 320 occludes the pump cavity 296 to displace water form the outlet 298 to the desired site. During backward linear stroke motion the plunger 320 moves in an outward direction from the pump cavity 296 and water is drawn into the cavity 296 through the inlet 294.

Powered Handpiece

FIG. 39 shows the powered handpiece 20 including the cover or housing 74, the video camera 78, the motor assembly 80 and a distal interface member 322 for connecting to the interface member 102 and coupling 104 of the distal tip assembly 18. The interface member 322 has an opening 324 substantially aligned with the interface opening 158 which allow passage of the fiber optic probes 124, 126 for connection to the camera 78.

The proximal end 70 of the distal tip assembly 18 and the handpiece's distal end or portion 326 are configured and adapted to provide a quick and reliable connection or mating. This includes, but is not limited to, mechanical docking, electrical docking, optical docking and hydraulic docking.

The housing 74 and motor assembly 80 are steam sterilizable. The steam sterilization process involves the application of hot water and steam under pressure to kill germs followed by a partial drying process. The drying process is not always fully complete in that the instruments and parts processed, often come back partially wet. Usually there are small pockets of standing water trapped in small pools created by part shapes with water-titer pockets that end up facing upward due to there placement in the holding trays used to contain the parts and instruments to be steam sterilized.

With the routine use of steam sterilization it is desirable that any optical or electronic parts that are used with the steam sterilized instruments be designed to provide solutions to residual water and the problems it can create with electromechanical and opto-mechanical components. As discussed further below, the motor housing also houses the video camera module, which in inserted into the freshly sterilized motor housing. The hermetically sealed video camera module is designed to specifically address the specialized problems of residual water in a freshly steam sterilized surgical instrument in a sterile surgical setup environment.

The handpiece housing 74 has a motor housing 328 that receives the motor assembly 80 and the video housing 76 that receives the video camera 78. The video camera 78 is contained in the video housing 76 which provides a hermetically sealed housing. The video housing 76 desirably provides a water and gas sealed environmentally protective housing. The video camera 78 optically connects to the proximal end 70 of the distal tip assembly 18 and interfaces with the imaging fiberoptics.

The cable 16, the cover 68 and the components of the handpiece 20 are sterilizable except for the video camera 78 that is hard to sterilize. During assembly in a sterile field operating room, the non-sterile video camera 78 is inserted into a freshly sterilized handpiece housing 74. A hermetic (gas and liquid) seal is created by O-ring seals or the like. The O-rings are part of the interface at the handpiece's proximal end 330 and the distal end interface 322. Advantageously, this hardware and procedure combined together enables a non-sterile delicate electronic video camera to be made bacteriologically safe inside the sterile outer housing 74 of the sterilized handpiece 20.

The housing 74 also contains an LED illuminator 332 that connects to the illumination fiberoptics of the distal tip assembly 18. The LED (Light Emitting Diode) 332 is also mounted into the video housing 74 in a waterproof and gas-tight method to prevent intrusion and damage from water or water vapor accumulation. In one embodiment, a distal video imaging lens 334 is recessed to help prevent accidental damage.

The camera 78 can be provided in a mount 336 with an outer shape that is designed to prevent the incorrect insertion into the housing 74. The mount 336 has a male structure 338 that is received within a mating female receptor opening 340 within the housing 74. The male structure 338 provides the mount 336 with an asymmetrical cross sectional shape that is intended to create a visually obvious shape that can be readily inserted into its mating female receptor opening 340 in the correct or desired orientation.

In one embodiment, the camera 78 and the mount 336 comprise a video module 342 with the camera 78 housed in a waterproof and air-tight manner as discussed above in connection with the video housing 74. The hermetically sealed video module 342 can then be fitted within in the housing 74. The LED 332 can also be hermetically sealed within the module 342, for example, in an opening 344.

The camera 78 can comprise any one of a number of suitable video or digital devices. In one embodiment, the video camera 78 comprises a device as available from Toshiba. Advantageously, the integration of the video camera 78 within the handpiece 20 greatly enhances the capability, compactness, utility and versatility of the system.

As discussed above, the sterilizable powered handpiece 20 contains a non-sterile non-sterilizable video camera 78 contained inside the sterile hand piece assembly. Advantageously, the sterile powered handpiece 20 hermetically seals the non-sterile video camera 78 in a sterile housing 74 or 336, which permits safely using the sealed assembly in the sterile field and inside a patient's body.

The handpiece 20 can include one or more switches or buttons that allows the user to operably control the surgical file operation. Alternatively, or in addition, the controls can be provided on a separate platform and/or on the control system 14.

The precision motor 80 can comprise any one of a number of suitable rotary motion creating devices such as, but not limited to, gas turbines and electric motors and the like. In one embodiment, the motor 80 comprises a gas or air turbine rotary motor that is fed pressurized air or gas through the umbilical cord 16.

In one embodiment, the gas turbine motor 80 is provided air or gas at about 80 psi to run the device. In another embodiment, air or gas is provided at a pressure in the range from about 50 psi to about 100 psi, including all values and subranges therebetween. In modified embodiments, the pressure can be lower or higher, as needed or desired.

The motor assembly 80 at its distal end or portion 342 includes a rotatable power shaft 344 connected to a rotatable drive shaft 346. The motor distal end 342 docks with the proximal end 70 of the distal tip assembly 18. The power shaft 344 is generally received in the distal tip assembly holes 162, 160 and 149.

The motor 80 powers the reciprocating blade 106. The male drive shaft 346 is substantially irrotationally received within the matching female receptor hole of the drive shaft 140 to provide rotary motion to the transmission system 98 that converts it into linear reciprocating motion.

Figure 40A:
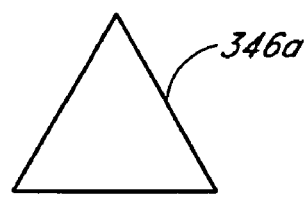
FIG. 40A is a sectional view along line 40-40 of FIG. 39 illustrating features and advantages in accordance with an embodiment of the invention.

FIG. 40A shows a simple triangular shaft 346*a* that can engage the triangular receptor hole 254*a*. When the distal tip assembly 18 and the powered handpiece 20 are connected both the female triangular receptor hole 254*a* and the motor's male triangular drive shaft 346*a* can rotate in tandem. The male and female features are free to mesh and align during the axial motion of connecting the disposable cutting tip assembly 18 onto the reusable sterilizable motor handpiece 20. This docking feature has a simplified rotary triangular shaped drive shaft, even though it drives a reciprocating (push-pull) motion-cutting blade.

A triangular shaped male mating drive 346a is desirable because it facilitates sterilization of the male triangular shaft 346a. The surfaces that are steam sterilized and reused are desirably simple surfaces that are easy to wash and clean. The surfaces should also enable reliable cleaning prior to sterilization. The triangular male shaft 346a has three flat surfaces that are both easy to see and clean.

Figure 40B:
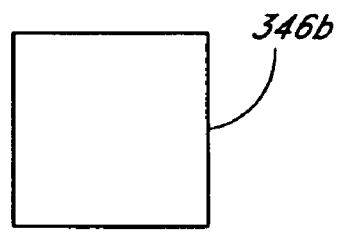
FIG. 40B is a sectional view along line 40-40 of FIG. 39 illustrating features and advantages in accordance with another embodiment of the invention.
Figure 40C:
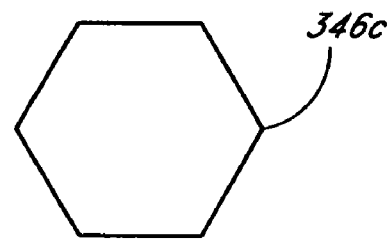
FIG. 40C is a sectional view along line 40-40 of FIG. 39 illustrating features and advantages in accordance with yet another embodiment of the invention.

In modified embodiments, other suitable male-female mating drive polygonal or non-polygonal interlocking configurations may be utilized with efficacy, as needed or desired. For example, FIG. 40B shows a generally square or rectangular male shaft 346b and FIG. 31C shows a generally hexagonal male shaft 346c.

Surgical Methods

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

The surgical instrument of embodiments of the invention enable the removal of obstructions in the tubular spaces (neuroforamen) between the vertebras of the neck and back. Desirably, this allows surgeons to navigate into the tiny (neuroforamen) canals between delicate nerve roots and remove small amounts of bony overgrowth (osteophytes) under direct vision.

Embodiments of the invention allow a surgeon to safely navigate down into the neuroforamen canal next to the nerve roots and see and remove obstructions that cause nerve compression with direct vision. The surgeons can perform a new surgical procedure, a "micro foramentomy" through as small as about a ½ inch to about 1 inch incision. This advantageously represents a truly minimally invasive surgical procedure which would serve to benefit patients and surgeons.

Figure 41:
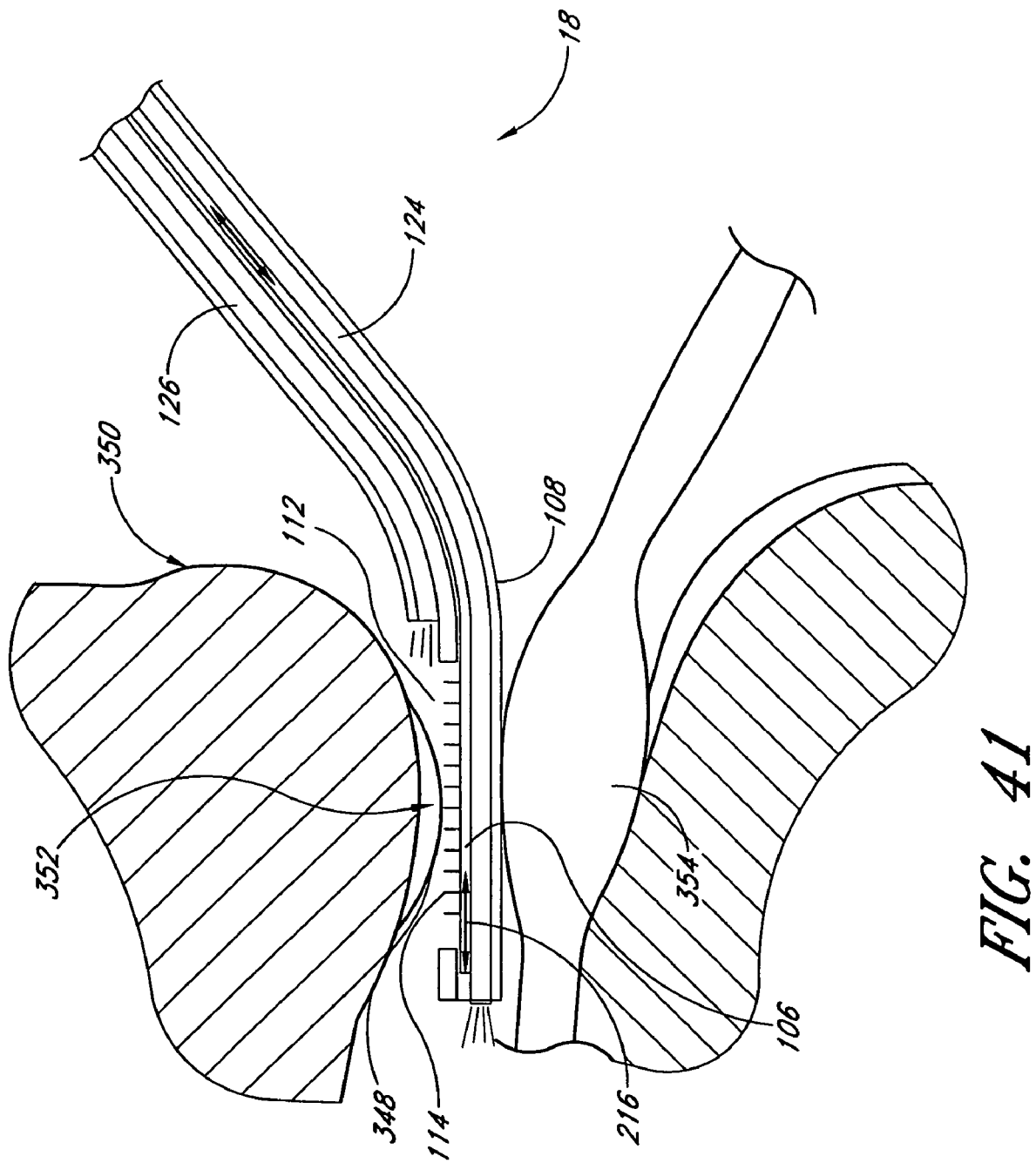
FIG. 41 is a schematic view of a bone and/or tissue removal procedure illustrating features and advantages in accordance with an embodiment of the invention.
Figure 42:
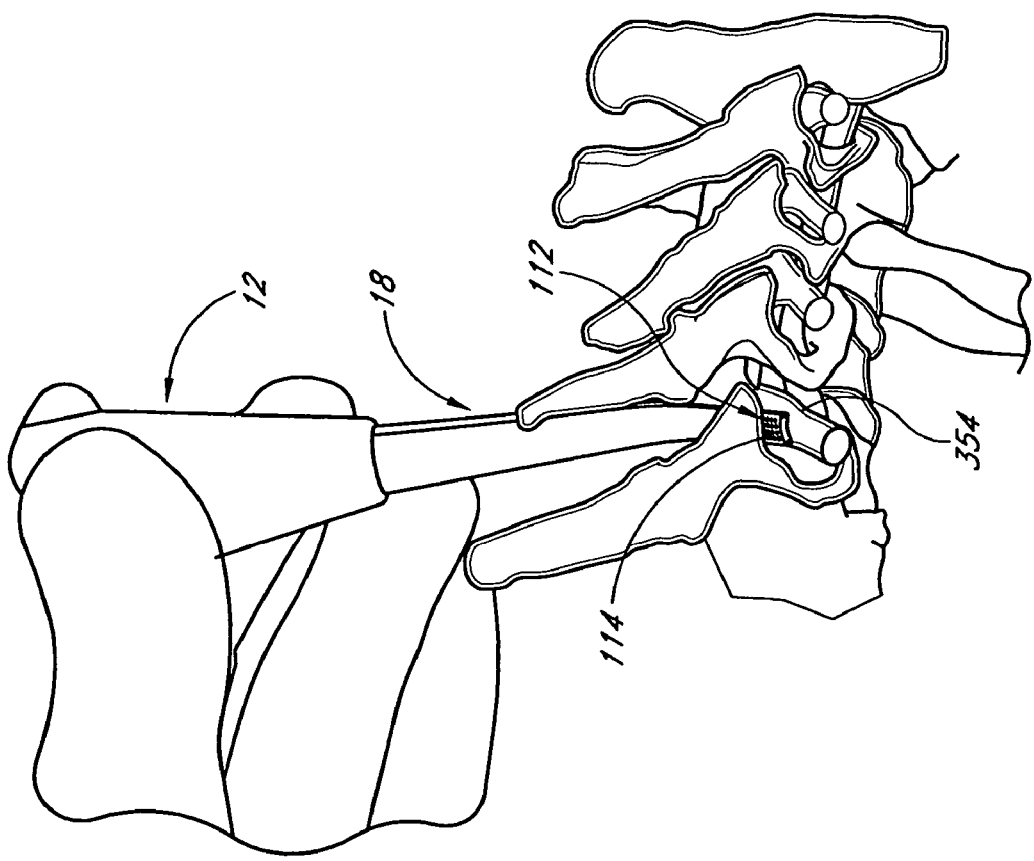
FIG. 42 is a simplified perspective view of a bone and/or tissue removal procedure on a plastic anatomical model of the human spine illustrating features and advantages in accordance with an embodiment of the invention.

FIGS. 41 and 42 show a bone and/or tissue cutting procedure using the surgical instrument 12. The shielded cutting blade 106 is inserted into a neuroforamen 348 between a vertebra 350, unwanted bone and/or tissue 352 and a nerve root 354. The shield 108 protects the nerve root 354 while the blade cutting surface 114 removes the bone and/or tissue 354 to relieve nerve compression by enlarging the neuroforamen 348.

Advantageously, embodiments of the invention provide a high level of cutting blade control and enable surgeons to reach into previously inaccessible areas to remove unwanted bone with precision, sensitivity and complete safety and confidence. The shielded cross sectional profile of embodiments of the cutting tip permit protection of delicate nerves during the neuroforamen enlargement process to relieve nerve compression.

As seen in FIG. 42, the shielded portion 108 of the file is facing the delicate nerve 354 and the opposite cutting surface 114 is facing the bone that is to be removed 352 to enlarge the bony and cartilage structural opening. Advantageously, the surgical instrument of embodiments of the invention has a cutting surface 114 that can travel around corners. A direct vision system allows surgeons to safely navigate into blind cavities of the patient's body and also assists visualization of the actual tissue cutting action and its results.

In the embodiments of a sterile disposable (one time use) cutting tip assembly 18, the cutting tip assembly 18 is used typically, in one embodiment, for about three minutes in a two-hour surgical procedure. The tip of the distal assembly 18 can provide the surgeon with a picture of the area, and enable the doctor to see the cavity and its anatomical features.

The view is magnified so the user sees a full screen image of the small tunnel, which is typically, in one embodiment, about one quarter of an inch in diameter. The enlarged view of the area allows surgeons to inspect and find the exact location and size of nerve irritation and compression, and determine where and how much bone and cartilage to remove to eliminate the nerve compression and relieve the pain.

Orthopaedic File Embodiments, Components, and Procedures

Figure 43:
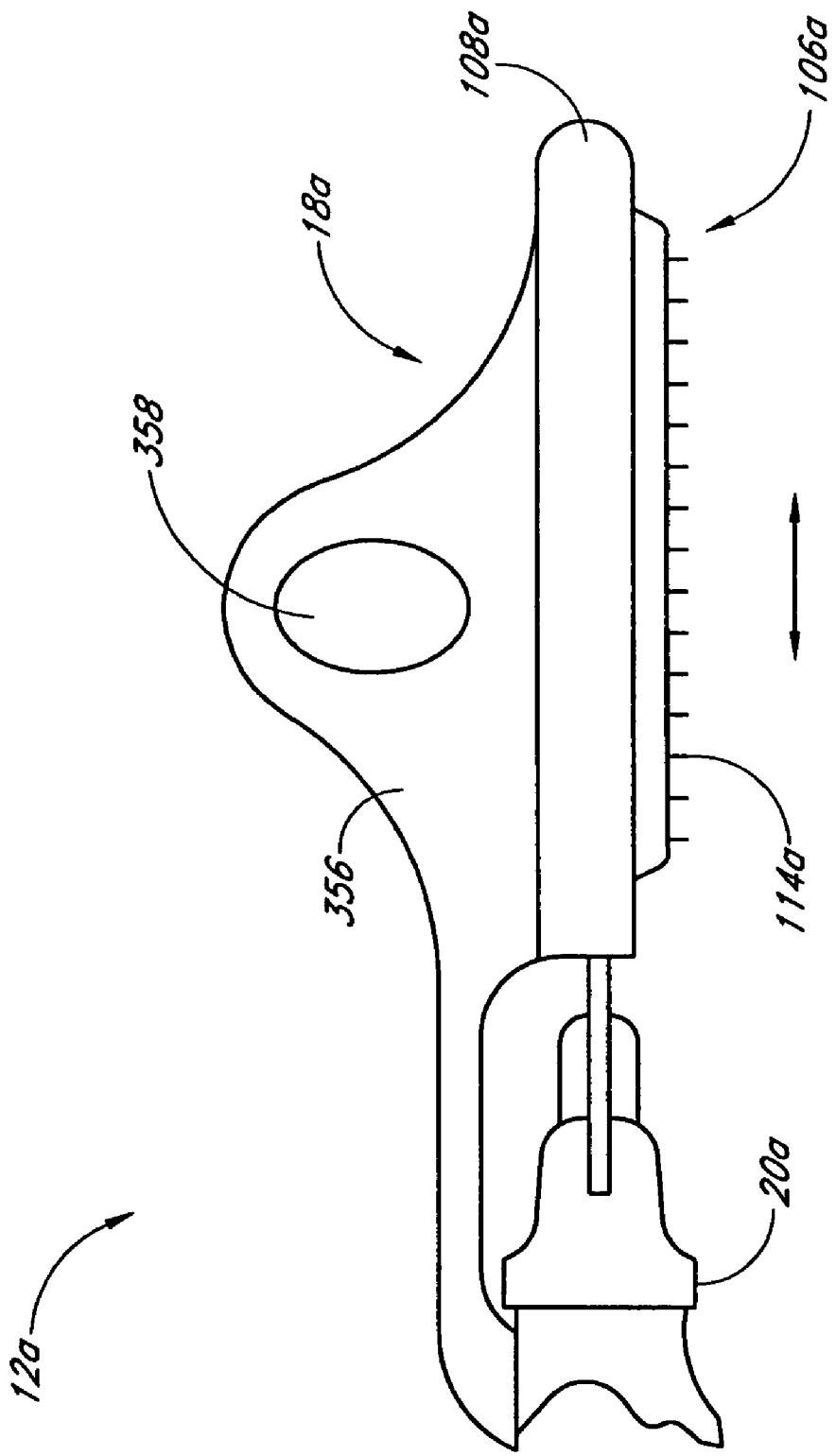
FIG. 43 simplified side view of an orthopaedic surgical file instrument illustrating features and advantages in accordance with an embodiment of the invention.

FIGS. 43-45 show different views of an orthopaedic shielded reciprocating surgical file instrument or apparatus 12a. The surgical file instrument 12a generally comprises a distal tip assembly 18a docked to and powered by a handpiece 20a.

The distal blade assembly 18a generally comprises a reciprocating blade 106a with a cutting surface 114a and a shield or guard 108a. The cutting surface 114 has an abrasive material or abrasives 206a.

The distal blade assembly 18a further includes a handle 356 above the blade 106a. The handle 356 is used by a surgeon to press against or down on the bone and/or tissue material to be removed. The handle 356 is shaped to facilitate manipulation and has a suitable ergonomic shape or the like. The handle 356 further includes an opening 358 to facilitate operation.

Figure 46:
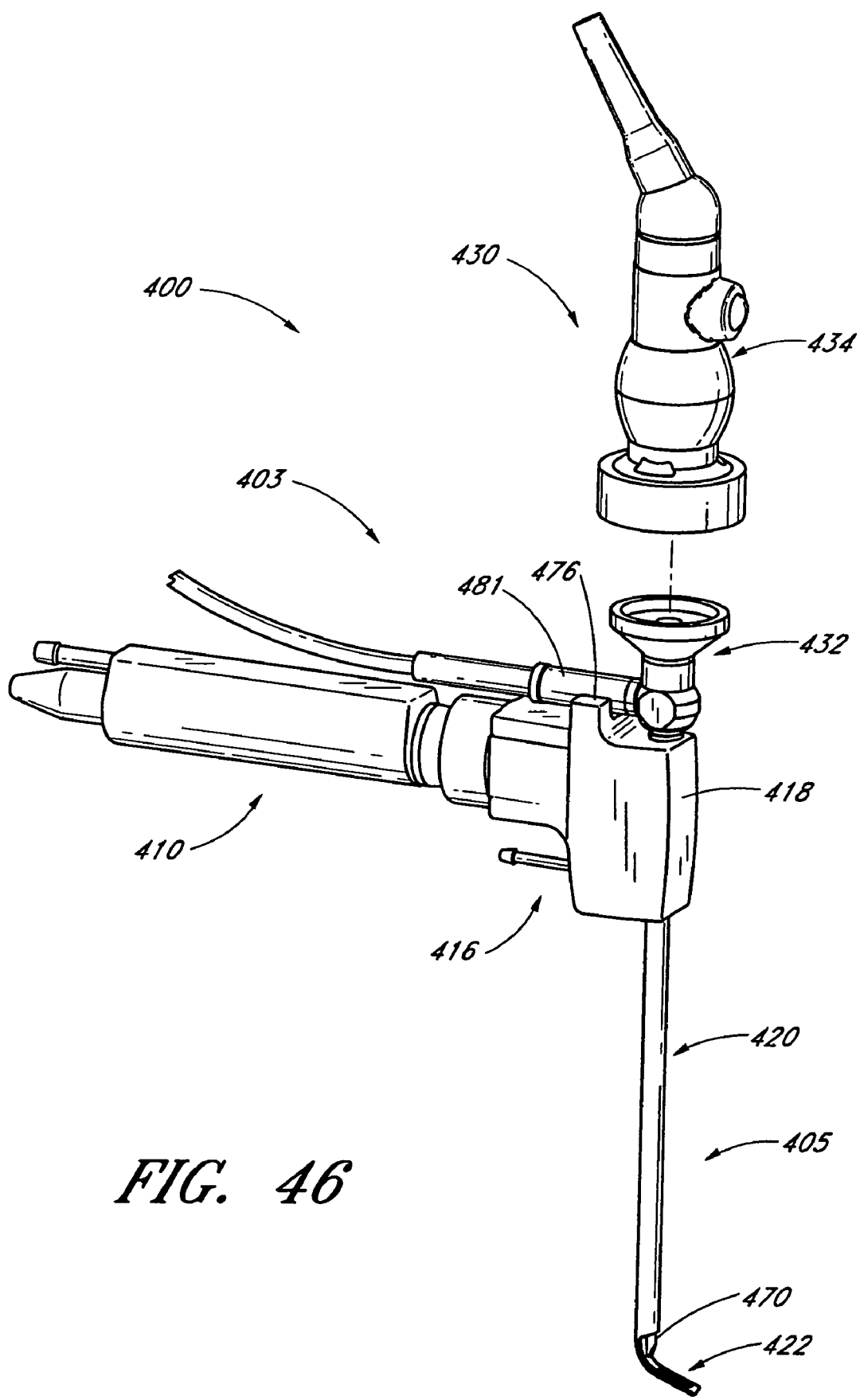
FIG. 46 is a perspective view of a surgical instrument in accordance with another embodiment.
Figure 47:
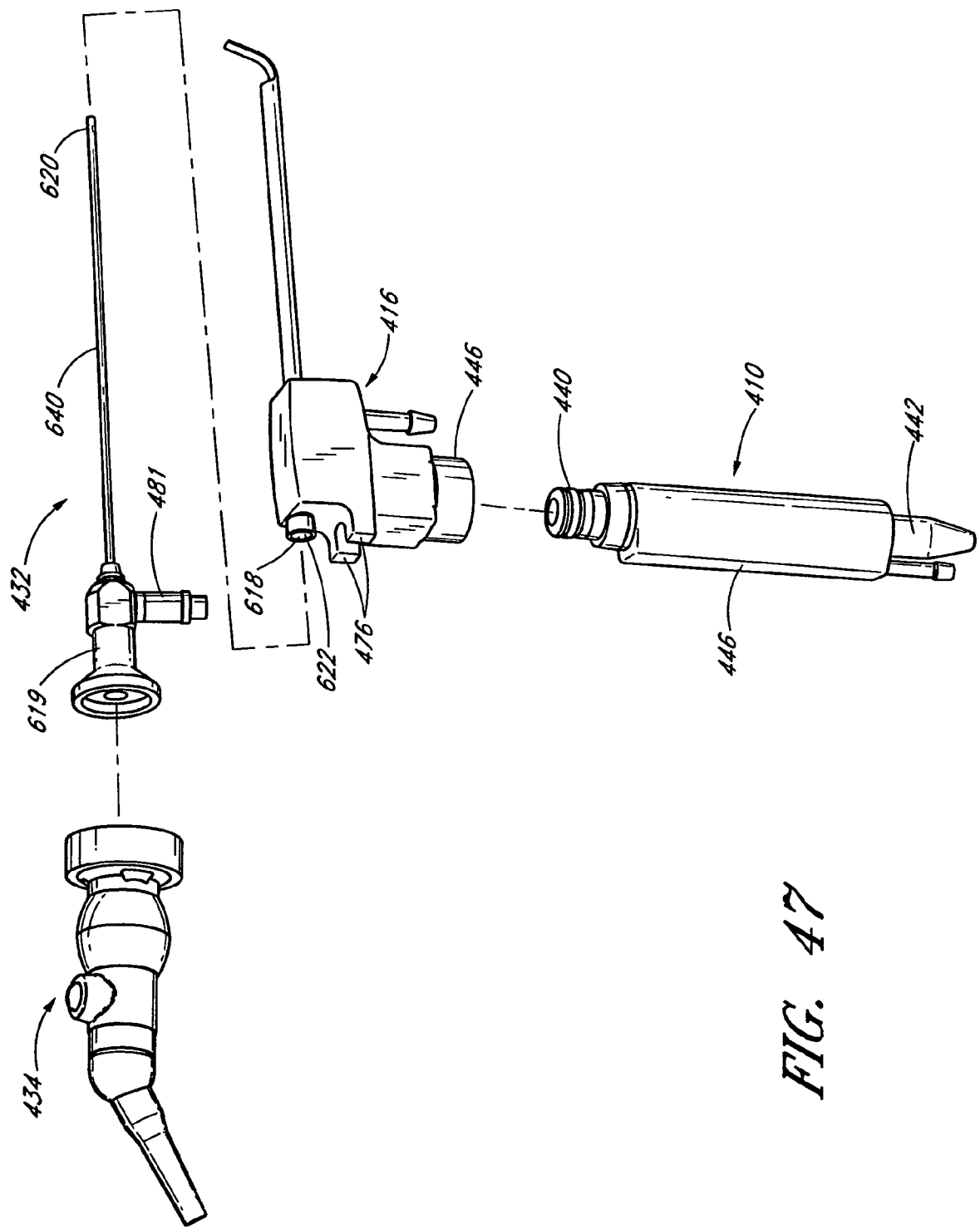
FIG. 47 is an exploded view of the surgical instrument of FIG. 46.
Figure 48:
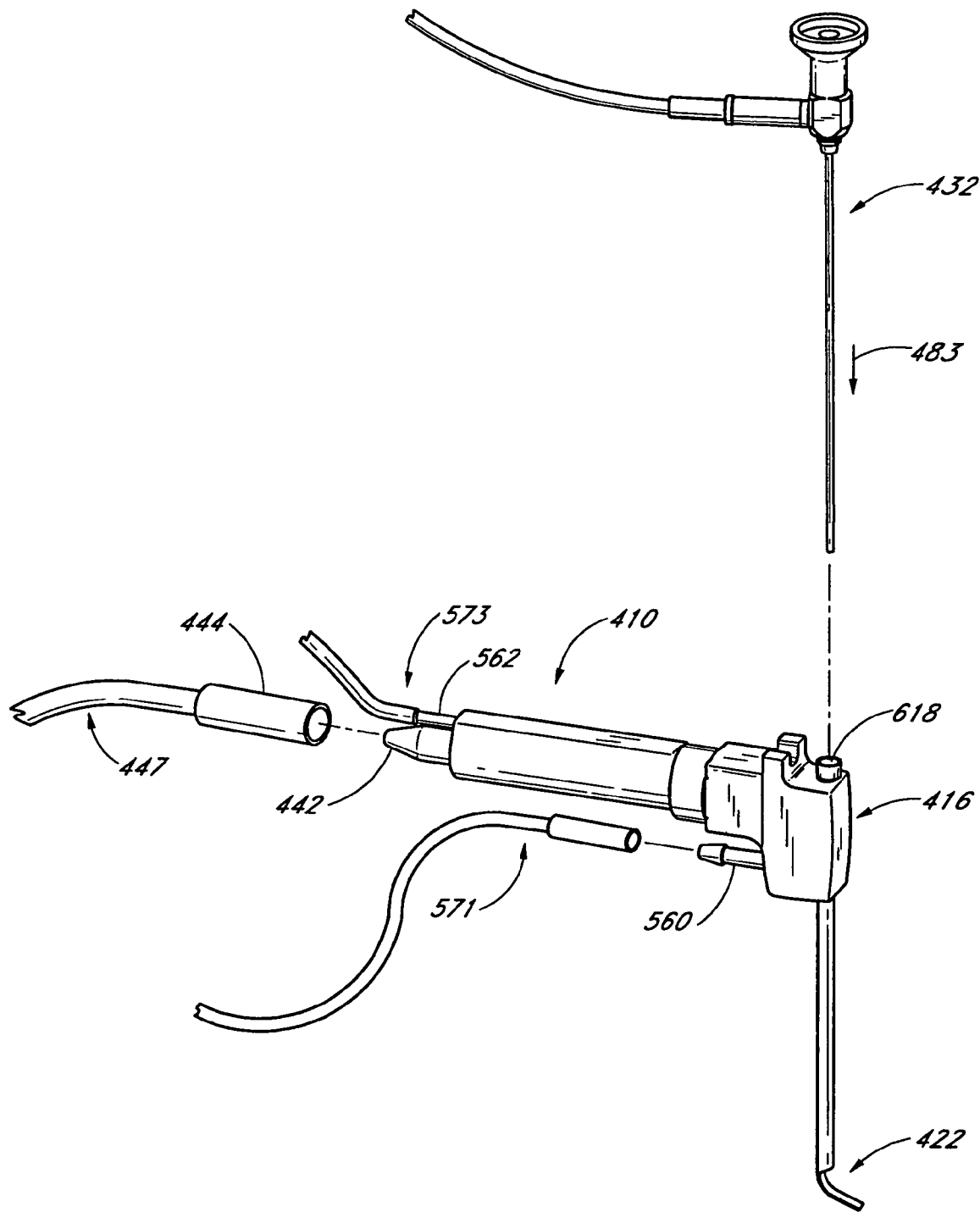
FIG. 48 is a perspective view of the surgical instrument of FIG. 46 being assembled.

FIGS. 46-48 illustrate a surgical instrument 400 in accordance with another embodiment. The illustrated surgical instrument 400 is a surgical file device that includes a handle assembly 403 and a distal tip assembly 405. The handle assembly 403 has a powered handpiece 410 that is connected to a modular body assembly 416. The modular body assembly 416 comprises a housing 418 that is connected to the distal tip assembly 405. The distal tip assembly 405 includes a distal tip portion 420 that has a somewhat L-shaped distal tip 422. The surgical file device 400 also includes a visualization system 430 that provides viewing of a target surgical area. When the distal tip 422 is used to perform a surgical procedure, the visualization system 430 provides viewing, preferably direct viewing, of the surgical site. The illustrated visualization system 430 includes an endoscope 432 that can be connected to an imaging capturing device 434. The endoscope 432 can extend through the modular body assembly 416 such that a viewing element 470 is positioned to provide viewing of the distal tip 422.

FIG. 47 illustrates the surgical file device 400 when unassembled. The powered handpiece 410 is a powered device that can be used to operate the body assembly 416. The illustrated powered handpiece 410 is in the form of a standard motorized rotary handpiece that can be pneumatically powered, electricity powered, and/or mechanically powered. Other types of handpieces can also be used to drive the body assembly 416.

The handpiece 410 has a distal handpiece connector 440 and a proximal handpiece connector 442. A body 446 of the handpiece 410 extends between the connectors 440, 442. The distal handpiece connector 440 is configured to mate with a handpiece docketing assembly 446 of the body assembly 416. Preferably, the distal handpiece connector 440 is in the form of a quick connector that can be easily coupled to and removed from the handpiece docketing assembly 446. Various types of connectors can be utilized depending on the configuration of the body assembly 416 and the handpiece 410.

To switch handpieces, the illustrated handpiece 410 can be decoupled from the handpiece docking assembly 446. Another handpiece can then be coupled to the handpiece docketing assembly 446. The quick connection thus allows a user to quickly change between any number of handpieces. A single handpiece can be used with more than one body assembly.

With reference again to FIGS. 46-48, the proximal handpiece connector 442 is configured to be connected to an umbilical cord 447 that can deliver power to the handpiece 410. Non-limiting exemplary umbilical cords can be pressurized air lines, electrical lines, and other types of lines that are used for effectively powering surgical devices. The illustrated umbilical cord 447 of FIG. 48 has an umbilical cord connector 444 for coupling to the proximal handpiece connector 442. To couple the line 447 to the handpiece 410, the connector 444 can be inserted over the proximal handpiece connector 442.

Figure 49:
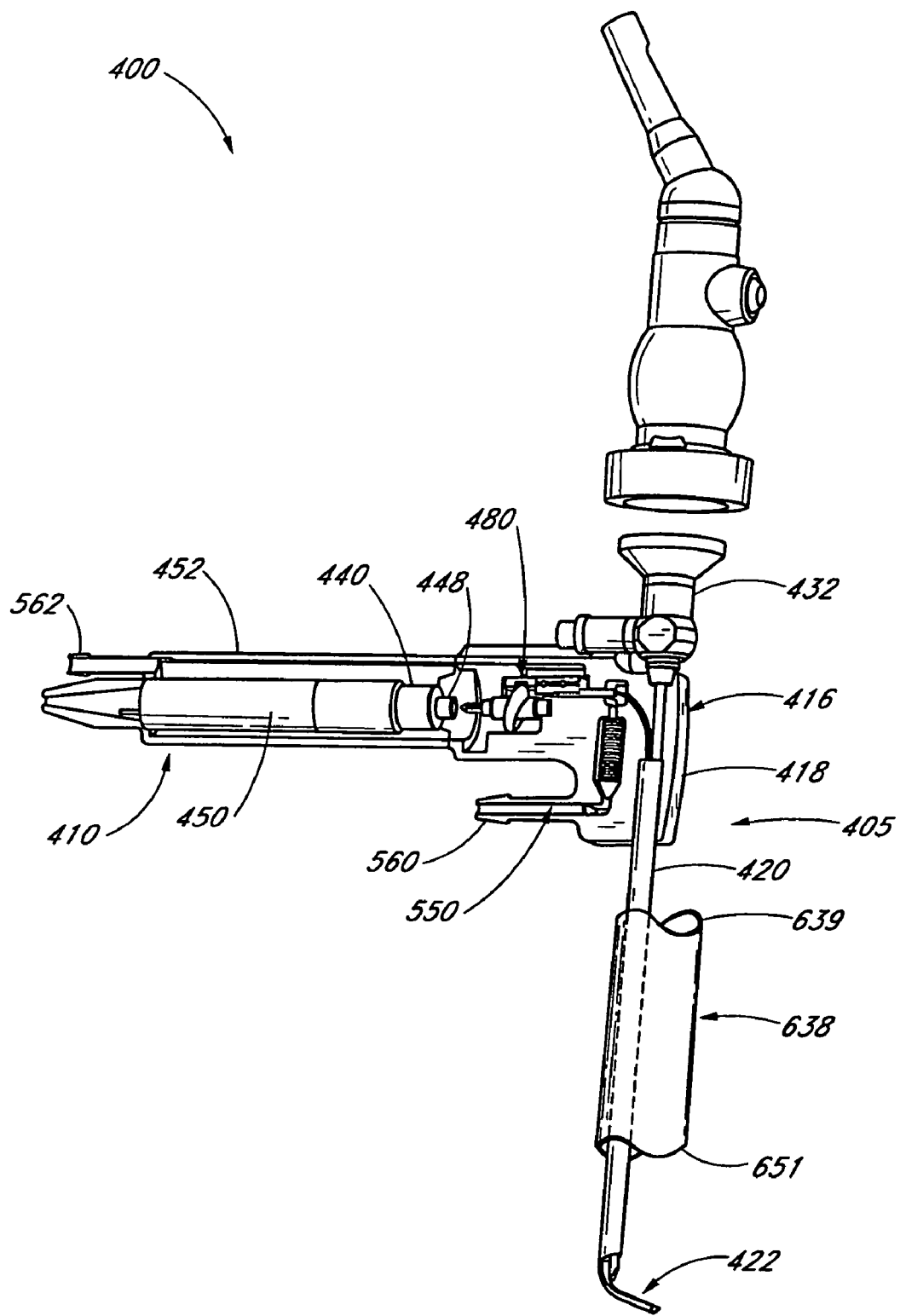
FIG. 49 is a partial cross-sectional view of the surgical instrument of FIG. 46. A portion of the surgical instrument is positioned through an access device.

As shown in FIG. 49, the distal handpiece connector 440 includes a drive shaft 448 that can be coupled to a proximal end of a drive system 480. The illustrated drive shaft 448 can be moved distally until it is coupled to the drive system 480. The drive shaft 448 can be rotated by a drive motor 450. The motor 450 is surrounded and protected by a housing 452. The housing 452 provides a comfortable gripping surface for the user. The housing 452 can advantageously provide a thermal barrier to limit heating of an outer gripping surface of the handpiece 410. As such, the housing 452 can form a surface that is maintained at a suitable temperature for gripping, even when the motor 450 reaches elevated temperatures. In some cases, the handpiece 410 can drive a disposable distal tip assembly 405. After the distal tip assembly 405 is spent, the distal tip assembly 405 can be discarded and replaced with another distal tip assembly. If desired, the handpiece can be a standard handpiece. These types of powered handpieces are often found in hospital surgical rooms. Accordingly, the modular body 416 can be used with standard power devices without the need of additional tools or power sources.

With reference again to FIG. 46, the modular body assembly 416 is configured to receive the endoscope 432. The endoscope 432 extends through the housing 418 and the distal tip portion 420 so that the viewing element 470 is positioned near the distal tip 422. When the endoscope 432 is in the illustrated position, the body assembly 416 can securely hold the endoscope 432. If desired, the endoscope 432 can be retracted and pulled out of the body assembly 416 to perform maintenance on the endoscope, replace the endoscope, or for any other reason.

To position the endoscope 432, the housing 418 has a pair of guides 476 (see FIG. 47) configured to receive an illumination light port 481 of the endoscope 432. The illumination light port 481 of the endoscope 432 can extend outwardly between the guides 476 such that the guides 476 inhibit rotation of the endoscope 432 with respect to the housing 418. The guides 476 can advantageously maintain proper alignment of the endoscope 432 during a surgical procedure, even if the surgical file device 400 is subjected to external forces or sudden acceleration, for example. The illustrated guides 476 are protrusions that define a U-shaped channel that is sized to receive the light port 481. Other types of guides can also be used to position the endoscope 432. One or more clamps, pins, ties, brackets, or other suitable structures can be used to position the endoscope 432. Thus, various types of arrangements can be used to lock an endoscope to body assembly 416.

With respect to FIG. 49, the body assembly 416 includes the drive system 480 for drivingly connecting the powered handpiece 410 to a cutting blade at the distal tip 422. The drive assembly 480 is a mechanical transmission that converts rotary motion of the powered handpiece 410 to reciprocating, linear motion for driving the cutting blade.

Figure 50:
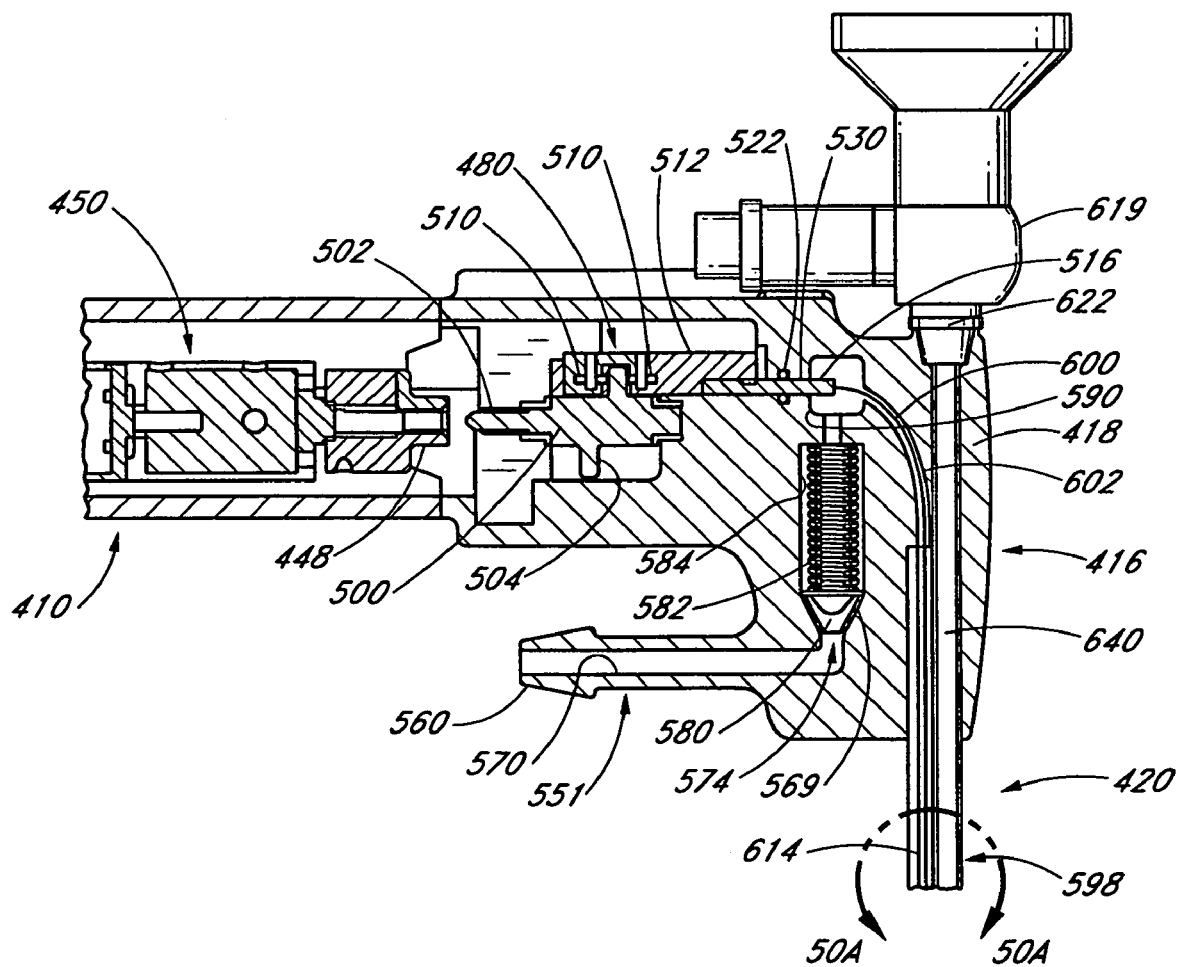
FIG. 50 is a cross-sectional side view of a body assembly of the surgical instrument of FIG. 49.

FIG. 50 illustrates the drive system 480 disposed in the housing 418. The drive system 480 comprises a toroidal drive 500 that is driven by the motor 450 of the handpiece 410. A drive shaft 502 of the toroidal drive 500 can be permanently or temporarily coupled to the drive shaft 448 of the handpiece 410. A rim cam 504 of the toroidal drive 500 is interposed between and contacts follower bearings 510 of a slide plate 512. When the toroidal drive 500 rotates about its longitudinal axis, the cam 504 pushes and pulls on the bearings 510 because the slide plate 512 is restrained so that it slides linearly along the housing 418.

The drive system 480 also includes a drive member 516 extending through a drive member passageway 530 formed in the housing 418. The drive member 516 connects the slide plate 512 to the drive ribbon 600. Alternatively, the drive member 516 can be directly connected to the blade.

A sealing member 522 can surround the drive member 516 to inhibit fluid flow past the drive member 516 through the drive member passageway 530. The drive member 516 and sealing member 522 cooperate to isolate fluid in the body assembly 416 in order to avoid damage to components of the surgical file device 400.

The drive member 516 can have any suitable configuration to engage the sealing member 522. Non-limiting exemplary drive members 516 can have a polygonal, elliptical, circular, or any other suitable axial cross-section depending on the intended application. The drive member 516 can be a tube, plate, rod, and the like. The drive member 516 is preferably securely coupled to the slide plate 512. As the toroidal drive 500 rotates, the slide plate 512 and the drive member 516 are actuated together in a linear direction.

The sealing member 522 can be disposed in a recess formed in the drive member passageway 530. The sealing member 522 is somewhat compressed against the outer surface of the drive member 516 and the wall of the passageway 530. In such a configuration, the sealing member 522 can effectively inhibit fluid flow along the drive member passageway 530 past the sealing member 522. Other sealing arrangements can also be employed to seal portions of the body assembly 416.

With respect again to FIG. 49, the body assembly 416 can have a fluid system 550 for providing fluid irrigation and/or fluid removal at the surgical site. When the distal tip 422 is positioned at a surgical site, the fluid system 550 can deliver irrigation fluid (preferably sterile irrigation fluid) to the surgical site to enhance tissue removal. Alternatively, or in addition, the fluid system 550 can remove substances, such as irrigation fluid, tissue (including detached tissue, particulate, debris, contaminants) and the like, from the surgical site.

The body assembly 416 has an inlet connector 560 and an outlet connector 562 that are configured to connect to an input fluid line 571 and an output fluid line 573, respectively. See FIG. 48. Fluid delivered into the inlet connector 560 can be circulated through the body assembly 416 and is eventually expelled out of the distal tip 422 at the surgical site.

In some embodiments, material at the surgical site (e.g., tissue and the irrigation fluid) can be sucked into the distal tip 422 and is eventually drawn through the surgical file device 400 until it reaches the outlet connector 562. The fluid can then be delivered out of the outlet connector 562 and into the outlet line 573. Thus, fluid can flow continuously into and out of the surgical file device 400 to irrigate a surgical site and/or remove undesirable substances at the surgical site.

The irrigation fluid can be delivered by any suitable means to the inlet connector 560. To aid fluid flow through the fluid system 550, one or more pressurization devices can be employed to pressurize the irrigation fluid. For example, pumps, such as a peristaltic pump, can be connected to the fluid line. The pump can pressurize the irrigation fluid to enhance fluid flow through the fluid system 550.

The inlet connector 560 and the outlet connector 562 can have various configurations as are known in the art. Preferably, the connectors 560, 562 are quick connectors configured to couple to standard fluid lines. In some embodiments, the connectors 560, 562 have a different configuration from each other so that a clinician can visually distinguish between the connectors. This can help the clinician determine which line should be attached to a particular connector. The inlet connector 560 of FIG. 48 can be specifically designed to receive the inlet fluid line 571 but not the outlet fluid line 573. Similarly, the outlet connector 562 can be specifically designed to receive the outlet fluid line 573 but not the inlet fluid line 571. Accordingly, the connectors 560, 562 may reduce the likelihood that an improper line is connected to the corresponding connector. Alternatively, the connectors 560, 562 can have similar or identical configurations, if desired.

With reference to FIG. 50, an irrigation system 551 includes an inlet connector passageway 570 of that extends to a valve system 574. The valve system 574 of the irrigation system 551 regulates fluid flow through the body assembly 416. The valve system 574 is in the form of a check valve that permits one way flow therethrough. The illustrated valve system 574 comprises a movable valve member 580 and a biasing member 582. A valve member chamber 584 houses the members 580, 582. The movable valve member 580 bears against a narrowing portion 569 of the valve member chamber 584. The biasing member 582 is interposed between the valve member 580 and an upper end of the valve member chamber 584. Fluid can flow through the valve system 574 by lifting the valve member 580 away from the surface of the narrowing portion 569, but pressure in the opposite direction will force the valve member 580 against the narrowing portion 569 inhibit fluid flow in the reverse direction.

The illustrated biasing member 582 permits fluid flow through the valve system 574 when a relatively low pressure differential exists. For example, when the upstream pressure is equal to or greater than 3 psi greater than the downstream pressure, the valve system 574 can open. The pressure differential moves the valve member 580 thereby compressing the biasing member 582 to open the valve system 574. Once the pressure differential drops to less than 3 psi, the biasing member 582 moves the valve member 580 to the closed position. The stiffness of the biasing member 582 can be chosen based on the desired actuation pressure for opening and closing of the valve system 574. Other types of check valves, gate valves, flow regulators, and the like can be used to control fluid flow through the device 400.

The fluid system 550 can also have a pumping chamber 590 that is in fluid communication with the valve system 574 and the distal tip 422 illustrated in FIG. 46. The pumping chamber 590 is configured to contain fluid that can be pressurized to a sufficiently high pressure such that the fluid flows through a delivery lumen 614 that extends along the length of the distal tip portion 420. The pressurized fluid ultimately can be expelled out of the distal tip 422.

To pressurize fluid in the pumping chamber 590, the drive member 516 can be actuated between a first position and a second position. In some embodiments, including the illustrated embodiment of FIG. 50, the drive member 516 reciprocates in a forward and backward motion.

The pressure in the pumping chamber 590 is increased or decreased as the drive member 516 is moved distally or proximally, respectively. When the drive member 516 is displaced proximally, the pressure in the pumping chamber 590 can be sufficiently reduced so that fluid flows through the valve system 574 and into the pumping chamber 590. When the drive member 516 moves distally through the pumping chamber 590, the pressure within the chamber 590 is increased. The increased pressure causes the valve system 574 to close. Additionally, the pressurized fluid flows from the pump chamber 590 through a ribbon passage 602 and the delivery lumen 614.

Figure 50A:
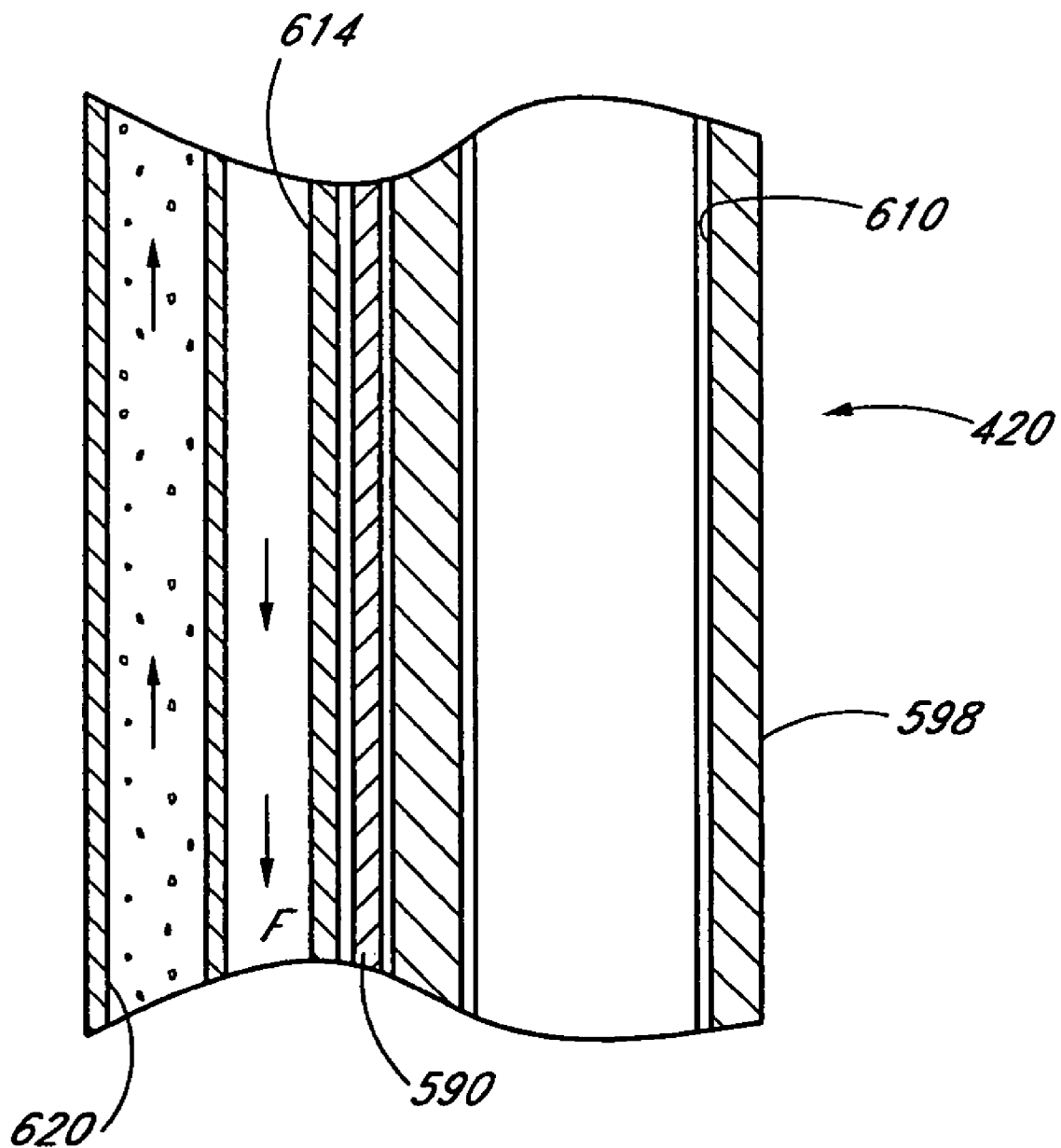
FIG. 50A is an enlarged cross-sectional side view of the surgical instrument of FIG. 49 taken along 50A-50A.

With reference to FIGS. 50 and 50A, the delivery lumen 614 of the distal tip portion 420 extends from the ribbon passage 602 to the distal tip 422. Fluid flowing distally through the delivery lumen 614 can proceed along the distal tip portion 420 until it is ultimately expelled out of the distal tip 422. One of ordinary skill in the art can select the size of the delivery lumen 614 to achieve a desired fluid flow through the distal tip portion 420.

Figure 51:
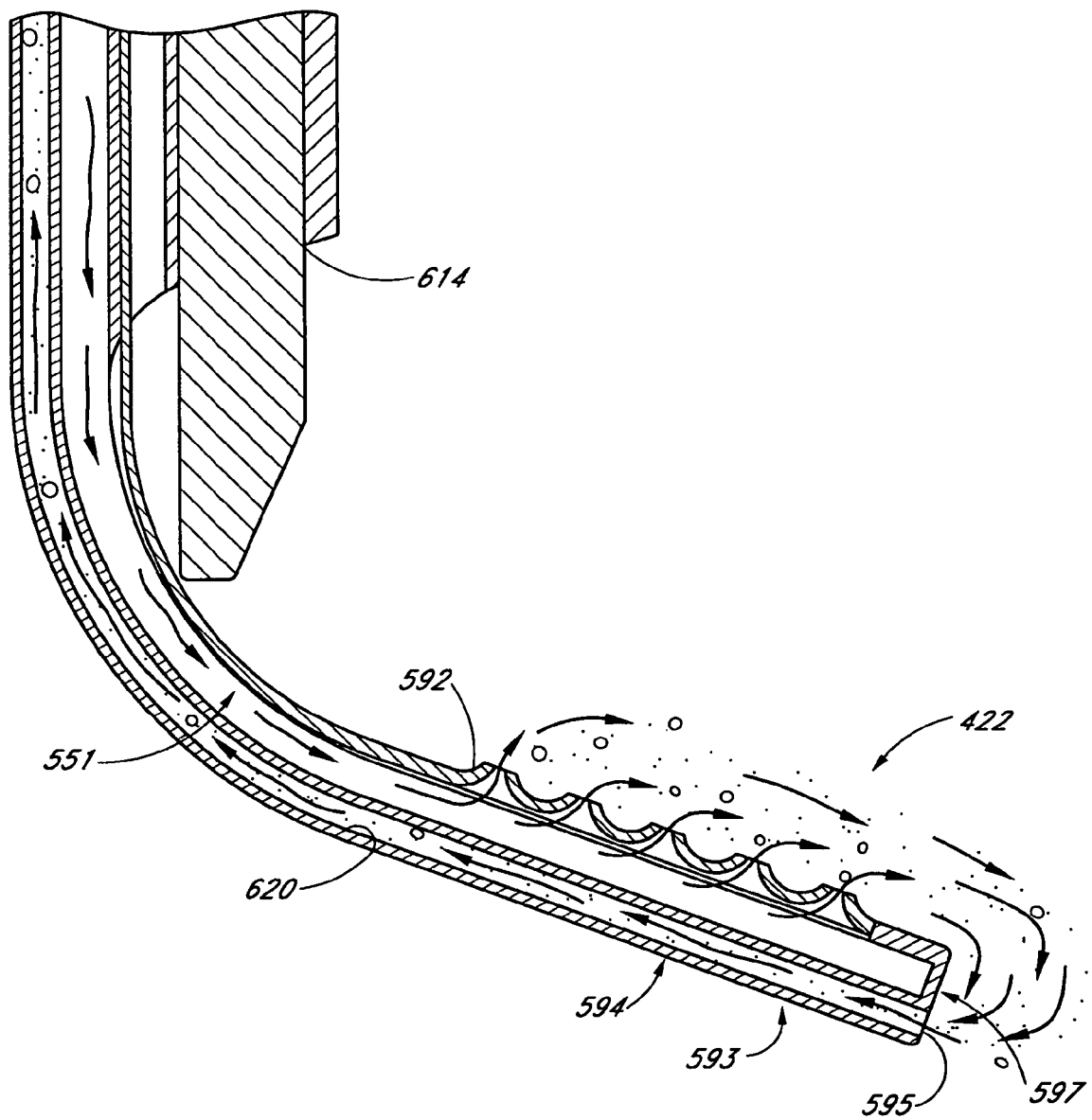
FIG. 51 is a cross-sectional side view of a distal end of the surgical instrument of FIG. 49 performing a procedure.

As shown in FIG. 51, the distal tip 422 outputs irrigation fluid, F, to irrigate a surgical site. In the illustrated embodiment, the irrigation fluid F flows out of a blade 592 mounted to a lower blade structure 593. To remove the freshly cut tissue and expelled irrigation fluid, the fluid system 550 can also comprise an optional removal system 594. The removal system 594 can draw in the mixture of freshly cut tissue and irrigation fluid to improve visibility of the surgical site.

The removal system 594 includes an inlet port 595 positioned so that material at the surgical site can be drawn into the distal tip 422. The position and configuration of the inlet port 595 can be chosen based on the flow dynamics of the irrigation fluid. The illustrated inlet port 595 is position at the distal-most portion of the lower blade structure 593 of the distal tip 422. A distal face 597 of the lower blade structure 593 can define the inlet portion 595. Irrigation fluid can flow distally along the blade 592. Once the fluid reaches the end of the distal tip 422, the fluid flows around the distal tip 422 towards the inlet port 595. As shown in FIG. 51, the mixture of solids (e.g., particulate, contaminates, tissue, etc.) and irrigation fluid can be pulled into the inlet port 595 and then flows proximally along a return lumen 620 towards the housing 418.

The illustrated inlet port 595 is a single aperture. However, the inlet port 595 can include a plurality of apertures for receiving material at the surgical site. The positions and the sizes of the apertures can be selected to achieve the desired flow dynamics for effective irrigation of the surgical site. In some embodiments, the distal tip 422 can have a plurality of inlet ports positioned along the lateral sides and/or the front surface of the distal tip 422.

With reference to FIGS. 50 and 51, the return lumen 620 provides fluid communication between the inlet port 595 and the outlet connector 562 (see FIG. 49) of the removal system 594. In some embodiments, the return lumen 620 extends through the distal tip portion 420, the housing 418, and the handpiece 410. Suction or aspiration can be provided by the fluid line 573 attached to the outlet connector 562. Thus, the removal system 594 and the outlet line 573 can cooperate to remove material from the surgical site that may undesirably obstruct a physician's viewing. As such, the visual sight field can remain substantially free of debris for a clear line of sight for enhanced viewing of the cutting blade and the tissue removal process. The removal system 594 can also remove contaminates, debris, detached tissue, and the like. Alternatively, or in addition, the surgical file device 400 can have one or more pumps for drawing fluid through the return lumen 620.

With reference again to FIG. 50, the reciprocating drive ribbon 600 couples the drive member 516 to the cutting blade 592. In some embodiments, the reciprocating drive ribbon 600 can be a somewhat thin, flexible band that is sized to fit within a ribbon passageway 602. In some non-limiting embodiments, the drive ribbon 600 is constructed of metal (e.g., stainless steel) and has a thickness of about 0.004 to 0.008 inches. In such an embodiment, the drive ribbon 600 can bend easily through the curved ribbon passageway 602. Other materials can also be used to form the drive ribbon 600. The drive ribbon 600 can preferably flex and assume a curved shape, even when drive ribbon 600 is reciprocated. As used herein, the term "reciprocate" is a broad term and includes, but is not limited to, the concept of moving an object alternatingly in substantially opposite directions. If the drive ribbon 600 is made of a stainless steel, the ribbon 660 can be flexible with high deflection limits. In alternative embodiments, the drive member 516 can be connected to the blade 592 by a flexible rod or other suitable structure. The rod can comprise a flexible material so that it can assume various curved configurations. The rod can be a single element or may comprise multiple elements. Alternatively, the drive member 516 can be directly coupled to the proximal end of the cutting blade 592.

Because the drive ribbon 600 of FIG. 50 can assume a curved configuration, the toroidal drive 500 can be positioned away from the longitudinal axis of the distal tip portion 420. The toroidal drive 500 can thus be spaced from the endoscope 432 extending through the housing 418. Accordingly, the housing 418 can have a somewhat compact configuration.

The distal tip portion 420 of FIGS. 50 and 50A has a body 598 that has a working lumen 610 extending the entire length of a body 598. The delivery lumen 614 and the return lumen 620 also extend axially through the body 598. The upper portion of the blade 590 may or may not be disposed within the delivery lumen 614 or the working lumen 610. The illustrated working lumen 610 extends axially along the distal tip portion 420 to a distal tip portion opening 614 of FIG. 51. During a surgical procedure, irrigation fluid can flow through the body 598 via the delivery lumen 614. The irrigation can flow out into the surgical site. Fluid and cut tissue can be sucked in the distal tip 422 and can flow proximally through the return lumen 620. As detailed above, the fluid can then flow through the housing 418 and through the powered handpiece 410 until it eventually flows out of the fluid outlet connector 562 and into the outlet line 573.

The body 598 can be constructed of metal, polymers, plastics, combinations thereof, or any other suitable material having appropriate structural properties for the intended application of the device 400. Additionally, the body 598 can have any number of lumens. The illustrated body 598 has four lumens, but the body can have any number of lumens depending on the application. The lumens of the body 598 can have polygonal (including rounded polygonal), elliptical, circular, or any other cross-section as desired.

FIG. 47 illustrates a receptor port 618 of the housing 418 that is configured to receive a distal end 620 of the endoscope 432. To assemble the modular body assembly 416 and the endoscope 432, the distal end 620 of the endoscope 432 can be inserted into the receptor port 618. The endoscope 432 can then be advanced along the instrument lumen 610, until an enlarged proximal portion 619 of the endoscope 432 contacts a seat 622 of the housing 418, as shown in FIG. 50. The enlarged portion 619 and the seat 622 can have a similar shape. When the endoscope 432 is assembled with the body assembly 416, the guides 476 and seat 622 cooperate to hold securely the endoscope 432.

An elongated body 640 of the endoscope 432 can have such a length that the endoscope 432 extends through the housing 418 and the distal tip portion 420. The distal end 620 of the endoscope 432 preferably extends out of the distal portion opening 614 (see FIG. 51). The illustrated elongated body 640 is a cylindrical body sized to fit within the working lumen 610 of the distal tip portion 420.

As shown in FIG. 48, the endoscope 432 can be inserted into the receptor 618 in the direction indicated by the arrow 483. The endoscope 432 can be inserted into the body assembly 418 until the enlarged portion 619 of the endoscope 432 rests against the seat 622 of the housing 418.

Figure 52:
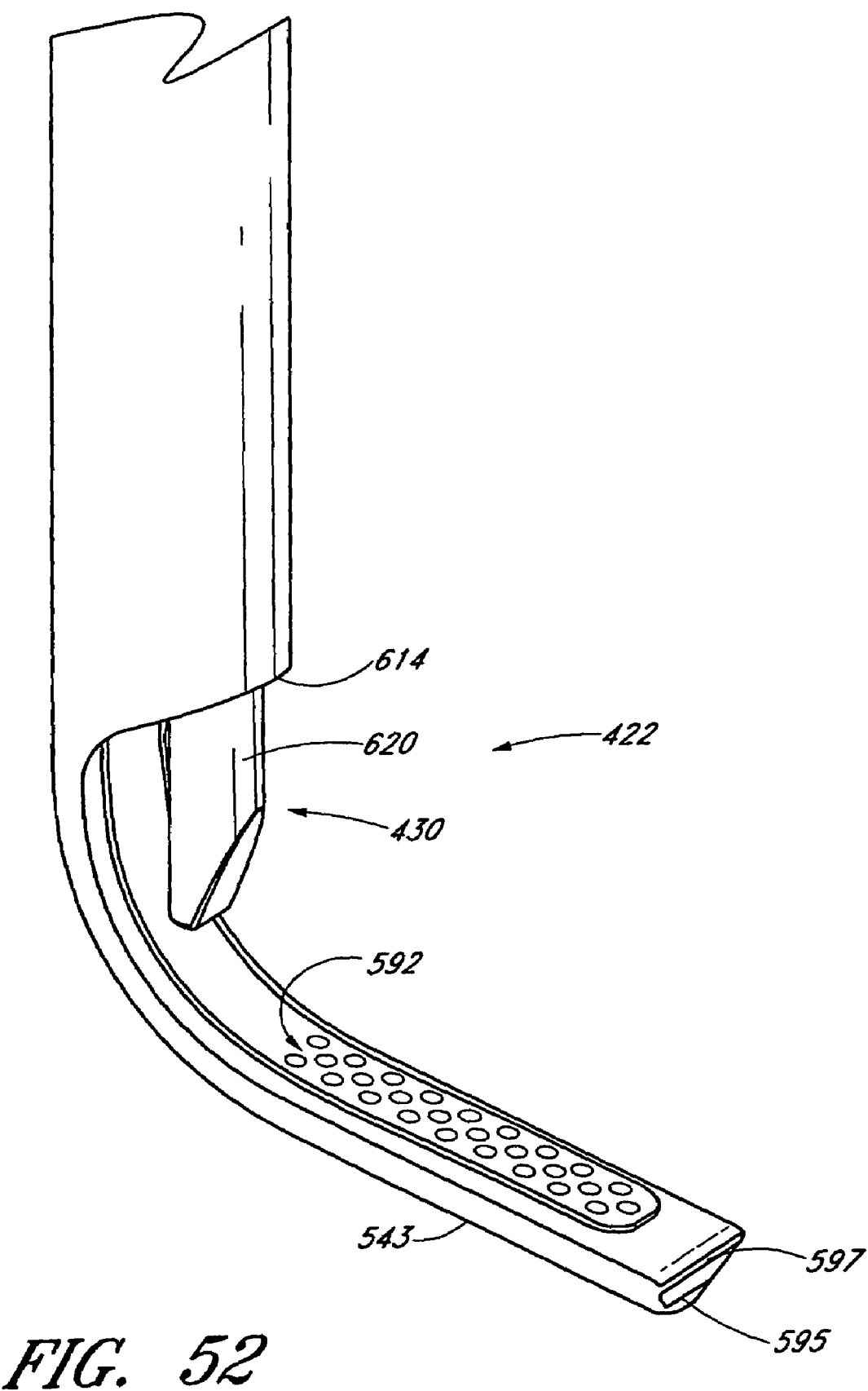
FIG. 52 is a perspective view of the distal end of the surgical instrument of FIG. 51.
Figure 53:
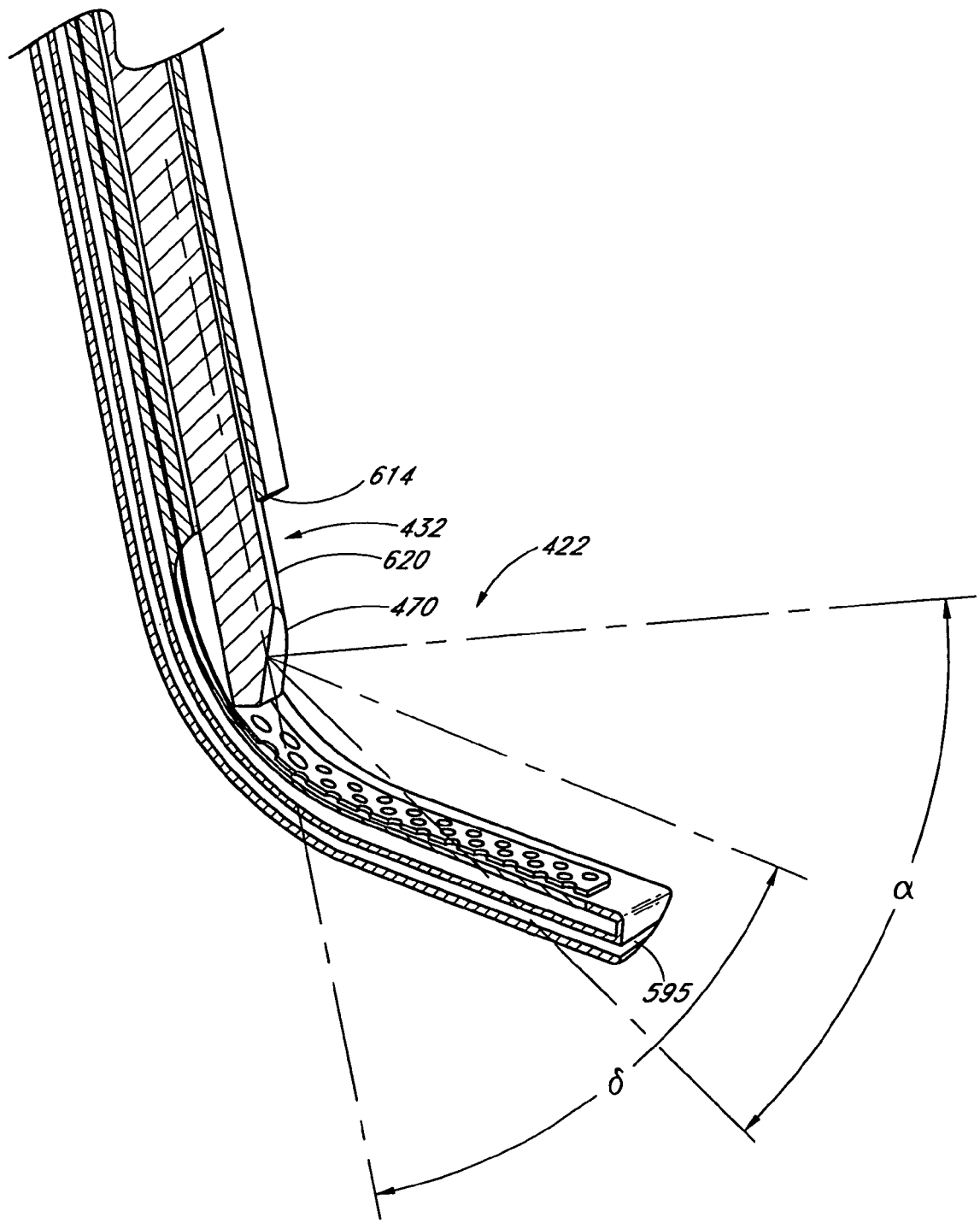
FIG. 53 is a longitudinal cross-sectional view of the distal end of the surgical instrument of FIG. 51.

FIG. 52 illustrates the distal tip 422 of the surgical file device 400. The distal end 620 of the endoscope 432 extends out of the distal portion opening 614 and is near the cutting surfaces of the cutting blade 592. The illustrated endoscope 432 of FIG. 53 is aligned to provide a field of vision for direct visualization of a surgical site. The line of sight of the endoscope 432 can be generally aligned with the longitudinal axis of the blade 592. If the endoscope is in such a position, the user can view the cutting blade 592 cutting tissue during a surgical procedure. However, the endoscope 432 can be at other orientations depending on the surgical procedure. For example, the endoscope 432 can have a line of sight that is offset or angled from the centerline of the cutting blade 592. In the illustrated embodiment, the distal tip portion 420 has a longitudinal axis 453. The endoscope 432 provides viewing of a distal tip 422 when the distal tip 422 is offset from the longitudinal axis 453.

In the illustrated embodiment of FIG. 53, the distal end 620 of the endoscope 432 defines the viewing element 470 in the form of optical prism. The configuration of the prism can be chosen based on the desired range of viewing. The illustrated viewing element 470 is in a 70 degree prism (i.e., $\delta$ is about 70 degrees) that defines a field of vision having an angle a. The illustrated viewing element 470 has a 50 degree field of vision, although the viewing element 470 can have any desire field of vision. For example, field of vision can have an angle $\alpha$ that is about 40 degrees, 50 degrees, 60 degrees, or any other angle suitable for providing adequate visualization to an operator. This viewing element 470 provides direct visualization during navigation of the surgical file device 400 and positioning of the distal tip 422. This enables an operator to navigate in areas of the body having sensitive nerve roots, blood vessels, or other delicate structures under direct vision.

Various types of diagnostic tests can be performed to evaluate and determine an appropriate treatment for a patient. A patient may have a disorder (e.g., facet joint disorder) that adversely affects the patient. The surgical file device 400 can be used to perform a procedure that may alleviate discomfort, improve spine functioning, or otherwise improve functioning or health of a patient.

The distal tip portion 420 extends away from the housing 418 and terminates at a distal tip 422 that is curved away from the longitudinal axis of the distal tip portion 420. The illustrated distal tip 422 has a somewhat L-shape. However, the distal tip 422 can have other configurations depending on the intended use of the surgical file device 400. For example, the distal tip 422 can have a somewhat J-shaped configuration. The blade 592 is positioned above the lower blade structure 543. The lower blade structure 543 supports the blade 592 when the blade 592 is actuated. The illustrated lower blade structure 543 is wider then the blade 592.

Figure 54:
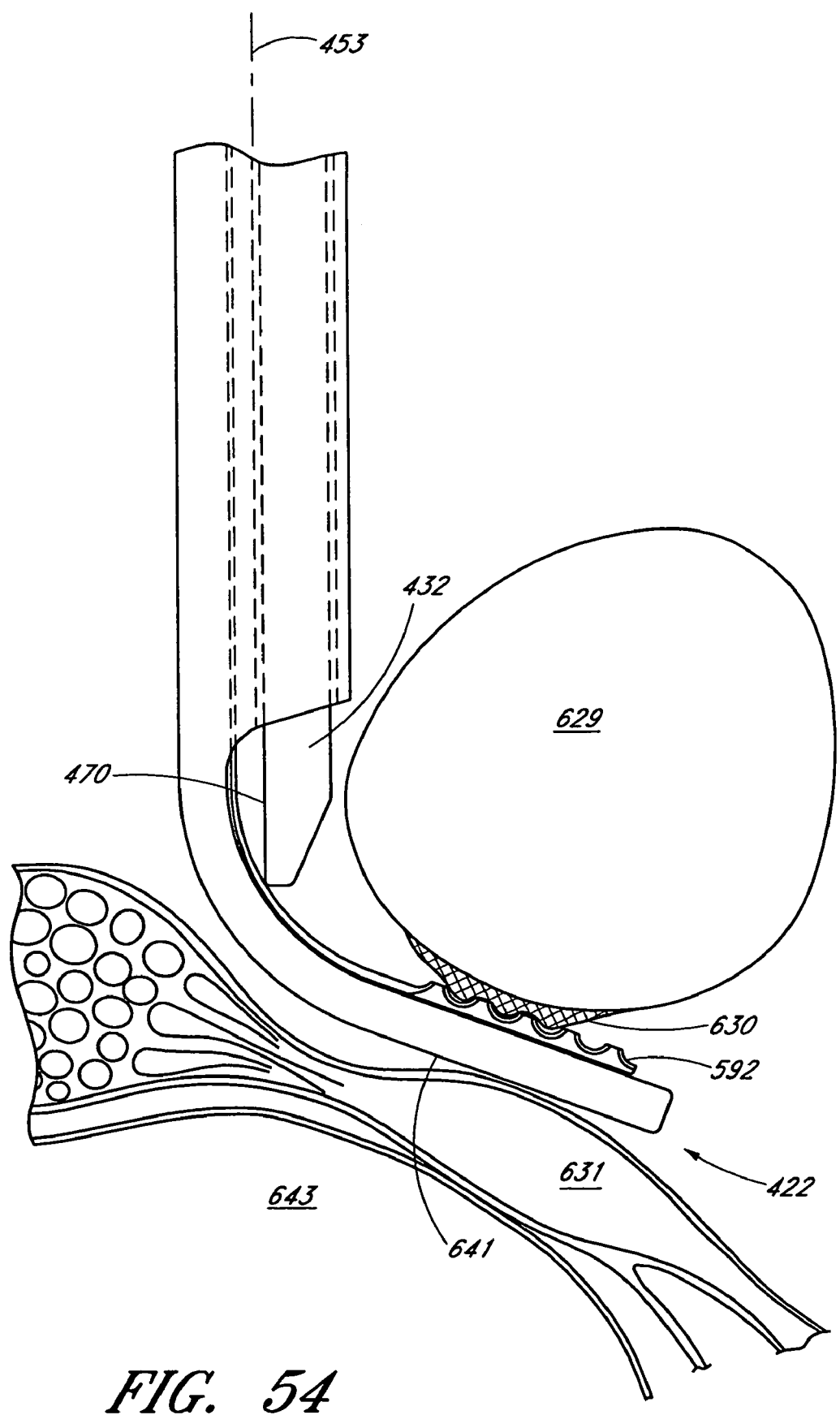
FIG. 54 is a simplified side view of a bone and/or tissue removal procedure on a human spine.

FIG. 54 illustrates the cutting blade 592 of the distal tip 422 engaging tissue 630 on a facet joint 629. The upwardly facing cutting surface of the cutting blade 592 can cut off tissue 630 (e.g., boney overgrowth). In some instances, the tissue 630 can be a bone spur or a portion of an enlarged region of the joint 629. The cutting blade 592 can be actuated to remove (e.g., grind, cut, file, etc.) a desired amount of tissue 630. The physician can view the surgical procedure using the visualization instrument 430 to ensure accuracy of the treatment. In the illustrated procedure, the viewing element 470 of the endoscope 432 is proximate to the surgical site for viewing the cutting blade 592 and the tissue 630.

The illustrated distal tip 422 is interposed between the facet joint 629 and a nerve root 631. The distal tip 422 can be slid between the facet joint 629 and the nerve root 631 without injuring the sensitive nerve root 631. The blunt, atraumatic tip 422 has a shield 641 that protects the nerve root 631. Thus, the distal tip 422 can be configured to fit safely between the anterior portion of the facet joint 629 and nerves (e.g., nerve roots 631 or ganglion) for safely removing a portion of the facet joint 629. The curve and angle of the distal tip portion 420 can be chosen such that the distal tip 422 can be easily inserted between the facet joint 629 and an adjacent vertebral body 643. In some embodiments, the distal tip 422 is shaped to match the angle of a neural foramen canal. For example, if the neural foramen canal is angled at 20 degrees sloping down from horizontal when a patient is positioned face down, the distal dip 422 can also have a 20 degree angle. As such, the configuration of the tip 422 can be selected to match the patient's physiology. The surgical instrument described herein can be used in neuroforamina anywhere in the body, including the spine, skull, and other bones through which nerves extend.

As tissue is removed from the facet joint 629, the irrigation system 551 and removal system 594 can be used for continuously (or intermittently) irrigating and cleaning the surgical site thereby avoiding debris buildup and improving viewing of the surgical site. The distal tip 422 can be moved along the facet joint 629 as the blade 592 reciprocates to remove target tissue. The distal tip 422 can also be used for general bone sculpturing, if desired.

Figure 55:
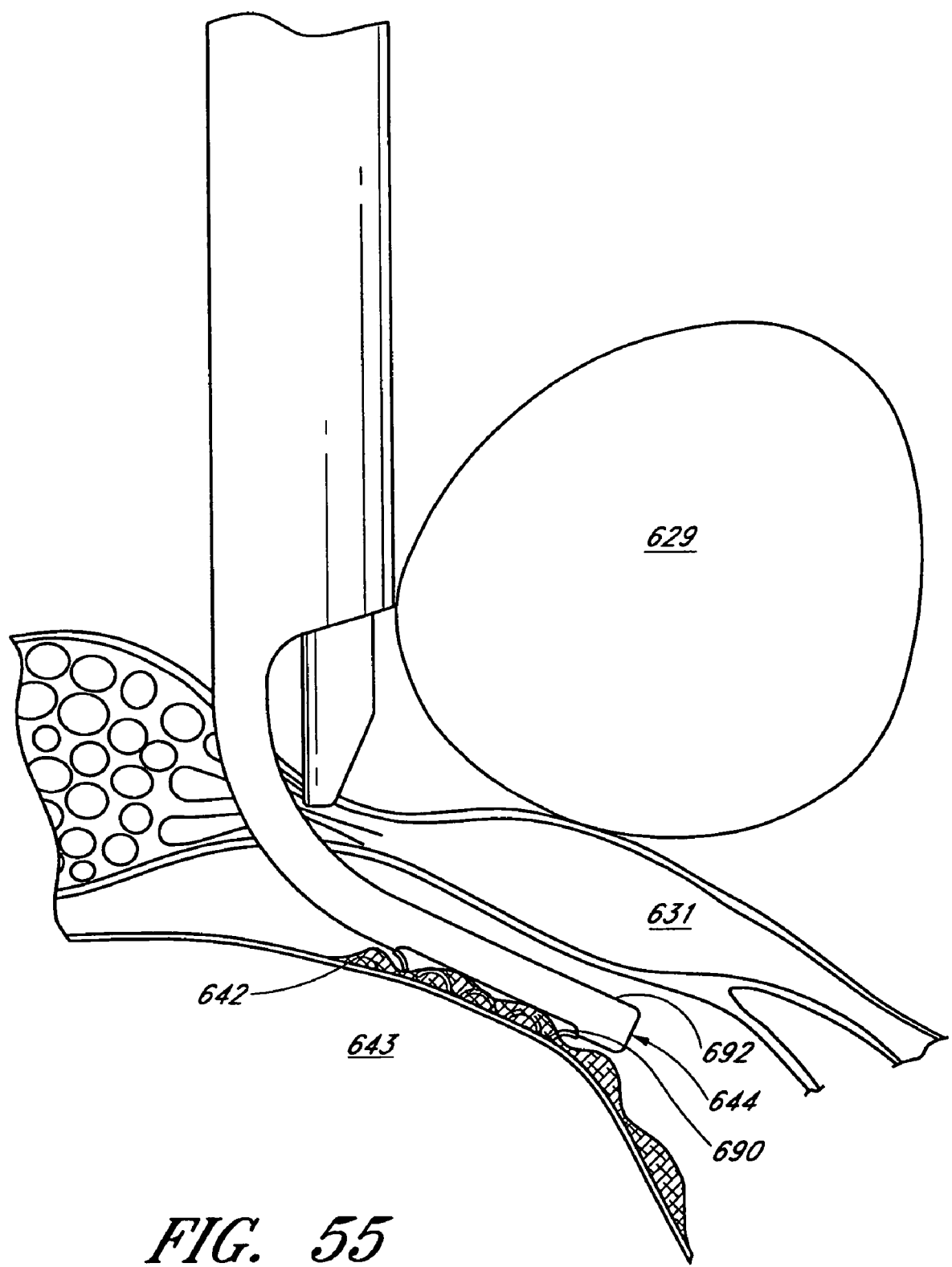
FIG. 55 is a side view of a bone and/or tissue removal procedure on a human spine in accordance with another embodiment.

The distal tip 422 can also have other configurations to treat other portions of a patient's body. FIG. 55 illustrates another distal tip 644 that is positioned to remove tissue from a vertebral body 643. The distal tip 644 is generally similar to the distal tip 422, except as detailed below.

The distal tip 644 has a downwardly facing cutting blade 690 and an opposing shield 692. To remove tissue 642 from the vertebral body 643, the distal tip 644 can be inserted between the nerve root 631 and the vertebral body 643. The shield 692 can contact and protect the nerve 631. The distal tip 644 can be utilized to remove tissue from the posterior portion of the vertebral body 643 in the neural foramen area. To move the distal tip 644 to the illustrated position, the distal tip 644 can be slid over the dura mater and then between the nerve 631 and the vertebral body. The dura mater is a tough fibrous membrane that envelopes the spinal nerves that can be navigated through to remove tissue from the spine. The distal tip 644 can be delivered to the target site with or without using an access device, such as the introducer discussed above. Additionally, the distal tip 644 may or may not have an irrigation system and/or removal system.

An access device can optionally be used for positioning a surgical instrument, such as the file device 400. FIG. 49 illustrates the distal tip portion 420 extending through an access device 638 in accordance with one embodiment. In some embodiments, including the illustrated embodiment, the access device 638 is an introducer. A standard tubular introducer for lumber spine surgery has an inner diameter of about 22 mm. If such an introducer is used, the distal tip portion 420 can have a spin diameter that is less than 22 mm. However, the distal tip portion 420 can have other spin diameters, if desired. The spin diameter can be selected based on the surgical procedure and/or the type and size of introducer utilized.

After the introducer 638 is positioned in the patient, the distal tip 422 can be inserted through an upper end 639 of the introducer 638 and then advanced through the introducer 638. The distal tip portion 420 can be advanced distally until the distal tip 422 is exposed from lower end 651 the introducer 638 and is positioned at the target surgical site. The introducer 638 provides a delivery path to the target surgical site. Non-limiting exemplary access devices can be a tube, sleeve, or other device capable of providing a delivery path for insertion of a surgical instrument to a target surgical site.

In some embodiments, one or more of the components of the surgical file device 400 are disposable. As used herein, the term "disposable" when applied to a component, such as a body assembly (e.g., the body assembly 416, distal tip assembly, etc.) is a broad term and means, without limitation, that the component in question is used a finite number of times and then discarded. Some disposable components are used only once and then discarded. Other disposable components are used more than once and then discarded. In some embodiments, the body assembly of the surgical file device is a single-use component. Such body assemblies assures that sterile irrigation fluid is delivered to a surgical site, if the surgical file device has a fluid system. In alternative embodiments, the body assembly of the surgical device 400 is a multiuse component that may or may not be sterilized after each use.

Figure 56:
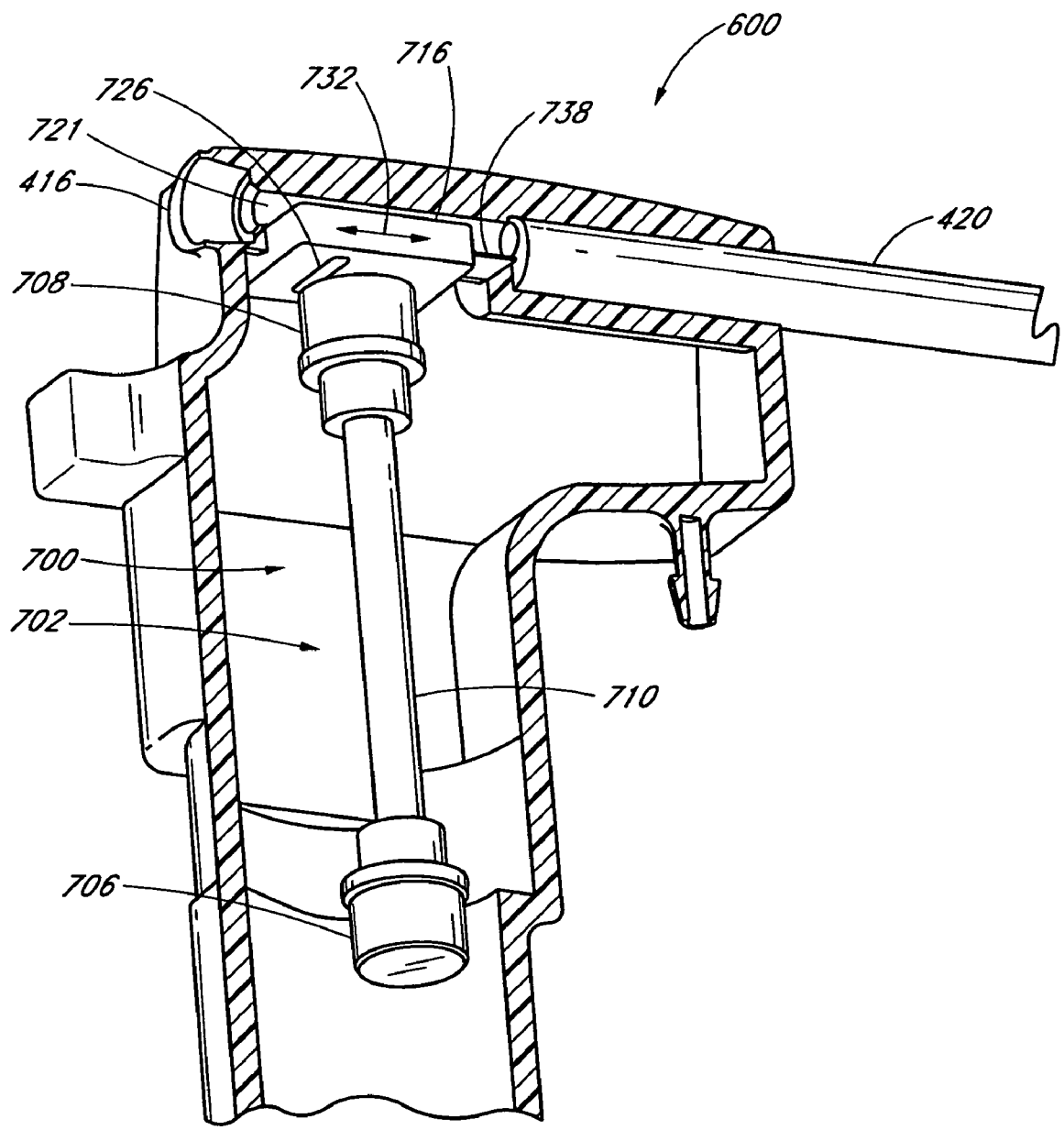
FIG. 56 is a partial cross-sectional view of a surgical instrument having a drive system in accordance with another embodiment.
Figure 57:
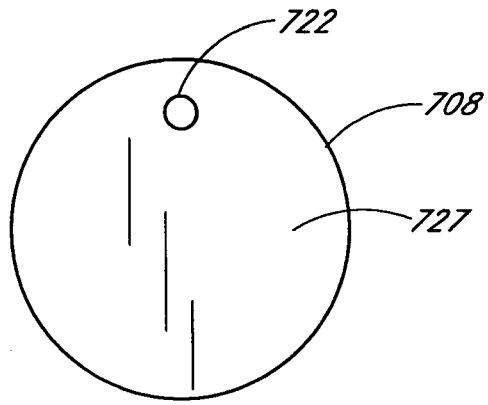
FIG. 57 is a front view of a slide plate connector of a drive member of the drive system of FIG. 56.
Figure 58:
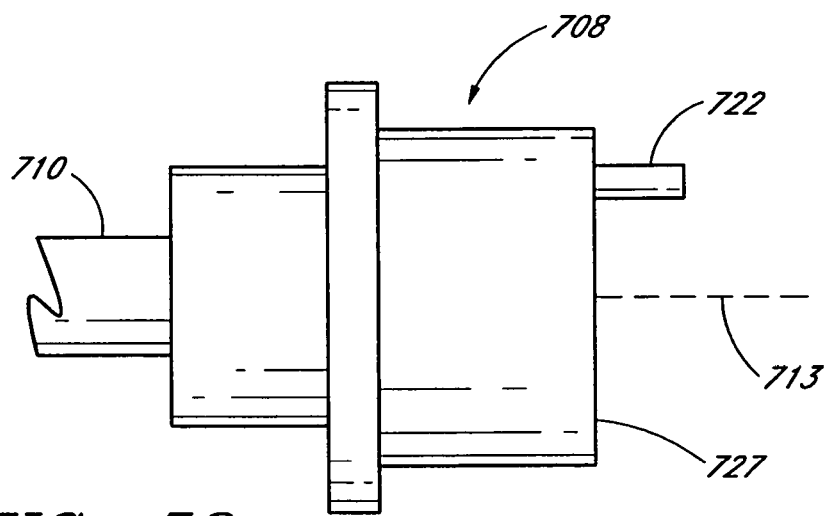
FIG. 58 is a side view of the slide plate connector of FIG. 57.

FIG. 56 illustrates a drive system 700 of a surgical instrument for actuating a cutting blade. The surgical instrument 699 can be similar to the surgical instrument 400, except as detailed below. In FIG. 56, many of the internal components of the instrument have been removed to more clearly illustrate the drive system 700.

The drive system 700 translates rotary motion to linear motion. The illustrated drive system 700 comprises a drive member 702 that has a drive connector 706, a slide plate connector 708, and a drive member body 710 therebetween.

The drive connector 706 is configured to engage a portion of a powered handpiece, such as the handpiece 410 of FIG. 46. The drive connector 706 can be coupled to a rotatable output shaft of a handpiece. If the handpiece 410 of FIG. 46 powers the body assembly 416 of FIG. 56, the drive connector 706 can be adapted to mate and lock with the receptor shaft 448 of the handpiece 410. Alternatively, the drive connector 706 can be adapted to mate with other output structures based on the design of the powered handpiece. The drive connector 706 is preferably coupled to a structure that imparts rotary motion to the drive member 702.

The drive member body 710 extends between the drive connector 706 and the slide plate connector 708. The drive member body 710 can be a shaft, rod, tubular member, or other suitable member for imparting rotary motion. The body assembly 416 can have brackets, a drive member passageway, or other structure for pivotally holding the drive member 710. As such, the body assembly 416 and drive member body 710 are arranged so that the drive member 702 is rotatable about its longitudinal axis.

The slide plate connector 708 is connected to an axially movable slide plate 716. As shown in FIGS. 56-59, the slide plate connector 708 can have a pin 722 that extends through a slot 726 of the slide plate 716. The pin 722 extends outwardly from a distal face 727 of the slide plate connector 708. As the drive member 702 rotates, the pin 722 travels along a somewhat circular path about the longitudinal axis 713 of the drive member 702. The traverse dimension of the travel path of the pin 722 determines the axial travel stroke of the slide plate 716. The pin 722 slides back and forth in the slot 726 when the drive member 702 rotates about its longitudinal axis. The rotating pin 722 also axially displaces the slide plate 716 towards or away from the elongate distal tip portion 420 as indicated by the arrows 732. Hence, the slide plate 716 is reciprocated as the drive member 702 is rotated.

Figure 59:
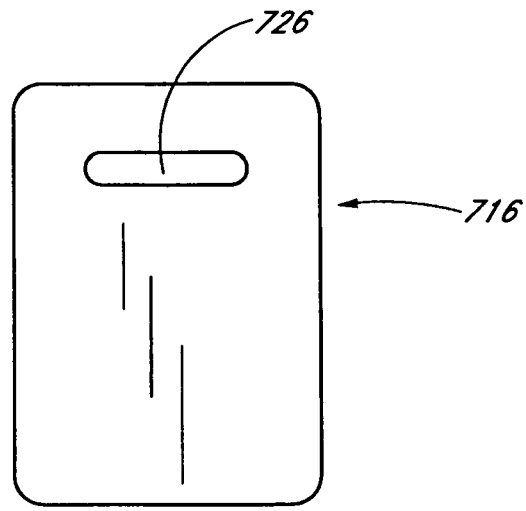
FIG. 59 is a front view of a slide plate of the drive system of FIG. 56.

The slide plate 716 of FIGS. 56 and 59 has the elongated slot 726 that is sized to receive the pin 722. The longitudinal axis of the slot 726 is somewhat perpendicular to the direction of travel of the slide plate 716. The length of the slot 726 is preferably greater than the diameter of the travel path of the pin 722. The slide plate 716 is connected to the upper end 738 of the cutting blade. In such embodiments, the slide plate 716 and cutting blade can be reciprocated together.

With continued reference to FIG. 56, the instrument 699 also includes a working lumen for receiving a visualization instrument. The illustrated instrument 699 has a working lumen 721 configured to receive a visualization instrument, such as an endoscope, although other visualization instruments can be employed.

FIGS. 60-64 illustrate another embodiment of a surgical instrument. In the illustrated embodiment, the surgical instrument 800 comprises a straight distal tip cutting blade, straight ribbon drive or tube drive, with suction and irrigation. This design can be powered by a standard specialized power handpiece. This illustrated distal tip assembly 802 is configured to be mated to an existing rotary motor powered handpiece 816.

The distal tip assembly 802 can have a relatively simple design and can be mounted onto a standard powered surgical hand piece. These standard powered surgical hand pieces are often built to drive rotary cutting tools. The distal tip assembly 802 converts the rotary handpiece into a reciprocating cutting instrument. Rotary instruments may often have a rotating cutter. Unfortunately, these rotating cutters skip sideways, especially when the rotating cutter touches hard to cut tissue, such as bone. Additionally, rotary cutting tools may not be suitable for forming a smooth or flat sculptured surface. By comparison, the illustrated reciprocating cutting instrument 800 can avoid sideways skipping. The distal tip assembly 802 cuts an inherently smoother and flatter surface with dramatically improved control, and therefore reduces fatigue of the surgeon's hands. Thus, the surgical file system 800 is easier to operate and can be safer for the patient than systems employing rotary cutting instruments.

Figure 60:
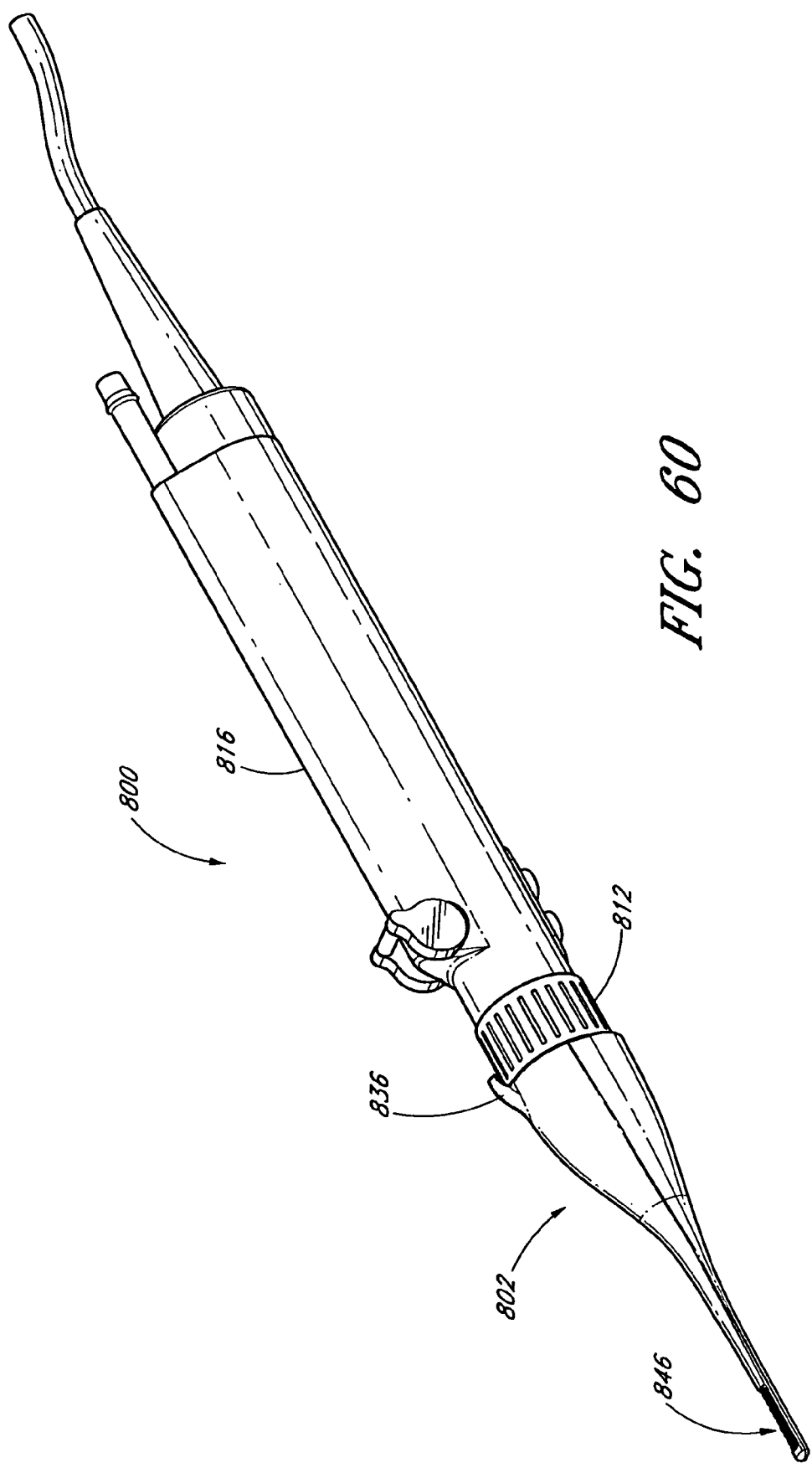
FIG. 60 is a perspective view of a surgical instrument in accordance with another embodiment. The surgical instrument has a removable distal tip assembly attached to a handle assembly.
Figure 61A:
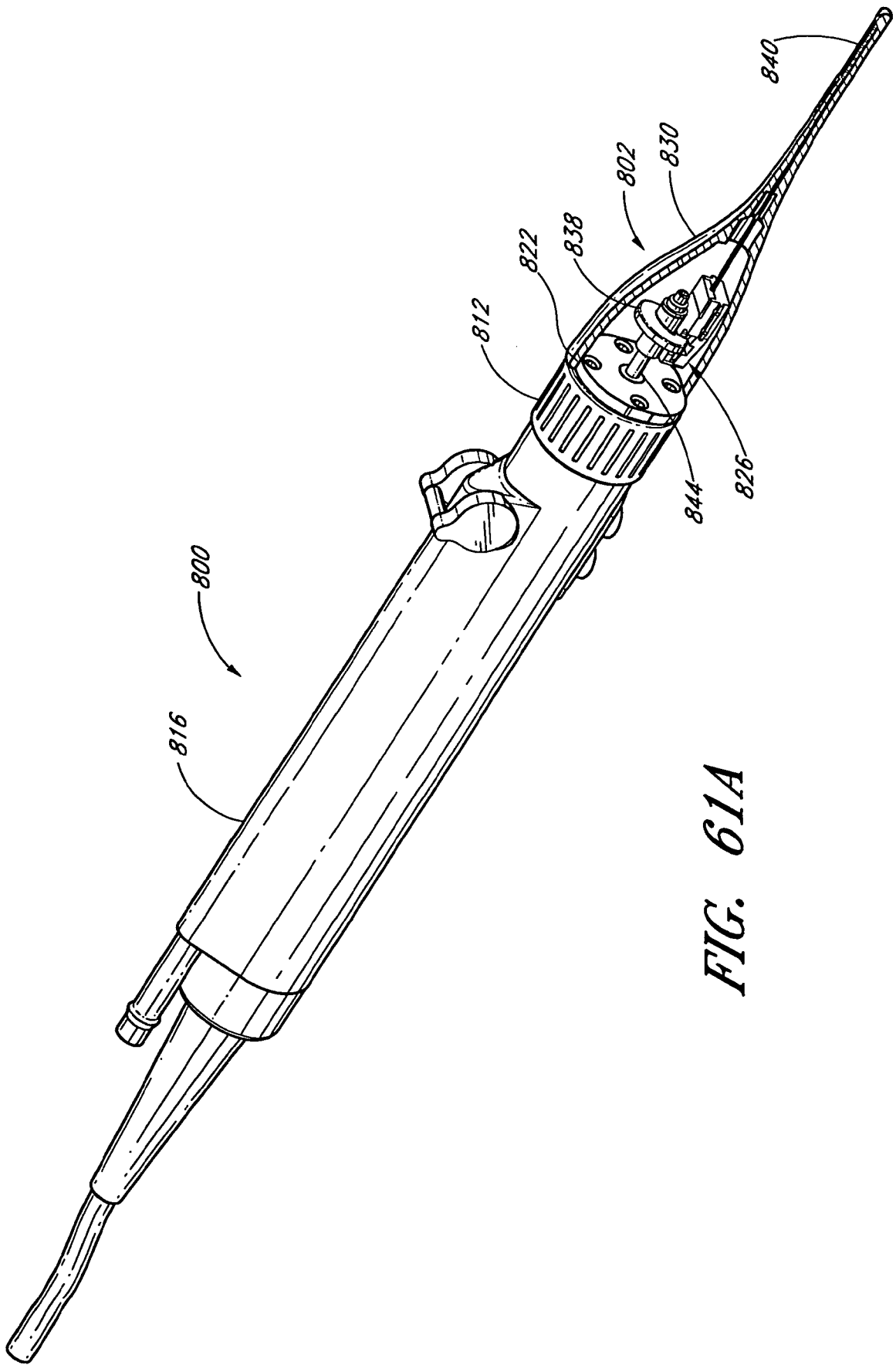
FIG. 61A is a cross-sectional view of a distal tip assembly that is attached to a handle assembly.
Figure 61B:
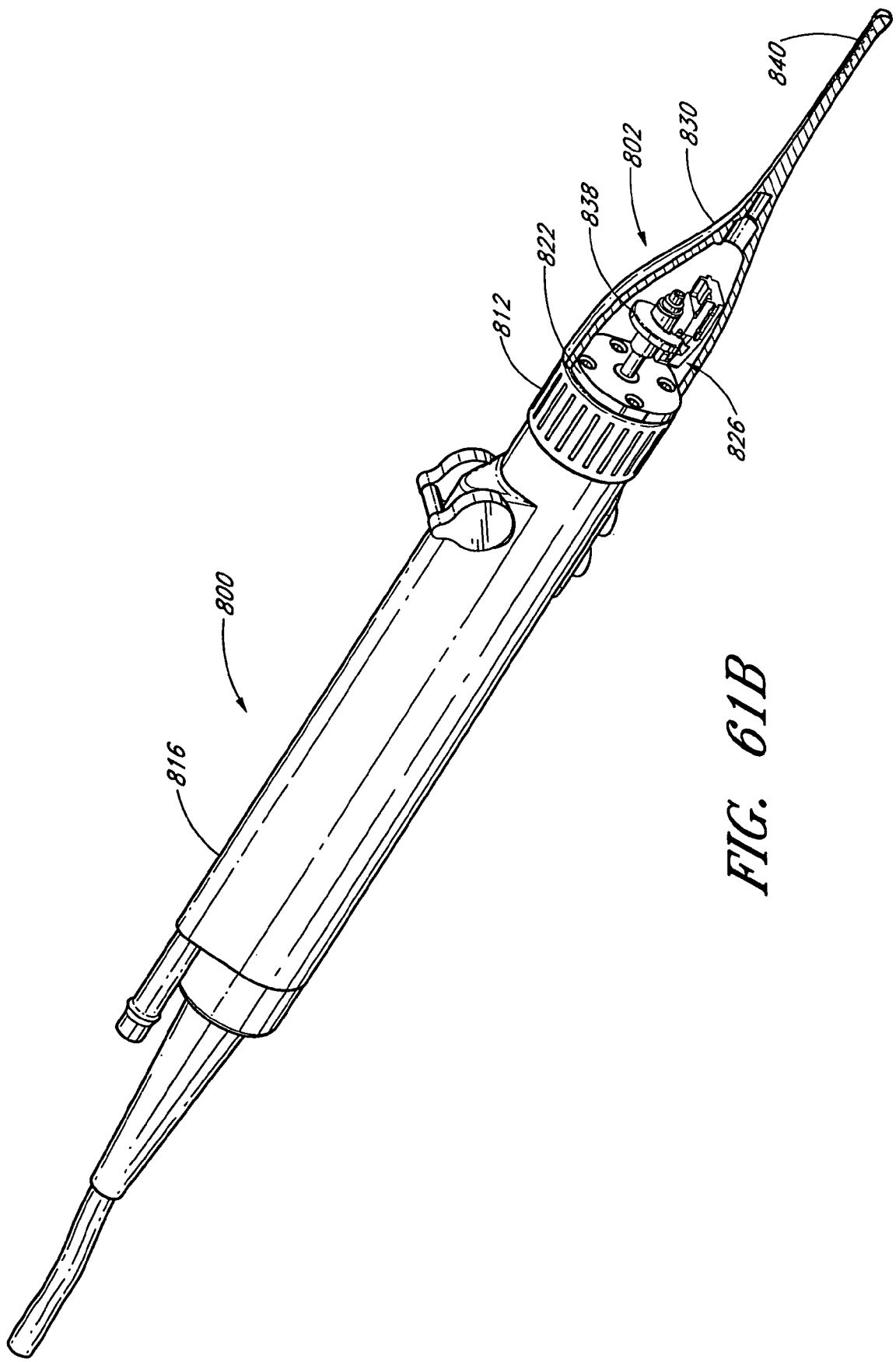
FIG. 61B is a cross-sectional view of the distal tip assembly of FIG. 61A having a blade assembly removed.

As shown in FIGS. 60 and 61A, the distal tip assembly 802 is coupled to a distal end 812 of a handle assembly 816. A quick connect docking mechanism 822 connects the distal tip assembly 802 to the handpiece or handle assembly 816. In some embodiments, the distal tip assembly 802 is removably coupled to the handle assembly 816. Threads of the distal tip assembly 802 can engage threads of the handle assembly 816. For example, the mechanism 822 can have internal threads that mate with external threads of the distal tip assembly 802. Alternatively, pins, screws, snap structures, or the like can be utilized to temporarily couple the distal tip assembly 802 to the handle assembly 816. If desired, the distal tip assembly 802 can also be permanently coupled to the handle assembly 816

The distal tip assembly 802 has a drive system 826 and a housing 830 that surrounds the drive system 826. An inlet connector 836 of FIG. 60 of a fluid system extends outwardly from the housing 830. The modified distal tip assembly 802 of FIGS. 61A and 61B does not have an inlet connector. The distal tip assembly 802 tapers distally and has a substantially straight distal tip 840.

In the illustrated embodiment, the distal tip assembly 802 is in the form of a removal, disposable tip. As such, the distal tip assembly 802 can be conveniently removed from the handle assembly 816 when desired. Accordingly, one or more distal tip assemblies can be used to perform a surgical procedure. The embodiment of FIG. 61 is illustrated without an irrigation system. However, the distal tip assembly 802 can have an irrigation system and/or a removal system, as shown in FIGS. 62-64.

Figure 62:
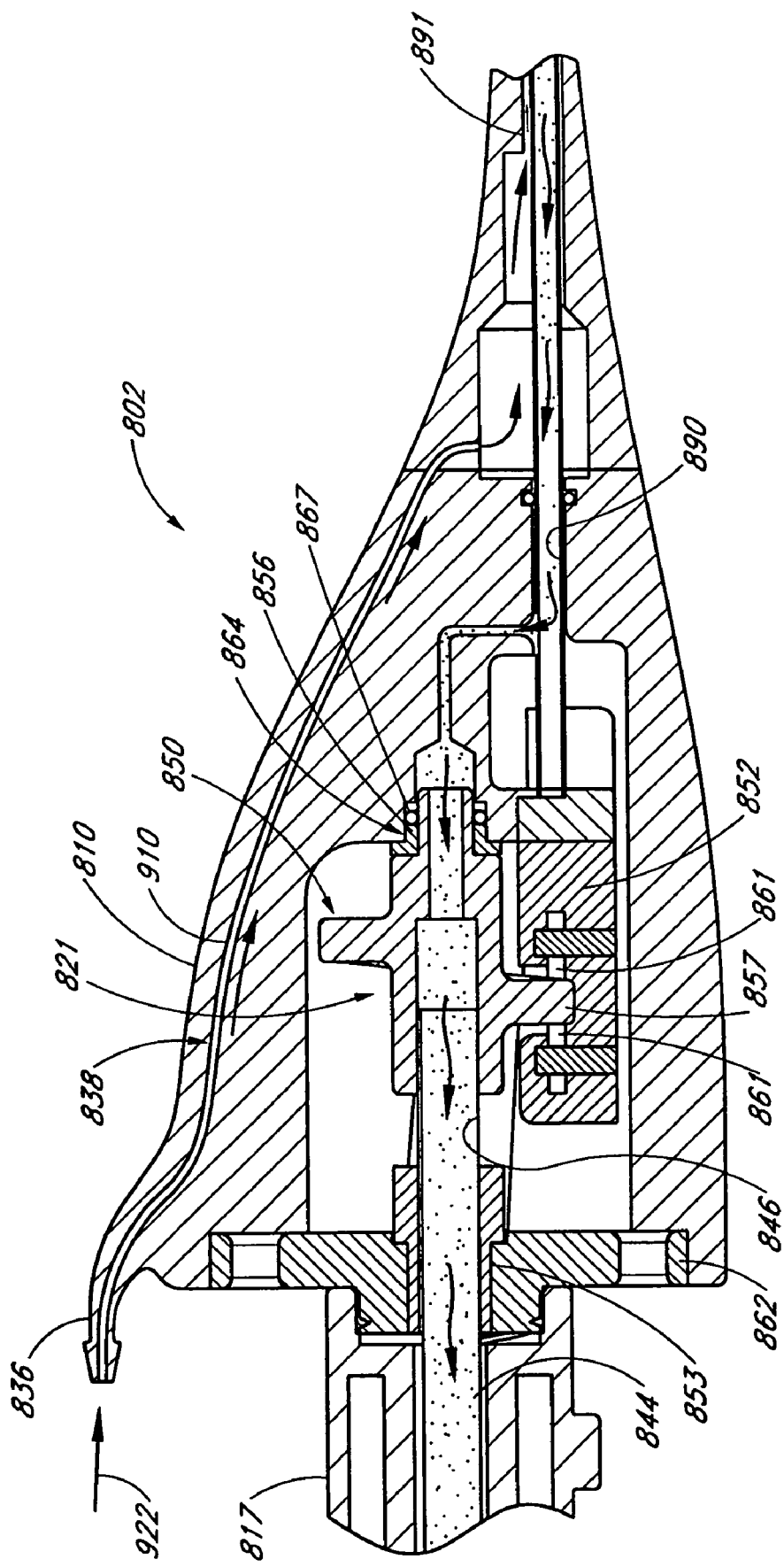
FIG. 62 is a cross-sectional view of a distal tip assembly in accordance with another embodiment.
Figure 63:
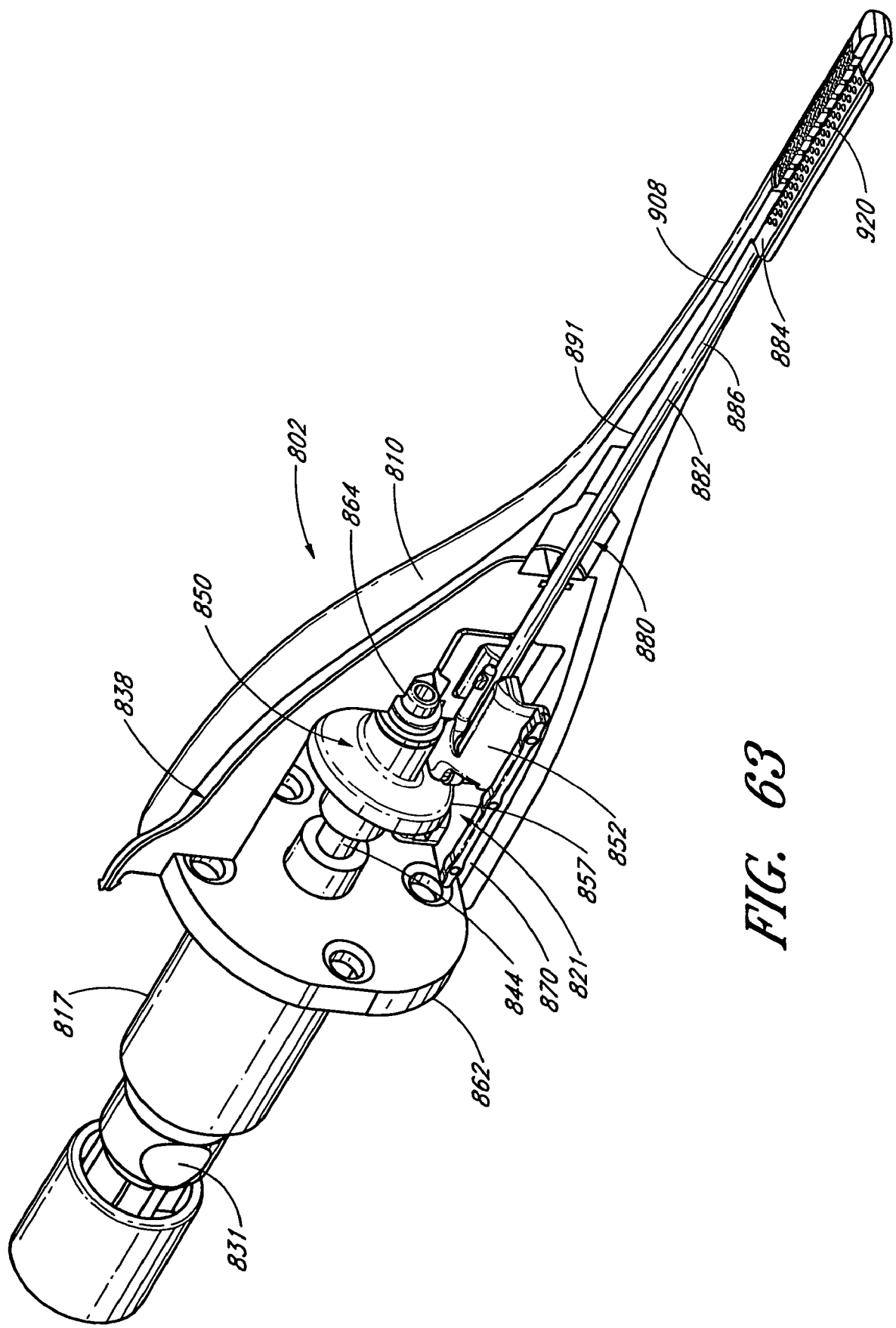
FIG. 63 is a perspective cross-sectional view of the distal tip assembly of FIG. 62.
Figure 64:
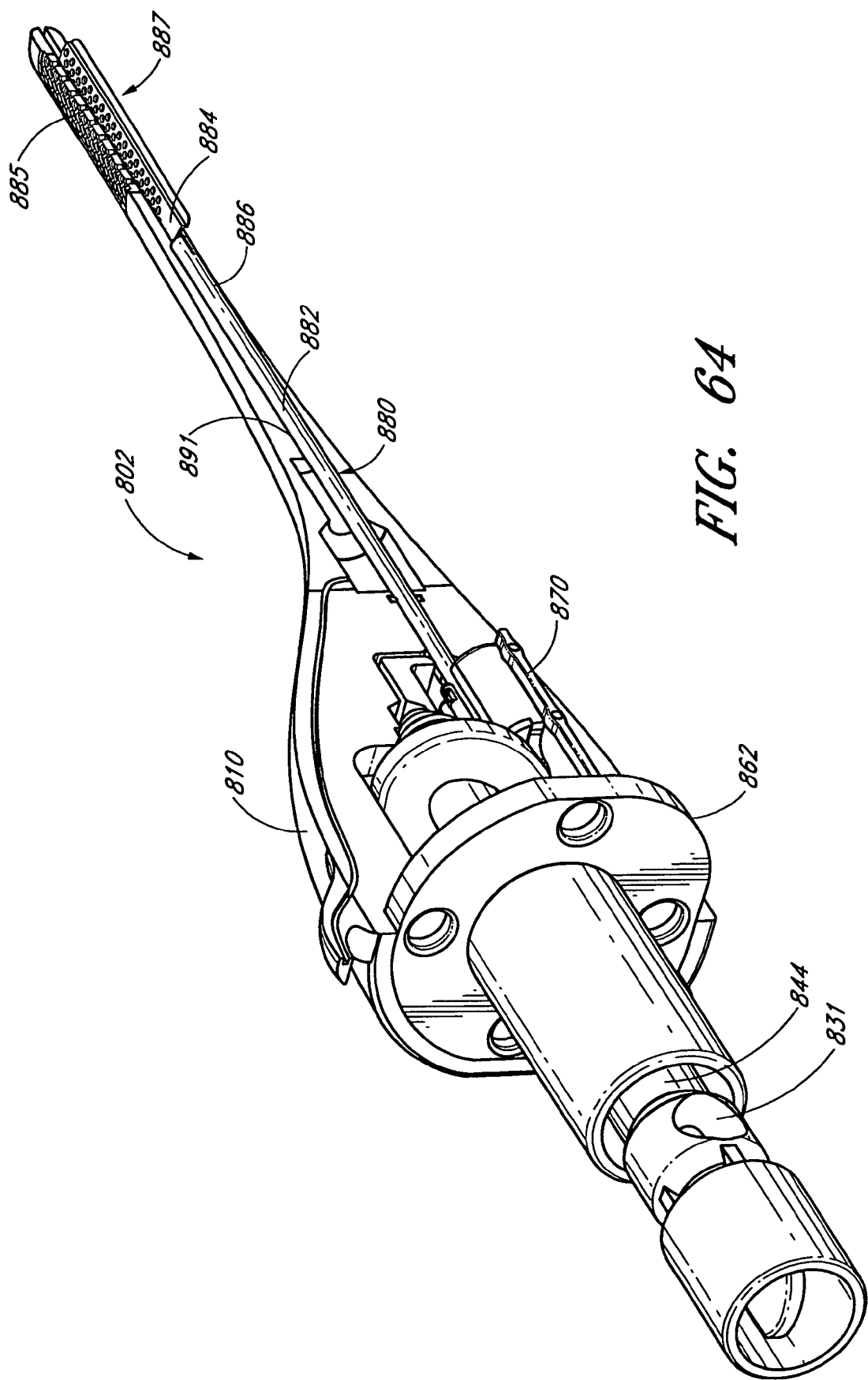
FIG. 64 is another perspective cross-sectional view of the distal tip assembly of FIG. 62.

With respect to FIGS. 62-63, a coupling assembly 817 is configured to be coupled to a handle assembly. The coupling assembly 817 is operatively connected to a shaft 844 of the drive system 821. The illustrated coupling assembly 817 is rotatable about its longitudinal axis and one or more ports 831 in fluid communication with the shaft 844. That is, the coupling assembly 817 is fixedly attached to the shaft 844. In such an arrangement, the coupling assembly 817 and the shaft 844 can rotate together. The coupling assembly design can be selected based on the handpiece.

The shaft 844 can form part of the fluid system 838. The illustrated shaft 844 has a shaft passageway 846 that permits transportation of waste fluids from the distal tip assembly 802 into the handle assembly 816. A shown in FIG. 62, the shaft 844 can be a hollow or tubular shaft that is suitable for transporting fluids while also being capable of transmitting rotational forces. If the distal tip assembly 802 does not have the fluid system 838, the shaft 844 can be a solid shaft that extends between the drive motor of the handle assembly 816 and the distal tip assembly 802. Thus, various types of shafts can be used for operatively coupling the distal tip assembly 802 to the handle assembly 816. Of course, other types of coupling structures can also be utilized.

The drive system 821 includes the shaft 844, a toroidal drive 850, and a slide plate 852 operatively connected to a cutting blade. The drive system 821 preferably converts rotary motion into linear motion. The toroidal drive 850 is rotatably mounted to a face plate 862 and a toroidal holder 864. In some embodiments, the toroidal drive 850 is supported by a pair of bearings.

In the illustrated embodiment of FIG. 62, the toroidal drive 850 and the rotating shaft 844 are supported by two bearings 853, 856, respectively. The shaft passageway 846 extends proximally from the bearing 856 through the face plate 862 and into the handle assembly 816. To seal the fluid from the toroidal drive, a sealing member 867 (e.g., an O-ring) is positioned between the housing 810 and the shaft 844. In such an embodiment, the drive system 821 can remain dry during operation to avoid contamination and damage of its components.

An outer rim 857 of the toroidal drive 850 is positioned somewhat midway between the face plate 862 and the holder 864. The toroid outer rim 857 warbles as the toroidal drive 850 rotates. The toroid rim 857 drives a pair of follower bearings 861 that are connected to the slide plate 852. Rotation of the toroidal drive 850 causes liner movement of the slide plate 852.

The slide plate 852 can be guided in its linear travel by one or more linear guides 870 as shown in FIGS. 63 and 64. The slide plate 852 is preferably connected to a blade assembly 880. The slide plate 852 drives the cutting assembly 880 as the toroidal drive 850 rotates. The cutting assembly 880 extends distally from the slide plate 852 through the distal tip assembly 802. The cutting assembly 880 includes an elongated body 882 and a cutting blade 884 at the distal end 886 of the body 882. The illustrated cutting assembly can be a multi-piece structure that has a movable upper cutting surface 885 mounted to slidable plate 887. Alternatively, the cutting assembly can be similar to blade assembly of the instrument illustrated in FIG. 69.

The elongated body 882 has an elongated body passageway 891 for transporting fluids. The illustrated elongated body 882 is a tubular body that defines the elongated passageway 891 extending between the passageway 846 and the cutting blade 884. Fluid (including irrigation fluid, tissue, etc.) can flow proximally from the distal end of distal tip assembly 802 through the elongated body 882 via the passageway 891. The fluid then proceeds along the passageway 891 and into the passageway 846.

Because the elongated body 882 is subjected to axial loads during operation, its axial cross section can be chosen to avoid buckling or other failure modes. The elongated body 882 can be comprised of metal, such as steel (including stainless steel), titanium, or other suitable material. For example, the elongated body 882 can be comprised of a high strength plastic.

The elongated body passageway 891 of the housing 810 surrounds at least a portion of the elongated body 882, and can limit flexing of the elongated body 882. Hence, the elongated body passageway 891 can inhibit buckling of the elongated body 882.

With reference again to FIG. 62, the fluid system 838 has an inlet connector 836 in communication with a delivery passageway 910. The delivery passageway 910 extends through the housing 810. A tapered or narrowing portion of the housing 810 defines the elongated passageway 891 that cooperates with the outer surface of the elongated body 882 of the blade assembly 880 to form a distal portion 908 of the delivery passageway 910.

Irrigation fluid 922 can be introduced through the inlet connector 836 into the housing 810. The fluid proceeds through the delivery passageway 910 until it reaches the distal portion 908. The fluid then flows through the distal portion 908 of the delivery passageway 910. In some embodiments, the irrigation fluid acts as a lubricant to the cutting blade guides and also cleanses the cutting blade 884 by exhausting out cutting holes 920.

Figure 63A:
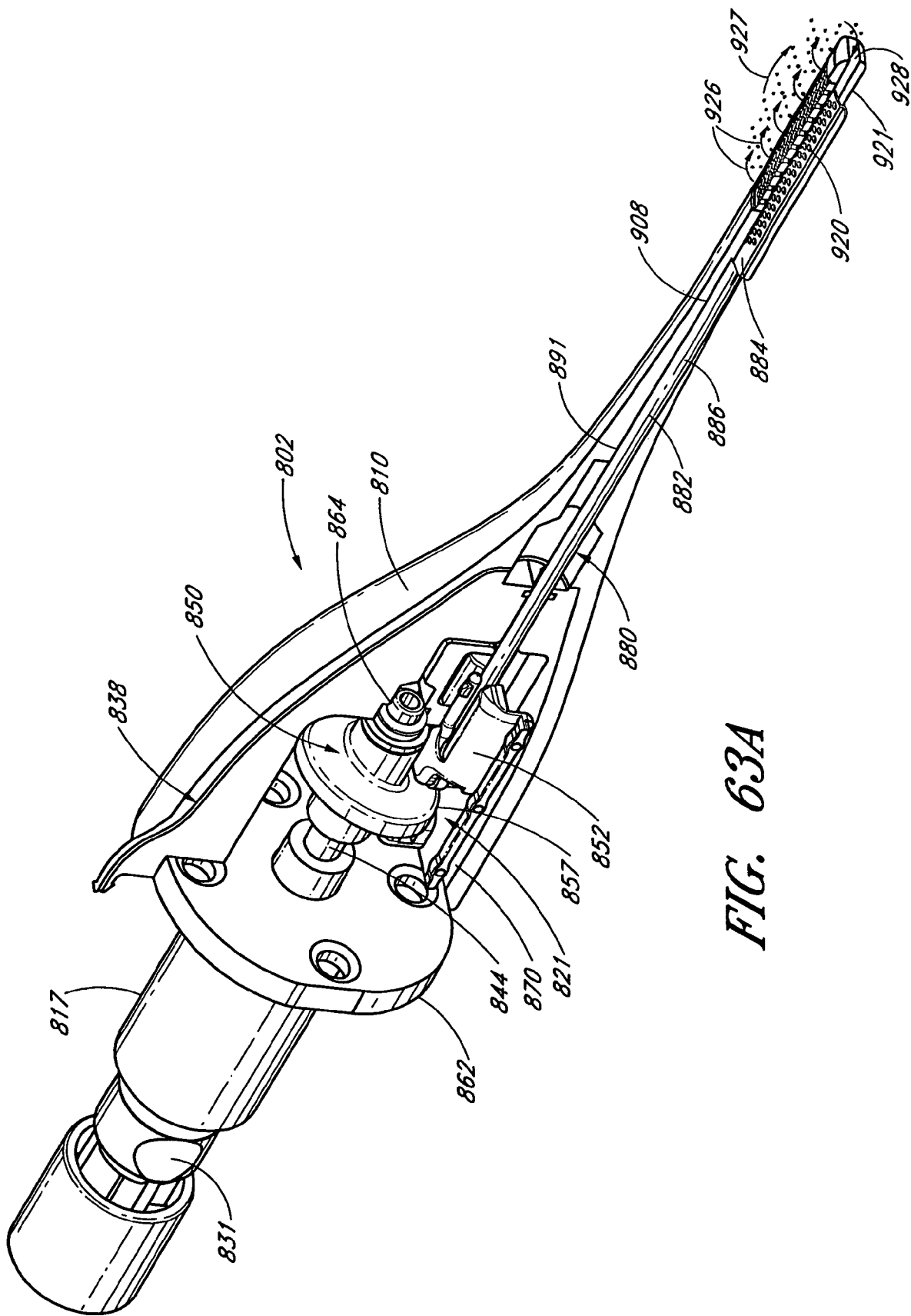
FIG. 63A is a perspective cross-sectional view of the distal tip assembly of FIG. 62 outputting a fluid.

The irrigation fluid can clean the surgical site. As shown in FIG. 63A the cleansing fluid and the freshly cut bone and tissue debris 926 are hydrodynamically drawn along a flow path 927 away from the cutting surface and into the lower blade structure 921. In particular, the tissue and fluid are drawn into the inlet port 928. The mixture then flows proximally through the elongated body passageway 891. After the mixture exits the elongated body passageway 891, it flows through the drive system 821, and is ultimately removed from the distal tip assembly 802.

Figure 65:
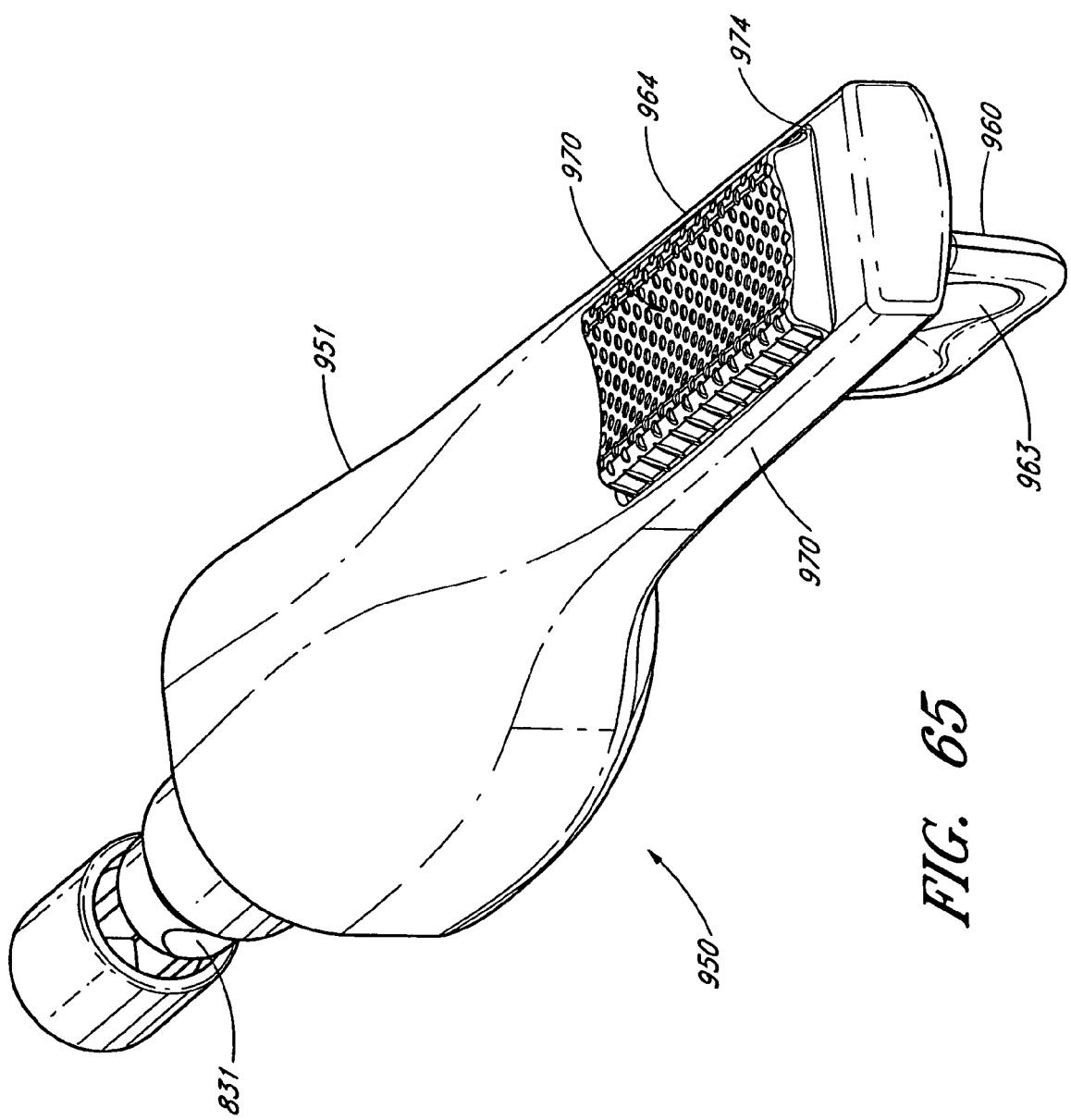
FIG. 65 is a perspective view of a distal tip assembly in accordance with another embodiment.
Figure 66:
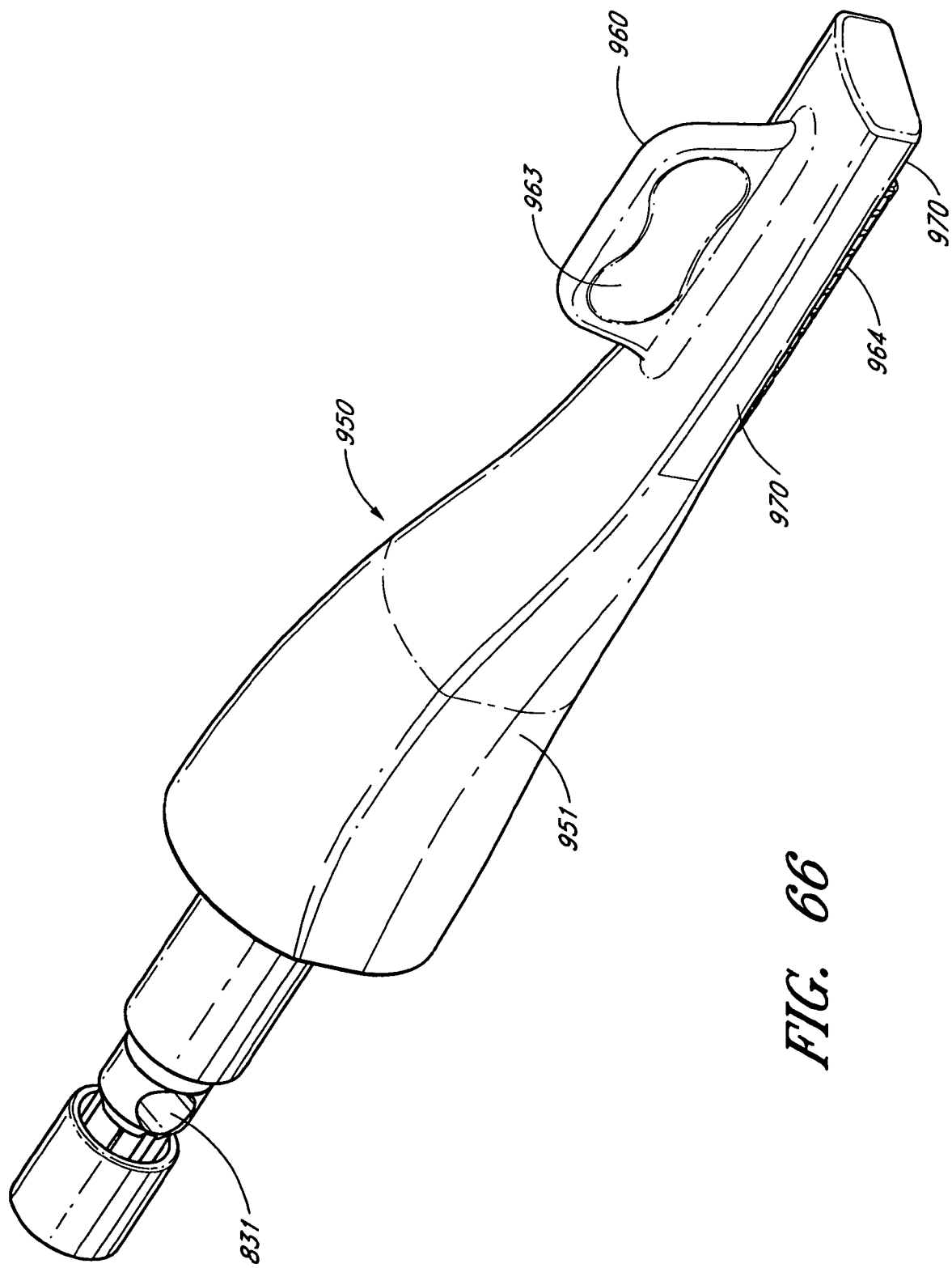
FIG. 66 is another perspective view of the distal tip assembly of FIG. 65.
Figure 67:
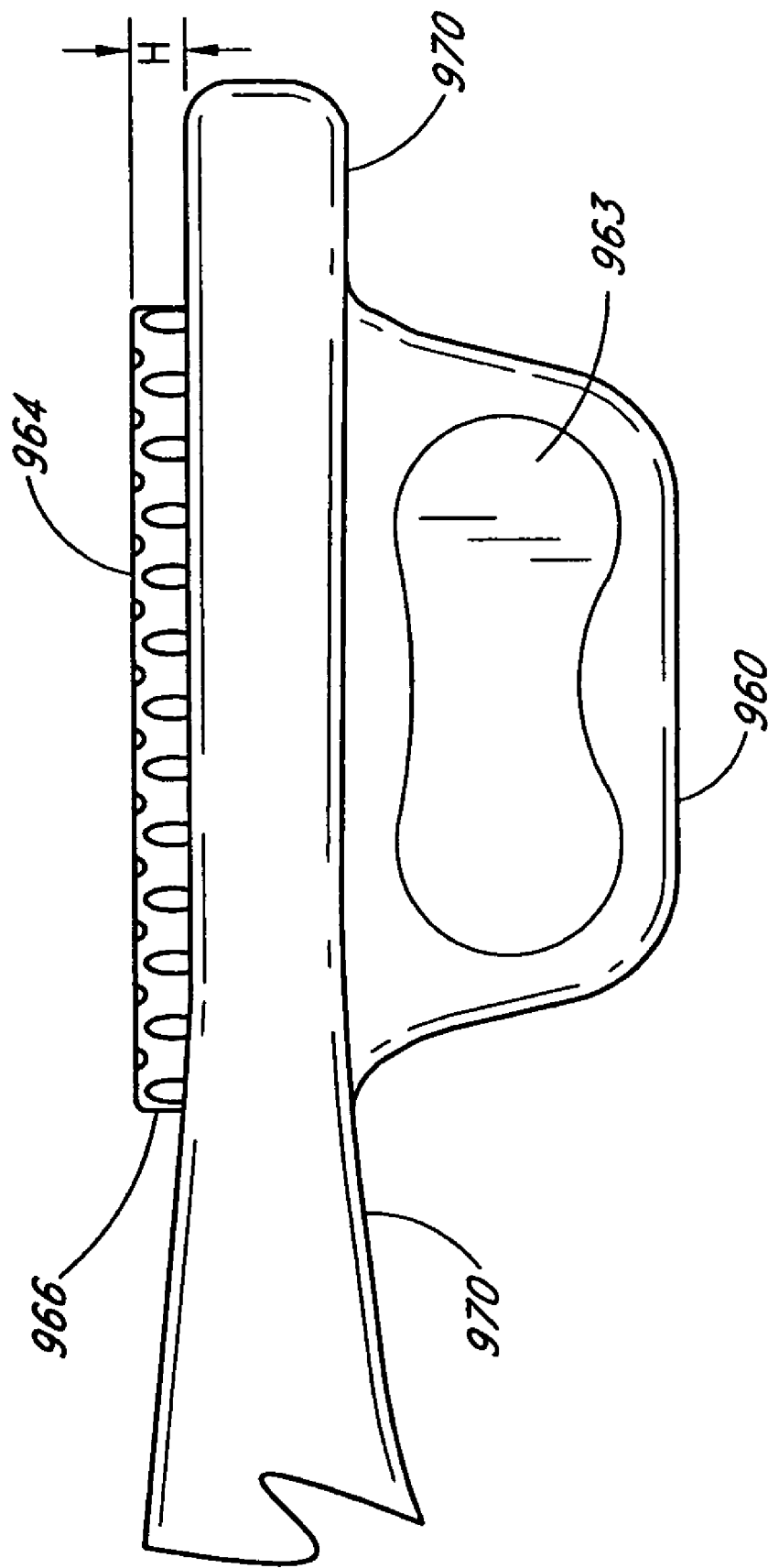
FIG. 67 is a side view of the distal tip assembly of FIG. 65.

FIGS. 65-67 illustrate another distal tip assembly 950 in accordance with another embodiment. The distal tip assembly 950 has a distal tip body 951 and a handle 960 connected to the distal tip body 951. The handle 960 is used to help a user control the movement of the distal tip assembly 950. Additionally, the handle 960 can be used for pressing an actuatable cutting blade 964 against tissue.

The cutting blade 964 and the handle 960 are on opposing sides of a distal end 970 of the distal tip assembly 950. The cutting blade 964 protrudes out of an aperture 974. The illustrated cutting blade 964 has a somewhat concave cutting surface 970 as shown in FIG. 65. In some embodiments, the cutting surface 970 is concave along the length of the cutting blade 964. However, the cutting surface 970 can have other shapes, if needed or desired. For example, the cutting blade 964 can have a generally flat cutting surface for preparing a flat surface. Alternatively, the cutting blade 964 can have a convex cutting surface 970.

As shown in FIG. 67, the portion 966 of the cutting blade 964 extending out of the aperture 974 has a height, H, of about 1 mm, 2 mm, 3 mm, 5 mm, and ranges encompassing such distances. In some non-limiting embodiments, the portion 966 has a height H of more than about 5 mm. In some non-limiting embodiments, the portion 966 has a height H of more than about 8 mm, 10 mm, and 20 mm. The portion 966 can have other heights also. In other embodiments, the cutting blade 964 is generally flush with the aperture 974. The cutting blade 964 can also be similar to the cutting blades described above.

The handle 960 is designed to be comfortably gripped between a user's thumb and index finger while the user's other hand holds an handle assembly to which the distal tip assembly is attached. The operator can use the handle 960 to provide a mechanical advantage in order to remove tissue at a desired rate. As the cutting blade 964 cuts tissue, for example, the handle 960 can be used to press the cutting blade 964 against the tissue. As such, the applied pressure and rate of tissue cutting can be accurately controlled. Thus, the handle 960 can be used for accurately positioning the cutting blade 964 and/or controlling the rate of cutting.

The illustrated handle 960 has depressions to enhance traction. The illustrated handle 960 has depressions 963 on either side for receiving a finger or thumb of a user. Surface texturing, protrusions, or other structures can be used to help a user grip the handle 960. The illustrated handle 960 extends longitudinally along the distal tip assembly 950. However, the handle 960 can be at other orientations, if desired.

The illustrated distal tip assembly 950 has a single handle 960. Other distal tip assemblies can have a plurality of handles. The configurations and positions of the handles can be selected based on the intended use of the surgical file device. In alternative embodiments, the structure 960 can be a guide that assists in positioning of the cutting blade 964. The guide 960 can be positioned against tissue to help align the distal tip 950.

Figure 68:
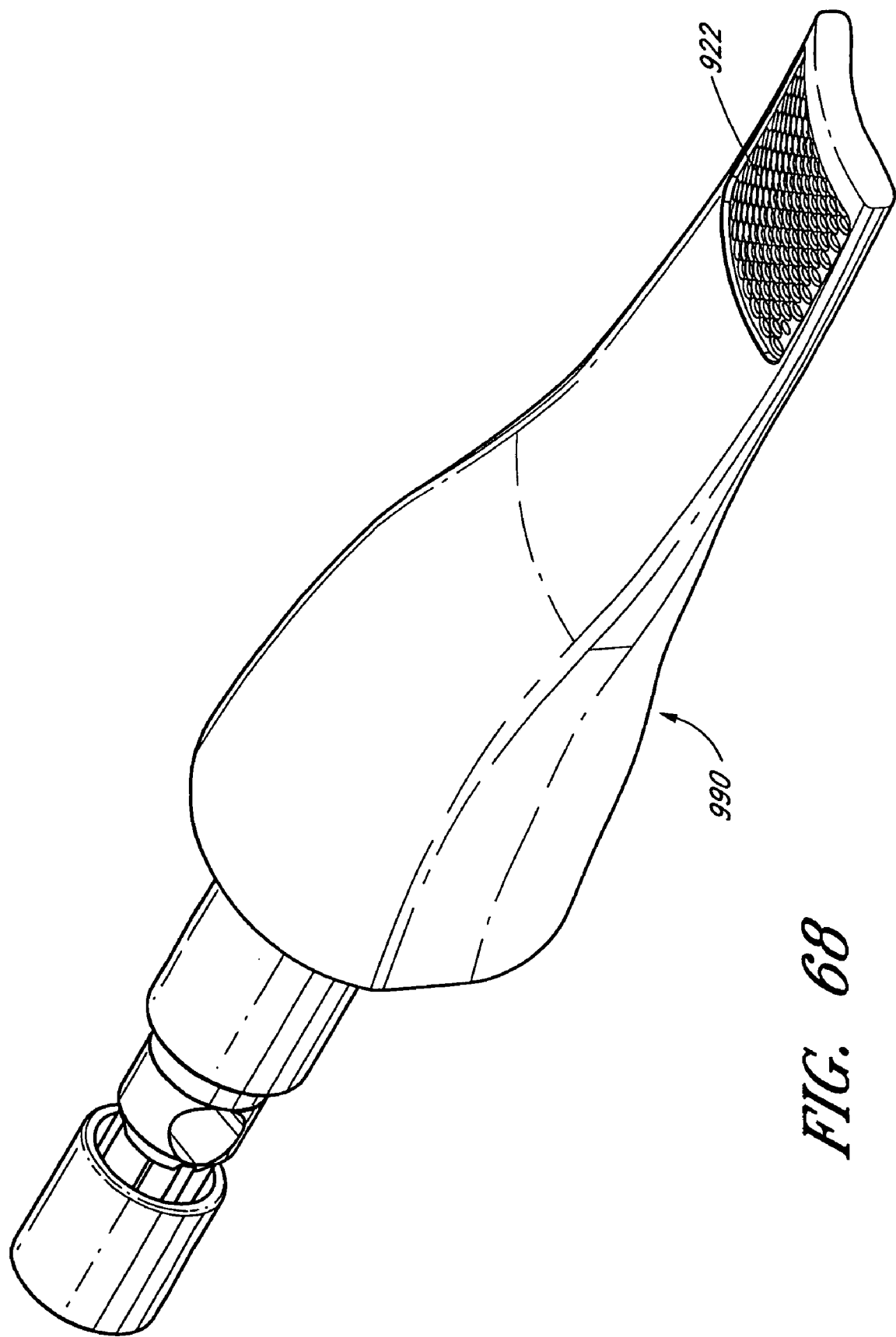
FIG. 68 is a perspective view of a distal tip assembly in accordance with another embodiment.

FIG. 68 illustrated another distal tip assembly. The illustrated distal tip assembly 990 has a cutting blade 992 that is somewhat recessed. The distal tip assembly 990 may or may not have a handle depending on its intended use. The illustrated distal tip assembly 990 does not have a handle and has a low profile configuration.

Advantageously, a single handpiece or handle assembly can be used with more than one distal tip assembly. During a single surgical procedure, the surgeon can use a plurality of distal tip assemblies to perform specific procedures. Thus, various portions of a patient's body can be treated without the need of several handpieces.

Figure 69:
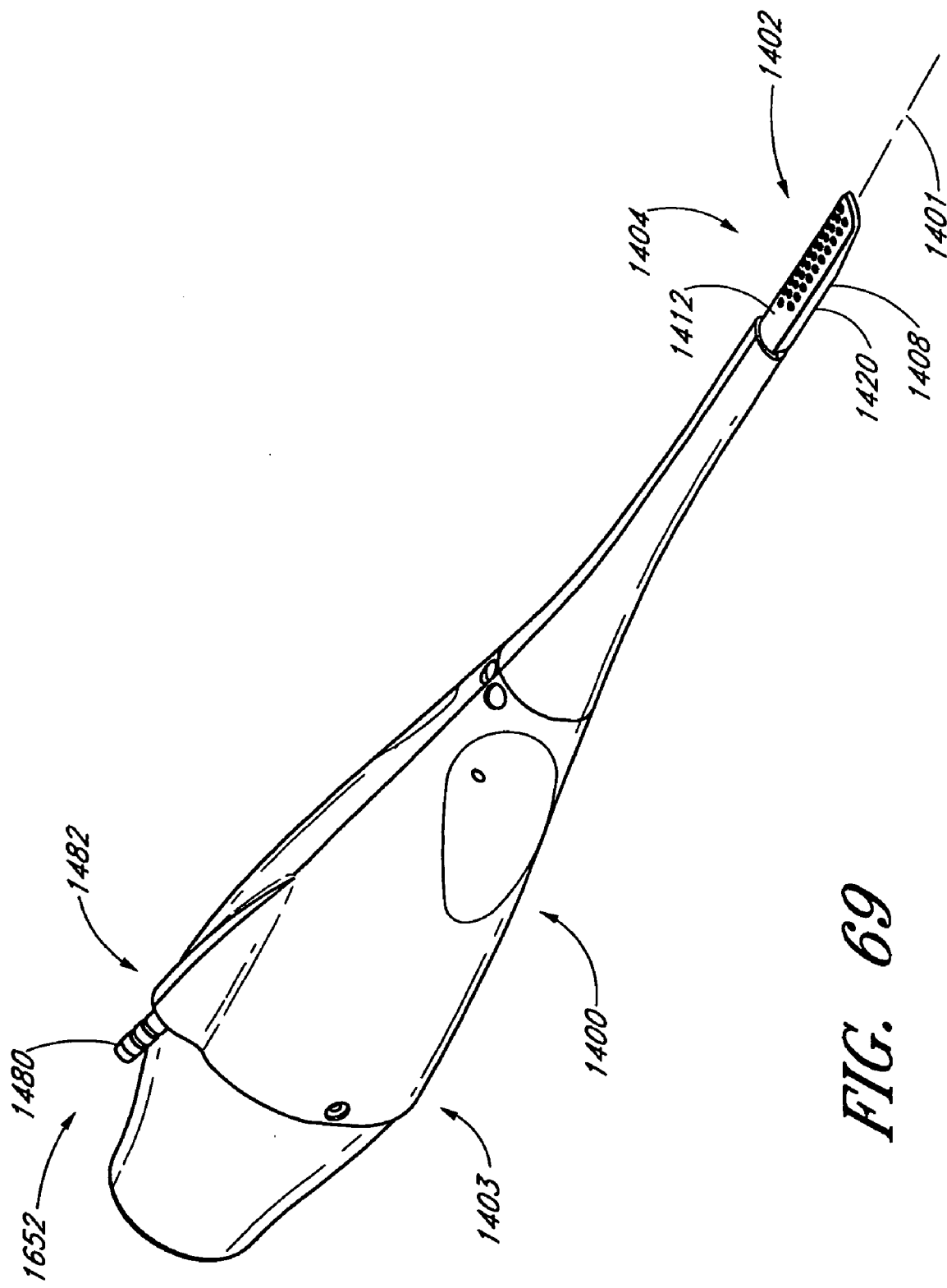
FIG. 69 is a perspective view of a surgical instrument in accordance with another embodiment.

FIG. 69 shows another embodiment of a surgical instrument. The surgical instrument 1400 can be generally similar to the embodiments described above, except as detailed below. Generally, the surgical instrument 1400 can be used to remove tissue, such as unwanted bony overgrowth of the spine. Bony overgrowths can affect the neural foramen and can cause nerve root compression. The illustrated instrument 1400 is well suited for treating this type of nerve compression, although the instrument can be used to treat other conditions.

The distal tip assembly 1402 extends from a handle assembly 1403 and has a long axis 1401. Generally, the distal tip assembly 1402 comprises a distal tip portion 1404 that includes a cutting implement or filing blade 1412 (e.g., the blade of the blade assembly shown in FIG. 48).

The distal tip portion 1404 preferably comprises the blade 1412 that overlays at least a portion of a lower blade structure 1420. The blade 1412 is preferably slidably coupled with the lower blade structure 1420. The illustrated distal tip portion 1404 preferably forms an atraumatic tip. In some embodiments, the atraumatic tip is configured to engage a patient's body without causing traumatic injury. Such atraumatic tip can be a generally blunt tip, although the atraumatic tip can have any suitable design for minimizing trauma to a patient. The shape and configuration of the atraumatic distal tip portion 1404 can be chosen based on the application of the surgical file instrument 1400. In some embodiments, however, the distal tip portion may not comprise an atraumatic tip. For example, the distal tip portion may form a cutting edge for severing tissue. Thus, both sides of the distal tip portion 1404 can be used to perform a procedure on a patient.

A shield 1408 can be formed by a lower portion of the lower blade structure 1420. The blade 1412 can be positioned on one side of the distal tip portion 1404 and the shield 1408 can be positioned on the opposing side of the distal tip portion 1404. The blade 1412 can be movably mounted to the lower blade structure 1420 to provide cutting action. The exposed portion of the blade 1412 is unrestrained by the lower blade structure 1420. Irrigation of a surgical site can be provided via the distal tip portion 1404, as detailed below. Additionally, the distal tip portion 1404 can also have one or more inlet ports for tissue removal, although not illustrated.

FIGS. 70-71 are elevation views of the instrument 1400 that has the blade 1412 having a similar shape to the lower blade structures 1420. The lower blade structure 1420 can have an average width that is similar to the average width of the blade 1412. An outer periphery 1493 of the blade 1412 can have a similar shape as a periphery 1405 of the lower blade structure 1420. Thus, the overall shapes of the blade 1412 and lower blade structure 1420 can be similar to one another, as viewed from above.

FIG. 72A is a cross-sectional view of the instrument 1400 taken along the line 72A-72A of FIG. 71. A lower surface 1415 of the blade 1412 can mate with an upper face 1416 of the lower blade structure 1420. The blade 1412 preferably extends longitudinally along the upper face 1416.

The blade 1412 can extend laterally across a substantial portion of the distal tip portion 1404. In some embodiments, the average width, $W_b$, of the blade 1412 is at least 50%, 60%, 70%, 80%, 90%, or 95% of the average width, $W_{dt}$, of the shield 1408, lower blade structure 1420, and/or upper face 1416. In the illustrated embodiments, the blade 1412 has a width that is substantially similar to the width of the lower blade structure 1420. The lower blade structure 1420 has the upper face 1416 (see FIGS. 73 and 74) that mates with the blade 1412. In non-limiting embodiments, the width of the blade 1412 is equal to or less than the width of the upper face 1416. In some embodiments, the width of the blade 1412 is at least about 95%, 90%, 85%, 85%, and ranges encompassing such percentages of the width of the upper face 1416. In one exemplary non-limiting embodiment, the width of the blade 1412 is at least about 95% of the width of the upper face 1416. In another exemplary non-limiting embodiment, the width of the blade 1412 is at least about 80% of the width of the upper face 1416.

The blade 1412 can have a shape that is generally similar to the shape of the upper face 1416 of the lower blade structure 1420. In the illustrated embodiment, the blade 1412 and the upper face 1416 of the lower blade structure 1420 have a curved shape. However, the blade 1412 can have other suitable shapes for cutting tissue. For example, the blade 1412 can have a substantially arcuate, U-shaped, V-shaped, curved, linear, polygonal, combinations thereof, or any other suitable cross-sectional profile. Although not illustrated, the blade 1412 can have a generally U-shaped cross-sectional profile and can extend vertically along both sides of the lower blade structure 1420.

When the blade 1412 is utilized to treat tissue, the lower blade structure 1420 may not limit cutting of the blade 1412. That is, the lower blade structure 1420 preferably does not extend laterally from the blade 1412 to limit appreciably the vertical movement of the blade 1412 into tissue. Of course, the lower blade structure 1420 can extend slightly from the blade 1412 without appreciably limiting the vertical cutting ability of the blade 1412. Additionally, if the lower blade structure 1420 extends laterally from the blade 1412, the blade 1412 can be moved horizontally (e.g., the blade 1412 can be slid across tissue) for effective cutting action of the surgical file instrument 1400.

Figure 73:
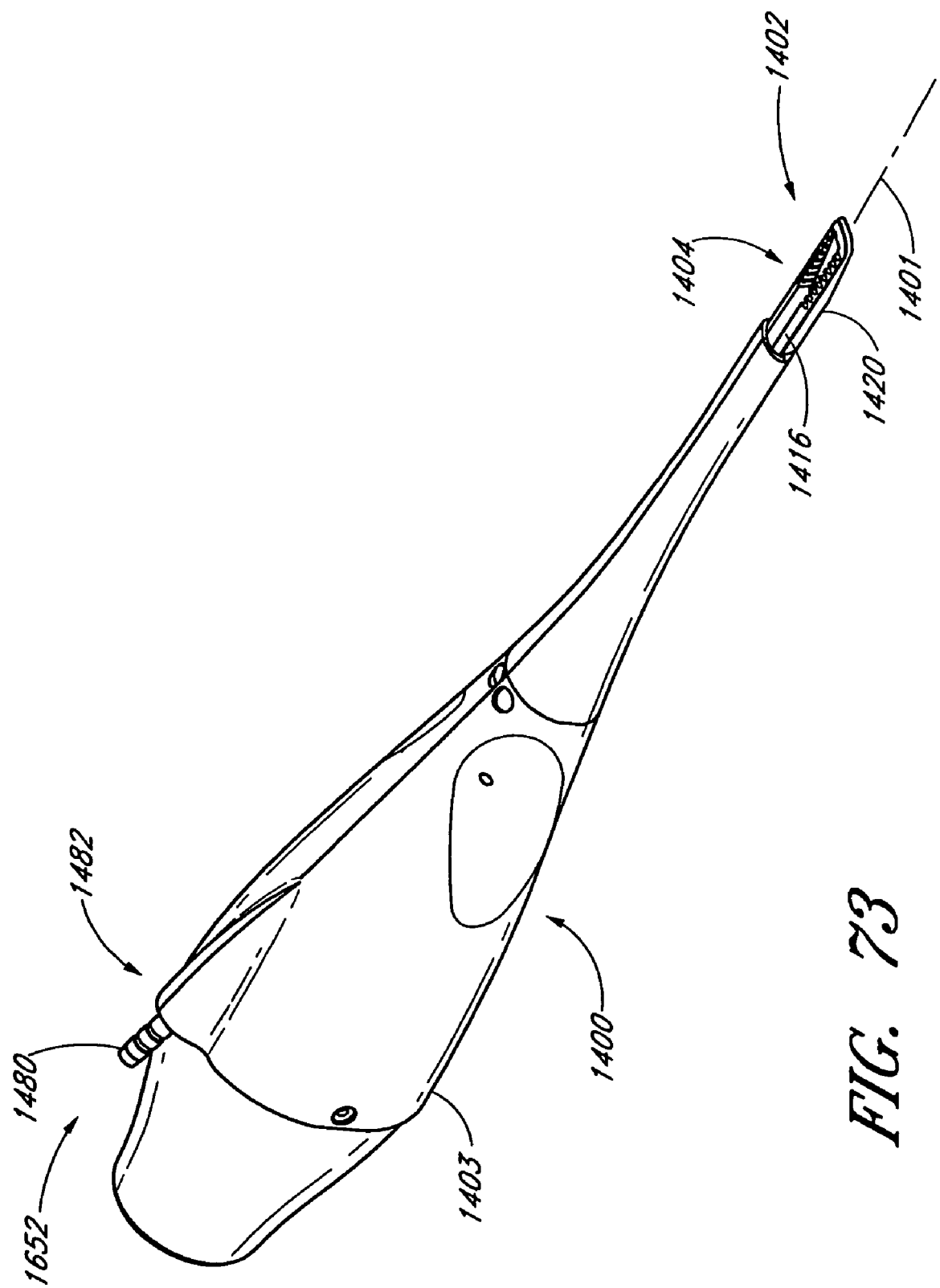
FIG. 73 is a perspective view of the surgical instrument of FIG. 69. A blade of the instrument has been removed.
Figure 74:
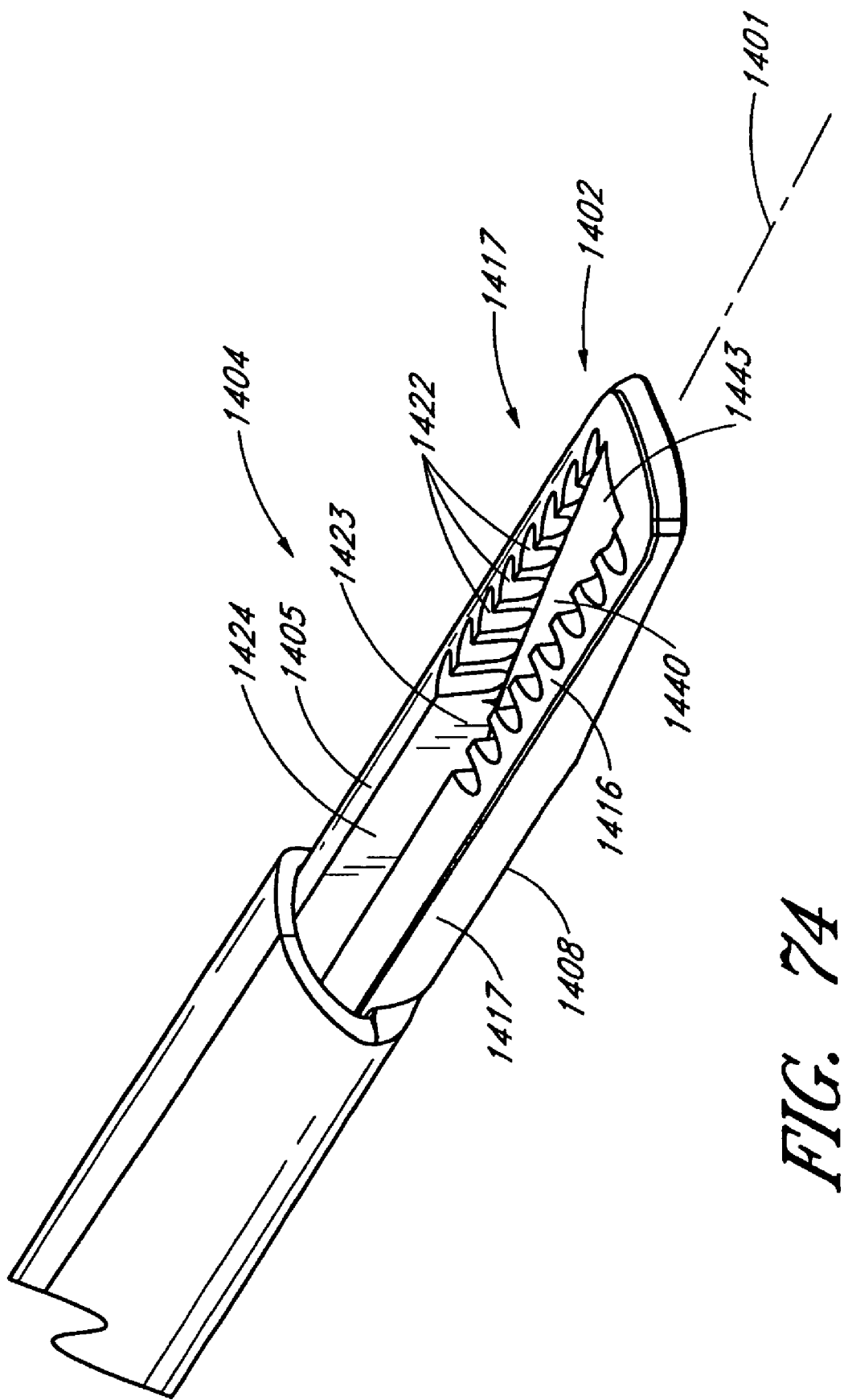
FIG. 74 is a perspective view of a distal end of the surgical instrument of FIG. 73.

FIGS. 73 and 74 illustrated the distal tip assembly 1402 with the blade 1412 removed. The lower blade structure 1420 has a long axis 1401 and the upper face 1416 extending between a first lateral side 1417 and an opposing second lateral side 1419 (see FIG. 72). The device 1400 has an irrigation system 1417 having a fluid delivery channel system 1423 of the lower blade structure 1420. The delivery channel system 1423 extends longitudinally along the upper face 1416.

The delivery channel system 1423 can cooperate with the blade 1412 to expel irrigation fluid. The delivery channel system 1423 includes an elongate delivery channel 1424 and a plurality of side delivery channels 1422. The elongate delivery channel 1424 can be in communication with an irrigation fluid source via an inlet connector 1480 of an adapter 1652 (see FIG. 71). Irrigation fluid can flow through the handle assembly 1403, the delivery channel system 1423, and ultimately out of the distal tip portion 1404.

With respect to FIG. 74, the elongate delivery channel 1424 can be sloped in the distal direction. In the illustrated embodiment, a bottom surface 1440 of the elongate delivery channel 1424 is sloped towards the upper surface 1416 in the distal direction. The elongate delivery channel 1424 can have a generally uniform or varying width along its length. The illustrated elongate delivery channel 1424 has a generally constant width and has a generally flat bottom surface 1440, although the bottom surface 1440 can have other configurations. Although not illustrated, the elongate delivery channel 1424 can have a generally uniform height and can have any suitable cross-section for delivering fluid to the channels 1422. For example, the elongate delivery channel 1424 can have a generally U-shaped, V-shaped, semi-circular, or curved axial cross-section.

The channels 1422 are spaced along a portion of the lower blade structure 1420 and are in fluid communication with the elongate delivery channel 1424. The elongate delivery channel 1424 is interposed between two rows of channels 1422. Any suitable number of channels 1422 can be positioned along the distal tip portion 1404. In the illustrated embodiment, eight channels 1422 are positioned on either side of the elongate delivery channel 1424. Each channel 1422 can have a generally semi-circular shape, polygonal shape (including rounded polygonal), or other shape suitable for delivering fluid out of the distal tip portion 1404. The channels 1422 can be depressions formed in the lower blade structure 1420. The number, sizes, and configurations of the channels 1422 can be selected to achieve the desired fluid flow out of the distal tip portion 1404. When the blade 1412 mates with the upper surface 1416, at least one of the channels 1422 can be covered by the blade 1412. The side delivery channels 1422 can be formed by any suitable process, such as by a molding process (e.g., an injection molding process), cutting or machining process, or other suitable manufacturing process.

Figure 75:
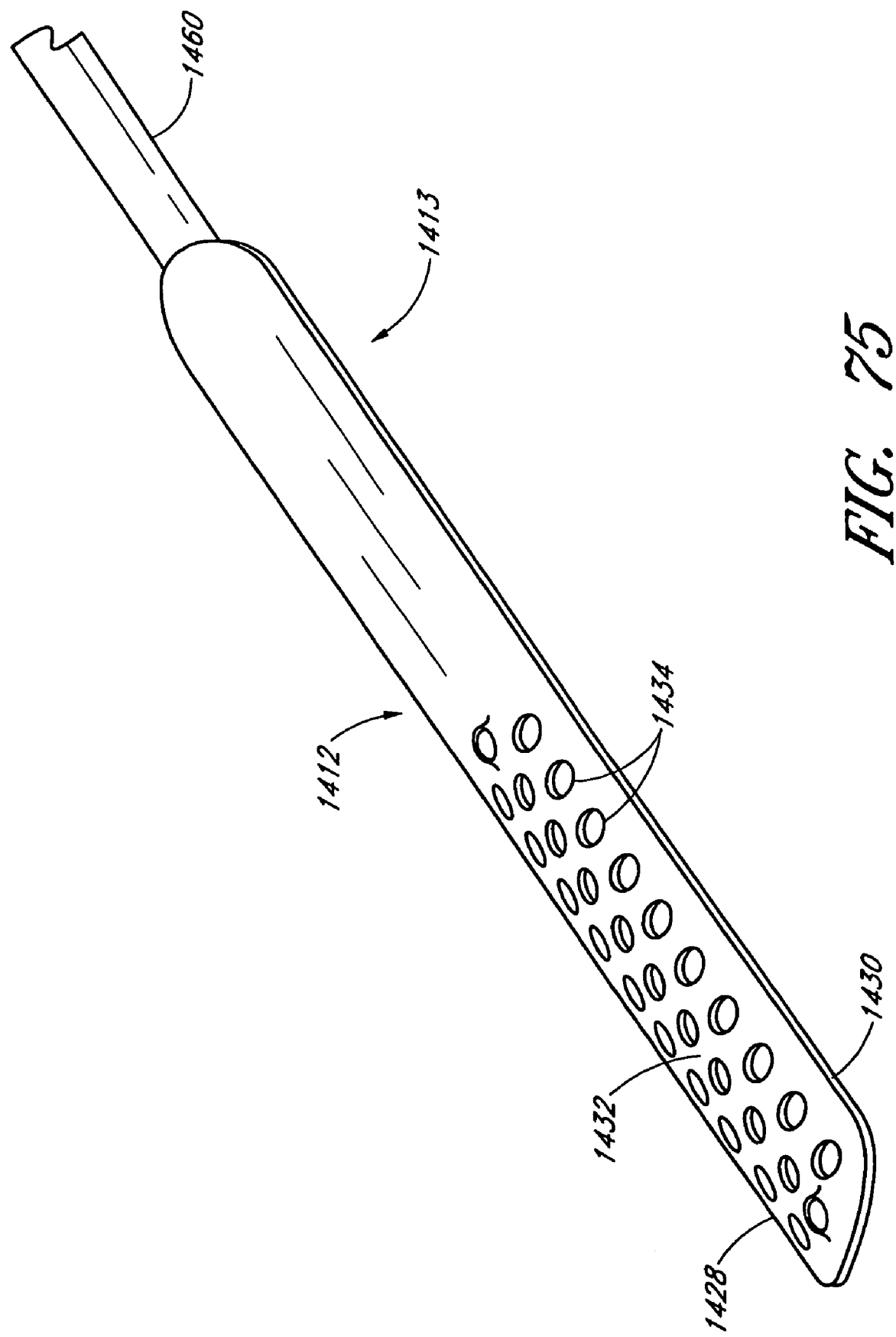
FIG. 75 is a perspective view of a blade assembly of the surgical instrument of FIG. 69.

FIG. 75 illustrates the blade assembly 1413 having the blade 1412 connected to an elongated body 1460. The blade 1412 can comprise a cutting zone or cutting surface 1432 configured to remove tissue as the blade 1412 is actuated. In some embodiments, the cutting zone 1432 comprises a plurality of cutting members, cutting teeth, sharp edges, and combinations thereof. The blade 1412 can have a first blade edge 1428 and a second blade edge 1430. The illustrated first blade edge 1428 and the second blade edge 1430 are free edges that are not restrained by the lower blade structure 1420. The cutting zone 1432 can be positioned between the blade edges 1428, 1430. The blade 1412 can be perforated for providing fluid flow therethrough. The illustrated cutting zone 1432 comprises an array of throughholes 1434. In some embodiments, at least one throughhole 1434 is positioned near the first blade edge 1428 and at least one throughhole 1434 is positioned near the second blade edge 1430. The throughholes 1434 can be positioned near the sides of the cutting zone 1432. Any number of throughholes 1434 can be positioned along the cutting zone 1432. The cutting zone 1432 can have a transverse width that is similar to, less than, or greater than a transverse width of the blade 1412.

In some embodiments, a plurality of throughholes 1434 is positioned near the first blade edge 1428 and a plurality of throughholes 1434 is positioned near the second blade edge 1430. In some embodiments, at least one throughhole 1434 is positioned near the first lateral side 1417 and at least one throughhole 1434 is positioned near the second lateral side 1419 of the lower blade structure 1420. For example, in the embodiment of FIG. 72A, the plurality of throughholes (e.g., cutting elements having a throughhole) is positioned near the first lateral side 1417 and a plurality of throughholes is positioned near the second lateral side 1419 of the lower blade structure 1420. The throughholes 1434 can be evenly or unevenly spaced along the cutting zone 1432.

Figure 76:
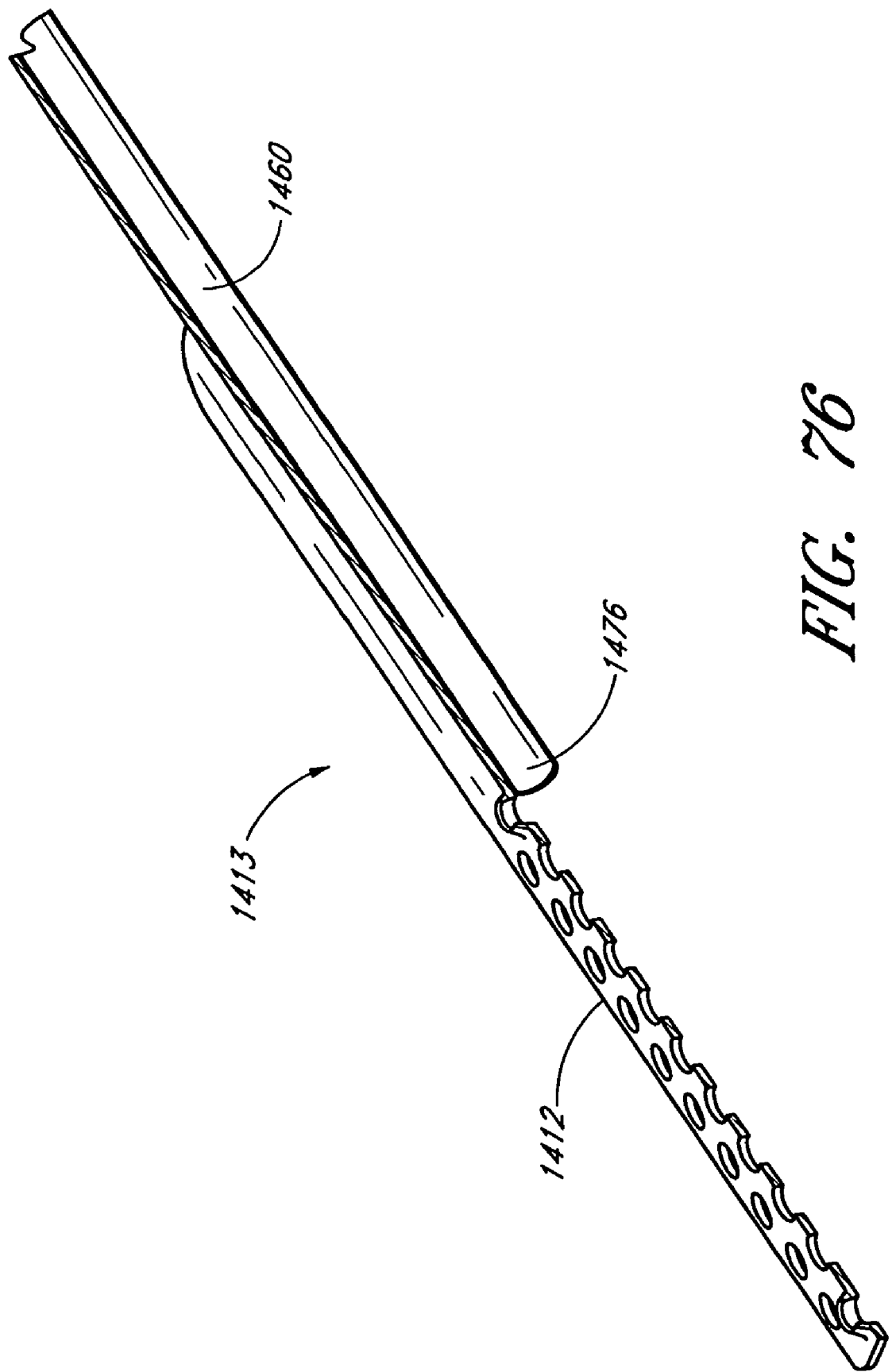
FIG. 76 is a longitudinal cross-sectional view of the blade assembly of FIG. 75.

With respect to FIG. 76, the blade assembly 1413 can be actuated linearly by the elongated body 1460 in the form of a drive member. The drive member 1460 can be temporarily or permanently coupled to the blade 1412. The blade 1412 can be used for a single procedure, or a plurality of procedures. In some embodiments, the blade assembly 1413 is disposable and can be easily replaced with a new blade assembly after use. Alternatively, the blade assembly 1413 can be a non-disposable component configured for one or more procedures. Any suitable attachment means, such as welding, mechanical fasteners, adhesives, or the like can be used to attach the blade 1412 to the drive member 1460.

In some embodiments, the drive member 1460 is operatively coupled to the blade 1412 by a plurality of welds. The welds can have significant structure integrity and reliability. The blade assembly 1413 can comprise one or more of the following: metals (e.g., titanium, aluminum, steel and its alloys, such as stainless steel), plastics, polymers, ceramics, composites, and combinations thereof. Alternatively, the blade assembly 1413 can have a one-piece construction. For example, the blade assembly 1413 can be monolithically formed through a machining or molding process. Thus, the blade assembly 1413 can have a one-piece or multi-piece construction.

Figure 78:
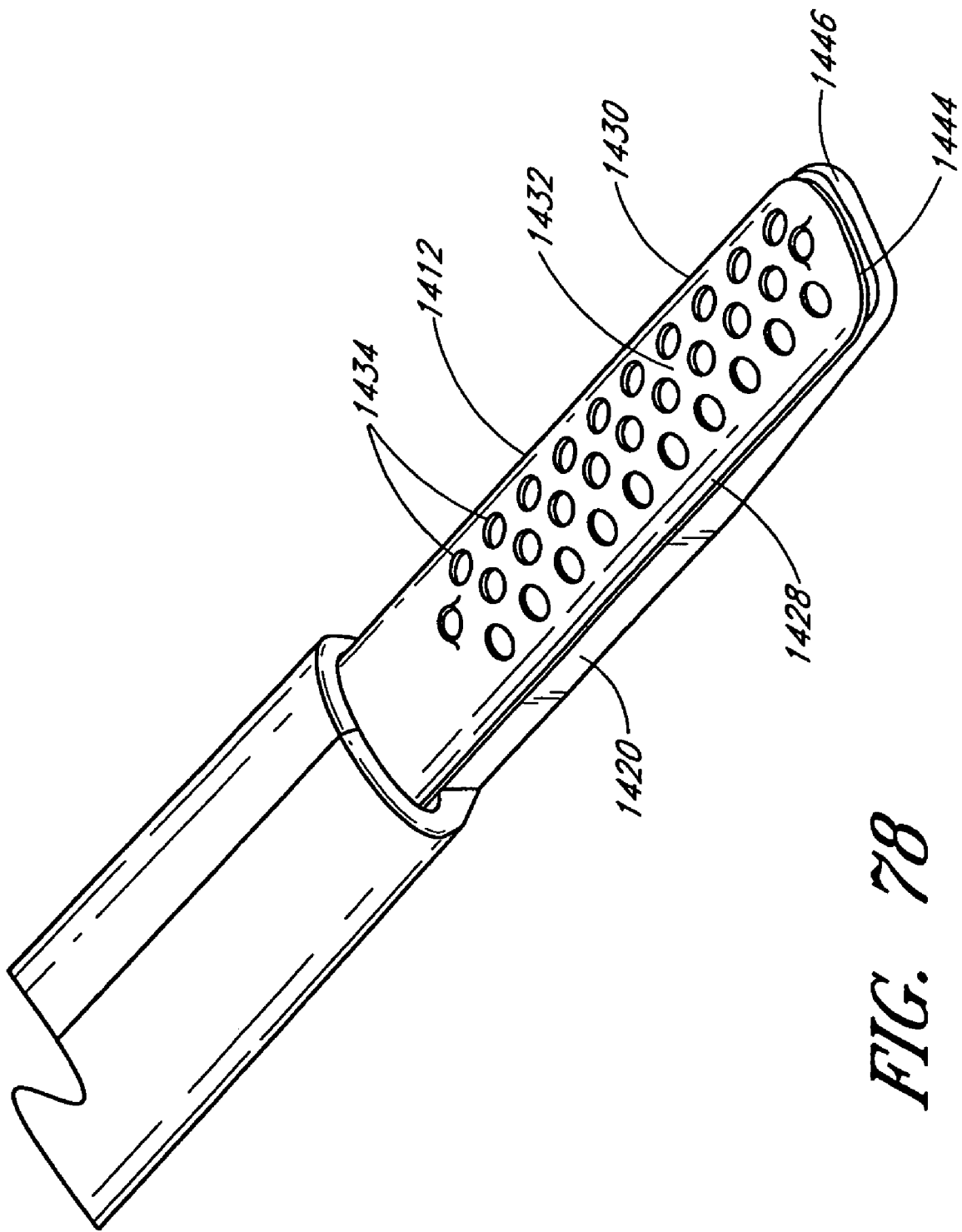
FIG. 78 is a perspective view of the distal end of the surgical instrument of FIG. 69 having a blade in a distal position.
Figure 79:
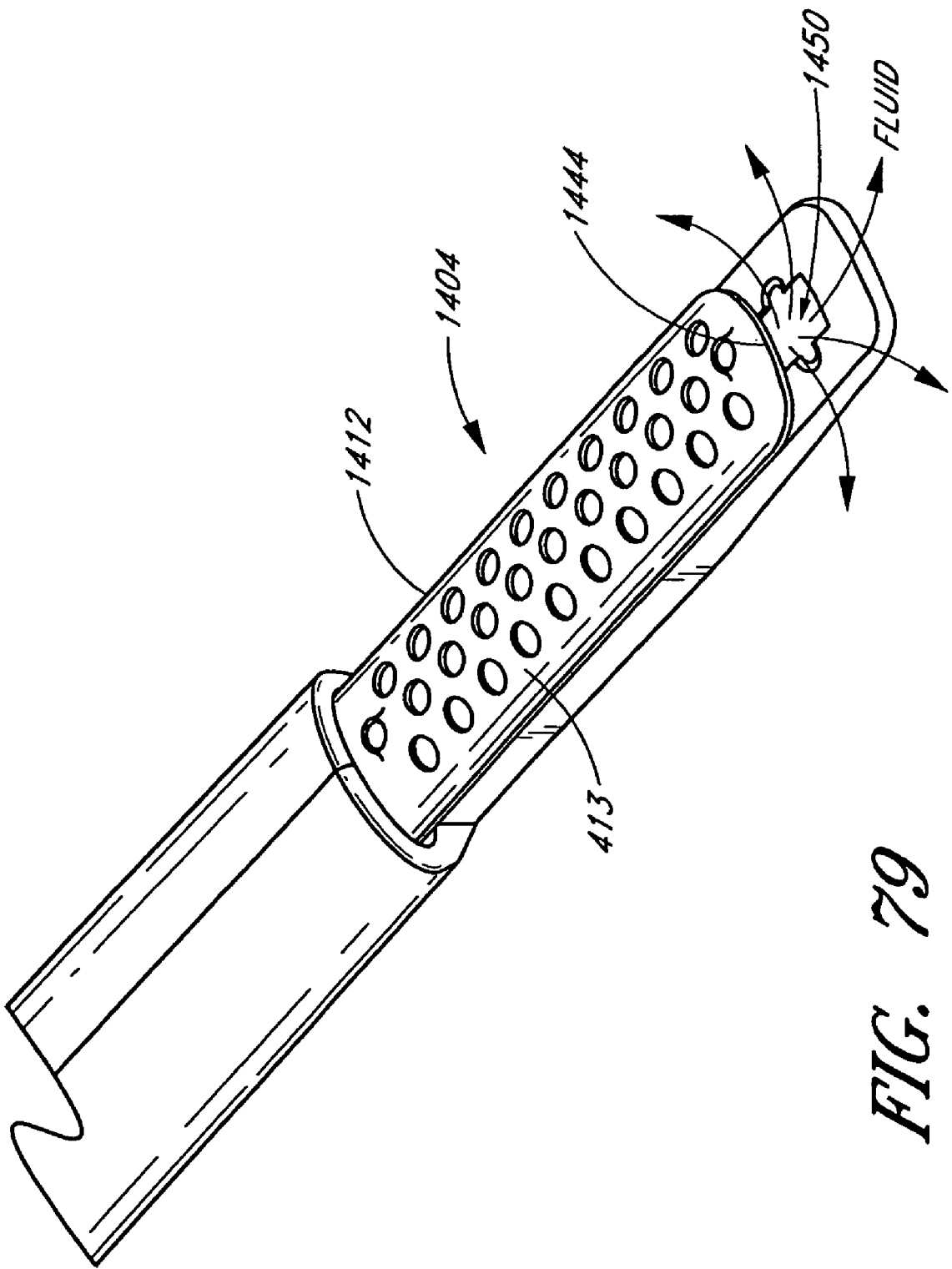
FIG. 79 is a perspective view of the distal end of the surgical instrument of FIG. 69 having the blade in a proximal position.

The blade 1412 is preferably movable between a distal position (FIGS. 77-78) and a proximal position (FIG. 79). The blade 1412 can be rapidly reciprocated between the distal position and the proximal position to remove tissue. In non-limiting embodiments, the blade 1412 can be actuated 1,000 times/min., 2,000 times/min., 3,000 times/min., or 4,000 times/min. The blade 1412 can also be actuated at other rates. As the blade 1412 slides along the lower blade structure 1420, at least some of the throughholes 1434 of the blade 1412 can be matched and unmatched with the channels 1422 to provide pulse irrigation. In some embodiments, a substantial number or all of the throughholes 1434 can cooperate with the elongate delivery channel 1424 to provide pulse irrigation. The illustrated blade 1412 and the lower blade structure 1420 can cooperate to provide pulsatile flow even if the fluid is delivered to the distal tip at a constant or varying pressure.

Figure 77:
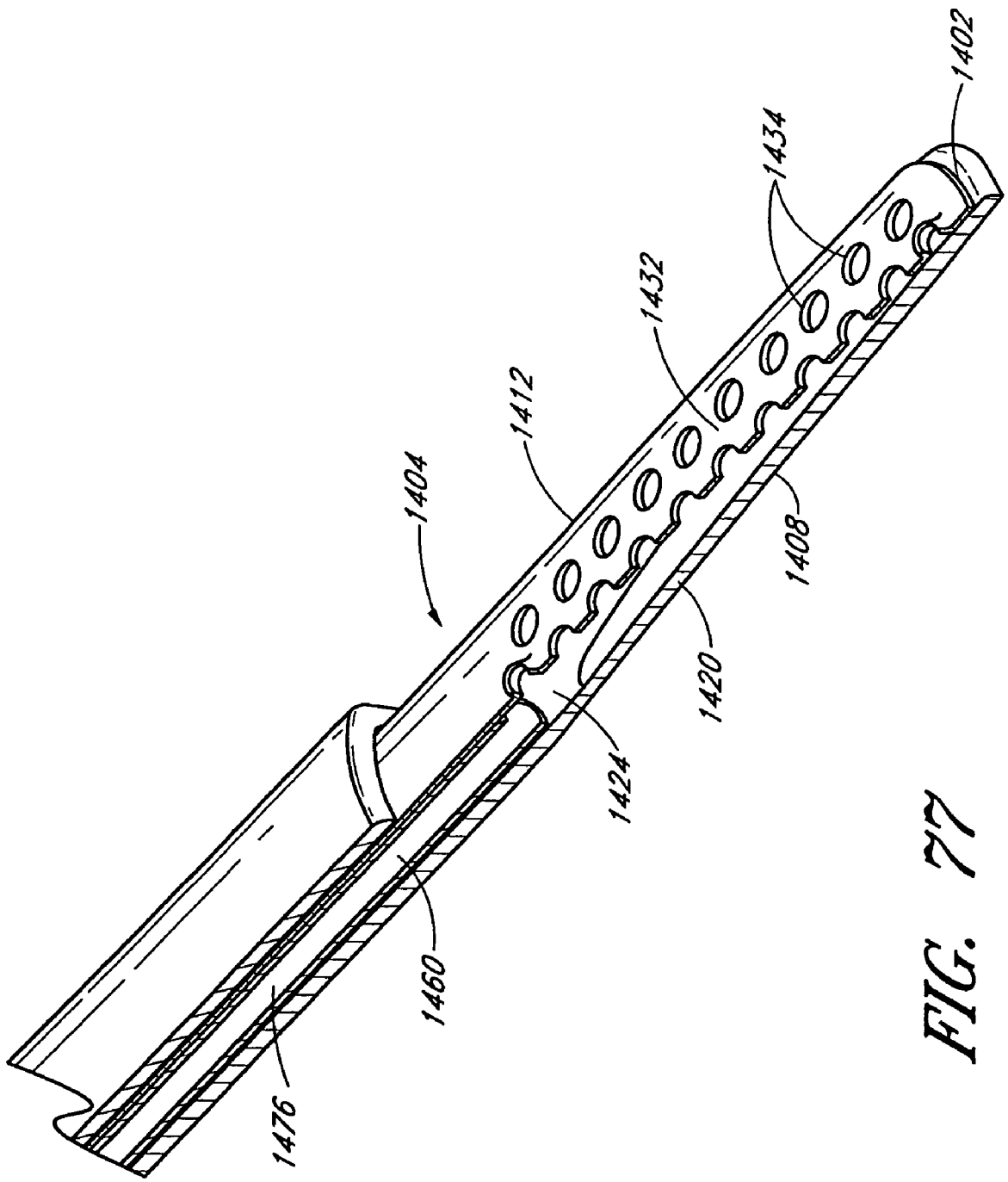
FIG. 77 is a longitudinal cross-sectional view of the distal end of the surgical instrument of FIG. 69.

Any number of the throughholes 1434 can be positioned over the elongate delivery channel 1424. As shown in FIG. 77, a series of throughholes 1434 is adjacent the elongate delivery channel 1424. Thus, some of the throughholes 1434 can be periodically aligned with the channels 1422 while at least some of the throughholes 1434 can be disposed over the elongate delivery channel 1424. As such, some of the throughholes 1434 can provide pulse irrigation while other throughholes 1434 can provided somewhat continuous irrigation.

In the illustrated embodiment of FIG. 77, a center row of throughholes 1434 is constantly fed irrigation fluid. The fluid can be provided at a generally constant or varying pressure, although the irrigation fluid can be provided at any pressure depending on the application. In some embodiments, the center row of throughholes 1434 is fed irrigation fluid at varying pressures, preferably delivered in synchronization with the reciprocating rate of the blade 1412. However, the irrigation fluid can be delivered in other relationships with the movement of the blade 1412. The pressurized irrigation fluid can be delivered at varying rates to create an enhanced cleaning action to keep the cutting zone 1432 clean and to remove tissue debris.

The centrally disposed throughholes 1434 can remove a substantial portion or most of the debris material and therefore may need constant fluid flushing. The flushing can be accomplished by variations in the pressure and flow rate of the irrigation fluid. The laterally offset throughholes 1434 may remove less material during operation and can also benefit from variations in irrigation flow. In some embodiments, the nearly on and nearly off flow of the irrigation fluid effectively cleans the laterally offset throughholes 1434. The variations in irrigation fluid temperature, flow rates, and pressure can be chosen to clean effectively tissue debris from the blade 1412.

The irrigation fluid can also be used to control the temperature of at least a portion of the distal tip portion 1404. For example, the frictional interaction between the blade 1412 and the lower blade structure 1420 can cause localized heating at the interface of the blade 1412 and the upper surface 1416. During operation, the irrigation fluid can be at a relatively low temperature and used to absorb heat generated by the frictional interaction. Accordingly, heat can be transferred to the irrigation fluid which then carries the heat away from the distal tip portion 1404 to cool the components of the distal tip portion 1404. In some cases, the irrigation fluid can be a chilled fluid to ensure that the distal tip portion 1404 is maintained below a target temperature. The irrigation fluid can be heated/cooled as desired.

Irrigation fluid can function as a lubricant for the interface between the moving blade 1412 and the stationary lower blade structure 1420. The irrigation fluid can thus be used to clean the blade 1412 and transport the cut tissue away while also lubricating the distal tip portion 1404. The lubricant irrigation fluid can minimize wear of one or more components of the surgical file instrument 1400.

FIG. 78 illustrates the blade 1412 in a distal position. When the blade 1412 occupies the distal position, the distal end 1444 of the blade 1412 is preferably proximate to a distal end 1446 of the lower blade structure 1420. The blade 1412 can be actuated proximally along the lower blade structure 1420 to a proximal position shown in FIG. 79. When the blade 1412 occupies the proximal position, the distal end 1444 is preferably distanced from the distal end 1446 such that at least a portion of the delivery channel system 1423 is exposed. In some embodiments, the blade 1412 is moved laterally and/or longitudinally between two or more positions, if needed or desired.

With respect to FIG. 79, when the blade 1412 occupies a proximal position, the blade 1412 and the lower blade structure 1420 cooperate to define a window 1450. A fluid can be expelled through the window 1450. The irrigation fluid delivered from the window 1450 can be used to dislodge and flush tissue debris from the distal tip portion 1404, as well as for irrigating the surgical site. As the blade 1412 moves in the distal direction, the window 1450 is reduced in size. In some embodiments, when the blade 1412 reaches its distal position (FIGS. 77 and 78), the blade 1412 completely covers the elongate delivery channel 1424 thereby completely closing the window 1450. In the illustrated embodiment, the blade 1412 and the lower blade structure 1420 are configured to open and close the window 1450 repeatedly for a somewhat on and off fluid flow. The pulsing fluid flow from the window 1450 can aid in breaking up of clots and tissue debris. However, in other embodiments, the blade 1412 and the lower blade structure 1420 can be configured to provide continuous fluid flow out of the window 1450. For example, the distal end 1444 of the blade 1412 can be positioned at some point above the delivery channel system 1423 when the blade 1412 occupies its distal-most position and its proximal-most position. In such an embodiment, fluid can be continuously delivered during reciprocation of the blade 1412.

The cyclic nature of the perturbated irrigation fluid can enhance cleaning and debris removal. The frequency and magnitude of the pulsed irrigation fluid flow can be selected to achieve the desired cleaning and debris removal effect. In some embodiments, the fluid perturbations can hold the tissue debris (e.g., bone particles, cartilage, and other debris material) in suspension. The suspension can be easily removed from the surgical site. For example, the suspension can be sucked out of the surgical area by a surgical suction wand, suction tube, or other tissue or removal device. Alternatively, or in addition, the device 1400 can have a removal system for waste fluid removal. In some embodiments, for example, the device 1400 can have a removal system similar to the removal system illustrated in FIG. 51.

Figure 80:
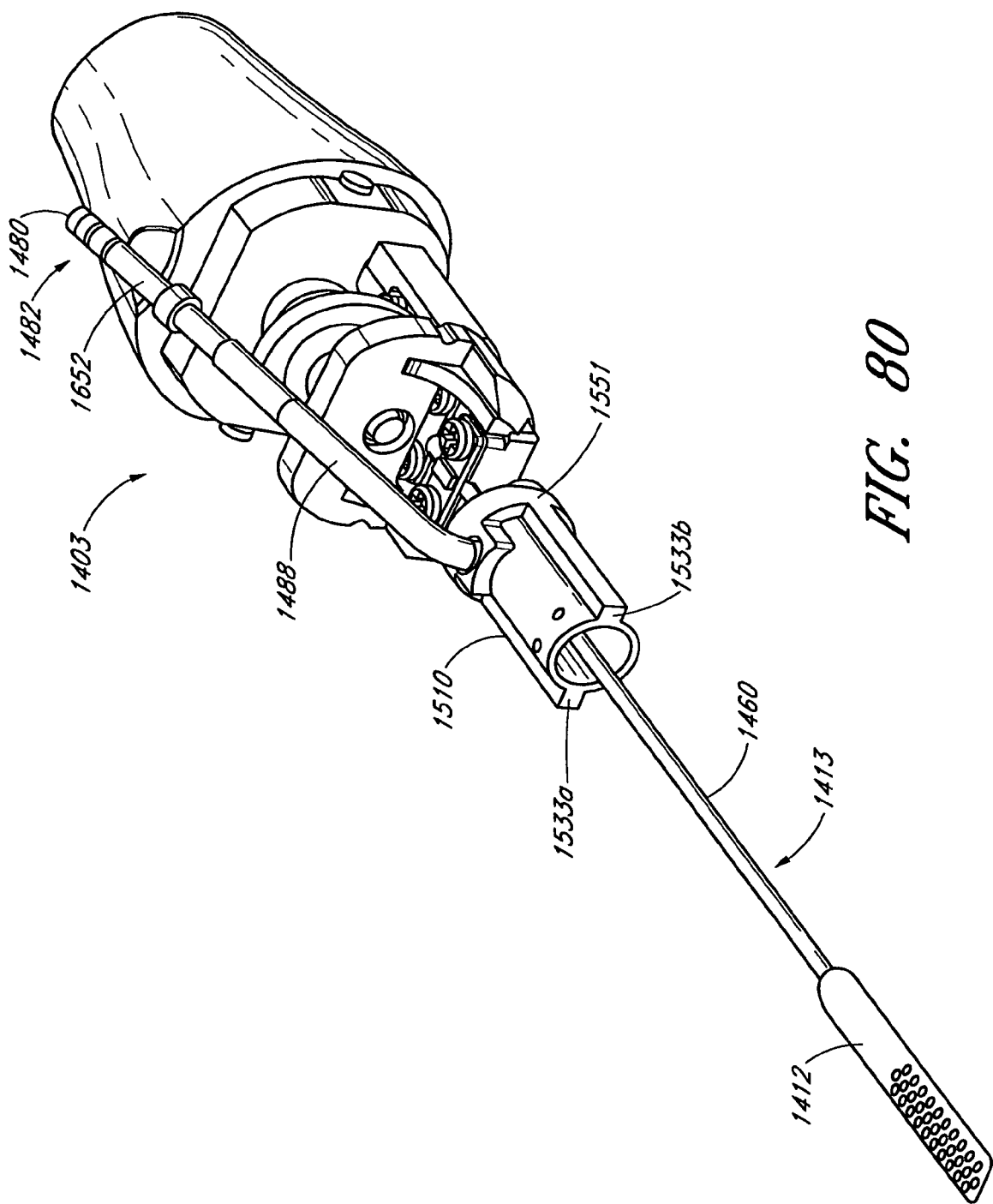
FIG. 80 is a perspective view of internal components of the surgical instrument of FIG. 69.

FIG. 80 illustrates the blade assembly 1413 connected to internal components of the handle assembly 1403. The drive member 1460 extends from the handle assembly 1403. As shown in FIG. 77, the drive member 1460 can be a generally tubular member that defines at least one lumen 1476. As such, the drive member 1460 can have a reduced weight to therefore reduce the overall weight of the surgical file instrument 1400. The drive member 1460 can have any suitable cross-section. Exemplary drive members 1460 can have a generally circular cross-section, elliptical cross-section, polygonal (including rounded polygonal) cross-section, although the drive members 1460 can have other cross-sections depending on the application. The size and configuration of the drive member 1460 can be selected to minimize or avoid buckling, deflection, bending, and/or fatigue failure.

In some embodiments, the lumen 1476 can be in communication with the distal tip portion 1404. The lumen 1476 can be used to transport water to and/or from the distal tip portion 1404. Alternatively, the lumen 1476 can be used to provide suction to draw in material (e.g., debris and suspension) from the surgical area through the distal tip portion 1404. Any fluid (e.g., lubricants, medicants, irrigation fluid, or combinations thereof) or material can be passed through the lumen 1476 depending on the application.

Figure 81:
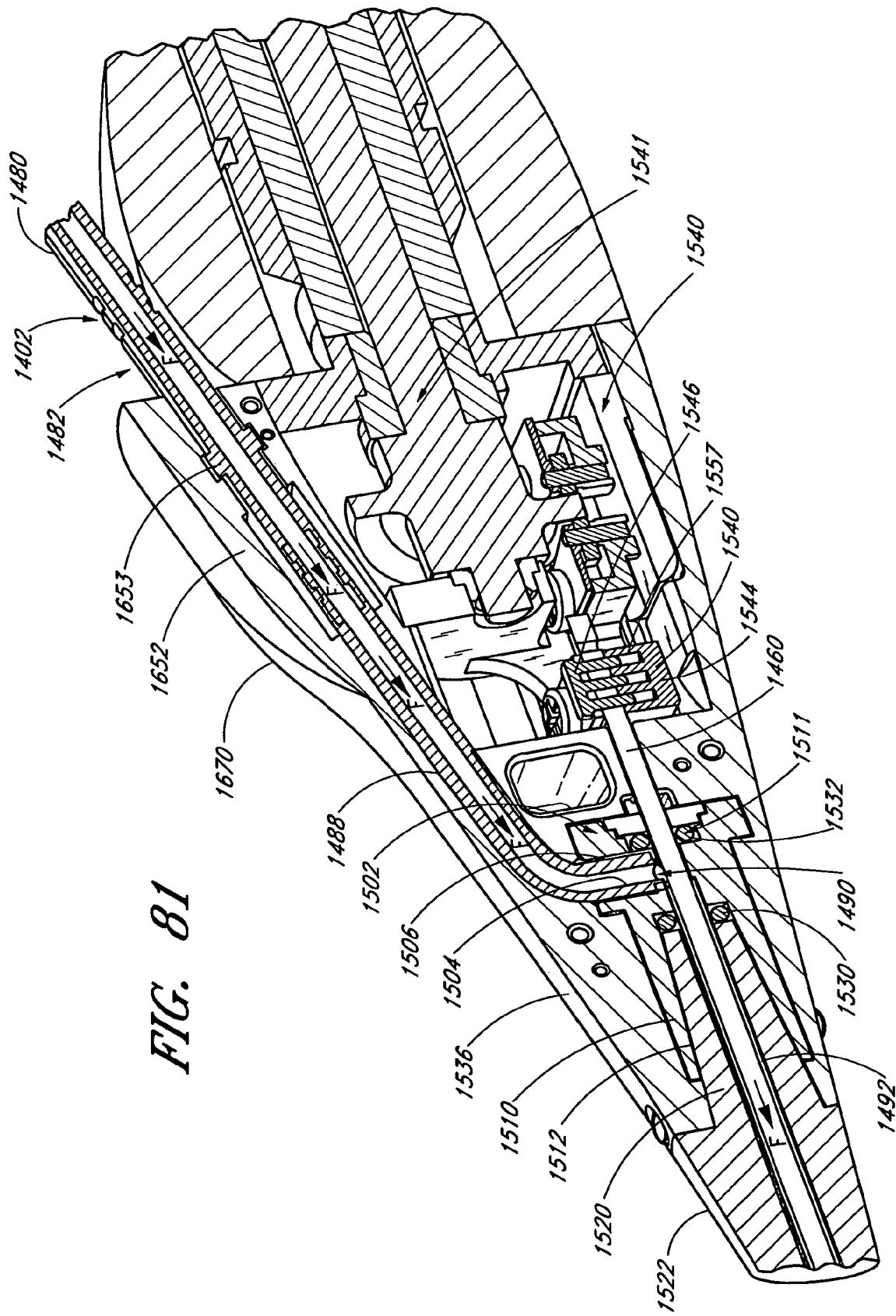
FIG. 81 is a longitudinal cross-sectional view of a portion of the surgical instrument of FIG. 69.

With respect to FIG. 81, to deliver fluid F (e.g., irrigation fluid) through the distal tip portion 1404, fluid can be delivered to the inlet port 1480 of a fluid delivery system 1482. The fluid delivery system 1482 also comprises an adapter 1652 and a fluid supply tube 1488 that connects the inlet port 1480 to the drive member 1460. The irrigation fluid can pass through the inlet port 1480 and the adapter 1652. The irrigation fluid then flows through the supply tube 1488 and eventually through the distal tip portion 1404.

The fluid F can flow distally along the supply tube 1488 and eventually to a junction 1490. The fluid F can then flow distally between a delivery tube 1492 and the drive member 1460. The drive member 1460 extends through the length of the delivery tube 1492. In some embodiments, the drive member 1460 and the delivery tube 1492 are generally concentric and define a fluid channel. The fluid channel can be defined by the outer surface of the drive member 1460 and the inner surface of the delivery tube 1492. The fluid F can flow distally through the fluid channel.

The supply tube 1488 can be made of a flexible material, such as silicon, rubber, or other suitable flexible material. However, the supply tube 1488 can also be made of generally rigid materials, such as metals or hard plastics. In the illustrated embodiment, the supply tube 1488 is connected to a coupler 1502. A distal end 1504 of the supply tube 1488 is received by a female receptor hole 1506 of the connector 1502. Preferably, a water-tight seal is accomplished by coating the supply tube 1488 with a sealant (e.g., silicon rubber sealant, gels, and the like) and inserting the distal end 1504 into the female receptor hole 1506. Additionally, one or more sealing members (e.g., annular sealing members) can be used to further seal in irrigation fluid. It is contemplated that other arrangements can be employed to connect the supply tube 1488 to the junction 1490.

Figure 82:
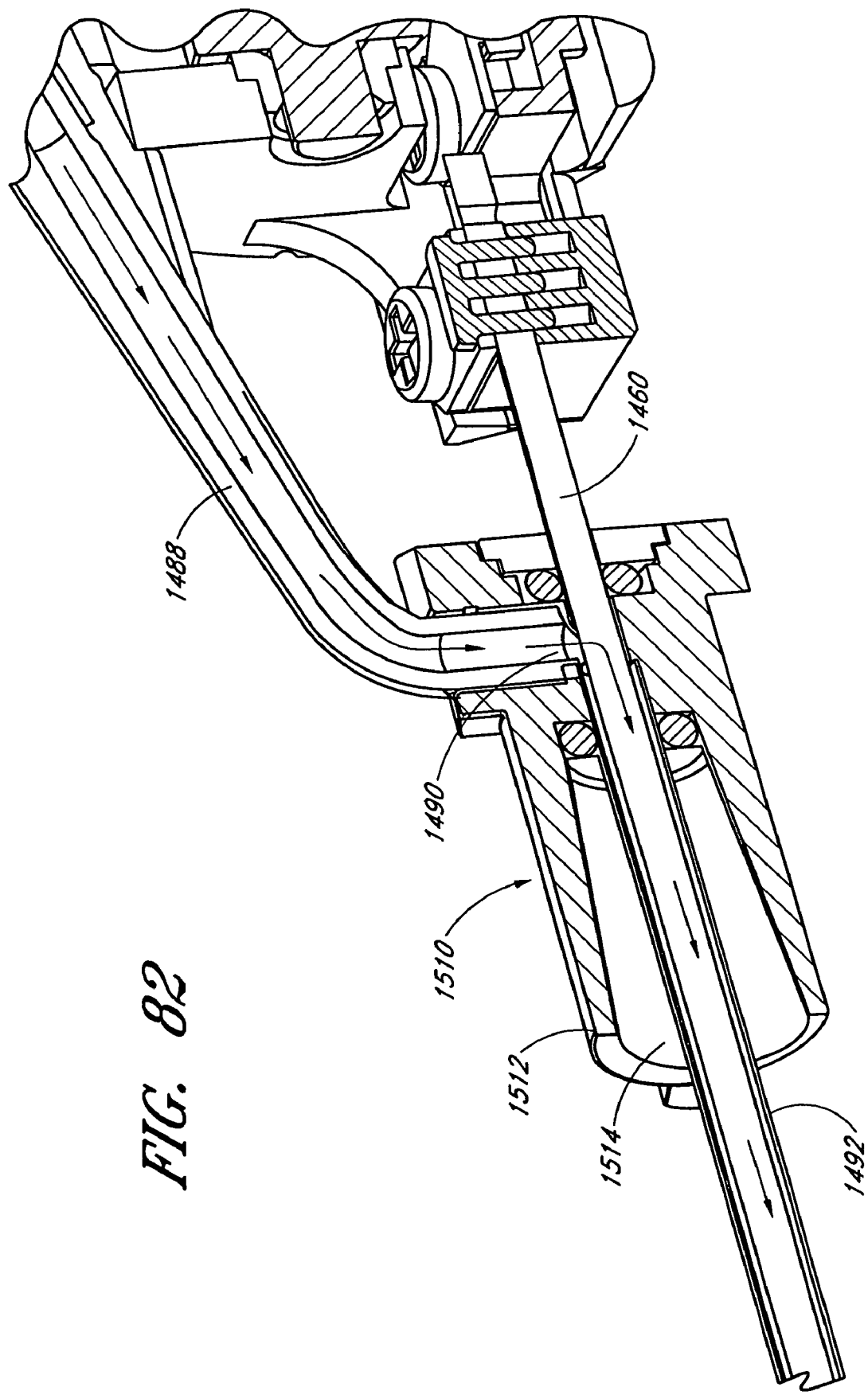
FIG. 82 is a longitudinal cross-sectional view of a portion of the surgical instrument of FIG. 69, wherein components have been removed.

In operation, as shown in FIG. 82, the fluid F flows through the junction 1490 and through a flow chamber defined by the drive member 1460 and the delivery tube 1492. The fluid F flows distally along the fluid chamber until it reaches the distal tip portion 1404 and is eventually expelled out of the surgical file instrument 1400. In some embodiments, however, the fluid F can be delivered through a lumen within the drive member 1460. For example, the fluid F can be delivered through the lumen 1476 of the drive member 1460 illustrated in FIG. 77. The drive member 1460 can be disposed in the elongated channel 1424.

With reference again to FIGS. 81 and 82, the connector assembly 1510 can hold the distal end 1504 of the tube 1488 and both the delivery tube 1492 and the drive member 1460. The connector assembly 1510 surrounds both the delivery tube 1492 and the drive member 1460. In some embodiments, the drive member 1460 extends all the way through the connector assembly 1510. The distal end 1504 of the tube 1488 is positioned within the connector assembly 1510.

The connector assembly 1510 can include a connector housing 1512 that can define a connector chamber 1514. The delivery tube 1492 and the drive member 1460 can extend centrally through the chamber 1514. In the illustrated embodiment, the chamber 1514 is tapered in the proximal direction. However, the connector chamber 1514 can have any other suitable shape and configuration depending on the application.

As shown in FIG. 81, the connector housing 1512 is configured to receive a distal tip structure proximal end 1520 of the distal tip 1522. The distal tip structure proximal end 1520 is configured to fit within the connector chamber 1514. As such, the connector chamber 1514 and the distal tip structure proximal end 1520 can have a similar shape so that the distal tip structure proximal end 1520 is tightly held by the connector housing 1512. The illustrated distal tip structure proximal end 1520 has a generally frusto-conical shape, although the distal tip can have other configurations.

The connector system 1510 can comprise a sealing system 1511 used to seal the fluid within the surgical file instrument 1400. The sealing system 1511 can comprise a plurality of sealing members that are strategically positioned at various points throughout the surgical file system 1400 to inhibit or prevent fluid from leaking. In the illustrated embodiment, the sealing system 1511 comprises a first O-ring 1530 that is positioned between the distal tip structure proximal end 1520 and the connector housing 1512. The sealing member 1530 surrounds the tube 1492 and substantially prevents fluid flow from escaping between the tube 1492 and the end 1520 and the connector housing 1512.

A second sealing member 1532 can be positioned proximal of the junction 1490. The illustrated sealing member 1532 surrounds the drive member 1460 and prevents fluid flow proximally past the sealing member 1532. The sealing members 1530, 1532 can be any suitable sealing members for containing the fluid F. For example, the sealing members can comprise one or more O-rings, gaskets, sealing gels, or other suitable sealing. structures and can comprise plastic, polymers, rubber, and the like.

The connector housing 1512 can comprise one or more ribs extending along its side. In the illustrated embodiment of FIG. 80, the connector housing 1512 comprises a pair of diametrically opposed longitudinally extending ribs 1533*a*, 1533*b*. The longitudinal ribs 1533*a*, 1533*b* can lock the connector assembly 1510 into position relative to the distal tip 1522. The ribs 1533*a*, 1533*b* can be spaced at any location along the periphery of the housing 1512. Any number of longitudinally extending ribs can be used to orient the connector assembly 1510 with the distal tip 1522. Exemplary ribs can have generally U-shaped, V-shaped, semi-circular, polygonal, or any other shaped cross-sections.

The connector housing 1512 can comprise a cylindrical collar 1551 that engages the tip 1522. The cylindrical collar 1551 can be positioned somewhat proximally along the connector housing 1512. The cylindrical collar 1551 can engage sealing members to absorb excessive linear forces, which may be due to reciprocation of the blade assembly 1413.

With reference again to FIG. 81, the surgical file instrument 1400 can comprise a drive assembly 1540. The drive assembly 1540 can comprise a shear pin 1546. The pin 1546 is configured to shear by linear forces caused by the drive plate or sled 1557 and the linear cylindrical drive shaft. The illustrated shear pin 1546 has a plurality of elements extending through the drive member 1460. The elements are movably retained in a retainer member 1544. Other retaining means can be employed to connect the drive member 1460 to the drive assembly 1540. The drive assembly 1540 can comprise a toroidal drive system or transmission, or other type of drive system. The illustrated assembly has a toroidal drive system 1541.

Figure 83:
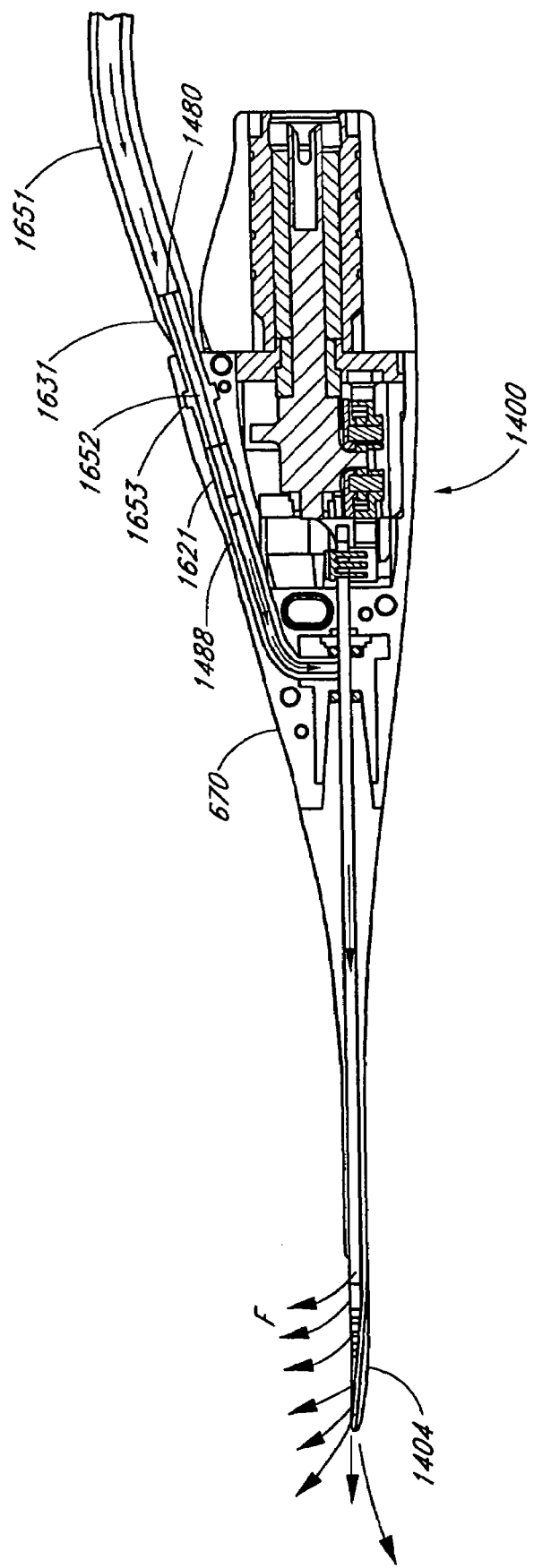
FIG. 83 is a longitudinal cross-sectional view of a portion of the surgical instrument of FIG. 69 delivering out a fluid.

FIG. 83 illustrates the instrument 1400 outputting irrigation fluid F (preferably a sterile fluid). An inlet line 1651 delivers the fluid to the surgical file instrument 1400. The fluid is transported by means of the adapter 1652 via the inlet port 1480. The adapter 1652 extends into the body housing and is in communication with the supply tube 1488. The adapter 1652 can be attached to various types of conduits or supply systems. In view of the present disclosure, the adapter 1652 can be designed to couple temporarily or permanently to the inlet line 1651. One end of the adapter 1652 is connected to the distal end 1631 of the conduit 1651. The other end of adapter 1652 is connected to a proximal end 1621 of the supply tube 1488.

Relatively large axial compressive forces can be applied to the adapter 1652, especially because of its relatively small size, when conduits are connected and disconnected. The adapter 1652 can have a fitting structure to locate the adapter 1652 relative to the outer housing 1670. The illustrated fitting feature is in the form of a cylindrical ring 1653 configured to fit within a corresponding annular recess in the outer housing 1670. The fitting structure can comprise one or more of the following: a ring, flange, recess, pin, and adhesives. The fitting structure can be positioned at any point between the ends of the adapter 1652.

The adapter 1652 operatively connects to the supply tube 1488. The fluid path continues running distally into the delivery lumen between the drive member 1460 and the delivery tube 1492. The fluid continues to flow distally until it is expelled out of the instrument 1400 at the distal tip portion 1404 and thru the tissue cutting holes. The pulsatile nature of the exiting fluid that is expelled directly thru the actual cutting teeth has several advantages. As detailed above, the fluid can cool the device mechanism or other moving components. The fluid can also lubricate the moving components of the instrument 1400. The fluid suspends the bone debris so it can be safely extracted from the tissue removal site by a surgical wand vacuum.

Figure 84:
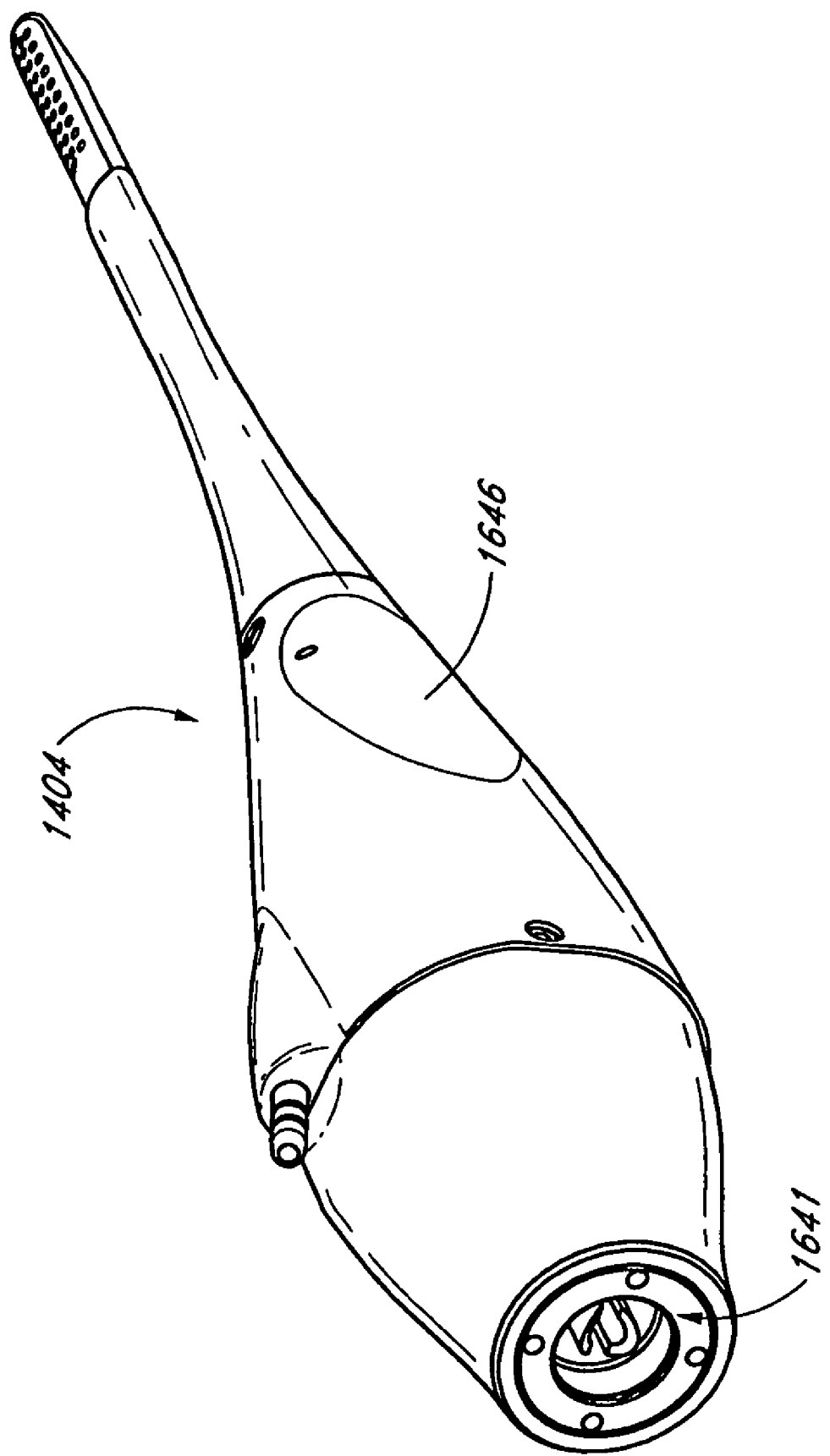
FIG. 84 is another perspective view of the surgical instrument of FIG. 69.
Figure 85:
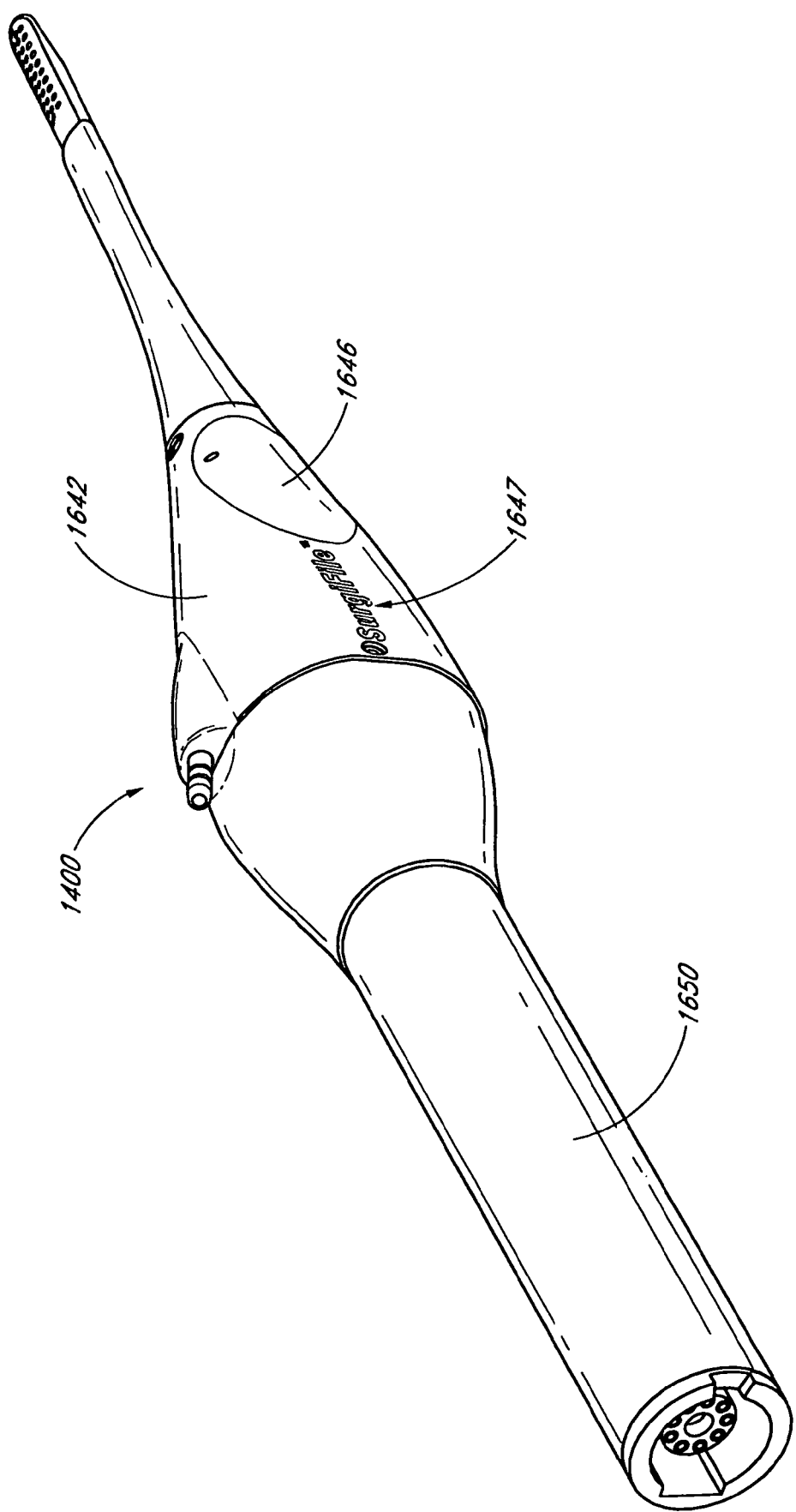
FIG. 85 is perspective view of a power device attached to the surgical instrument of FIG. 84.

With respect to FIGS. 84 and 85, a power device 1650 is connected to a proximal adapter 1641 of the surgical file instrument 1400. The surgical file instrument 1400 can be driven by various types of electrical motors, power devices and other motor systems known in the art. Power devices can be rotary devices for driving the surgical file instrument 1400. The power device 1650 can be small and light. In some cases, the small motors that can be used to power the surgical file instrument 1400 may become very hot to the touch. The surgeon can advantageously grip the surgical file instrument 1400 without touching the hot motor housing.

Figure 86:
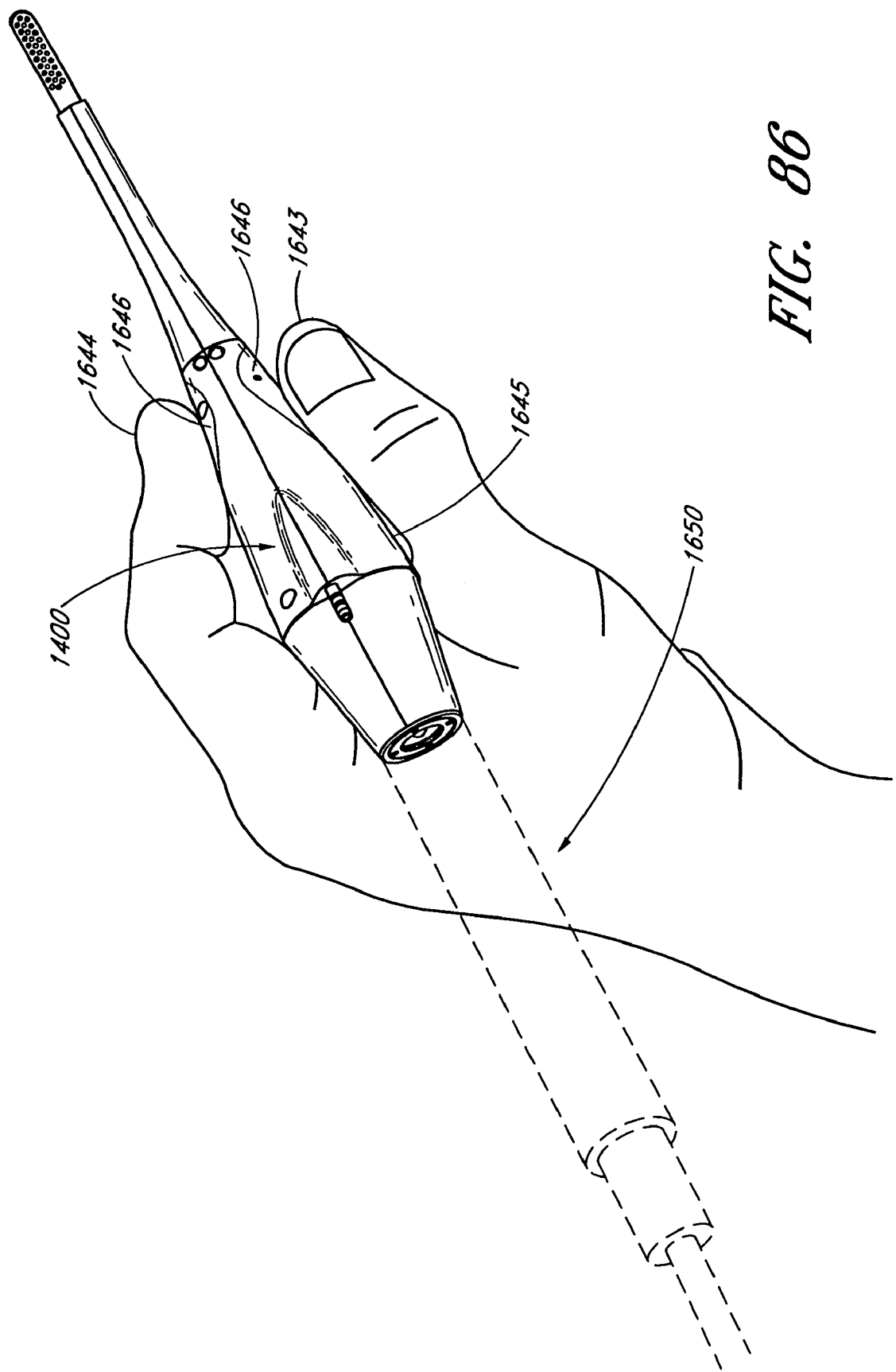
FIG. 86 is a perspective view of the assembled instrument of FIG. 85 held in a clinician's hand.

The overall geometric shape of the surgical file instrument 1400 provides for comfortable gripping. As shown above in FIG. 86, surgical file instrument 1400 can be designed to fit the human hand by a natural grip between the thumb 1643 and an index finger 1644.

The illustrated surgical file instrument 1400 has a body shape that is somewhat similar to the shape of a radish. The relaxed human hand generally features a curved opening between the thumb and index finger that fits the general shape and curve of an outer body handle grip area 1645 of the surgical file instrument 1400.

The outer body of the surgical file instrument 1400 features finger grip depressions 1646 (on both sides) that assist in adding hand traction without the tiring of a hard grip. This enables a surgeon to relax their grip and work in more comfort, and with better hand control and long term stamina. Indicia (e.g., the instrument name, trademark, etc.) can be featured in raised letters 1647 (see FIG. 85) in an area of the finger grip areas to improve grip traction. The illustrated instrument has raised indicia comprising SURGIFILE™ to improve traction. The superior grip and hand traction can be achieved even if the surgeon wears a glove. A wet surgical gloved hand can engage the indicia to enable the surgeon to have a good grip.

Figure 87:
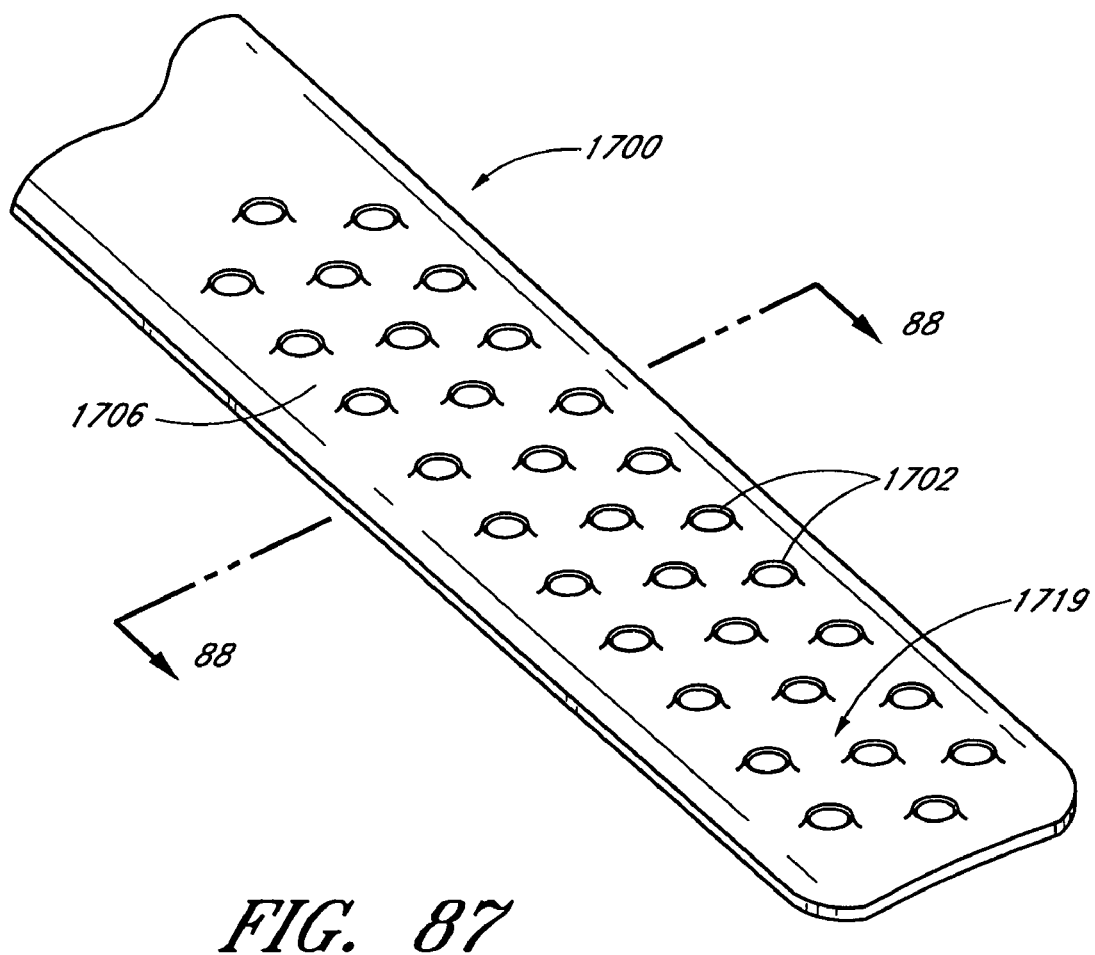
FIG. 87 is a perspective view of a blade for a surgical instrument.
Figure 88:
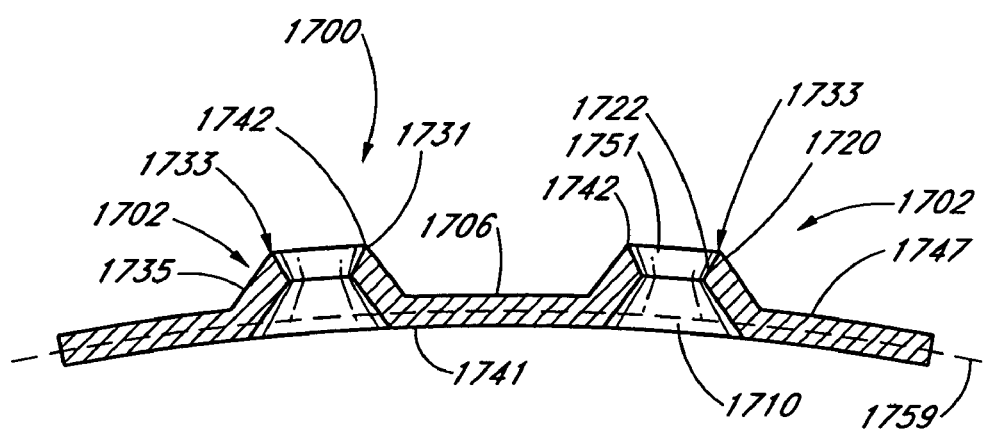
FIG. 88 is a cross-sectional view of the blade of FIG. 87 taken along the line 88-88.

FIG. 87 illustrates one embodiment of a blade of a surgical file instrument. The blade 1700 is perforated and comprises a cutting zone 1719. The illustrated cutting zone 1719 comprises a plurality of cutting elements 1702. The cutting elements 1702 also define throughholes extending through the blade 1700. As shown in FIG. 88, the cutting elements 1702 extend outwardly from an upper face 1706 of the blade 1700. The cutting elements 1702 can have any configuration suitable for grinding, cutting, filing, or otherwise removing tissue. A blade body 1747 of the blade 1700 is defined between the upper face 1706 and a lower face 1741.

The illustrated cutting elements 1702 are raised elements that are somewhat conical in shape and define throughholes 1710. In some embodiments, an irrigation fluid can pass through the throughholes 1710 as discussed in detail above. Each of the cutting elements 1702 can comprise one or more cutting edges for engaging tissue. In the illustrated embodiment of FIG. 88, each of the cutting elements 1702 comprises a tip 1733 that defines an outer cutting surface 1720 and an inner cutting surface 1722. As the cutting surfaces 1720, 1722 move along tissue, the cutting elements 1702 remove tissue.

Tips 1733 of the cutting elements 1702 can have cutting edges 1742 for engaging tissue. The cutting edges 1742 define upper ends 1751 of the throughholes 1710. The cutting edges 1742 can be general parallel to the upper face 1706 and/or the lower face 1741 of the blade 1700. The illustrated body 1747 has a somewhat arcuate transverse axis 1759, as shown in FIG. 88. The cutting edges 1742 can be somewhat arcuate to match the curvature of the body 1747. In some embodiments, the cutting edges 1742 are substantially concentric to the arcuate transverse axis 1759 of the blade 1700. In alternative embodiments, the cutting edges 1742 are substantially flat. Thus, the cutting edges 1742 can be curved, flat, or combinations thereof. The cutting edges 1742 are preferably capable of grinding, cutting, or filing tissue (e.g., bone or other somewhat hard tissue).

The cutting edges 1742 can be formed at the junction of the surfaces 1702, 1722. In the illustrated embodiment, the tips 1733 have a substantially V-shaped portion forming the cutting edges 1742. However, the tips 1733 can have other configurations. The cutting edges 1742 can form substantially contiguous cutting edges.

In alternatively embodiments, the cutting zone 1719 does not comprise throughholes corresponding to each cutting element. For example, cutting elements, without throughholes, can extend from a substantial planar surface.

The blade 1700 can be self-sharpening to retain effectiveness over extended periods of use. As the cutting elements 1702 treat tissue (e.g., remove tissue), the cutting elements 1702 generally do not become dull. In the illustrate embodiment, the cutting elements 1702 are generally circular as view from above. However, in exemplary embodiments, the cutting elements 1702 can be ellipsoidal, polygonal, or having any other shape and size suitable for treating tissue. The cutting elements may or may not define throughholes. For example, the blade may have throughholes spaced from the cutting elements.

The blade 1700 can be formed by a punching process to form the cutting elements 1702. Etching processes (e.g., chemical etching), machining, molding, or other manufacturing techniques can be employed to form the cutting elements 1702.

Figure 89:
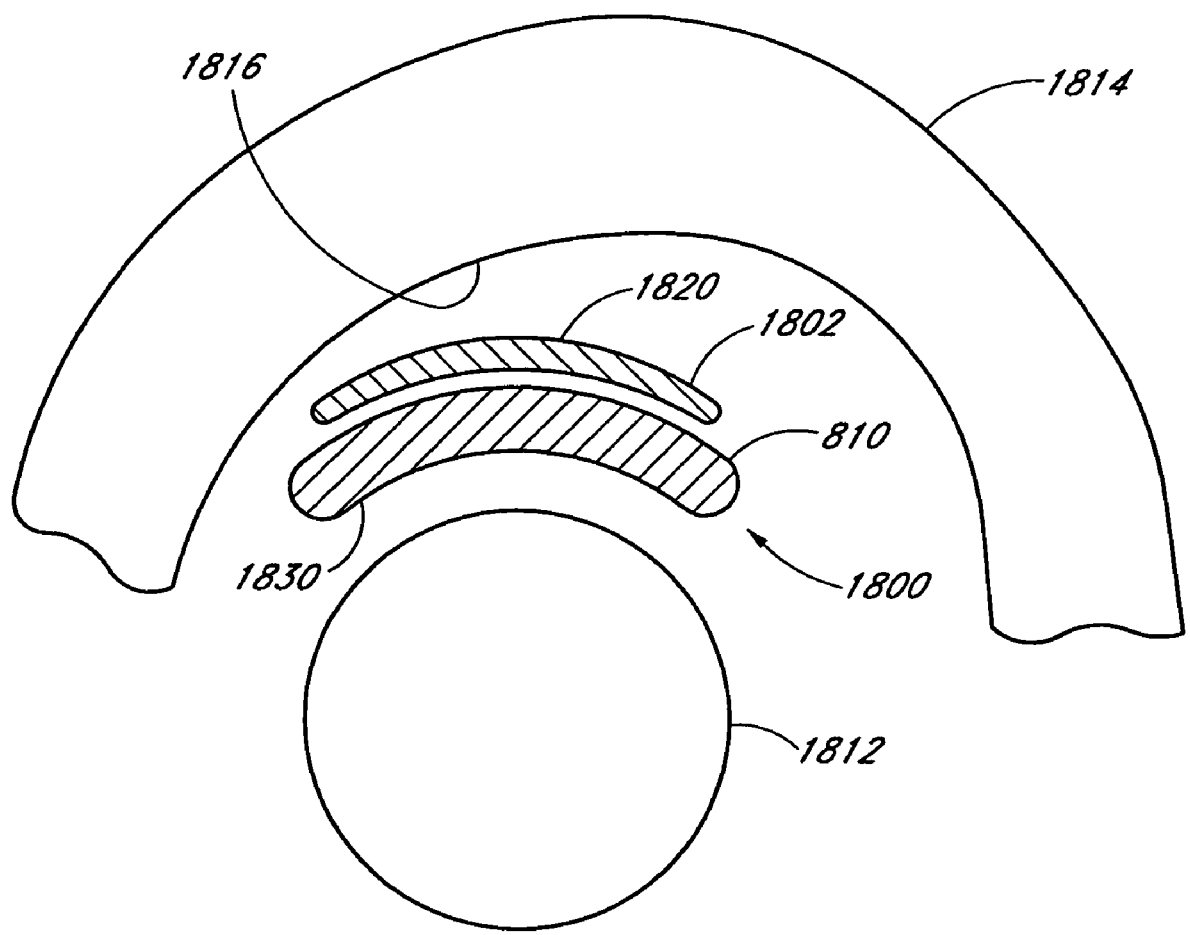
FIG. 89 is a cross-sectional view of a distal tip assembly of a surgical file instrument in which the distal tip assembly is positioned between vertebral bone and a nerve.

FIG. 89 is a cross-sectional view of the distal tip assembly of a surgical file instrument positioned to treat tissue of a patient. The distal tip assembly can be similar to the distal tip assembly of FIGS. 69-72B.

A distal tip assembly 1800 of the surgical file instrument comprises a blade 1802 and a lower blade structure 1810. The illustrated distal tip assembly 1800 is positioned between a nerve 1812 and tissue 1814, although the distal tip assembly 1800 can be positioned at other treatment sites in a patient's body.

In some embodiments, the distal tip assembly 1800 can be used to remove tissue 1814 in a form of vertebral bone made up of one or more facets. In the illustrated embodiment, the distal tip assembly 1800 is positioned to remove material from the inner periphery 1816 of the vertebral bone.

The blade 1802 can comprise an upper filing surface 1820 configured to engage the tissue 1814. The blade 1802 is configured to mate with the lower blade structure 1810. The blade 1802 and the lower blade structure 1810 can be configured to promote and guide movement of the blade 1802. In some embodiments, including the illustrated embodiment, the blade 1802 is slidably coupled to the lower blade structure 1810. The blade 1802 and the lower blade structure 1810 are convex away from the filing surface 1820.

The lower blade structure 1810 can be configured to reduce or minimize trauma to the nerve 1812. The lower blade structure 1810 can define an atraumatic surface 1830 suitable for contacting the tissue 1812. In some embodiments, the atraumatic surface 1830 is concaved towards the nerve 1812. As such, the distal tip assembly 1800 can be positioned between the bone 1814 and the nerve 1812 without substantially traumatizing the nerve 1812. That is, this atraumatic distal tip assembly 1800 is dimensioned so as to fit into a neuroforamen without appreciable trauma to a nerve extending through the neuroforamen. In some embodiments, the distal tip assembly 1800 can have a shape similar to the shape of the opening defined between the bone 1814 and the nerve 1812. The target tissue is removed by reciprocating the blade 1802 while the distal tip assembly 1800 remains in the neuroforamen.

The blade 1802 can have a transverse width that is generally similar to a transverse width of the lower blade structure 1810. In some embodiments, the blade 1802 has a transverse width that is greater than the transverse width of the lower blade structure 1810. In some embodiments, the blade 1802 has a width that is generally similar to the transverse width of the lower blade structure 1810. In some embodiments, the blade 1802 has a transverse width that is less than the transverse width of the lower blade structure. In some embodiments, the blade 1802 can overhang or extend vertically along the edges of the lower blade structure 1810.

The blade 1802 can have a cutting zone. A plurality of cutting elements can define the zone which has a width that is generally similar to the transverse width of the blade 1802. That is, the lateral most cutting elements on either side of the blade 1802 can define a width that is substantially similar to the width of the lower blade structure 1810. In some embodiments, the lateral most cutting elements of the blade 1802 can define a width that is about 95%, 90%, 85%, 80%, 70%, 60%, or other percentages of the width of the lower blade structure 1810. The cutting elements can therefore define an enlarged cutting zone for effectively and rapidly removing tissue from the bone 1814.

FIGS. 90 and 91 illustrate a surgical instrument 2000 in accordance with another embodiment. The surgical instrument 2000 has a curved distal tip assembly 2010 and is generally similar to the surgical instrument 1400, except as detailed below.

Figure 92:
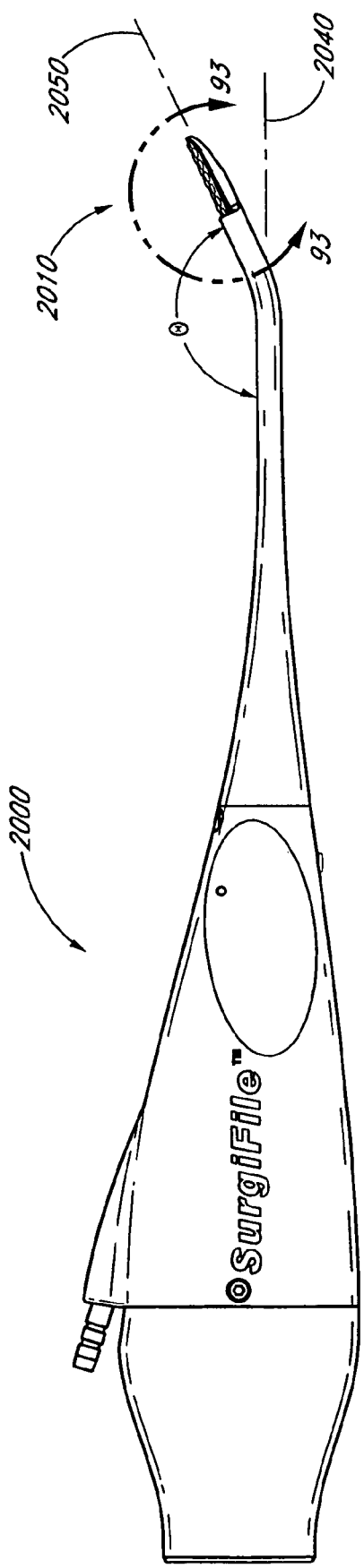
FIG. 92 is a side elevational view of the surgical instrument of FIG. 90.
Figure 93:
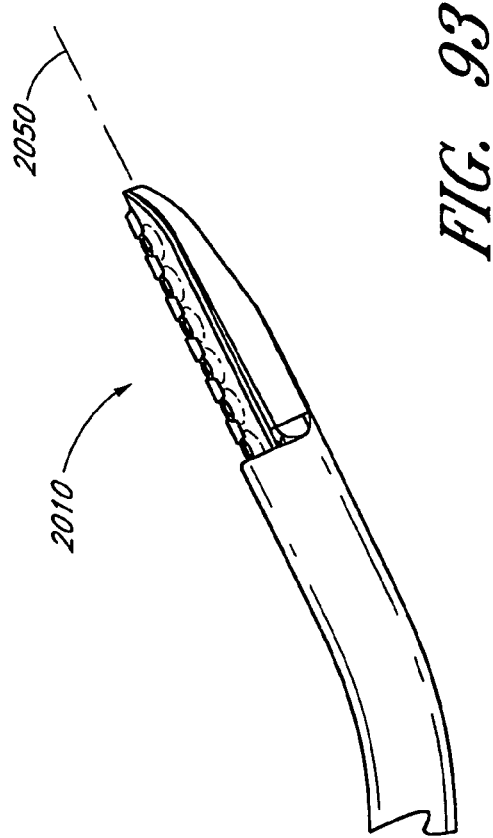
FIG. 93 is an enlarged side view of a distal tip of the surgical instrument of FIG. 92 taken along 93-93.
Figure 94:
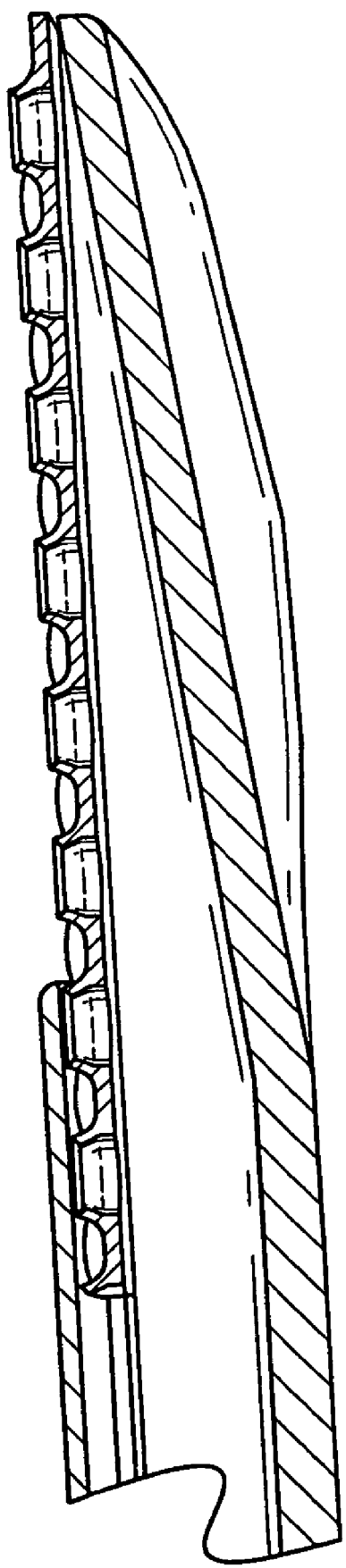
FIG. 94 is a longitudinal cross-sectional view of the distal tip of the surgical instrument of FIG. 90.

The distal tip assembly 2010 has a blade 2014 positioned above a lower blade structure 2016. The distal tip assembly 2010 has an angled section 2020. As shown in FIG. 92, the angle section 2020 defines an angle θ. The angle θ is the angle between the longitudinal axis 2040 of the upper portion of the distal tip assembly 2010 and the distal tip 2050. The angle θ can be about 110 degrees, 120 degrees, 130 degrees, 140 degrees, or ranges encompassing such angles. Distal tip assemblies can also be at other angles or orientations. Such distal tip assemblies can be used for general bone sculpturing, for example. The illustrated instrument 2000 can be used to remove tissue from the spine or any other region of the body, such as a shoulder. For example, the instrument 2000 can be used remove tissue from the scapula, humerus, clavicle, cartilage or any other tissue. The instrument 2000 can also be used in neuroforamina anywhere in the body, including the spine, skull, and other bones through which nerves extend. The shape and size of the distal tip assembly 2010 can be chosen based on the surgical procedures.

Except as further described herein, the embodiments, features, systems, devices, materials, methods and techniques described herein may, in some embodiments, be similar to any one or more of the embodiments, features, systems, devices, materials, methods and techniques described in U.S. application Ser. No. 10/675,068 (U.S. Publication No. 2004-0122459) entitled SHIELDED RECIPROCATING SURGICAL FILE, filed Sep. 29, 2003.

From the foregoing description, it will be appreciated that a novel approach for precision bone and/or tissue removal surgery has been disclosed. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A blade assembly for removing tissue, said blade assembly comprises:
    an elongated blade body having a first surface and an opposing second surface, the blade body having elongate proximal, medial and distal portions;
    at least the medial portion of the blade body being substantially flat and having a width axis transverse to a length of the blade body, the medial portion of the blade body being flexible about the width axis;
    an elongate blade guide comprising a first bearing surface and a second bearing surface, the first bearing surface being adjacent the first blade body surface and the second bearing surface being adjacent the second blade body surface, the blade body and blade guide configured so that the blade can reciprocate along its length between the first and second bearing surfaces of the blade guide, the blade guide having proximal, medial and distal portions, an arcuate bend being disposed in the blade guide medial portion so that a longitudinal axis of the blade guide proximal portion is angled relative to a longitudinal axis of the blade guide distal portion;
    the blade body flexing in the blade body medial portion so as to conform to the bend in the blade guide medial portion; and
    the blade body distal portion having a plurality of raised cutting elements extending from said first surface, each of said cutting elements defining a cutting edge for removing tissue, said cutting edge being elongate and substantially parallel to at least one of said first surface and second surface.

2. The blade of claim 1, wherein said raised cutting elements are adapted to remove bone by at least one of grinding, cutting, and filing.

3. The blade of claim 1, wherein said raised cutting elements each have a throughhole extending through said elongated blade body.

4. The blade of claim 1, wherein said raised cutting elements each have a substantially frusto-conical shape.

5. The blade of claim 4, wherein at least one of the raised cutting elements has a substantially contiguous cutting edge.

6. The blade of claim 1, wherein the first surface in the distal portion of said elongated blade body has an arcuate transverse axis.

7. The blade of claim 6, wherein said cutting edge has substantially the same curvature as said arcuate transverse axis.

8. The blade of claim 6, wherein said cutting edge is arcuate.

9. The blade of claim 1, wherein said cutting edge is substantially flat.

10. The blade of claim 1, wherein said raised cutting elements are substantially self-sharpening.

11. The blade of claim 1, wherein said blade is movably coupled to a lower blade structure of a surgical instrument.

12. The blade of claim 1, wherein said blade is dimensioned so as to fit at least partially within a neuroforamen.

13. The blade assembly of claim 1, wherein the distal portion of the blade body has a longitudinal axis, and the first and second blade body surfaces in the distal portion are arcuate about the distal portion longitudinal axis.

14. The blade assembly of claim 13, wherein the second bearing surface in the blade guide distal portion is arcuate adjacent the arcuate second blade body second surface.

15. The blade assembly of claim 14 additionally comprising a housing, the housing comprising the blade guide and having a distal portion, wherein an outer surface of the housing distal portion is arcuate opposite the arcuate second bearing surface.

16. The blade assembly of claim 15, wherein the housing comprises a channel configured to accommodate a fluid flow, the channel communicating with at least one opening through the second bearing surface in the blade guide distal portion.

17. A blade for removing tissue, said blade comprising:
    a blade body having a first face and a second face, said first face and said second face extending between a first edge and a second edge, the blade body having proximal, medial and distal portions;
    at least the medial portion of the blade body being substantially flat and having a width axis transverse to a length of the blade body, the medial portion of the blade body being flexible about the width axis;
    an elongate blade guide comprising a first bearing surface and a second bearing surface, the first bearing surface being adjacent the first blade body surface and the second bearing surface being adjacent the second blade body surface, the blade body and blade guide configured so that the blade can reciprocate along its length between the first and second bearing surfaces of the blade guide, the blade guide having proximal, medial and distal portions, an arcuate bend being disposed in the blade guide medial portion so that a longitudinal axis of the blade guide proximal portion is angled relative to a longitudinal axis of the blade guide distal portion;

the blade body flexing in the blade body medial portion so as to conform to the bend in the blade guide medial portion; and the blade body distal portion having a plurality of raised elements for removing tissue, said raised elements extending from said first face, each of said raised elements having a cutting edge that is substantially concentric to an arcuate transverse axis of said blade body.

18. The blade of claim 17, wherein said blade body is dimensioned so as to fit at least partially within a neuroforamen.

19. The blade of claim 17, wherein said raised elements form an array of cutting elements that effectively remove tissue when said blade is reciprocated.

20. The blade of claim 17, wherein said raised elements each have a throughhole extending through said blade body.

21. The blade of claim 17, wherein said raised elements are substantially frusto-conical in shape.

22. The blade of claim 21, wherein said cutting edge is defined at a junction of an outer surface and an inner surface of said raised element.

23. The blade of claim 22, wherein said cutting edge is substantially contiguous.

24. The blade of claim 17, wherein said raised elements are substantially self sharpening.

* * * * *

UNITED STATES PATENT AND TRADEMARK OFFICE
CERTIFICATE OF CORRECTION

PATENT NO.        : 7,666,186 B2                                        Page 1 of 1
APPLICATION NO.   : 11/258841
DATED             : February 23, 2010
INVENTOR(S)       : Richard J. Harp It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this

Twenty-eighth Day of December, 2010

David J. Kappos
*Director of the United States Patent and Trademark Office*